US011702709B2

(12) United States Patent
Eggers et al.

(10) Patent No.: US 11,702,709 B2
(45) Date of Patent: Jul. 18, 2023

(54) COMBINATORIAL MICROARRAY ASSAY FOR CLADE VARIANT DETECTION

(71) Applicants: Frederick Henry Eggers, Sahuarita, AZ (US); Benjamin Alan Katchman, Tucson, AZ (US); Fushi Wen, Tucson, AZ (US); Candy Mavis Rivas, Tucson, AZ (US); Cory Scott Newland, Tucson, AZ (US); Michael Edward Hogan, Stony Brook, NY (US)

(72) Inventors: Frederick Henry Eggers, Sahuarita, AZ (US); Benjamin Alan Katchman, Tucson, AZ (US); Fushi Wen, Tucson, AZ (US); Candy Mavis Rivas, Tucson, AZ (US); Cory Scott Newland, Tucson, AZ (US); Michael Edward Hogan, Stony Brook, NY (US)

(73) Assignee: PathogenDx, Inc., Scottsdale, AZ (US)

( * ) Notice: Subject to any disclaimer, the term of this patent is extended or adjusted under 35 U.S.C. 154(b) by 0 days.

(21) Appl. No.: 17/529,666

(22) Filed: Nov. 18, 2021

(65) Prior Publication Data

US 2022/0267867 A1 Aug. 25, 2022

Related U.S. Application Data

(63) Continuation-in-part of application No. 17/332,837, filed on May 27, 2021.

(60) Provisional application No. 63/147,613, filed on Feb. 9, 2021.

(51) Int. Cl.
*C12Q 1/70* (2006.01)
*C12Q 1/68* (2018.01)
*C12Q 1/686* (2018.01)

(52) U.S. Cl.
CPC ............ *C12Q 1/701* (2013.01); *C12Q 1/686* (2013.01); *C12Q 2600/16* (2013.01)

(58) Field of Classification Search
CPC ................................ C12Q 1/686; C12Q 1/701
See application file for complete search history.

(56) References Cited

U.S. PATENT DOCUMENTS

| | | | | |
|---|---|---|---|---|
| 11,149,320 | B1 * | 10/2021 | Brambati | C12Q 1/70 |
| 2018/0251758 | A1 * | 9/2018 | Hogan | C12N 15/1086 |
| 2018/0251822 | A1 * | 9/2018 | Hogan | C12Q 1/6895 |
| 2019/0085414 | A1 * | 3/2019 | Hogan | G16B 30/00 |
| 2019/0085415 | A1 * | 3/2019 | Hogan | C12Q 1/6837 |
| 2022/0195539 | A1 * | 6/2022 | Hogan | C12Q 1/701 |
| 2022/0251635 | A1 * | 8/2022 | Eggers | C12Q 1/686 |
| 2022/0267867 | A1 * | 8/2022 | Eggers | C12Q 1/701 |
| 2022/0364157 | A1 * | 11/2022 | Hogan | C12Q 1/6816 |

FOREIGN PATENT DOCUMENTS

WO WO-2022173707 A1 * 8/2022

OTHER PUBLICATIONS

Blow, J.A., Mores, C.N., Dyer, J. and Dohm, D.J., 2008. Viral nucleic acid stabilization by RNA extraction reagent. Journal of virological methods, 150(1-2), pp. 41-44 (Year: 2008).*
Casagrande et al., 2020. Detection of SARS-CoV-2 in human retinal biopsies of deceased COVID-19 patients. Ocular immunology and inflammation, 28(5), pp. 721-725. (Year: 2020).*
Chan et al., 2020. Improved molecular diagnosis of COVID-19 by the novel, highly sensitive and specific COVID-19-RdRp/Hel real-time reverse transcription-PCR assay validated in vitro and with clinical specimens. Journal of clinical microbiology, 58(5), e00310-20 pp. 1-10. (Year: 2020).*
Corman et al., 2012. Detection of a novel human coronavirus by real-time reverse-transcription polymerase chain reaction. Eurosurveillance, 17(39), 20285 pp. 1-6. (Year: 2012).*
Corman et al., 2020. Detection of 2019 novel coronavirus (2019-nCoV) by real-time RT-PCR. Eurosurveillance, 25(3), 2000045 pp. 23-30. (Year: 2020).*
Damin et al., 2021. CovidArray: A microarray-based assay with high sensitivity for the detection of Sars-Cov-2 in nasopharyngeal swabs. Sensors, 21(7), 2490 pp. 1-13. (Year: 2021).*
Daum et al., 2011. A clinical specimen collection and transport medium for molecular diagnostic and genomic applications. Epidemiology & Infection, 139(11), pp. 1764-1773. (Year: 2011).*
Dhar, B.C., 2022. Diagnostic assay and technology advancement for detecting SARS-CoV-2 infections causing the COVID-19 pandemic. Analytical and Bioanalytical Chemistry, pp. 1-32. (Year: 2022).*
Guan et al., 2020. A genetic barcode of SARS-CoV-2 for monitoring global distribution of different clades during the COVID-19 pandemic. International Journal of Infectious Diseases, 100, pp. 216-223. (Year: 2020).*
Han et al., 2008. Simultaneously subtyping of all influenza A viruses using DNA microarrays. Journal of virological methods, 152(1-2), pp. 117-121. (Year: 2008).*
Huang et al., 2009. Multiplex assay for simultaneously typing and subtyping influenza viruses by use of an electronic microarray. Journal of clinical microbiology, 47(2), pp. 390-396. (Year: 2009).*
Jalandra et al., 2020. Strategies and perspectives to develop SARS-CoV-2 detection methods and diagnostics. Biomedicine & Pharmacotherapy, 129, 110446 pp. 1-10. (Year: 2020).*
Le et al., 2020. Development of a multiplex RT-qPCR for the detection of different clades of avian influenza in poultry. Viruses, 12(1), 100 pp. 1-14. (Year: 2020).*

(Continued)

*Primary Examiner* — Teresa E Strzelecka
*Assistant Examiner* — Olayinka A Oyeyemi
(74) *Attorney, Agent, or Firm* — Benjamin Aaron Adler

(57) ABSTRACT

Provided herein is a method for detecting the presence of clade variants in the COVID-19 virus in a human sample and/or an environmental sample. Samples are processed to obtain total RNA. The RNA is used as a template in a combined reverse transcription and amplification reaction to obtain fluorescent COVID-19 virus amplicons. These amplicons are hybridized on a microarray with nucleic acid probes having sequences that discriminate among the various clade variants. The microarray is imaged to detect the clade variant and each clade variant is distinguished from others by generating an intensity distribution profile from the image, which is unique to each of the clade variants.

13 Claims, 48 Drawing Sheets

Specification includes a Sequence Listing.

(56) References Cited

OTHER PUBLICATIONS

Lee, S.H., 2020. Testing for SARS-CoV-2 in cellular components by routine nested RT-PCR followed by DNA sequencing. International Journal of Geriatrics and Rehabilitation 2(1):69-96. (Year: 2020).*
Luna et al., 2007. Generic detection of coronaviruses and differentiation at the prototype strain level by reverse transcription-PCR and nonfluorescent low-density microarray. Journal of clinical microbiology, 45(3), pp. 1049-1052. (Year: 2007).*
Mercatelli, D. and Giorgi, F.M., 2020. Geographic and genomic distribution of SARS-CoV-2 mutations. Frontiers in microbiology, 1800. pp. 1-13. (Year: 2020).*
Mollaei et al., 2020. Comparison five primer sets from different genome region of COVID-19 for detection of virus infection by conventional RT-PCR. Iranian Journal of Microbiology, 12(3), p. 185-193. (Year: 2020).*
Murugan et al., 2021. COVID-19: A review of newly formed viral clades, pathophysiology, therapeutic strategies and current vaccination tasks. International Journal of Biological Macromolecules, 193, pp. 1165-1200. (Year: 2021).*
Ortiz-Prado et al., 2020. Clinical, molecular, and epidemiological characterization of the SARS-CoV-2 virus and the Coronavirus Disease 2019 (COVID-19), a comprehensive literature review. Diagnostic microbiology and infectious disease, 98(1), p. 115094. (Year: 2020).*
Rogers et al., 2020. Evaluation of transport media and specimen transport conditions for the detection of SARS-CoV-2 by use of real-time reverse transcription-PCR. Journal of clinical microbiology, 58(8), e00708-20, pp. 1-5. (Year: 2020).*
Sengupta et al., 2003. Molecular detection and identification of influenza viruses by oligonucleotide microarray hybridization. Journal of Clinical Microbiology, 41(10), pp. 4542-4550. (Year: 2003).*
Shi et al., 2003. Design and application of 60mer oligonucleotide microarray in SARS coronavirus detection. Chinese Science Bulletin, 48(12), pp. 1165-1169. (Year: 2003).*
Vogels et al., 2020. Analytical sensitivity and efficiency comparisons of SARS-CoV-2 RT-qPCR primer-probe sets. Nature microbiology, 5(10), pp. 1299-1305. (Year: 2020).*
Wang et al., 2016. Detection and typing of human-infecting influenza viruses in China by using a multiplex DNA biochip assay. Journal of virological methods, 234, pp. 178-185. (Year: 2016).*
Zhang et al., 2005. Sensitive detection of SARS coronavirus RNA by a novel asymmetric multiplex nested RT-PCR amplification coupled with oligonucleotide microarray hybridization. In Microarrays in Clinical Diagnostics (pp. 59-78). Humana Press. (Year: 2005).*
Islam et al., 2021. A rapid and cost-effective multiplex ARMS-PCR method for the simultaneous genotyping of the circulating SARS-CoV-2 phylogenetic clades. Journal of medical virology, 93(5), pp. 2962-2970. (Year: 2021).*
De Souza Luna et al., 2007. Generic detection of coronaviruses and differentiation at the prototype strain level by reverse transcription-PCR and nonfluorescent low-density microarray. Journal of clinical microbiology, 45(3), pp. 1049-1052. (Year: 2007).*
Guo, X., Geng, P., Wang, Q., Cao, B. and Liu, B., 2014. Development of a single nucleotide polymorphism DNA microarray for the detection and genotyping of the SARS coronavirus. Journal of microbiology and biotechnology, 24(10), pp. 1445-1454. (Year: 2014).*
Hindson et al., 2008. Diagnostic evaluation of multiplexed reverse transcription-PCR microsphere array assay for detection of foot-and-mouth and look-alike disease viruses. Journal of clinical microbiology, 46(3), pp. 1081-1089. (Year: 2008).*
Liu, Q., Zhou, Q., Bai, Y., Ge, Q. and Lu, Z., 2005. Detection and analysis system for hybridization images of lab-in-a-tube microarray. Chinese Science Bulletin, 50(24), pp. 2896-2900. (Year: 2005).*
Liu, Q., Bai, Y., Ge, Q., Zhou, S., Wen, T. and Lu, Z., 2007. Microarray-in-a-tube for detection of multiple viruses. Clinical chemistry, 53(2), pp. 188-194. (Year: 2007).*
Poddar, S.K., 2000. Symmetric vs asymmetric PCR and molecular beacon probe in the detection of a target gene of adenovirus. Molecular and Cellular probes, 14(1), pp. 25-32. (Year: 2000).*
Tao et al., 2009. Detection and differentiation of four poultry diseases using asymmetric reverse transcription polymerase chain reaction in combination with oligonucleotide microarrays. Journal of veterinary diagnostic investigation, 21(5), pp. 623-632. (Year: 2009).*
Graybill et al., 2019. Multiplexed microRNA expression profiling by combined asymmetric PCR and label-free detection using silicon photonic sensor arrays. Analytical methods, 10(14), pp. 1618-1623. (Year: 2019).*
Guo et al., 2014. Development of a single nucleotide polymorphism DNA microarray for the detection and genotyping of the SARS coronavirus. Journal of microbiology and biotechnology, 24(10), pp. 1445-1454. (Year: 2014).*
Guo et al., 2019. Fluorescence resonance energy transfer combined with asymmetric PCR for broad and sensitive detection of porcine reproductive and respiratory syndrome virus 2. Journal of virological methods, 272, 113710, pp. 1-8. (Year: 2019).*

* cited by examiner

COMBINATORIAL MICROARRAY ASSAY FOR CLADE VARIANT DETECTION

CROSS-REFERENCE TO RELATED APPLICATIONS

This continuation-in-part application claims the benefit of priority under 35 U.S.C. § 120 of pending non-provisional application U.S. Ser. No. 17/332,837, filed May 27, 2021, which claims the benefit of priority under 35 U.S.C. § 119(e) of provisional application U.S. Ser. No. 63/147,613, filed Feb. 9, 2021, both of which are hereby incorporated by reference in their entireties.

BACKGROUND OF THE INVENTION

Field of the Invention

The present invention relates to the field of multiplex based viral pathogen detection and analysis. More particularly, the present invention relates to detecting the presence of clade variants of SARS-COVID-2 virus in patient and environmental samples.

Description of the Related Art

The COVID-19 pandemic has increased awareness that viral infection can be an existential threat to health, public safety and the US economy. More fundamentally, there is a recognition that the viral risks are exceedingly dangerous and complex and require new approaches to diagnostics and screening.

The next pandemic wave is expected to have more pronounced flu-like symptoms (seasonal influenza A and/or B) coupled with the COVID-19, or COVID-19 variants that will coexist with the Coronavirus already responsible for the common cold. These complexities are expected to pose significant challenges to public health and the healthcare system in diagnosing multi-symptom conditions accurately and efficiently.

The COVID-19 pandemic has also led to the realization of an additional level of complexity that the realization that human health and environmental contamination are linked in a fundamental way that affects collection efficiency and increases risk to the healthcare workers (1, 2). Alternatives to nasopharyngeal collection methods such as for example, saliva collection are needed to enable scalability among millions of individuals.

Q-RT-PCR technology has dominated COVID-19 diagnostics and public health screening. Independent of the test developer, Q-RT-PCR has been shown to have an unusually high false negative rate (15% up to 30%). As of May 2020, the CDC has recorded 613,041 COVID-19 tests. With a 15% false negative rate, approximately 91, 956 people would thus be falsely classified as free of infection. Meta-analysis has shown that the false negative rate for Q-RT-PCR is high below day 7 of infection when viral load is still low. This renders Q-RT-PCR ineffective as a tool for early detection of weak symptomatic carriers while also lessening its value in epidemiology.

As for other organisms, genetic variations in SARS-COVID-2 are grouped into clades. There are over 52,600 complete and high-coverage genomes available on the Global Initiative on Sharing Avian Influenza Data (GISAID). Presently, WHO has identified 10,022 SARS-COVID-2 genomes from 68 different countries and detected 65,776 variants and 5,775 distinct variants that comprised missense mutations, synonymous mutations, mutations in non-coding regions, non-coding deletions, in-frame deletions, non-coding insertions, stop-gained variants, frameshift deletions and in-frame insertions among others. Identifying these clade variants in population and environmental samples while a daunting task, is critical for global public health management directed to controlling the pandemic.

When first identified, it was widely assumed that COVID-19 would mutate slowly, based on a relatively stable genome that would experience minimal genetic drift as the pandemic spread. Unfortunately, perhaps as a function of environmental selection pressure (crowding) physical selection pressure (PPE) and therapeutic selection pressure (vaccination) the original Wuhan clade has evolved into a very large number of clade variants. Consequently, in the past 3 months there has been an international effort to discover and track the full range of clade variant evolution.

Next Generation Sequencing (NGS), primarily Targeted Resequencing of the CoV-2 Spike gene, has been instrumental in elucidating the patterns of genetic variation which define the growing set of clade variants of present international concern (UK, South Africa, Brazil, India, US California, US NY, US Southern) with others emerging at an expanding rate. Whereas NGS is without equal as a discovery tool in genetic epidemiology, it is not ideally suited for field-deployed, public health screening at population scale due to complexities associated with purchasing and managing the kits supply chain, setting up and training personnel, especially when compared to Q-RT-PCR, which is the present standard for nucleic acid based COVID-19 screening. Conversely, while Q-RT-PCR (especially TaqMan) is now the clear standard in COVID-19 testing laboratories for simple positive/negative screening, its suitability for screening clade variants is limited. Deploying TaqMan for COVID-19 clade Identification requires running about 10-15 TaqMan kits on each sample to generate sequence content equivalent to Spike targeted NGS, thereby negating the benefits of costs and logistics with Q-RT-PCR.

Thus, there is a need in the art for superior tools to not only administer and stabilize sample collection for respiratory viruses from millions of samples in parallel obtained from diverse locations including, clinic, home, work, school and in transportation hubs, but also to detect and identify clade variants in the population at the highest levels of sensitivity and specificity. The present invention fulfills this longstanding need and desire in the art.

SUMMARY OF THE INVENTION

The present invention is directed to a method for detecting clade variants in the Coronavirus disease 2019 virus in a sample. The sample is obtained from which viruses are harvested. Total RNA is isolated from the harvested viruses. A combined reverse transcription and first amplification reaction is performed on the total RNA using at least one first primer pair selective for all COVID-19 viruses to generate COVID-19 virus cDNA amplicons. A second amplification is performed using the COVID-19 virus cDNA amplicons as template and at least one fluorescent labeled second primer pair selective for a target nucleotide sequence in the COVID-19 virus cDNA to generate at least one fluorescent labeled COVID-19 virus amplicon. The fluorescent labeled COVID-19 virus amplicons are hybridized to a plurality of nucleic acid probes. Each nucleic acid probe is attached to a solid microarray support and has a sequence corresponding to a sequence determinant that discriminates among clade variants of the COVID-19 virus. After hybridization, the array is washed at least once and imaged to detect at least one fluorescent signal from the hybridized fluorescent labeled COVID-19 virus amplicons. An intensity distribution profile is generated from the at least one fluorescent signal that is unique to one of the clade variants, thereby detecting the clade variant of the COVID-19 virus in the sample. The present invention is directed to a related method where prior to the harvesting step, the method further comprises mixing the sample with an RNA stabilizer.

The present invention is further directed to a method for detecting clade variants in the Coronavirus disease 2019 virus in a sample. The sample is obtained from which, viruses are harvested. Total RNA is isolated from the harvested viruses. A combined reverse transcription and first amplification reaction is performed on the total RNA using at least one fluorescent labeled primer pair comprising an unlabeled primer, and a fluorescently labeled primer, selective for a target sequence in all COVID-19 viruses to generate at least one fluorescent labeled COVID-19 virus amplicon. The fluorescent labeled COVID-19 virus amplicons are hybridized to a plurality of nucleic acid probes. Each nucleic acid probe is attached to a solid microarray support, and has a sequence corresponding to a sequence determinant that discriminates among clade variants of the COVID-19 virus. After hybridization, the array is washed at least once and imaged to detect at least one fluorescent signal from the hybridized fluorescent labeled COVID-19 virus amplicons. An intensity distribution profile is generated from the at least one fluorescent signal that is unique to one of the clade variants, thereby detecting the clade variant of the COVID-19 virus in the sample. The present invention is directed to a related method where prior to the harvesting step, the method further comprises mixing the sample with an RNA stabilizer.

Other and further aspects, features, and advantages of the present invention will be apparent from the following description of the presently preferred embodiments of the invention. These embodiments are given for the purpose of disclosure.

BRIEF DESCRIPTION OF THE FIGURES

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 12A shows the multiplex analysis data normalized to Universal probe. FIG. 12B shows the multiplex analysis data normalized to Wild-type probe.

FIG. 13A shows the multiplex analysis data normalized to Universal probe. FIG. 13B shows the multiplex analysis data normalized to Wild-type probe.

FIG. 14A shows DETECTX-Cv analysis for the indicated variants corresponding to the Brazil region. FIG. 14Y shows DETECTX-Cv analysis for the indicated variants corresponding to the UK region.

FIG. 15A shows the analysis using synthetic Clade Variant standard corresponding to Brazil. FIG. 15B shows the analysis using synthetic Clade Variant standard corresponding to California 452 (CA 452). FIG. 15C shows the analysis using synthetic Clade Variant standard corresponding to India. FIG. 15D shows the analysis using synthetic Clade Variant standard corresponding to South Africa. FIG. 15E shows the analysis using synthetic Clade Variant standard corresponding to United Kingdom.

FIG. 18A shows a histogram analysis for the South Africa synthetic cocktail, D80A–, E484K, N501Y, A701V. FIG. 18B shows a histogram analysis for the California synthetic cocktail, W152C, L452R. FIG. 18C shows a histogram analysis for the India synthetic cocktail, N440K. FIG. 18D shows a histogram analysis for the Brazil P.1 synthetic cocktail, D138Y, E484K, N501Y. FIG. 18E shows a histogram analysis for the UK (B.1.1.7) synthetic cocktail, 69-70 deletion, N501Y, P681H.

FIG. 19A shows a histogram analysis for a sample comprising Wuhan/European progenitor variants. FIG. 19B shows a histogram analysis for a sample comprising California variants, W152C AND L452R. FIG. 19C shows a histogram analysis for a sample comprising California variants, W152C and L452R. FIG. 19D shows a histogram analysis for a sample comprising UK variants, 69-70 deletion, N501Y and P681H. FIG. 19E shows a histogram analysis for a sample comprising UK variants, 69-70 deletion, N501Y and P681H. FIG. 19F shows a histogram analysis for a sample comprising, 69-70 deletion, and P681H. FIG. 19G shows a histogram analysis for a sample comprising variant P681H. FIG. 19H shows a histogram analysis for a sample comprising variant P681H. FIG. 19I shows a histogram analysis for a sample comprising California variants, W152C and L452R. FIG. 19J shows a histogram analysis for a sample that did not pass QA/QC. FIG. 19K shows a histogram analysis for a sample that did not pass QA/QC.

FIG. 20A shows a histogram analysis for a sample comprising California variants W152C and L452R. FIG. 20B shows a histogram analysis for a sample comprising likely California variant L452R. FIG. 20C shows a histogram analysis for a sample comprising California variants, W152C and L452R. FIG. 20D shows a histogram analysis for a sample that did not pass QA/QC. FIG. 20E shows a histogram analysis for a sample comprising California variants W152C and L452R. FIG. 20F shows a histogram analysis for a sample comprising California variant, W152C and L452R. FIG. 20G shows a histogram analysis for a sample comprising California variants, W152C and L452R. FIG. 20H shows a histogram analysis for a sample comprising variant P681H. FIG. 20I shows a histogram analysis for a sample comprising variant P681H. FIG. 20J shows a histogram analysis for a sample comprising Wuhan/European progenitor variants.

DETAILED DESCRIPTION OF THE INVENTION

Figure 1:
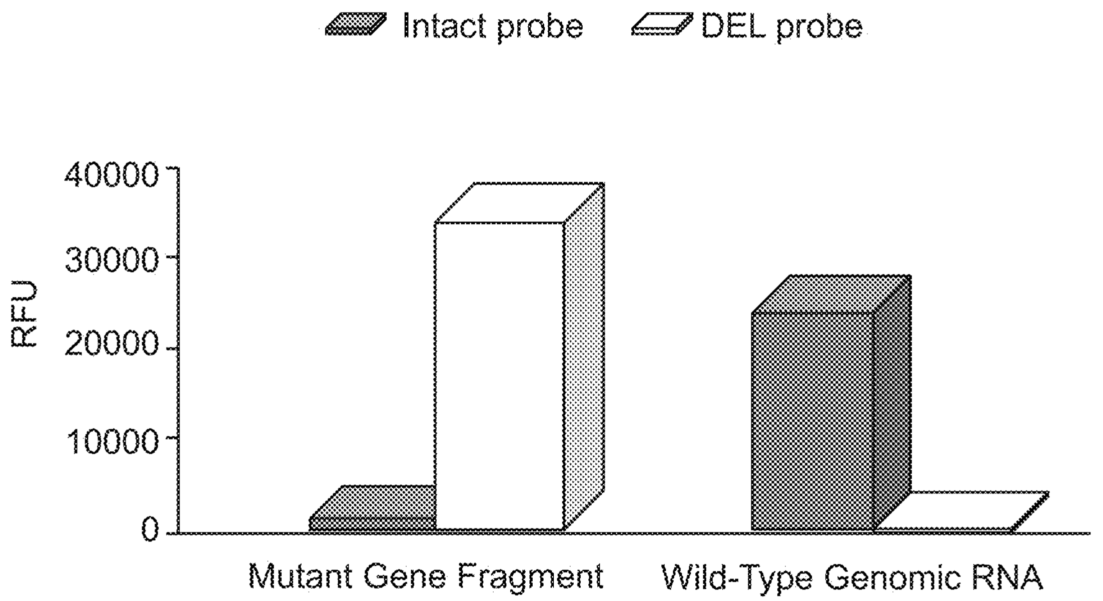
FIG. 1 shows clade Chip target site performance data for the Spike 69-70 deletion.
Figure 2:
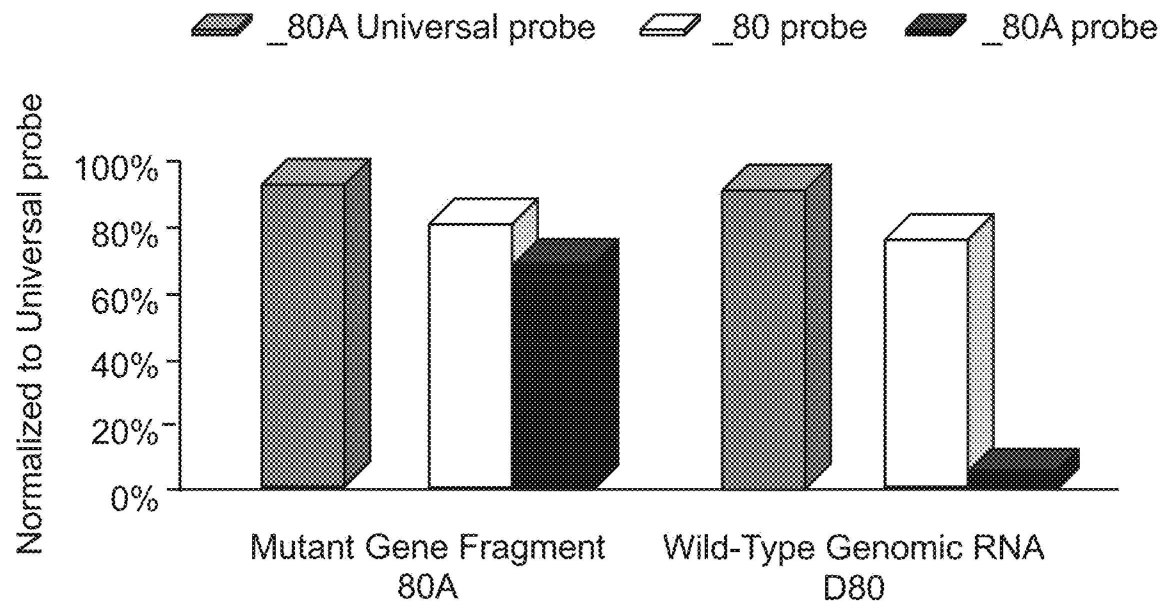
FIG. 2 shows clade Chip target sites performance data normalized to a universal probe for the Spike D80A mutation.
Figure 3:
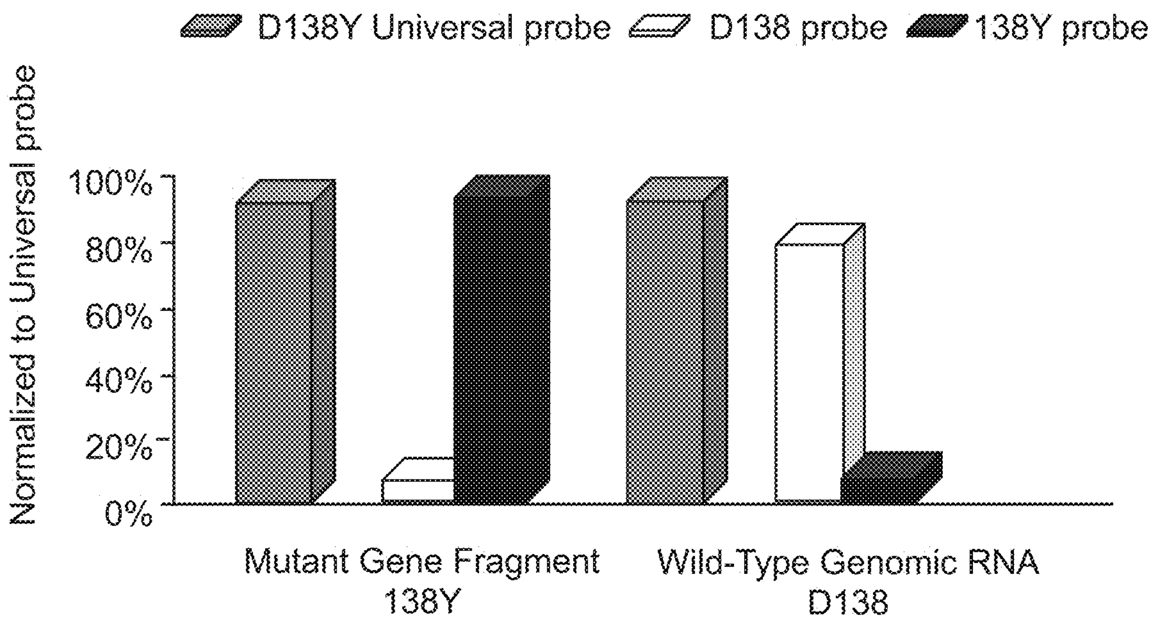
FIG. 3 shows clade Chip target sites performance data normalized to a universal probe for the Spike D138Y mutation.
Figure 4:
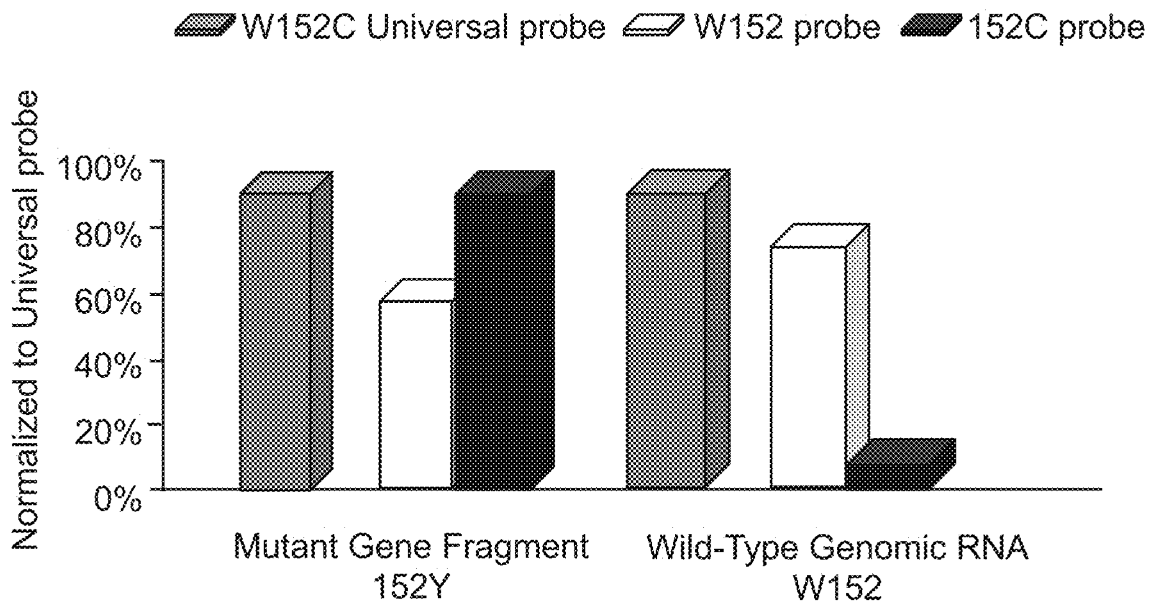
FIG. 4 shows clade Chip target sites performance data normalized to a universal probe for the Spike W152C mutation.
Figure 5:
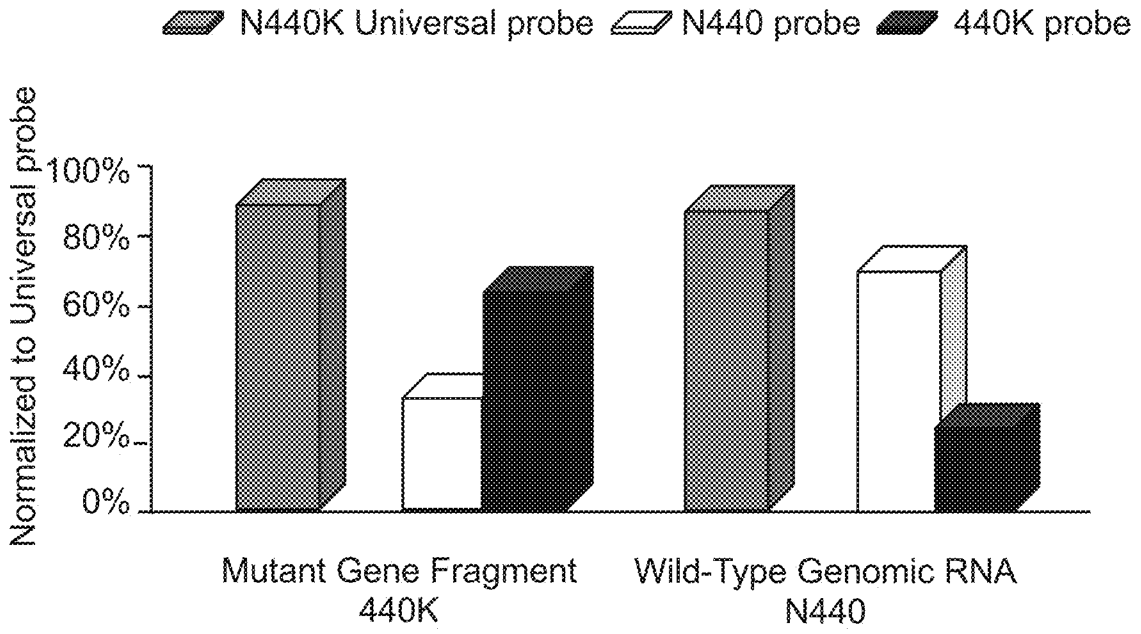
FIG. 5 shows clade Chip target sites performance data normalized to a universal probe for the Spike N440K mutation.
Figure 6:
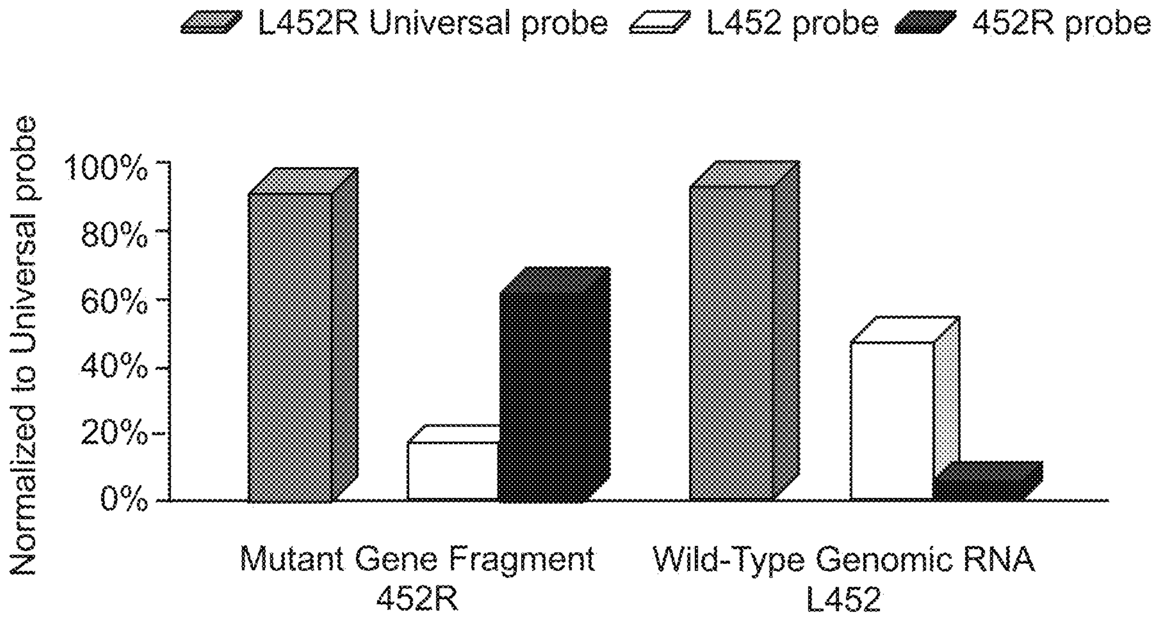
FIG. 6 shows clade Chip target sites performance data normalized to a universal probe for the Spike L452R mutation.
Figure 7:
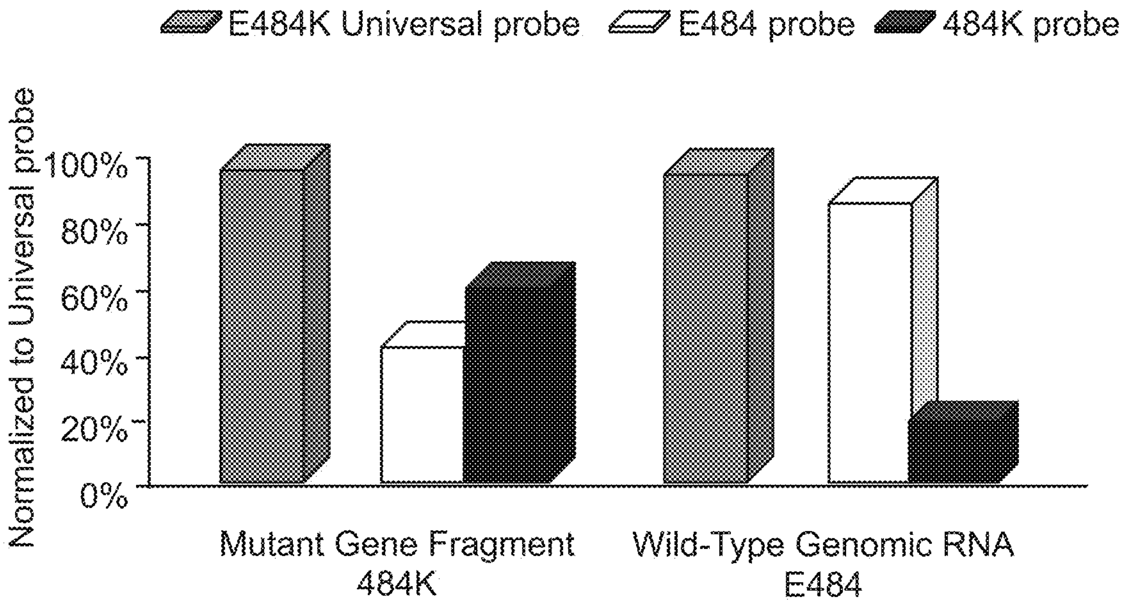
FIG. 7 shows clade Chip target sites performance data normalized to a universal probe for the Spike E484K mutation.
Figure 8:
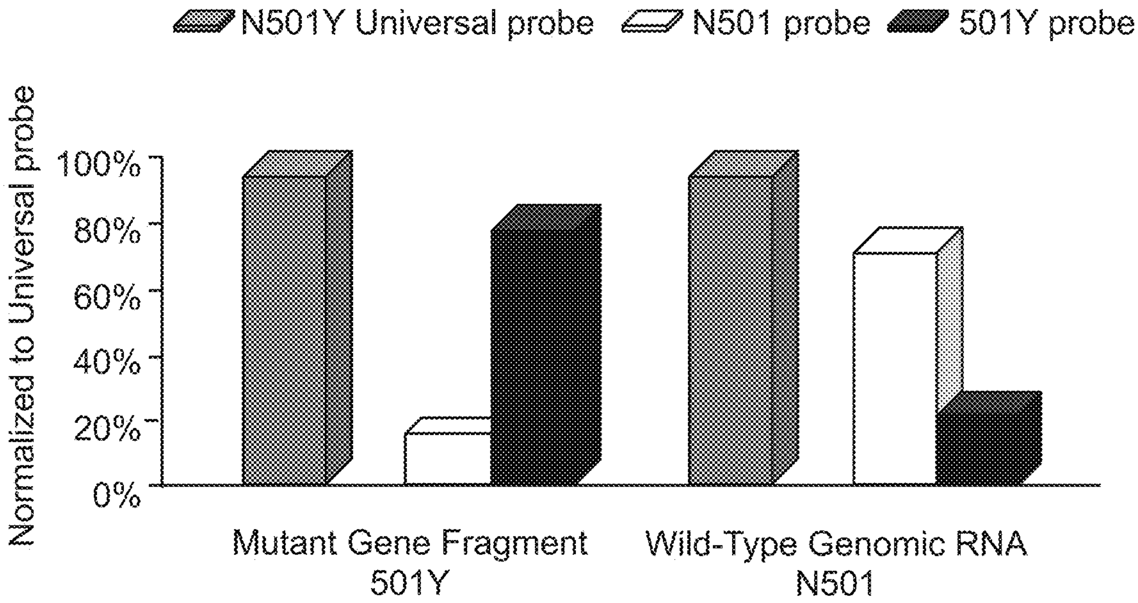
FIG. 8 shows clade Chip target sites performance data normalized to a universal probe for the Spike N501Y mutation.
Figure 9:
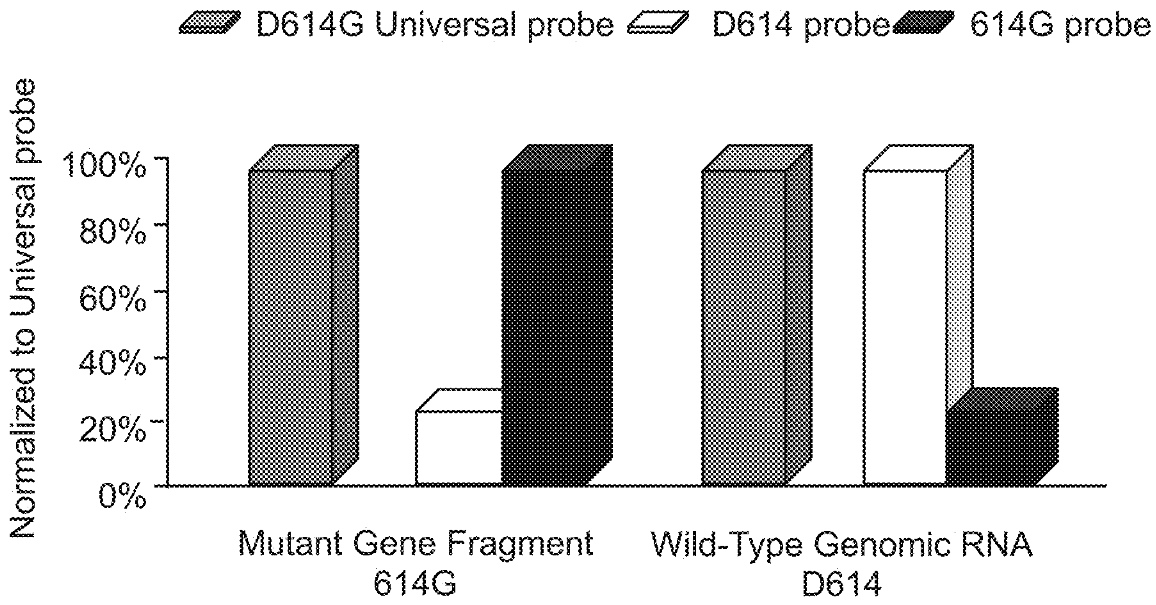
FIG. 9 shows clade Chip target sites performance data normalized to a universal probe for the Spike D614G mutation.
Figure 10:
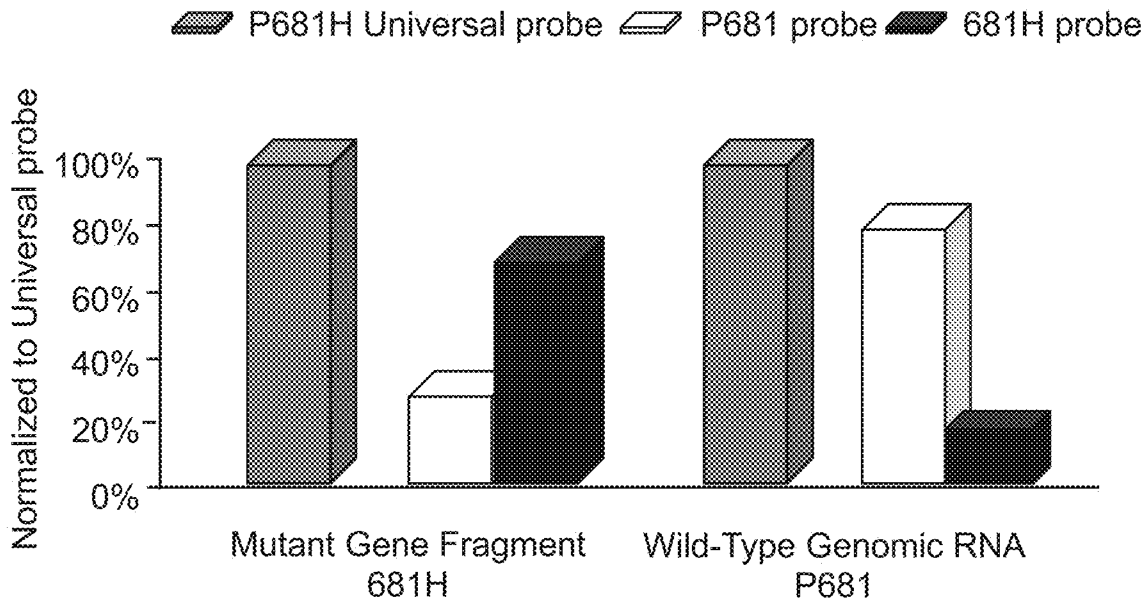
FIG. 10 shows clade Chip target sites performance data normalized to a universal probe for the Spike P681H mutation.
Figure 11:
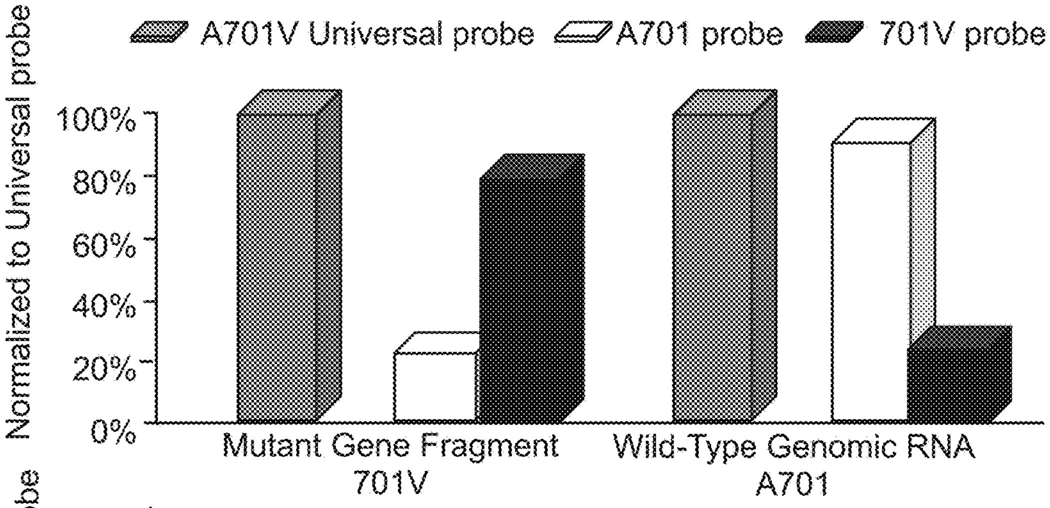
FIG. 11 shows clade Chip target sites performance data normalized to a universal probe for the Spike A701V mutation.

As used herein, the term "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method described herein can be implemented with respect to any other method described herein.

As used herein, the term "or" in the claims is used to mean "and/or" unless explicitly indicated to refer to alternatives only or the alternatives are mutually exclusive, although the disclosure supports a definition that refers to only alternatives and "and/or".

As used herein, "comprise" and its variations, such as "comprises" and "comprising" will be understood to imply the inclusion of a stated item, element or step or group of items, elements or steps but not the exclusion of any other item, element or step or group of items, elements or steps unless the context requires otherwise. Similarly, "another" or "other" may mean at least a second or more of the same or different claim element or components thereof.

In one embodiment of the present invention there is provided a method for detecting clade variants in a Coronavirus disease 2019 virus (COVID-19) in a sample, comprising obtaining the sample; harvesting viruses from the sample; isolating a total RNA from the harvested viruses; performing a combined reverse transcription and first amplification reaction on the total RNA using at least one first primer pair selective for all COVID-19 viruses to generate COVID-19 virus cDNA amplicons; performing a second amplification using the COVID-19 virus cDNA amplicons as template and at least one fluorescent labeled second primer pair selective for a target nucleotide sequence in the COVID-19 virus cDNA to generate at least one fluorescent labeled COVID-19 virus amplicon; hybridizing the fluorescent labeled COVID-19 virus amplicons to a plurality of nucleic acid probes, each having a sequence corresponding to a sequence determinant that discriminates among the clade variants of the COVID-19 virus, where the nucleic acid probes are attached to a solid microarray support; washing the microarray at least once; and imaging the microarray to detect at least one fluorescent signal from the hybridized fluorescent labeled COVID-19 virus amplicons, thereby detecting the clade variants of the COVID-19 virus in the sample. In a related embodiment after the imaging step, a step is performed of generating an intensity distribution profile from the at least one fluorescent signal that is unique to one of the clade variants thereby detecting the clade variant of the COVID-19 virus in the sample.

A total RNA potentially comprising RNA from COVID-19 virus and other contaminating pathogens and human cells is isolated from the sample. Commercially available RNA isolation kits such as for example, a Quick-DNA/RNA Viral MagBead Kit from Zymo Research are used for this purpose. The total RNA thus isolated is used without further purification. Alternatively, intact virus may be captured with magnetic beads, using kits such as that from Ceres Nanosciences (e.g., CERES NANOTRAP technology), or by first precipitating the virus with polyethylene glycol (PEG), followed by lysis of the enriched virus by heating with a "PCR-Friendly" lysis solution such as 1% NP40 in Tris-EDTA buffer and then used without additional purification.

COVID-19 virus cDNA to generate at least one fluorescent labeled COVID-19 virus amplicon.

The fluorescent labeled COVID-19 virus amplicons hybridize to the nucleic acid probes, which are attached at specific positions on a microarray support, for example, a 3-dimensional lattice microarray support. After hybridization, the microarray is washed at least once to remove unhybridized amplicons. Washed microarrays are imaged to detect a fluorescent signal from the hybridized fluorescent labeled COVID-19 virus amplicons to detect the clade variants of the COVID-19 virus in the sample.

TABLE 1

Primer sequences used for the first amplification reaction

| SEQ ID NOS. | Amplimer # | Target | Gene | Primer Sequence (5' to 3') |
|---|---|---|---|---|
| SEQ ID NO: 1 | 1/2 | AA 00-103 | Spike | TTTAACAGAGTTGTT ATTTCTAGTGATG |
| SEQ ID NO: 2 | 1/2 | AA 00-103 | Spike | TTTTCTAAAGTAGTA CCAAAAATCCAGC |
| SEQ ID NO: 3 | 3/4 | AA 124-262 | Spike | TTTCCCTACTTATTG TTAATAACGCTAC |
| SEQ ID NO: 4 | 3/4 | AA 124-262 | Spike | TTTAGATAACCCAC ATAATAAGCTGCAG |
| SEQ ID NO: 5 | 5/6 | AA 397-517 | Spike | TTTATCTCTGCTTTA CTAATGTCTATGC |
| SEQ ID NO: 6 | 5/6 | AA 397-517 | Spike | TTTACAAACAGTTG CTGGTGCATGTAGA |
| SEQ ID NO: 7 | 7/8 | AA 601-726 | Spike | TTTTGGTGTCAGTG TTATAACACCAGGA |
| SEQ ID NO: 8 | 7/8 | AA 601-726 | Spike | TTTTGTCTTGGTCAT AGACACTGGTAGA |
| SEQ ID NO: 264 | N:9 | (AA 167-174) | Nucleocapsid | TTTTGCCAAAAGGC TTCTACGCAGAA |
| SEQ ID NO: 265 | N:9 | (AA 254-262) | Nucleocapsid | TTGTTTTTGCCGAG GCTTCTTAGAAG |
| SEQ ID: 130 | — | RNAse P control | RNAse P | TTTACTTCAGCATG GCGGTGTTTGCAGA |
| SEQ ID: 131 | — | RNAse P control | RNAse P | TTTTGATAGCAACAA CTGAATAGCCAAG |

The COVID-19 virus RNA in the total RNA isolate is used as a template for amplifying a COVID-19 virus specific sequence. This comprises first performing a combined reverse transcriptase enzyme catalyzed reverse transcription reaction and a first amplification reaction using a first primer pair selective for the virus to generate COVID-19 virus cDNA amplicons. In this embodiment, the first primer pairs have forward (odd numbers) and reverse (even number) sequences shown in SEQ ID NO: 1 to SEQ ID NO: 8 (Table 1)). Commercially available reverse transcriptase enzyme and buffers are used in this step. Controls including, but not limited to a RNAse P control having first primer pair (forward primer SEQ ID NO: 130, reverse primer SEQ ID NO: 131) are also used herein (Table 1). The COVID-19 virus cDNA amplicons generated in the first amplification reaction are used as a template for a second amplification that employs at least one fluorescent labeled second primer pair selective for a target nucleotide sequence in the Further to this embodiment, prior to the harvesting step, the method comprises mixing the sample with an RNA stabilizer. A representative RNA stabilizer is a chemical stabilizer that protects the RNA from degradation during storage and transportation.

In both embodiments at least one of the fluorescent labeled second primer pair is selective for a panel of target nucleotide sequences within a target region of a gene in the COVID-19 virus; and the nucleic acid probes are specific to the target region of the gene, whereby the at least one fluorescent labeled COVID-19 virus amplicon generated is hybridized to the nucleic acid probe thereby discriminating the clade variants of the COVID-19 virus in the sample. Further to this embodiment the imaging and generating steps comprise detecting the at least one fluorescent signal from the hybridized at least one fluorescent labeled COVID-19 virus amplicons associated with the panel of target nucleotide sequences within the target region of the gene; and generating an intensity distribution profile unique to each of the clade variants, whereby each of the clade variants is distinguishable from others. Particularly, the gene may be a Spike gene.

In a non-limiting example, the target region may be in the Spike gene and/or Nucleoprotein gene in the COVID-19 virus and the fluorescent labeled second primer pairs may have forward (odd numbers) and reverse (even number) sequences shown in SEQ ID NO: 9 to SEQ ID NO: 29 (Tables 2 and 11) and the paired fluorescent labeled second primer sequences shown in Table 27. Controls including, but not limited to a RNAse P control having primer pair (forward primer SEQ ID NO: 132, reverse primer SEQ ID NO: 133) are also used herein (Table 2).

Any fluorescent label may be used in the fluorescent labeled second primer pairs including, but not limited to, a CY3, a CY5, SYBR Green, a DYLIGHT™ DY647, a ALEXA FLUOR 647, a DYLIGHT™ DY547 and a ALEXA FLUOR 550.

TABLE 2

Fluorescent labeled primer sequences used for amplification reactions

| SEQ ID NOS. | Amplimer # | Target | Gene | Primer Sequence (5' to 3') |
|---|---|---|---|---|
| SEQ ID NO: 9 | 2 | AA64-80 | Spike | ACCTTTCTTTTCCAATGT TACTTGGTTC |
| SEQ ID NO: 10 | 2 | AA64-80 | Spike | Cy3-TTTTATGTTAGA CTTCTCAGTGGAAGCA |
| SEQ ID NO: 11 | 3 | AA126-157 | Spike | TTTCTTATTGTTAATAAC GCTACTAATG |
| SEQ ID NO: 12 | 3 | AA126-157 | Spike | Cy3-TTTCATTCGCACT AGAATA AACTCTGAA |
| SEQ ID NO: 13 | 5 | AA408-456 | Spike | TGTAATTAGAGGTGATG AAGTCAGA |
| SEQ ID NO: 14 | 5 | AA408-456 | Spike | Cy3-TTTAAAGGTTTGA GATTAG ACTTCCTAA |
| SEQ ID NO: 15 | 6 | AA475-505 | Spike | TTTTATTTCAACTGAAAT YTATCAGGCC |
| SEQ ID NO: 16 | 6 | AA475-505 | Spike | Cy3-TTTAAAGTACTAC TACTCT GTATGGTTG |
| SEQ ID NO: 17 | 8 | AA677-707 | Spike | TTTTATATGCGCTAGTTA TCAGACTCAG |
| SEQ ID NO: 18 | 8 | AA677-707 | Spike | Cy3-TTTTGGTATGGC AATAGA GTTATTAGAG |
| SEQ ID NO: 19 | 1 | AA11-33 | Spike | TTTTTTTCTTGTTTTATTG CCACTAGTC |
| SEQ ID NO: 20 | 1 | AA11-33 | Spike | Cy3-TTTTTGTCAGGG TAATAAA CACCACGTG |
| SEQ ID NO: 21 | 4 | AA213-260 | Spike | TTTTAAGCACACGCCTA TTAATTTAGTG |
| SEQ ID NO: 22 | 4 | AA213-260 | Spike | Cy3-TTTCCACATAAT AAGCTGCAGCACCAGC |
| SEQ ID NO: 23 | 7 | AA603-618 | Spike | TTTAGTGTTATAACACCA GGAACAAATA |
| SEQ ID NO: 24 | 7 | AA603-618 | Spike | Cy3-TTTTGCATGAAT AGCAACAGGGACTTCT |
| SEQ ID NO: 137 | 1 | AA15-11 | Spike | TTTAGAGTTGTTATTTCT AGTGATGTTC |
| SEQ ID NO: 138 | 2 | AA98-105 | Spike | Cy3- TTTAATCCAGCCTCTTAT TATGTTAGAC |
| SEQ ID NO: 139 | 3 | AA161-169 | Spike | TTTCAAAAGTGCAATTAT TCGCACTAGA |
| SEQ ID NO: 140 | 6 | AA471-463 | Spike | TTTCTTTTGAGAGAGATA TTTCAACTGA |

TABLE 2-continued

| Fluorescent labeled primer sequences used for amplification reactions | | | | |
|---|---|---|---|---|
| SEQ ID NOS. | Amplimer # | Target | Gene | Primer Sequence (5' to 3') |
| SEQ ID NO: 141 | 8 | AA666-673 | Spike | TTTATTGGTGCAGGTAT ATGCGCTAG |
| SEQ ID NO: 142 | N:9 | AA167-175 | Nucleoprotein | TTTGCCAAAAGGCTTCT ACGCAGAAG |
| SEQ ID NO: 143 | N:9 | AA253-261 | Nucleoprotein | Cy3- TTTTTTGCCGAGGCTTC TTAGAAGCC |
| SEQ ID NO: 132 | — | RNAse P control | RNAse P | TTTGTTTGCAGATTTGG ACCTGCGAGCG |
| SEQ ID NO: 133 | — | RNAse P control | RNAse P | Cy3-TTTAAGGTGAG CGGCTGTCTCCACAAGT |

In all embodiments the clade variant of the COVID-19 virus is identified as a variant of concern, a variant of interest, or a Wuhan variant, or a combination thereof. Particularly, the clade variants of the COVID-19 virus may be Denmark, UK (B.1.1.7), South African (B.1.351), Brazil/Japan (P1), Brazil (B1.1.28), California USA, L452R (1.429), India (N440K), or Wuhan, or a combination thereof. The COVID-19 virus is a Severe Acute Respiratory Syndrome Coronavirus 2 (SARS-CoV 2) or a mutated form thereof. A combination of these variants also may be detected simultaneously.

Also in all embodiments the first primer pair may comprise the nucleotide sequences of SEQ ID NO: 1 and SEQ ID NO: 2, or SEQ ID NO: 3 and SEQ ID NO: 4, or SEQ ID NO: 5 and SEQ ID NO: 6, or SEQ ID NO: 7 and SEQ ID NO: 8, or SEQ ID. NO: 264 or SEQ ID NO: 265, or a combination thereof. Sequences of the first primer pairs for the Spike gene and Nucleocapsid gene are shown in Table 1.

In addition in all embodiments the fluorescent labeled second primer pair may comprise the nucleotide sequences of SEQ ID NO: 9 and SEQ ID NO: 10, or SEQ ID NO: 11 and SEQ ID NO: 12, or SEQ ID NO: 13 and SEQ ID NO: 14, or SEQ ID NO: 15 and SEQ ID NO: 16, or SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 24, SEQ ID NO: 137 and SEQ ID NO: 20, or SEQ ID NO: 9 and SEQ ID NO: 138, or SEQ ID NO: 11 and SEQ ID NO: 139, or SEQ ID NO: 140 and SEQ ID NO: 16, or SEQ ID NO: 141 and SEQ ID NO: 18, or SEQ ID NO: 142 and SEQ ID NO: 143 or a combination thereof. Sequences of the fluorescent labeled second primer pairs are shown in Tables 2, 11 and 27.

Furthermore, in all embodiments the nucleic acid probes may comprise at least one nucleotide sequence selected from the group consisting of SEQ ID NOS: 30-129 and/or 144-263. The nucleic acid probes may have a sequence corresponding to a sequence determinant that discriminates among the Clade variants of the COVID-19 virus. The nucleic acid probes are specific to the target region of the gene in the COVID-19 virus as discussed supra. This enables hybridization of the one fluorescent labeled COVID-19 virus amplicon generated to the Spike gene-specific nucleic acid probe thereby discriminating the Clade variants of the COVID-19 virus in the sample. In a non-limiting example, the target region is in a Spike gene or nucleoprotein gene in the COVID-19 virus and the nucleic acid probes have a sequence shown in SEQ ID NO: 30 to SEQ ID: 129 (Tables 3, 10 and 14) or SEQ ID NO: 144 to SEQ ID NO: 263 (Tables 28A and 28B). Controls including, but not limited to, a RNAse P control nucleic acid probe (SEQ ID NO: 68 and SEQ ID NO: 69) and a negative control nucleic acid probe (SEQ ID NO: 70) are also used herein (Table 3).

TABLE 3

| Nucleic acid probe sequences used for hybridization | | | | |
|---|---|---|---|---|
| SEQ ID NOS. | Amplimer # | Target | Gene | Probe Sequence (5' to 3') |
| SEQ ID NO: 31 | 2 | AA69-70 HV | S* | TTTTTCCCATGCTATACATGTCTCT GTTTTTT |
| SEQ ID NO: 32 | 2 | AA69-70 DEL | S | TTTTTTTTTCCATGCTATCTCTGGG ATTTTTT |
| SEQ ID NO: 33 | 2 | AA D80A | S | TTTTTCAGAGGTTTGMTAACCCTG TCTTTTTT |
| SEQ ID NO: 34 | 2 | AA D80_ | S | TTTTTTTGGTTTGATAACCCTGCTT TTTTT |
| SEQ ID NO: 35 | 2 | AA_80A | S | TTTTTTTGGTTTGCTAACCCTGCTT TTTTT |

TABLE 3-continued

Nucleic acid probe sequences used for hybridization

| SEQ ID NOS. | Amplimer # | Target | Gene | Probe Sequence (5' to 3') |
|---|---|---|---|---|
| SEQ ID NO: 36 | 3 | AA D138Y | S | TTTTATTTTGTAATKATCCATTTTT GTTTT |
| SEQ ID NO: 37 | 3 | AA D138_ | S | TTTTTCTTTGTAATGATCCATTTTC TTTTT |
| SEQ ID NO: 38 | 3 | AA_138Y | S | TTTTTTTTTGTAATTATCCATTTTCT TTTT |
| SEQ ID NO: 39 | 3 | AA W152C | S | TTTTTAGTTGKATGGAAAGTGAGT TCTTTT |
| SEQ ID NO: 40 | 3 | AA W152_ | S | TTTCTCTAAAAGTTGGATGGAAAC TCTTCT |
| SEQ ID NO: 41 | 3 | AA_152C | S | TTTCTTCAAAGTTGTATGGAAAGC CTTCTT |
| SEQ ID NO: 42 | 5 | AA 439K + N440K | S | TTTTTAATTCTAAMAAKCTTGATTC TAATTTT |
| SEQ ID NO: 43 | 5 | AA N439_ + N440 | S | TTTTTAATTCTAACAATCTTGATTT CTTTT |
| SEQ ID NO: 44 | 5 | AA N439_ + _440K | S | TTTTTTATTCTAACAAGCTTGATTT TTTTT |
| SEQ ID NO: 45 | 5 | AA_439K + N440_ | S | TTTTCTATTCTAAAAATCTTGATTT CTTTT |
| SEQ ID NO: 46 | 5 | AA L452R | S | TTTCTATAATTACCTGTATAGATTG TCTTT |
| SEQ ID NO: 47 | 5 | AA L452_ | S | TTTTTTTAATTACCTGTATAGATTT CTTTT |
| SEQ ID NO: 48 | 5 | AA_452R | S | TTTTTCATAATTACTGGTATAGATC TTTTT |
| SEQ ID NO: 49 | 6 | AA S477_ | S | TTTTTTCGCCGGTAGCACACCTCT TTTTTT |
| SEQ ID NO: 50 | 6 | AA_477N | S | TTTTCTTCCGGTAACACACCTTTTT TTTTT |
| SEQ ID NO: 51 | 6 | AA V483A + E484K | S | TTTTTTAATGGTGTTRAAGGTTTTA ATTTTTT |
| SEQ ID NO: 52 | 6 | AA V483_ + E484 | S | TTTTTTCTGGTGTTGAAGGTTTTA CTTTTT |
| SEQ ID NO: 53 | 6 | AA V483_ + _484K | S | TTTTTTTATGGTGTTAAAGGTTTTC TTTTT |
| SEQ ID NO: 54 | 6 | AA_483A + E484_ | S | TTTTTTTATGGTGCTGAAGGTTCT TTTTTT |
| SEQ ID NO: 55 | 6 | AA N501Y | S | TTTTTTTCCAACCCACTWATGGT GTTTTTTTT |
| SEQ ID NO: 56 | 6 | AA N501_ | S | TTTTTTTTACCCACTAATGGTGTCT TTTTT |
| SEQ ID NO: 57 | 6 | AA N_501Y | S | TTTTTTTTACCCACTTATGGTGTCT TTTTT |
| SEQ ID NO: 58 | 8 | AA P681H | S | TTTTTCAGACTAATTCTCMTCGG CTTTTT |
| SEQ ID NO: 59 | 8 | AA P681_ | S | TTTTTTTCTAATTCTCCTCGGCGTT TTTTT |
| SEQ ID NO: 60 | 8 | AA_681H | S | TTTTTTTTTAATTCTCATCGGCGTT TTTTT |

TABLE 3-continued

Nucleic acid probe sequences used for hybridization

| SEQ ID NOS. | Amplimer # | Target | Gene | Probe Sequence (5' to 3') |
|---|---|---|---|---|
| SEQ ID NO: 61 | 8 | AA A701V | S | TTTTCACTTGGTGYAGAAAATTCA GTTTTT |
| SEQ ID NO: 62 | 8 | AA A701_ | S | TCTTCTTCTTGGTGCAGAAAATTA TTCTTT |
| SEQ ID NO: 63 | 8 | AA_701V | S | TCTTCTTCTTGGTGTAGAAAATTAT TCTTT |
| SEQ ID NO: 144 | 1 | AA L5F | S | TTTTCGTTTGTTTTTYTTGTTTTATT GCTTTT |
| SEQ ID NO: 145 | 1 | AA L5_ | S | TTTTCGTTTGTTTTTCTTGTTTTAT TTTTT |
| SEQ ID NO: 146 | 1 | AA_5F | S | TTTTCGTTTGTTTTTTTTGTTTTATT TTTT |
| SEQ ID NO: 147 | 1 | AA_18F | S | TTTTTCTTGTTAATTTTACAACCAT TTTTT |
| SEQ ID NO: 148 | 1 | AA_19R | S | TTTTTCTTTAATCTTAGAACCAGAC TTTTT |
| SEQ ID NO: 149 | 2 | AA A67_.HV69-70 | S | TTTTTCTCCATGCTATACATGTCCT TTTTT |
| SEQ ID NO: 150 | 2 | AA A67_.69-70DEL | S | TTTTTTTTTCCATGCTATCTCTGTT TTTTT |
| SEQ ID NO: 151 | 2 | AA_67V.69-70DEL | S | TTTTTTTTTCCATGTTATCTCTGTT TTTTT |
| SEQ ID NO: 152 | 2 | AA_80G | S | TTTTTTTGGTTTGGTAACCCTGCT TTTTTT |
| SEQ ID NO: 153 | 2 | AA T95I | S | TTTCTTTTTGCTTCCAYTGAGAAG TCTTTTTT |
| SEQ ID NO: 154 | 2 | AA T95_ | S | TTTTTTCCGCTTCCACTGAGAAGC ATTTTT |
| SEQ ID NO: 155 | 2 | AA_95I | S | TTTTTTCCGCTTCCATTGAGAAGC ATTTTT |
| SEQ ID NO: 156 | 3 | AA Y144_ | S | TTTCTTTGGGTGTTTATTACCACA AAAATTTT |
| SEQ ID NO: 157 | 3 | AA_144DEL_ | S | TTTTTTTTTGGGTGTTTACCACAAA AACTTTT |
| SEQ ID NO: 158 | 3 | AA_144T.145insS | S | TTTATTTTTGGGTGTTACTTATTAC CACATTT |
| SEQ ID NO: 159 | 3 | AA_143G_ | S | TTCTTTTGGATGTTTATTACCACAA AAACTTT |
| SEQ ID NO: 160 | 3 | AA_141Y.142-144DEL | S | TTCGTAATGATCCATTTTATTACCA CAAATTT |
| SEQ ID NO: 161 | 3 | AA_152L | S | TCTCTTCAAAAGTTTGATGGAAAT CTCTTT |
| SEQ ID NO: 162 | 3 | AA_152R | S | TTTCTTTACAAAAGTAGGATGGAT TTCTTT |
| SEQ ID NO: 163 | 3 | AA_154K | S | TTTCTTTGTTGGATGAAAAGTGAT CTTCTT |
| SEQ ID NO: 164 | 3 | AA F157_ | S | TTTTGAAAGTGAGTTCAGAGTTTA CCTTTT |
| SEQ ID NO: 165 | 3 | AA_157del | S | TTCTTTGGAAAGTGGAGTTTATTC TCTTTT |

TABLE 3-continued

Nucleic acid probe sequences used for hybridization

| SEQ ID NOS. | Amplimer # | Target | Gene | Probe Sequence (5' to 3') |
|---|---|---|---|---|
| SEQ ID NO: 166 | 4 | AA 241-243 LLA | S | TTTTTTTTCAAACTTTACTTGCTTTACTCTTT |
| SEQ ID NO: 167 | 4 | AA_241-243DEL | S | TTTTTTTTCAAACTTTACATAGAAGCCTTTTT |
| SEQ ID NO: 168 | 4 | AA_R246_ | S | TTTTCTACATAGAAGTTATTTGACTCCCTTTT |
| SEQ ID NO: 169 | 4 | AA_246N. 247-253DEL | S | TTTTCTGCTTTACATATGACTCCTGGTTTTTT |
| SEQ ID NO: 170 | F | AA D253G | S | TTTCTACTCCTGGTGRTTCTTCTTCATTTT |
| SEQ ID NO: 171 | 4 | AA D253_ | S | TTTTTTCCCTGGTGATTCTTCTTTCTTTTT |
| SEQ ID NO: 172 | 4 | AA_253G | S | TTTTTTCCCTGGTGGTTCTTCTTTTTTTTT |
| SEQ ID NO: 173 | 5 | AA_452Q | S | TTTTTTTAATTACCAGTATAGATCCTTTTT |
| SEQ ID NO: 174 | 6 | AA T478K | S | TTTTTCGGTAGCAMACCTTGTAATGTTTTT |
| SEQ ID NO: 175 | 6 | AA T478_ | S | TTTTTTTGTAGCACACCTTGTATTTTTTTT |
| SEQ ID NO: 176 | 6 | AA_478K | S | TTTTTTTGTAGCAAACCTTGTATTTTTTTT |
| SEQ ID NO: 177 | 6 | AA_484Q | S | TTTTTTATGGTGTTCAAGGTTTTCTTTTTT |
| SEQ ID NO: 178 | 6 | AA F490S | S | TTTTCTAATTGTTACTTTCCTTTACAATTTTT |
| SEQ ID NO: 179 | 6 | AA F490_ | S | TTTTTTTTTGTTACTTTCCTTTACTTTTTT |
| SEQ ID NO: 180 | 6 | AA_490S | S | TTTTTTTTTGTTACTCTCCTTTACTTTTTT |
| SEQ ID NO: 181 | 6 | AA S494P | S | TTTTTCTCCTTTACAAYTATATGGTTTTTTTT |
| SEQ ID NO: 182 | 6 | AA S494_ | S | TTTTTCTCTTTACAATCATATGGTCTTTTT |
| SEQ ID NO: 183 | 6 | AA_494P | S | TTTTTCTCTTTACAACCATATGGTCTTTTT |
| SEQ ID NO: 184 | 6 | AA_501T | S | TTTTTTTACCCACTACTGGTGTTTTTTTTT |
| SEQ ID NO: 185 | 8 | AA Q677P/H | S | TTTTTTATCAGACTCMGACTAATTCTCTTTTT |
| SEQ ID NO: 186 | 8 | AA Q677_ | S | TTTTTTCCAGACTCAGACTAATTTCTTTTT |
| SEQ ID NO: 187 | 8 | AA_677P | S | TTTTTCTTCAGACTCCGACTAATCTTTTTT |
| SEQ ID NO: 188 | 8 | AA_677H2 | S | TTTTTTCCAGACTCACACTAATTTCTTTTT |
| SEQ ID NO: 189 | 8 | AA_677H1 | S | TTTTTTCCAGACTCATACTAATTTCTTTTT |
| SEQ ID NO: 190 | 8 | AA_681R | S | TTTTTTTTTAATTCTCGTCGGCGTTTTTTT |

TABLE 3-continued

| Nucleic acid probe sequences used for hybridization | | | | |
|---|---|---|---|---|
| SEQ ID NOS. | Amplimer # | Target | Gene | Probe Sequence (5' to 3') |
| SEQ ID NO: 191 | N:9 (AA183-252) | AA S194L | N* | TTTTCCGCAACAGTTYAAGAAATT CATTTT |
| SEQ ID NO: 192 | N:9 (AA183-252) | AA S194_ | N | TTTTTTTAACAGTTCAAGAAATTTT TTTTT |
| SEQ ID NO: 193 | N:9 (AA183-252) | AA_194L | N | TTTTTTTAACAGTTTAAGAAATTTT TTTTT |
| SEQ ID NO: 194 | N:9 (AA183-252) | AA S197L | N | TTTTCTCAAGAAATTYAACTCCAG GCTTTT |
| SEQ ID NO: 195 | N:9 (AA183-252) | AA S197_ | N | TTTTTCTAAGAAATTCAACTCCATT TTTTT |
| SEQ ID NO: 196 | N:9 (AA183-252) | AA_197L | N | TTTTTCTAAGAAATTTAACTCCATT TTTTT |
| SEQ ID NO: 197 | N:9 (AA183-252) | AA P199L | N | TTTTTAAATTCAACTCYAGGCAGC ATCTTT |
| SEQ ID NO: 198 | N:9 (AA183-252) | AA P199_ | N | TTTTTTTTTCAACTCCAGGCAGCT TTTTTT |
| SEQ ID NO: 199 | N:9 (AA183-252) | AA_199L | N | TTTTTTTTTCAACTCTAGGCAGCTT TTTTT |
| SEQ ID NO: 200 | N:9 (AA183-252) | AA S201I | N | TTTTTACTCCAGGCAKCWSTADRS GATTTT |
| SEQ ID NO: 201 | N:9 (AA183-252) | AA S201_ | N | TTTTTTTTCCAGGCAGCAGTADRT TTTTTT |
| SEQ ID NO: 202 | N:9 (AA183-252) | AA_201I | N | TTTTTTTTCCAGGCATCAGTAGGT TTTTTT |
| SEQ ID NO: 203 | N:9 (AA183-252) | AA S202N | N | TTTTCCCAGGCAGCARTADRSGAA CCTTTT |
| SEQ ID NO: 204 | N:9 (AA183-252) | AA S202_ | N | TTTTTTTAGGCAGCAGTADRSGAT TTTTTT |
| SEQ ID NO: 205 | N:9 (AA183-252) | AA_202N | N | TTTTTTTAGGCAGCAATAGGGGAT TTTTTT |
| SEQ ID NO: 206 | N:9 (AA183-252) | AA R203M/K G204R | N | TTTTGCAGCWSTADRSGAACTTCT CTTTTT |
| SEQ ID NO: 207 | N:9 (AA183-252) | AA R203_ G204_ | N | TTTTTTTCAGCAGTAGGGGAACTC TTTTTT |
| SEQ ID NO: 208 | N:9 (AA183-252) | AA_203M G204_ | N | TTTTTTTCAGCAGTATGGGAACTC TTTTTT |

TABLE 3-continued

Nucleic acid probe sequences used for hybridization

| SEQ ID NOS. | Amplimer # | Target | Gene | Probe Sequence (5' to 3') |
|---|---|---|---|---|
| SEQ ID NO: 209 | N:9 (AA183-252) | AA_203K G204R | N | TTTTTTTCAGCAGTAAACGAACTC TTTTTT |
| SEQ ID NO: 210 | N:9 (AA183-252) | AA_203K G204R (2) | N | TTTTTTTCAGCTCTAAACGAACTCT TTTTT |
| SEQ ID NO: 211 | N:9 (AA183-252) | AA T205I | N | TTTTCSTADRSGAAYTTCTCCTGC TATTTT |
| SEQ ID NO: 212 | N:9 (AA183-252) | AA T205_ | N | TTTTTTTGGGGAACTTCTCCTGCC TTTTTT |
| SEQ ID NO: 213 | N:9 (AA183-252) | AA_205I | N | TTTTTTTGGGGAATTTCTCCTGCC TTTTTT |
| SEQ ID NO: 214 | N:9 (AA183-252) | AA A208G R209del | N | TTTTAAYTTCTCCTGCTAGAATGG CTGTTT |
| SEQ ID NO: 215 | N:9 (AA183-252) | AA A208G R209del (2) | N | TTTTACGAACTTCTCCTGGAATGG CTGTTT |
| SEQ ID NO: 216 | N:9 (AA183-252) | AA A208_ R209_ | N | TTTTCTCTCCTGCTAGAATGGCTG TTTTTT |
| SEQ ID NO: 217 | N:9 (AA183-252) | AA_208G_ 209del | N | TTTTTACTTCTCCTGGAATGGCTG TTTTTT |
| SEQ ID NO: 218 | N:9 (AA183-252) | AA G212V N213Y | N | TTTTTTGGCTGKCWATKGCKGTGA TTTTTT |
| SEQ ID NO: 219 | N:9 (AA183-252) | AA G212_ N213Y | N | TTTTTTTAATGGCTGGCWATKGCT TTTTTT |
| SEQ ID NO: 220 | N:9 (AA183-252) | SS_212B N213_ | N | TTTTTTTAATGGCTGTCAATGGCT TTTTTT |
| SEQ ID NO: 221 | N:9 (AA183-252) | AA G212V N213_ | N | TTTTTTTTGGCTGKCAATKGCKGC TTTTTT |
| SEQ ID NO: 222 | N:9 (AA183-252) | AA G213_ 213Y | N | TTTTTTTTGGCTGGCTATGGCGGC TTTTTT |
| SEQ ID NO: 223 | N:9 (AA183-252) | AA G214C G215C | N | TTTTTTGGCTGKCWATKGCKGTGA TTTTTT |
| SEQ ID NO: 224 | N:9 (AA183-252) | AA G214_ G215C | N | TTTTTTTTGKCWATGGCKGTGATT TTTTTT |
| SEQ ID NO: 225 | N:9 (AA183-252) | AA_214C G215_ | N | TTTTTTTTGGCAATTGCGGTGATT TTTTTT |
| SEQ ID NO: 226 | N:9 (AA183-252) | AA G214C G215_ | N | TTTTTTTCWATKGCGGTGATGCTT TTTTTT |

TABLE 3-continued

Nucleic acid probe sequences used for hybridization

| SEQ ID NOS. | Amplimer # | Target | Gene | Probe Sequence (5' to 3') |
|---|---|---|---|---|
| SEQ ID NO: 227 | N:9 (AA183-252) | AA G214_ _215C | N | TTTTTTTCAATGGCTGTGATGCTTT TTTTT |
| SEQ ID NO: 228 | N:9 (AA183-252) | AA M234I S235F | N | TTTTTGAGCAAAATDTYTGGTAAA GTTTTT |
| SEQ ID NO: 229 | N:9 (AA183-252) | AA M234_ S235_ | N | TTTTTTTCAAAATGTCTGGTAAATT TTTTT |
| SEQ ID NO: 230 | N:9 (AA183-252) | AA_234I S235_ | N | TTTTTCTAGCAAAATTTCTGGTATC TTTTT |
| SEQ ID NO: 231 | N:9 (AA183-252) | AA_234I S235_ (2) | N | TTTTTCTAGCAAAATATCTGGTATC TTTTT |
| SEQ ID NO: 232 | N:9 (AA183-252) | AA M234_ _235F | N | TTTTTCTCAAAATGTTTGGTAAATC TTTTT |
| SEQ ID NO: 134 | — | RNAse P | — | TTTTTTTTCTGACCTGAAGGCTCT GCGCGTTTTT |
| SEQ ID NO: 135 | — | RNAse P | — | TTTTTCTTGACCTGAAGGCTCTGC TTTTTT |
| SEQ ID NO: 136 | — | Negative Control | — | TTTTTTCTACTACCTATGCTGATTC ACTCTTTTT |

*S = Spike, N = Nucleoprotein

Further still in all embodiments the sample may comprise at least one of a nasopharyngeal swab, a nasal swab, a mouth swab, a mouthwash, an aerosol, or a swab from a hard surface. In one aspect the sample may be any sample obtained from a subject including, but not limited to, a nasopharyngeal swab, a nasal swab, a mouth swab, and a mouthwash (sample obtained by rinsing the subject's buccal cavity). A pooled sample obtained by combining two or more of these samples or by combining samples from multiple subjects also may be used. In another aspect, the sample is an environmental sample obtained from inanimate sources include, but are not limited to, an aerosol and a hard surface. The aerosol samples may be obtained using commercial air samplers such as for example a Coriolis Micro Air Sampler. A sample from a hard surface may be obtained using a swab. In both aspects, the viruses from samples obtained on swabs are dispersed in a liquid such as phosphate buffered saline. Aerosol samples are transferred into a volume of a liquid such as phosphate buffered saline.

In another embodiment of the present invention, there is provided a method for detecting clade variants in the Coronavirus disease 2019 virus (COVID-19) in a sample, comprising obtaining the sample; harvesting viruses from the sample; isolating total RNA from the harvested viruses; performing a combined reverse transcription and asymmetric PCR amplification reaction on the total RNA using at least one fluorescent labeled primer pair comprising an unlabeled primer, and a fluorescently labeled primer, selective fora target sequence in all COVID-19 viruses to generate at least one fluorescent labeled COVID-19 virus amplicon; hybridizing the fluorescent labeled COVID-19 virus amplicons to a plurality of nucleic acid probes, each having a sequence corresponding to a sequence determinant that discriminates among the clade variants of the COVID-19 virus, where the nucleic acid probes are attached to a solid microarray support; washing the microarray at least once; and imaging the microarray to detect at least one fluorescent signal from the hybridized fluorescent labeled COVID-19 virus amplicons, thereby detecting the clade variants of the COVID-19 virus in the sample. In a related embodiment after the imaging step, a step is performed of generating an intensity distribution profile from the at least one fluorescent signal that is unique to one of the clade variants thereby detecting the clade variant of the COVID-19 virus in the sample.

The total RNA is isolated as described supra and any COVID-19 virus RNA in the total RNA isolate is used as a template in a combined reverse transcription/amplification reaction (RT-PCR). In this step, the nucleic acid sequences in the COVID-19 virus RNA are transcribed using a reverse transcriptase enzyme to generate COVID-19 complementary DNA (cDNA) that is amplified in the same reaction using COVID-19 virus selective fluorescent labeled primer pairs to generate fluorescent labeled COVID-19 virus amplicons. Each fluorescent labeled primer pair comprises an unlabeled primer and a fluorescently labeled primer in about 4-fold to about 8-fold excess of the unlabeled primer whereby, upon completion of the reaction, the fluorescently labelled amplicon is primarily single stranded (that is, the reaction is a type of "asymmetric PCR").

Hybridization of the fluorescent labeled COVID-19 virus amplicons to the plurality of nucleic acid probes attached at specific positions on a microarray support is performed as described supra. The nucleic acid probes may have a sequence corresponding to a sequence determinant that discriminates among the clade variants of the COVID-19 virus and are specific to the target region of the gene in the COVID-19 virus, as discussed supra. This enables hybridization of the one fluorescent labeled COVID-19 virus amplicon generated to the Spike gene-specific nucleic acid probe or nucleoprotein specific nucleic acid probe thereby discriminating the clade variants of the COVID-19 virus in the sample. In a non-limiting example, the target region is in a Spike gene and/or a nucleoprotein gene in the COVID-19 virus and the nucleic acid probes have a sequence shown in SEQ ID NO: 31 to SEQ ID: 63 (Table 3). Controls are as described supra and shown in (Table 3).

Further to this embodiment, prior to the harvesting step, the method comprises mixing the sample with an RNA stabilizer. A representative RNA stabilizer is a chemical stabilizer, as described supra.

In both embodiments at least one of the fluorescent labeled second primer pair is selective for a panel of target nucleotide sequences within a target region of a gene in the COVID-19 virus; and the nucleic acid probes are specific to the target region of the gene, whereby the at least one fluorescent labeled COVID-19 virus amplicon generated is hybridized to the nucleic acid probe thereby discriminating the clade variants of the COVID-19 virus in the sample. Further to this embodiment the method comprises detecting the at least one fluorescent signal from the hybridized at least one fluorescent labeled COVID-19 virus amplicons associated with the panel of target nucleotide sequences within the target region of the gene; and generating an intensity distribution profile unique to each of the clade variants, whereby each of the clade variants is distinguishable from others. Particularly, the gene may be the Spike gene and/or a nucleoprotein gene.

In a non-limiting example, the target region may be in the Spike gene and/or a nucleoprotein gene in the COVID-19 virus and the fluorescent labeled second primer pairs may have forward (odd numbers) and reverse (even number) sequences shown in SEQ ID NO: 9 to SEQ ID NO: 29 (Tables 2 and 11) and the paired fluorescent labeled second primer sequences shown in Table 27. Controls including, but not limited to a RNAse P control having a primer pair with forward primer SEQ ID NO: 66 and reverse primer SEQ ID NO: 67 are also used herein (Table 2).

In all embodiments the COVID-19 gene, the clade variants of the COVID-19 virus, the at least one fluorescent labeled primer pair, the fluorescent label, the nucleic acid probes, and the samples are as described supra. Also in all embodiments the fluorescently labeled primer may be in an excess of about 4-fold to about 8-fold over the unlabeled primer in the fluorescent labeled primer pair. Exemplary nucleotide sequences for the fluorescent labeled primer pairs including, for example, RNAse P controls, are shown in Tables 2, 11 and 27. Exemplary nucleotide sequences for the nucleic acid probes, including, for example, RNAse P controls and negative controls, are shown in Tables 3, 28A and 28B.

Provided herein are methods of nucleic acid analysis to detect stable genetic variation such as a clade variation in a viral pathogen which is based on simultaneous analysis of multiple sequence domains in a gene, such as for example the Spike (S) gene in the RNA genome of CoV-2, or the Nucleoprotein (N) gene in SARS-CoV-2 or a combination of the Spike gene and the Nucleoprotein gene in SARS-CoV-2 to measure clade variation in SARS-CoV-2.

In one method for detecting the stable genetic variation, total RNA from the harvested viruses is isolated and used in a combined reverse transcription and first amplification reaction (RT-PCR) to generate COVID-19 virus cDNA amplicons. These amplicons are used as template in a second amplification reaction that uses fluorescent labeled second primer pair selective for a panel of target nucleotide sequences within a target region of a gene in the COVID-19 virus such as for example, the gene for the Spike protein, to generate fluorescent labeled COVID-19 virus amplicons. In a second method, a combined reverse transcription and asymmetric PCR amplification reaction is performed using at least one fluorescent labeled primer pair selective for the panel of target nucleotide sequences within a target region of a gene in the COVID-19 virus to generate fluorescent labeled COVID-19 virus amplicons. In either method, the fluorescent labeled COVID-19 virus amplicons are hybridized to nucleic acid probes attached at specific positions on a microarray.

This method allows positive hybridization signals to be validated on each sample tested based on internal "mismatched" and "sequence specific" controls. Additionally, at least one fluorescent signal from the hybridized amplicons associated with the panel of target nucleotide sequences within the target region of the gene is detected and an intensity distribution profile unique to each of the clade variants generated, whereby each of the clade variants is distinguishable from others.

In the embodiments described supra, the solid microarray support is made of any suitable material known in the art including but not limited to borosilicate glass, a thermoplastic acrylic resin (e.g., poly(methyl methacrylate-VSUVT) a cycloolefin polymer (e.g. ZEONOR 1060R), a metal including, but not limited to gold and platinum, a plastic including, but not limited to polyethylene terephthalate, polycarbonate, nylon, a ceramic including, but not limited to $TiO_2$, and Indium tin oxide (ITO) and engineered carbon surfaces including, but not limited to graphene. A combination of these materials may also be used. The solid support has a front surface and a back surface and is activated on the front surface by chemically activatable groups for attachment of the nucleic acid probes. In this embodiment, the chemically activatable groups include but are not limited to epoxysilane, isocyanate, succinimide, carbodiimide, aldehyde and maleimide. These materials are well known in the art and one of ordinary skill in this art would be able to readily functionalize any of these supports as desired. In a preferred embodiment, the solid support is epoxysilane functionalized borosilicate glass support.

The nucleic acid probes are attached either directly to the solid microarray support, or indirectly attached to the support using bifunctional polymer linkers. In this embodiment, the bifunctional polymer linker has a top domain and a bottom end. On the bottom end is attached a first reactive moiety that allows covalent attachment to the chemically activatable groups in the solid support. Examples of first reactive moieties include but are not limited to an amine group, a thiol group and an aldehyde group. In one aspect the first reactive moiety is an amine group. On the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. The bifunctional polymer linker may be an oligonucleotide such as OLIGOdT, an amino polysaccharide such as chitosan, a polyamine such as spermine, spermidine, cadaverine and putrescine, a polyamino acid, with a lysine or histidine, or any other polymeric compounds with dual functional groups which can be attached to the chemically activatable solid support on the bottom end, and the nucleic acid probes on the top domain. Preferably, the bifunctional polymer linker is OLIGOdT having an amine group at the 5' end.

The bifunctional polymer linker may be unmodified with a fluorescent label. Alternatively, the bifunctional polymer linker has a fluorescent label attached covalently to the top domain, the bottom end, or internally. The second fluorescent label is different from the fluorescent label in the fluorescent labeled primers. Having a fluorescent label (fluorescent tag) attached to the bifunctional polymer linker is beneficial since it allows the user to image and detect the position of the individual nucleic acid probes ("spot") printed on the microarray. By using two different fluorescent labels, one for the bifunctional polymer linker and the second for the amplicons generated from the viral RNA being queried, the user can obtain a superimposed image that allows parallel detection of those nucleic acid probes which have been hybridized with amplicons. This is advantageous since it helps in identifying the virus comprised in the sample using suitable computer and software, assisted by a database correlating nucleic acid probe sequence and microarray location of this sequence with a known RNA signature in viruses. Examples of fluorescent labels include, but are not limited to CY5, DYLIGHT™ DY647, ALEXA FLUOR 647, CY3, DYLIGHT™ DY547, or ALEXA FLUOR 550. The fluorescent labels may be attached to any reactive group including but not limited to, amine, thiol, aldehyde, sugar amido and carboxy on the bifunctional polymer linker. In one aspect, the bifunctional polymer linker is CY5-labeled OLIGOdT having an amino group attached at its 3'terminus for covalent attachment to an activated surface on the solid support.

Moreover, when the bifunctional polymer linker also is fluorescently labeled a second fluorescent signal image is detected in the imaging step. Superimposing the first fluorescent signal image and second fluorescent signal image allows identification of the virus by comparing the sequence of the nucleic acid probe at one or more superimposed signal positions on the microarray with a database of signature sequence determinants for a plurality of viral RNA. This embodiment is particularly beneficial since it allows identification of more than one type of virus in a single assay.

The following examples are given for the purpose of illustrating various embodiments of the invention and are not meant to limit the present invention in any fashion.

Example 1

Microarray Assay for Clade Variant Detection

Provided herein is a method of nucleic acid analysis to detect stable genetic variation in a pathogen which is based on simultaneous analysis of multiple sequence domains in a gene, such as the Spike gene in the RNA genome of CoV-2, to measure clade variation in SARS-CoV-2. For CoV-2, the sequence domains are processed for nucleic acid analysis by converting them into a set of amplicons via a multiplex RT-PCR reaction. In a present preferred implementation, the sequence of those multiplex RT-PCR products is identified relative to that of the underlying CoV-2 Spike gene, by the Horizontal Black Bars in the bottom of Tables 4-8.

The product of that multiplex RT-PCR reaction is analyzed by hybridization to a matrix of synthetic oligonucleotide probes positioned as a microarray test (see the boxes in Tables 4-8). As seen in Tables 4-8, in a preferred implementation of the present invention for CoV-2, there are (15) such Spike Gene Target Regions containing meaningful local sequence variation. (See top Row of Tables 4-8 for their identification).

In terms of detailed test design, the oligonucleotide probes resident at each Target Region of the Spike surface protein are each produced as 3 closely related probe variants, which may be referred to as "Wild Type", "Mutant" and "Universal".

Wild Type Probes

In the present invention, a "Wild Type" probe refers to an oligonucleotide probe sequence, generally 14-25 bases long that is specific to the Wuhan progenitor clade sequence. The pattern of Multiplex RT-PCR amplicon binding to such Wild Type Probes in the present invention are displayed as superscript "2" in Table 4 and as superscript "1" in Table 6.

Mutant Probes

"Mutant" probes correspond to an oligonucleotide probe sequence, also 15-25 bases long specific to the Sequence Change relative to the Wuhan progenitor manifest at the Spike gene location of interest are displayed as superscript "1" in Table 4 and as superscript "1" in Table 5.

Universal Probes

A "Universal" probe refers to an oligonucleotide probe sequence (15-30 bases long) which has been designed to bind to both "Wild Type" and "Mutant" sequences at each site with similar affinity. The patterns of Multiplex RT-PCR amplicon binding to such "Universal" Probes in the present invention are displayed are displayed as superscript "1" in Table 7.

TABLE 4

Combinatorial Analysis of CoV-2 Variants

| Spike Gene Target Region (Codon) Amino Amino Acid Change | | | S13I | L18F | T20N | P26S | Δ69-70 | D80A | D138Y | Y144DEL | W152C | R190S | D215G | A243del | R246I | K417N/T | N440L | L452R |
|---|---|---|---|---|---|---|---|---|---|---|---|---|---|---|---|---|---|---|
| Mutation specific Probe coverage | | | ✓$^1$ | | ✓$^1$ | | ✓$^1$ | ✓$^1$ | ✓$^1$ | | ✓$^1$ | | ✓$^1$ | | | ✓$^1$ | | |
| Wuhan reference specific probe/s coverage | | | ✓$^2$ | | ✓$^2$ | | ✓$^2$ | ✓$^2$ | ✓$^2$ | | ✓$^2$ | | ✓$^2$ | | | ✓$^2$ | | |
| Locus specific Probe coverage | | | ✓ | | ✓ | | ✓ | ✓ | ✓ | | ✓ | | ✓ | | | ✓ | | |
| REGION | LINEAGE DESIGNATION var | | | | | | | | | | | | | | | | | |
| Denmark | Mink V | B.1.1.298 | $S^2$ | $L^3$ | $T^2$ | $P^3$ | $A^1$ | $D^2$ | $D^2$ | $Y^3$ | $W^2$ | $R^3$ | $D^2$ | $A^3$ | $R^3$ | $K^2$ | $N^2$ | $L^2$ |
| UK | GR/501Y.V1 | B.1.1.7 | $S^2$ | $L^3$ | $T^2$ | $P^3$ | $A^1$ | $D^2$ | $D^2$ | $A^3$ | $W^2$ | $R^3$ | $D^2$ | $A^3$ | $R^3$ | $K^2$ | $N^2$ | $L^2$ |
| SA | GH/501Y.V2 | B.1.351 | $S^2$ | $L^3$ | $T^2$ | $P^3$ | $HV^2$ | $A^1$ | $D^2$ | $Y^3$ | $W^2$ | $R^3$ | $G^1$ | $A^3$ | $I^3$ | $N^1$ | $N^2$ | $L^2$ |
| Brazil/Japan | P.1 | | $S^2$ | $F^3$ | $N^1$ | $S^3$ | $HV^2$ | $D^2$ | $Y^1$ | $Y^3$ | $W^2$ | $S^3$ | $D^2$ | $A^3$ | $R^3$ | $T^1$ | $N^2$ | $L^2$ |
| Brazil | P.2 | | $S^2$ | $L^3$ | $T^2$ | $P^3$ | $HV^2$ | $D^2$ | $D^2$ | $Y^3$ | $W^2$ | $R^3$ | $D^2$ | $A^3$ | $R^3$ | $K^2$ | $N^2$ | $L^2$ |
| California | CAL.20C-GH/452R.V1 | B.1.429 | $I^1$ | $L^3$ | $T^2$ | $P^3$ | $HV^2$ | $D^2$ | $D^2$ | $Y^3$ | $C^1$ | $R^3$ | $D^2$ | $A^3$ | $R^3$ | $K^2$ | $N^2$ | $R^1$ |
| India | (Andhra Pradesh) | N440K | $S^2$ | $L^3$ | $T^2$ | $P^3$ | $HV^2$ | $D^2$ | $D^2$ | $Y^3$ | $W^2$ | $R^3$ | $D^2$ | $A^3$ | $R^3$ | $K^2$ | $K^1$ | $L^2$ |
| WUHAN | | WUHAN | $S^2$ | $L^3$ | $T^2$ | $P^3$ | $HV^2$ | $D^2$ | $D^2$ | $Y^3$ | $W^2$ | $R^3$ | $D^2$ | $A^3$ | $R^3$ | $K^2$ | $N^2$ | $L^2$ |
| PCR Amplimer length (bases) | | | | (1) 101 | | | | (2) 104 | | (3) 129 | | | | (4) 160 | | | (5) 199 | |

| Spike Gene Target Region (Codon) Amino Amino Acid Change | | | Y453F | E484K | N501Y | A570D | D614G | H655Y | P681H | I692V | A701V | T716I | S982A | T1027I | D1118H | V1176F | M1229I |
|---|---|---|---|---|---|---|---|---|---|---|---|---|---|---|---|---|---|
| Mutation specific Probe coverage | | | | ✓$^1$ | ✓$^1$ | | ✓$^1$ | | ✓$^1$ | | ✓$^1$ | | | | | | |
| Wuhan reference specific probe/s coverage | | | | ✓$^2$ | ✓$^2$ | | ✓$^2$ | | ✓$^2$ | | ✓$^2$ | | | | | | |
| Locus specific Probe coverage | | | | ✓ | ✓ | | ✓ | | ✓ | | ✓ | | | | | | |
| REGION | LINEAGE DESIGNATION var | | | | | | | | | | | | | | | | |
| Denmark | Mink V | B.1.1.298 | $F^3$ | $E^2$ | $N^2$ | $A^3$ | $G^1$ | $H^3$ | $P^2$ | V | $A^2$ | $T^3$ | $S^3$ | $T^3$ | $D^3$ | $V^3$ | $I^3$ |
| UK | GR/501Y.V1 | B.1.1.7 | $Y^3$ | $E^2$ | $Y^1$ | $D^3$ | $G^1$ | $H^3$ | $H^1$ | I | $A^2$ | $I^3$ | $A^3$ | $T^3$ | $H^3$ | $V^3$ | $M^3$ |
| SA | GH/501Y.V2 | B.1.351 | $Y^3$ | $K^1$ | $Y^1$ | $A^3$ | $G^1$ | $H^3$ | $P^2$ | I | $V^1$ | $T^3$ | $S^3$ | $T^3$ | $D^3$ | $V^3$ | $M^3$ |
| Brazil/Japan | P.1 | | $Y^3$ | $K^1$ | $Y^1$ | $A^3$ | $G^1$ | $Y^3$ | $P^2$ | I | $A^2$ | $T^3$ | $S^3$ | $I^3$ | $D^3$ | $F^3$ | $M^3$ |
| Brazil | P.2 | | $Y^3$ | $K^1$ | $N^2$ | $A^3$ | $G^1$ | $H^3$ | $P^2$ | I | $A^2$ | $T^3$ | $S^3$ | $T^3$ | $D^3$ | $F^3$ | $M^3$ |
| California | CAL.20C-GH/452R.V1 | B.1.429 | $Y^3$ | $E^2$ | $N^2$ | $A^3$ | $G^1$ | $H^3$ | $P^2$ | I | $A^2$ | $T^3$ | $S^3$ | $T^3$ | $D^3$ | $V^3$ | $M^3$ |
| India | (Andhra Pradesh) | N440K | $Y^3$ | $E^2$ | $N^2$ | $A^3$ | $G^1$ | $H^3$ | $P^2$ | I | $A^2$ | $T^3$ | $S^3$ | $T^3$ | $D^3$ | $V^3$ | $M^3$ |
| WUHAN | | WUHAN | $Y^3$ | $E^2$ | $N^2$ | $A^3$ | $D^2$ | $H^3$ | $P^2$ | I | $A^2$ | $T^3$ | $S^3$ | $T^3$ | $D^3$ | $V^3$ | $M^3$ |
| PCR Amplimer length (bases) | | | (5) 199 | (6) 151 | | | (7) 88 | | | (8) 135 | | | | | | | |

[1]AA mutation-hybridizes to mutation specific probe

[2]AA identical to hCoV-19/WUHAN/WIV04/2019 (WIV04-official reference sequence employed by GISAID (EPI_ISL_402124) Hybridizes to reference specific probe

[3]Potential probe target

TABLE 5

Combinatorial Analysis of CoV-2 Variants-Mutant Probes

| Spike Gene Target Region (Codon) Amino Acid Change | | | S13I | L18F | T20N | P26S | Δ69-70 | D80A | D138Y | Y144DEL | W152C | R190S | D215G | A243del |
|---|---|---|---|---|---|---|---|---|---|---|---|---|---|---|
| Mutation specific Probe coverage | | | ✓[1] | | ✓[1] | | ✓[1] | ✓[1] | ✓[1] | | ✓[1] | | ✓[1] | |
| REGION | LINEAGE DESIGNATION var | | | | | | | | | | | | | |
| Denmark | Mink V | B.1.1.298 | S | L | T | P | A[1] | D | D | Y | W | R | D | A |
| UK | GR/501Y.V1 | B.1.1.7 | S | L | T | P | A[1] | D | D | A | W | R | D | A |
| SA | GH/501Y.V2 | B.1.351 | S | L | T | P | HV | A | D | Y | W | R | G[1] | A |
| Brazil/Japan | P.1 | | S | F | N[1] | S | HV | D | Y1 | Y | W | S | D | A |
| Brazil | P.2 | | S | L | T | P | HV | D | D | Y | W | R | D | A |
| California | CAL.20C-GH/452R.V1 | B.1.429 | I[1] | L | T | P | HV | D | D | Y | C[1] | R | D | A |
| India | (Andhra Pradesh) | N440K | S | L | T | P | HV | D | D | Y | W | R | D | A |
| WUHAN | | WUHAN | S | L | T | P | HV | D | D | Y | W | R | D | A |
| | PCR Amplimer length (bases) | | | (1) 101 | | | | (2) 104 | | (3)129 | | | | (4) 160 |

| Spike Gene Target Region (Codon) Amino Acid Change | | | R246I | K417N/T | N440K | L452R | Y453F | E484K | N501Y | A570D | D614G | H655Y | P681H |
|---|---|---|---|---|---|---|---|---|---|---|---|---|---|
| Mutation specific Probe coverage | | | | ✓[1] | ✓[1] | ✓[1] | | ✓[1] | ✓[1] | | ✓[1] | | ✓[1] |
| REGION | LINEAGE DESIGNATION var | | | | | | | | | | | | |
| Denmark | Mink V | B.1.1.298 | R | K | N | L | F | E | N | A | G[1] | H | P |
| UK | GR/501Y.V1 | B.1.1.7 | R | K | N | L | Y | K[1] | Y[1] | D | G[1] | H | H[1] |
| SA | GH/501Y.V2 | B.1.351 | I | N[1] | N | L | Y | K[1] | Y[1] | A | G[1] | H | P |
| Brazil/Japan | P.1 | | R | T[1] | N | I | Y | K[1] | Y[1] | A | G[1] | Y | P |
| Brazil | P.2 | | R | K | N | L | Y | E | N | A | G[1] | H | P |
| California | CAL.20C-GH/452R.V1 | B.1.429 | R | K | N | R[1] | Y | E | N | A | G[1] | H | P |
| India | (Andhra Pradesh) | N440K | R | K | K[1] | L | Y | E | N | A | G[1] | H | P |
| WUHAN | | WUHAN | R | K | N | L | Y | E | N | A | D | H | P |
| | PCR Amplimer length (bases) | | (4) 160 | | (5) 199 | | | | (6) 151 | | (7) 88 | | (8) 135 |

| Spike Gene Target Region (Codon) Amino Acid Change | | | I692V | A701V | T716I | S982A | T1027I | D1118H | V1176F | M1229I |
|---|---|---|---|---|---|---|---|---|---|---|
| Mutation specific Probe coverage | | | | ✓[1] | | | | | | |
| REGION | LINEAGE DESIGNATION var | | | | | | | | | |
| Denmark | Mink V | B.1.1.298 | V | A | T | S | T | D | V | I |
| UK | GR/501Y.V1 | B.1.1.7 | I | A | I | A | T | H | V | M |
| SA | GH/501Y.V2 | B.1.351 | I | V[1] | T | S | T | D | V | M |
| Brazil/Japan | P.1 | | I | A | T | S | I | D | F | M |
| Brazil | P.2 | | I | A | T | S | T | D | F | M |
| California | CAL.20C-GH/452R.V1 | B.1.429 | I | A | T | S | T | D | V | M |
| India | (Andhra Pradesh) | N440K | I | A | T | S | T | D | V | M |
| | WUHAN WUHAN | | I | A | T | S | T | D | V | M |
| | PCR Amplimer length (bases) | | (8) 135 | | | | | | | |

[1]AA mutation-hybridizes to mutation specific probe

TABLE 6

Combinatorial Analysis of CoV-2 Variants-Wild Type Probes

| Spike Gene Target Region (Codon) Amino Acid Change | | | S13I | L18F | T20N | P26S | Δ69-70 | D80A | D138Y | Y144DEL | W152C | R190S | D215G | A243del |
|---|---|---|---|---|---|---|---|---|---|---|---|---|---|---|
| Wuhan reference specific probe/s coverage | | | ✓[1] | | ✓[1] | | ✓[1] | ✓[1] | ✓[1] | | ✓[1] | | ✓[1] | |
| REGION | LINEAGE DESIGNATION var | | | | | | | | | | | | | |
| Denmark | Mink V | B.1.1.298 | S[1] | L | T[1] | P | Δ | D[1] | D[1] | Y | W[1] | R | D[1] | A |
| UK | GR/501Y.V1 | B.1.1.7 | S[1] | L | T[1] | P | Δ | D[1] | D[1] | Δ | W[1] | R | D[1] | A |
| SA | GH/501Y.V2 | B.1.351 | S[1] | L | T[1] | P | HV | A | D[1] | Y | W[1] | R | G | Δ |
| Brazil/Japan | P.1 | | S[1] | F | N | S | HV | D[1] | Y | Y | W[1] | S | D[1] | A |
| Brazil | P.2 | | S[1] | L | T[1] | P | HV | D[1] | D[1] | Y | W[1] | R | D[1] | A |
| California | CAL.20C-GH/452R.V1 | B.1.429 | I | L | T[1] | P | HV | D[1] | D[1] | Y | C | R | D[1] | A |
| India | (Andhra Pradesh) | N440K | S[1] | L | T[1] | P | HV | D[1] | D[1] | Y | W[1] | R | D[1] | A |
| WUHAN | | WUHAN | S[1] | L | T[1] | P | HV | D[1] | D[1] | Y | W[1] | R | D[1] | A |
| | PCR Amplimer length (bases) | | | (1) 101 | | | | (2) 104 | | (3) 129 | | | (4) 160 | |

| Spike Gene Target Region (Codon) Amino Acid Change | | | R246I | K417N | N440K | L452R | Y453F | E484K | N501Y | A570D | D614G | H655Y | P681H |
|---|---|---|---|---|---|---|---|---|---|---|---|---|---|
| Wuhan reference specific probes/s coverage | | | | ✓[1] | ✓[1] | ✓[1] | | ✓[1] | ✓[1] | | ✓[1] | | ✓[1] |
| REGION | LINEAGE DESIGNATION var | | | | | | | | | | | | |
| Denmark | Mink V | B.1.1.298 | R | K[1] | N[1] | L[1] | F | E[1] | N[1] | A | G | H | P[1] |
| UK | GR/501Y.V1 | B.1.1.7 | R | K[1] | N[1] | L[1] | Y | E[1] | Y | D | G | H | H |
| SA | GH/501Y.V2 | B.1.351 | I | N | N[1] | L[1] | Y | K | Y | A | G | H | P[1] |
| Brazil/Japan | P.1 | | R | T | N[1] | L[1] | Y | K | Y | A | G | Y | P[1] |
| Brazil | P.2 | | R | K[1] | N[1] | L[1] | Y | K | N[1] | A | G | H | P[1] |
| California | CAL.20C-GH/452R.V1 | B.1.429 | R | K[1] | N[1] | R | Y | E[1] | N[1] | A | G | H | P[1] |
| India | (Andhra Pradesh) | N440K | R | K[1] | K | L[1] | Y | E[1] | N[1] | A | G | H | P[1] |
| WUHAN | | WUHAN | R | K[1] | N[1] | L[1] | Y | E[1] | N[1] | A | D[1] | H | P[1] |
| | PCR Amplimer length (bases) | | (4) 160 | | | (5) 199 | | (6) 151 | | | (7) 88 | | (8) 135 |

| Spike Gene Target Region (Codon) Amino Acid Change | | | I692V | A701V | T716I | S982A | T1027I | D1118H | V1176F | M1229I |
|---|---|---|---|---|---|---|---|---|---|---|
| Wuhan reference specific probes/s coverage | | | | ✓[1] | | | | | | |
| REGION | LINEAGE DESIGNATION var | | | | | | | | | |
| Denmark | Mink V | B.1.1.298 | V | A[1] | T | S | T | D | V | I |
| UK | GR/501Y.V1 | B.1.1.7 | I | A[1] | I | A | T | H | V | M |
| SA | GH/501Y.V2 | B.1.351 | I | V | T | S | T | D | V | M |
| Brazil/Japan | P.1 | | I | A[1] | T | S | I | D | F | M |
| Brazil | P.2 | | I | A[1] | T | S | T | D | F | M |
| California | CAL.20C-GH/452R.V1 | B.1.429 | I | A[1] | T | S | T | D | V | M |
| India | (Andhra Pradesh) | N440K | I | A[1] | T | S | T | D | V | M |
| WUHAN | | WUHAN | I | A[1] | T | S | T | D | V | M |
| | PCR Amplimer length (bases) | | (8) 135 | | | | | | | |

[1]AA identical to hCoV-19/Wuhan/WIV04/2019 (WIV04)-official reference sequence employed by GISAID (EPI_ISL_402124) Hybridizes to reference specific probe

TABLE 7

Combinatorial Analysis of CoV-2 Variants Universal Probes

| REGION | LINEAGE DESIGNATION | var | S13I | L18F | T20N | P26S | Δ69-70 | D80A | D138Y | Y144DEL | W152C | R190S | D215G | A243del |
|---|---|---|---|---|---|---|---|---|---|---|---|---|---|---|
| Spike Gene Target Region (Codon) Amino Acid Change | | | S13I | L18F | T20N | P26S | Δ69-70 | D80A | D138Y | Y144DEL | W152C | R190S | D215G | A243del |
| Locus specific Probe coverage | | | ✓[1] | | ✓[1] | | N/A | ✓[1] | ✓[1] | | ✓[1] | | ✓[1] | |
| Denmark | Mink V | B.1.1.298 | S[1] | L | T[1] | P | Δ | D[1] | D[1] | Y | W[1] | R | D[1] | A |
| UK | GR/501Y.V1 | B.1.1.7 | S[1] | L | T[1] | P | Δ | D[1] | D[1] | Δ | W[1] | R | D[1] | A |
| SA | GH/501Y.V2 | B.1.351 | S[1] | L | T[1] | P | HV | A[1] | D[1] | Y | W[1] | R | G[1] | Δ |
| Brazil/Japan | P.1 | | S[1] | F | N[1] | S | HV | D[1] | Y | Y | W[1] | S | D[1] | A |
| Brazil | P.2 | | S[1] | L | T[1] | P | HV | D[1] | D[1] | Y | W[1] | R | D[1] | A |
| California | CAL.20C-GH/452R.V1 | B.1.429 | I[1] | L | T[1] | P | HV | D[1] | D[1] | Y | C[1] | R | D[1] | A |
| India | (Andhra Pradesh) | N440K | S[1] | L | T[1] | P | HV | D[1] | D[1] | Y | W[1] | R | D[1] | A |
| WUHAN | | WUHAN | S[1] | L | T[1] | P | HV | D[1] | D[1] | Y | W[1] | R | D[1] | A |
| PCR Amplimer length (bases) | | | | (1) 101 | | | | (2) 104 | | (3) 129 | | | | (4) 160 |

| REGION | LINEAGE DESIGNATION | var | R246I | K417N/T | N440K | L452R | Y453F | E484K | N501Y | A570D | D614G | H655Y | P681H |
|---|---|---|---|---|---|---|---|---|---|---|---|---|---|
| Spike Gene Target Region (Codon) Amino Acid Change | | | R246I | K417N/T | N440K | L452R | Y453F | E484K | N501Y | A570D | D614G | H655Y | P681H |
| Locus specific Probe coverage | | | | ✓[1] | ✓[1] | ✓[1] | | ✓[1] | ✓[1] | | ✓[1] | | ✓[1] |
| Denmark | Mink V | B.1.1.298 | R | K[1] | N[1] | L[1] | F | E[1] | N[1] | A | G[1] | H | P[1] |
| UK | GR/501Y.V1 | B.1.1.7 | R | K[1] | N[1] | L[1] | Y | E[1] | Y[1] | D | G[1] | H | H[1] |
| SA | GH/501Y.V2 | B.1.351 | I | N[1] | N[1] | L[1] | Y | K[1] | Y[1] | A | G[1] | H | P[1] |
| Brazil/Japan | P.1 | | R | T[1] | N[1] | L[1] | Y | K[1] | Y[1] | A | G[1] | Y | P[1] |
| Brazil | P.2 | | R | K[1] | N[1] | L[1] | Y | K[1] | N[1] | A | G[1] | H | P[1] |
| California | CAL.20C-GH/452R.V1 | B.1.429 | R | K[1] | N[1] | R[1] | Y | E[1] | N[1] | A | G[1] | H | P[1] |
| India | (Andhra Pradesh) | N440K | R | K[1] | K[1] | L[1] | Y | E[1] | N[1] | A | G[1] | H | P[1] |
| WUHAN | | WUHAN | R | K[1] | N[1] | L[1] | Y | E[1] | N[1] | A | D[1] | H | P[1] |
| PCR Amplimer length (bases) | | | (4) 160 | | (5) 199 | | | (6) 151 | | | (7) 88 | | (8) 135 |

| REGION | LINEAGE DESIGNATION | var | I692V | A701V | T716I | S982A | T1027I | D1118H | V1176F | M1229I |
|---|---|---|---|---|---|---|---|---|---|---|
| Spike Gene Target Region (Codon) Amino Acid Change | | | I692V | A701V | T716I | S982A | T1027I | D1118H | V1176F | M1229I |
| Locus specific Probe coverage | | | | ✓[1] | | | | | | |
| Denmark | Mink V | B.1.1.298 | V | A[1] | T | S | T | D | V | I |
| UK | GR/501Y.V1 | B.1.1.7 | I | A[1] | I | A | T | H | V | M |
| SA | GH/501Y.V2 | B.1.351 | I | V[1] | T | S | T | D | V | M |
| Brazil/Japan | P.1 | | I | A[1] | T | S | I | D | F | M |
| Brazil | P.2 | | I | A[1] | T | S | T | D | F | M |
| California | CAL.20C-GH/452R.V1 | B.1.429 | I | A[1] | T | S | T | D | V | M |
| India | (Andhra Pradesh) | N440K | I | A[1] | T | S | T | D | V | M |
| WUHAN | | WUHAN | I | A[1] | T | S | T | D | V | M |
| PCR Amplimer length (bases) | | | (8) 135 | | | | | | | |

[1]Both Mutant and Wuhan reference sequence virus hybridize to Locus specific probe

TABLE 8

Combinatorial Analysis of CoV-2 Variants

| | | | Spike_ S13I | Spike_ L18F | Spike_ T20N | Spike_ P26S | Spike_ Δ69-70 | Spike_ D80A | Spike_ D138Y | Spike_ Y144DEL | Spike_ W152C | Spike_ R190S | Spike_ D215G | Spike_ A243del | Spike_ R246I | Spike_ K417N | Spike_ N440K | Spike_ L452R |
|---|---|---|---|---|---|---|---|---|---|---|---|---|---|---|---|---|---|---|
| Mutation specific Probe coverage | | | ✓[3] | | ✓[3] | | ✓[3] | ✓[3] | ✓[3] | | ✓[3] | | ✓[3] | | | ✓[3] | ✓[3] | ✓[3] |
| Wuhan reference specific probe/s coverage | | | ✓[1] | | ✓[1] | | ✓[1] | ✓[1] | ✓[1] | | ✓[1] | | ✓[1] | | | ✓[1] | ✓[1] | ✓[1] |
| Locus specific Probe coverage | | | ✓[4] | | ✓[4] | | N/A | ✓[4] | ✓[4] | | ✓[4] | | ✓[4] | | | ✓[4] | ✓[4] | ✓[4] |
| REGION | LINEAGE DESIGNATION var | | | | | | | | | | | | | | | | | |
| Denmark | Mink V | B.1.1.298 | S[2] | L[4] | T[2] | P[4] | Δ[3] | D[2] | D[2] | Y[4] | W[2] | R[4] | D[2] | A[4] | R[4] | K[2] | N[2] | L[2] |
| UK | GR/501Y.V1 | B.1.1.7 | S[2] | L[4] | T[2] | P[4] | Δ[3] | D[2] | D[2] | Δ[5] | W[2] | R[4] | D[2] | A[4] | R[4] | K[2] | N[2] | L[2] |
| SA | GH/501Y.V2 | B.1.351 | S[2] | L[4] | T[2] | P[4] | HV | A[3] | D[2] | Y[4] | W[2] | R[4] | G[3] | Δ[5] | I[5] | N[3] | N[2] | L[2] |
| Brazil/Japan | P.1 | | S[2] | F[5] | N[3] | S[5] | HV | D[2] | Y[3] | Y[4] | W[2] | S[5] | D[2] | A[4] | R[4] | T[3] | N[2] | L[2] |
| Brazil | P.2 | | S | L[4] | T[2] | P[4] | HV | D[2] | D[2] | Y[4] | W[2] | R[4] | D[2] | A[4] | R[4] | K[2] | N[2] | L[2] |
| California | CAL.20C-GH/ 452R.V1 | B.1.429 | I[3] | L[4] | T[2] | P[4] | HV | D[2] | D[2] | Y[4] | C[3] | R[4] | D[2] | A[4] | R[4] | K[2] | N[2] | R[3] |
| India | (Andhra Pradesh) | N440K | S[1] | L[4] | T[2] | P[4] | HV | D[2] | D[2] | Y[4] | W[2] | R[4] | D[2] | A[4] | R[4] | K[2] | K[3] | L[2] |
| WUHAN | | WUHAN | S[1] | L[4] | T[2] | P[4] | HV[1] | D[1] | D[1] | Y[4] | W[1] | R[4] | D[1] | A[4] | R[4] | K[1] | N[1] | L[1] |
| | | | | AMP 1 101 BASE | | | | AMP 2 104 BASE | | AMP 3 129 BASE | | | | AMP 4 160 BASE | | | AMP 5 199 BASE | |

| | | | Spike_ Y453F | Spike_ E484K | Spike_ N501Y | Spike_ A570D | Spike_ D614G | Spike_ H655Y | Spike_ P681H | Spike_ I692V | Spike_A 701V | Spike_ T716I | Spike_ S982A | Spike_ T1027I | Spike_ D1118H | Spike_ V1176F | Spike_ M1229I |
|---|---|---|---|---|---|---|---|---|---|---|---|---|---|---|---|---|---|
| Mutation specific Probe coverage | | | | ✓[3] | ✓[3] | | ✓[3] | | ✓[3] | | ✓[3] | | | | | | |
| Wuhan reference specific probe/s coverage | | | | ✓[1] | ✓[1] | | ✓[1] | | ✓[1] | | ✓[1] | | | | | | |
| Locus specific Probe coverage | | | | ✓[4] | ✓[4] | | ✓[4] | | ✓[4] | | ✓[4] | | | | | | |
| REGION | LINEAGE DESIGNATION var | | | | | | | | | | | | | | | | |
| Denmark | Mink V | B.1.1.298 | F[5] | E[2] | N[2] | A[4] | G[3] | H[4] | P[2] | V[5] | A[2] | T[4] | S[4] | T[4] | D[4] | V[4] | I[5] |
| UK | GR/501Y.V1 | B.1.1.7 | Y[4] | E[2] | Y[3] | D[5] | G[3] | H[4] | H[3] | I[4] | A[2] | I[5] | A[5] | T[4] | H[5] | V[4] | M[5] |
| SA | GH/501Y.V2 | B.1.351 | Y[4] | E[2] | Y[3] | A[4] | G[3] | H[4] | P[2] | I[4] | V[3] | T[4] | S[4] | T[4] | D[4] | V[4] | M[5] |
| Brazil/Japan | P.1 | | Y[4] | K[3] | Y[3] | A[4] | G[3] | Y[5] | P[2] | I[4] | A[2] | T[4] | S[4] | I[5] | D[4] | F[5] | M[5] |
| Brazil | P.2 | | Y[4] | K[3] | N[2] | A[4] | G[3] | H[4] | P[2] | I[4] | A[2] | T[4] | S[4] | T[4] | D[4] | F[5] | M[5] |
| California | CAL.20C-GH/ 452R.V1 | B.1.429 | Y[4] | K[3] | N[2] | A[4] | G[3] | H[4] | P[2] | I[4] | A[2] | T[4] | S[4] | T[4] | D[4] | V[4] | M[5] |
| India | (Andhra Pradesh) | N440K | Y[4] | E[2] | N[2] | A[4] | G[3] | H[4] | P[2] | I[4] | A[2] | T[4] | S[4] | T[4] | D[4] | V[4] | M[5] |
| WUHAN | | WUHAN | Y[4] | E[1] | N[1] | A[4] | D[1] | H[4] | P[1] | I[4] | A[1] | T[4] | S[4] | T[4] | D[4] | V[4] | M[5] |
| | | | AMP 5 199 BASE | AMP 6 151 BASE | | | AMP 7 88 BASE | | | AMP 8 135 BASE | | | | | | | |

[1]AA of hCoV-19/Wuhan/WIV04/2019 (WIV04)-official reference sequence employed by GISAID (EPI_ISL_402124)
[2]AA Identical to (WIV04)-hybridizes to Wuhan reference probe
[3]AA mutation-hybridizes to mutation specific probe
[4]Potential probe target identical to (WIV04)
[5]Potential AA mutation probe target Example 2

Biological Rationale for the Design of the Present Invention

The oligonucleotide probes of the microarray and the PCR primers to generate RT-PCR amplicons were developed to accommodate a specific CoV-2 clade Variant set of international interest in 2021, as specified in the Left-most Column in Tables 4-8. But, as can already be seen among the clade Variant strain these tables, the pattern of local sequence change manifest in each clade Variant comprises a unique combination derived from a larger set of specific local sequence variation chosen at discrete sites in the Spike gene.

For the Spike protein of the CoV-2 virus and for pathogens more universally, spontaneous local mutation in a surface protein such as Spike is likely to inactivate the protein, thus disabling the pathogen. As such, most spontaneous mutations in surface proteins do not propagate and hence go undetected.

On occasion, however, such random mutation produces a surface protein change that confers a selective advantage to a pathogen, such as enhanced infectivity, better resistance to vaccination or drug therapy and thus the mutation propagates in an infection and ultimately be detected at population scale. Such positively selected local mutational changes are generally rare and thus localized to a relatively small number of discrete segments within a pathogen surface protein such as Spike, often localized to specific sites where the protein contacts host cells, or sites which present peptides for interaction with a protective host antibody or sites where a drug might bind. In many cases such altered surface protein features may function in an additive way (enhanced cell binding+diminished neutralizing antibody binding may be selected for, concurrently) to produce a clade Variant presenting a combination derived from the set of available local sequence changes that confer functional superiority to the pathogen.

The present invention takes advantage of the fundamental matrix-like character of such selectable (discrete, local) surface protein changes and the ability of a matrix of hybridization probes (as in a microarray) to query many sites of local surface protein sequence change simultaneously (Tables 4-7). As such, this oligonucleotide probe set can interrogate (at the nucleic acid level) many possible combinations of such surface protein change as a single combinatorial test.

Based on the core design test design embodied in Tables 4-7, new, as-yet unknown, functionally relevant local sequence change can be added, once known, as new probes to the microarray (cells with superscript "3" in Table 4). It is expected that many other CoV-2 clades could be detected and discriminated, in a similar combinatorial fashion, via such relatively minor expansion of the core invention depicted in Table 4.

Example 3

Test Manufacturing Considerations

The present implementation of such an oligonucleotide probe panel for analysis of the CoV-2 Spike gene is based upon detection of 15 positively selected local mutational changes in the Spike gene, i.e. Tables 4-7, each with 3 probe sequence variants at each site, "Mutant", "Wild Type", "Universal", thus generating a set of 15×3=45 oligonucleotide probes to be used for the purpose of combinatorial Clade Variant Analysis.

In the present implementation, if that set of 45 probes is manufactured in triplicate, a 3×45=135 probe microarray is thus generated, which when printed along with positive and negative controls appropriate for CoV-2 testing (such as RNAse P) the present Clade Chip Assay consumes the full microarray content capacity presented by the standard 150 probe, 96-Well format described in applications U.S. Ser. No. 16/950,171 and U.S. Ser. No. 16/950,210, both hereby incorporated by reference in their entireties.

It is useful to note that the information content of such a 150-probe microarray becomes resident in a single well of the 96-well microarray format and thus generates information content similar to that of re-sequencing of the entire gene and content that is equivalent to that obtained from 150 q-RT-PCR assays performed in parallel. As seen below, a first preferred implementation of such a Clade Chip prototype has been fabricated via standard mass production methods described in the above-referenced patent applications.

Performance

In a first preferred implementation, the sample preparation methods of the Clade Chip are optimized for both NP-Swab and Saliva collection and designed to detect CoV-2 at 5 virus/RT-PCR reaction sensitivity (500 cp/ml) and resolve multiple CoV-2 Clade variants of present international concern (Denmark, UK, S Africa, Brazil/Japan, India, CA L452R, Wuhan), as depicted in Tables 4-7.

So long as any new CoV-2 Clade may be detected and discriminated via its pattern of Spike gene gRNA sequence change, that additional Clade sequence content (cells with superscript "3" in Table 4) can be designed and added to the manufacture of the present invention in less than 2-weeks, as the need for new or broader-range CoV-2 Clade Variant detection emerges.

The Clade-Chip Assay in the present preferred implementation is based on a standard 96-well plate microarray processing workflow already described in applications having U.S. Ser. No. 16/950,171 and U.S. Ser. No. 16/950,210 both hereby incorporated by reference in their entireties and is deployed in that standard 96-well format as a manual or automated test. However, the matrix of oligonucleotide probes of the present invention to detect CoV-2 clade Variants via Combinatorial Analysis could, in principle, be implemented by other methods of microarray manufacture or via alternative methods of bead-based solution phase nucleic acid hybridization. Additionally, the same principles of Combinatorial Analysis could be used to develop analogous tests for clade variation in other viruses, bacterial and fungi in the microarray or other hybridization formats.

Example 4

Clade Array Manufacturing Quality and Functional Characterization

The Clade Chip Test Design summary is shown in Table 9 and is suited for combinatorial analysis among multiple Spike Targets. The following are its features;

1. Core Content, Completed (11) Target Sites, ≥3 Probes Each (Universal, Mutant, Wild Type)=11×3×3=99 probe spots
2. Additional (Future Clade) Content Array Real-estate,
   a. Up to 8 additional Target sites can be added to current Clade Array
   b. 9×3×3=81 additional probe spots.

Clade Variant Content as Printed

A Clade Chip Probe layout was set up in duplicate. The probe content included three (3) probes for each Spike target site (Universal, Mutant, Wild Type). Validation testing was used to pick the best" of the two closely related "redundant" lead designs for each of the three probes. In addition to the core set of 11 spike targets, new probe designs were included to expand the content of the assay. The full set of redundant probe content was printed in duplicate as a 12×16 probe array in a 96-well format (Table 10). The forward (odd numbers) and reverse (even numbers) primer sequences for each amplimer employed in this assay are shown in Table 11.

TABLE 9

Validation of test design for the five prevalent Clade variants

| Spike Gene Target Region (Codon) Amino Acid Change | | | S13I | L18F | T20N | P26S | Δ69-70 | D80A | D138Y | Y144D | W152C | R190S | D215G | A243del | R246I | K417N | N440K | L452R |
|---|---|---|---|---|---|---|---|---|---|---|---|---|---|---|---|---|---|---|
| Mutation specific Probe coverage | | | | | | | ✓$^1$ | ✓$^1$ | ✓$^1$ | | ✓$^1$ | | | | | | ✓$^1$ | ✓$^1$ |
| Wuhan reference specific probe/s coverage | | | | | | | ✓$^2$ | ✓$^2$ | ✓$^2$ | | ✓$^2$ | | | | | | ✓$^2$ | ✓$^2$ |
| Locus specific Probe coverage | | | | | | | N/A | ✓ | ✓ | | ✓ | | | | | | ✓ | ✓ |
| REGION | LINEAGE DESIGNATION var | | | | | | | | | | | | | | | | | |
| Denmark | Mink V | B.1.1.298 | $S^3$ | $L^3$ | $T^3$ | $P^3$ | $Δ^1$ | $D^2$ | $D^2$ | $Y^3$ | $W^2$ | $R^3$ | $D^3$ | $A^3$ | $R^3$ | $K^3$ | $N^2$ | $L^2$ |
| UK | GR/501Y.V1 | B.1.1.7 | $S^3$ | $L^3$ | $T^3$ | $P^3$ | $Δ^1$ | $D^2$ | $D^2$ | $Δ^3$ | $W^2$ | $R^3$ | $D^3$ | $A^3$ | $R^3$ | $K^3$ | $N^2$ | $L^2$ |
| SA | GH/501Y.V2 | B.1.351 | $S^3$ | $L^3$ | $T^3$ | $P^3$ | $HV^2$ | $A^1$ | $D^2$ | $Y^3$ | $W^2$ | $R^3$ | $G^3$ | $Δ^3$ | $I^3$ | $N^3$ | $N^2$ | $L^2$ |
| Brazil/Japan | P.1 | | $S^3$ | $F^3$ | $N^3$ | $S^3$ | $HV^2$ | $D^2$ | $Y^1$ | $Y^3$ | $W^2$ | $S^3$ | $D^3$ | $A^3$ | $R^3$ | $T^3$ | $N^2$ | $L^2$ |
| Brazil | P.2 | | $I^3$ | $L^3$ | $T^3$ | $P^3$ | $HV^2$ | $D^2$ | $D^2$ | $Y^3$ | $W^2$ | $R^3$ | $D^3$ | $A^3$ | $R^3$ | $K^3$ | $N^2$ | $L^2$ |
| California | CAL.20C-GH/452R.V1 | B.1.429 | $S^3$ | $L^3$ | $T^3$ | $P^3$ | $HV^2$ | $D^2$ | $D^2$ | $Y^3$ | $C^1$ | $R^3$ | $D^3$ | $A^3$ | $R^3$ | $K^3$ | $N^2$ | $R^1$ |
| India | (Andhra Pradesh) | N440K | $S^3$ | $L^3$ | $T^3$ | $P^3$ | $HV^2$ | $D^2$ | $D^2$ | $Y^3$ | $W^2$ | $R^3$ | $D^3$ | $A^3$ | $R^3$ | $K^3$ | $K^1$ | $L^2$ |
| S. US | 20G/B.1.2 | Q677P/H | $S^3$ | $L^3$ | $T^3$ | $P^3$ | $HV^2$ | $D^2$ | $D^2$ | $Y^3$ | $W^2$ | $R^3$ | $D^3$ | $A^3$ | $R^3$ | $K^3$ | $N^2$ | $L^2$ |
| WUHAN | | WUHAN | $S^3$ | $L^3$ | $T^3$ | $P^3$ | $HV^2$ | $D^2$ | $D^2$ | $Y^3$ | $W^2$ | $R^3$ | $D^3$ | $A^3$ | $R^3$ | $K^3$ | $N^2$ | $L^2$ |
| | | | | | | | ✓$^4$ | ✓$^5$ | ✓$^4$ | | ✓$^4$ | | | | | | ✓$^4$ | ✓$^4$ |
| | | | | (1) 101 | | | | (2) | | (3) 129 | | | | (4) 160 | | | (5) 199 | |

| Spike Gene Target Region (Codon) Amino Acid Change | | | Y453F | E484K | N501Y | A570D | D614G | H655Y | Q677P/H | P681H | I692V | A701V | T716I | S982A | T1027I | D1118 | V1176 | M1229I |
|---|---|---|---|---|---|---|---|---|---|---|---|---|---|---|---|---|---|---|
| Mutation specific Probe coverage | | | | ✓$^1$ | ✓$^1$ | | ✓$^1$ | | | ✓$^1$ | | ✓$^1$ | | | | | | |
| Wuhan reference specific probe/s coverage | | | | ✓$^2$ | ✓$^2$ | | ✓$^2$ | | | ✓$^2$ | | ✓$^2$ | | | | | | |
| Locus specific Probe coverage | | | | ✓ | ✓ | | ✓ | | | ✓ | | ✓ | | | | | | |
| REGION | LINEAGE DESIGNATION var | | | | | | | | | | | | | | | | | |
| Denmark | Mink V | B.1.1.298 | $F^3$ | $E^2$ | $N^2$ | $A^3$ | $G^1$ | $H^3$ | $Q^3$ | $P^2$ | $V^3$ | $A^2$ | $T^3$ | $S^3$ | $T^3$ | $D^3$ | $V^3$ | $I^3$ |
| UK | GR/501Y.V1 | B.1.1.7 | $Y^3$ | $E^2$ | $Y^1$ | $D^3$ | $G^1$ | $H^3$ | $Q^3$ | $H^1$ | $I^3$ | $A^2$ | $I^3$ | $A^3$ | $T^3$ | $H^3$ | $V^3$ | $M^3$ |
| SA | GH/501Y.V2 | B.1.351 | $Y^3$ | $K^1$ | $Y^1$ | $A^3$ | $G^1$ | $H^3$ | $Q^3$ | $P^2$ | $I^3$ | $V^1$ | $T^3$ | $S^3$ | $T^3$ | $D^3$ | $V^3$ | $M^3$ |
| Brazil/Japan | P.1 | | $Y^3$ | $K^1$ | $Y^1$ | $A^3$ | $G^1$ | $Y^3$ | $Q^3$ | $P^2$ | $I^3$ | $A^2$ | $T^3$ | $S^3$ | $I^3$ | $D^3$ | $F^3$ | $M^3$ |
| Brazil | P.2 | | $Y^3$ | $K^1$ | $N^2$ | $A^3$ | $G^1$ | $H^3$ | $Q^3$ | $P^2$ | $I^3$ | $A^2$ | $T^3$ | $S^3$ | $T^3$ | $D^3$ | $F^3$ | $M^3$ |
| California | CAL.20C-GH/452R.V1 | B.1.429 | $Y^3$ | $E^2$ | $N^2$ | $A^3$ | $G^1$ | $H^3$ | $Q^3$ | $P^2$ | $I^3$ | $A^2$ | $T^3$ | $S^3$ | $T^3$ | $D^3$ | $V^3$ | $M^3$ |
| India | (Andhra Pradesh) | N440K | $Y^3$ | $E^2$ | $N^2$ | $A^3$ | $G^1$ | $H^3$ | $Q^3$ | $P^2$ | $I^3$ | $A^2$ | $T^3$ | $S^3$ | $T^3$ | $D^3$ | $V^3$ | $M^3$ |
| S. US | 20G/B.1.2 | Q677P/H | $Y^3$ | $E^2$ | $N^2$ | $A^3$ | $G^1$ | $H^3$ | P/H | $P^2$ | $I^3$ | $A^2$ | $T^3$ | $S^3$ | $T^3$ | $D^3$ | $V^3$ | $M^3$ |
| WUHAN | | WUHAN | $Y^3$ | $E^2$ | $N^2$ | $A^3$ | $D^2$ | $H^3$ | $Q^3$ | $P^2$ | $I^3$ | $A^2$ | $T^3$ | $S^3$ | $T^3$ | $D^3$ | $V^3$ | $M^3$ |
| | | | | ✓$^5$ | ✓$^4$ | | ✓$^4$ | | | ✓$^4$ | ✓$^4$ | | | | | | | |
| | | | (5) 199 | (6) 151 | | | (7) 88 | | | (8) 135 | | | | | | | | |

[1]AA mutation-hybridizes to mutation specific probe
[2]AA identical to hCoV-19/Wuhan/WIV04/2019 (WIV04)-official reference sequence employed by GISAID (EPI _ISL 402124). Hybridizes toreference specific probe
[3]Potential probe target
[4]No Probe Adjustment Necessary
[5]Minor Probe Adjustment Necessary

TABLE 10

| Clade chip probe layout | | | | | |
|---|---|---|---|---|---|
| Row | Col. | SEQ ID NOS. | Amplimer # | Target | Probe Sequence (5' to 3') |
| 1 | 1 | SEQ ID NO: 30 | 1 | AA S13I | TTTTTCTAGTCTCTAKTCAGTGTGTTTTTT |
| 1 | 2 | SEQ ID NO: 64 | 1 | AA S13_ (1) | TTTTTTTGTCTCTAGTCAGTGTTTTTTTTT |
| 1 | 3 | SEQ ID NO: 65 | 1 | AA S13_ (2) | TTTTTTTAGTCTCTAGTCAGTGTTTTTTTT |
| 1 | 4 | SEQ ID NO: 66 | 1 | AA_13I (1) | TTTTTTAGTCTCTATTCAGTGTTTTTTTTT |
| 1 | 5 | SEQ ID NO: 67 | 1 | AA_13I (2) | TTTTTTTAGTCTCTATTCAGTGTTTTTTTT |
| 1 | 6 | SEQ ID NO: 68 | 1 | AA T20N | TTTTTTAATYTTACAAMCAGAACTCTTTTT |
| 1 | 7 | SEQ ID NO: 69 | 1 | AA T20_ (1) | TTTTTTTATCTTACAACCAGAACCTTTTTT |
| 1 | 8 | SEQ ID NO: 70 | 1 | AA T20_ (2) | TTTTTTTATCTTACAACCAGAACTTTTTTT |
| 1 | 9 | SEQ ID NO: 71 | 1 | AA_20N (1) | TTTTTTATTTTACAAACAGAACTTTTTTTT |
| 1 | 10 | SEQ ID NO: 72 | 1 | AA_20N (2) | TTTTTCAATTTTACAAACAGAACTTTTTTT |
| 1 | 11 | SEQ ID NO: 68 | | RNAse P control | TTTTTTTTCTGACCTGAAGGCTCTGCGCGTTTTT |
| 1 | 12 | SEQ ID NO: 73 | 2 | AA69-70 HV (1) | TTTTTTATGCTATACATGTCTCTGTTTTTT |
| 2 | 1 | SEQ ID NO: 31 | 2 | AA69-70 HV (2) | TTTTTCCCATGCTATACATGTCTCTGTTTTTT |
| 2 | 2 | SEQ ID NO: 74 | 2 | AA69-70 DEL (1) | TTTTTTACCATGCTATCTCTGGGATTTTTT |
| 2 | 3 | SEQ ID NO: 32 | 2 | AA69-70 DEL (2) | TTTTTTTTTCCATGCTATCTCTGGGATTTTTT |
| 2 | 4 | SEQ ID NO: 33 | 2 | AA D80A | TTTTTCAGAGGTTTGMTAACCCTGTCTTTTTT |
| 2 | 5 | SEQ ID NO: 34 | 2 | AA D80_ (1) | TTTTTTTGGTTTGATAACCCTGCTTTTTTT |
| 2 | 6 | SEQ ID NO: 75 | 2 | AA D80_ (2) | TTTTTCTAGGTTTGATAACCCTGCTTTTTT |
| 2 | 7 | SEQ ID NO: 76 | 2 | AA_80A (1) | TTTTTTTAGGTTTGCTAACCCTCTTTTTTT |
| 2 | 8 | SEQ ID NO: 35 | 2 | AA_80A (2) | TTTTTTTGGTTTGCTAACCCTGCTTTTTTT |
| 2 | 9 | SEQ ID NO: 36 | 3 | AA D138Y | TTTTATTTTGTAATKATCCATTTTTGTTTT |
| 2 | 10 | SEQ ID NO: 37 | 3 | AA D138_ (1) | TTTTTCTTTGTAATGATCCATTTTCTTTTT |
| 2 | 11 | SEQ ID NO: 77 | 3 | AA D138_ (2) | TTTTTTCTTTGTAATGATCCATTTCTTTTT |
| 2 | 12 | SEQ ID NO: 38 | 3 | AA_138Y (1) | TTTTTTTTTGTAATTATCCATTTTCTTTTT |
| 3 | 1 | SEQ ID NO: 78 | 3 | AA_138Y (2) | TTTTTCTTTGTAATTATCCATTTTCTTTTT |
| 3 | 2 | SEQ ID NO: 39 | 3 | AA W152C | TTTTTAGTTGKATGGAAAGTGAGTTCTTTT |
| 3 | 3 | SEQ ID NO: 40 | 3 | AA W152_ (1) | TTTCTCTAAAAGTTGGATGGAAACTCTTCT |
| 3 | 4 | SEQ ID NO: 79 | 3 | AA W152_ (2) | TTTTCTTCAAAGTTGGATGGAAACTCTTTT |
| 3 | 5 | SEQ ID NO: 41 | 3 | AA_152C (1) | TTTCTTCAAAGTTGTATGGAAAGCCTTCTT |
| 3 | 6 | SEQ ID NO: 80 | 3 | AA_152C (2) | TTTCTCTAAAAGTTGTATGGAAACTCTTCT |
| 3 | 7 | SEQ ID NO: 81 | 4 | AA D215G | TTTTTTAGTGCGTGRTCTCCCTCATTTTTT |
| 3 | 8 | SEQ ID NO: 82 | 4 | AA D215_ (1) | TTTTTTCTGCGTGATCTCCCTCATTTTTTT |
| 3 | 9 | SEQ ID NO: 83 | 4 | AA D215_ (2) | TTTTTTTCTGCGTGATCTCCCTCTTTTTTT |
| 3 | 10 | SEQ ID NO: 84 | 4 | AA_215G (1) | TTTTTTTTGCGTGGTCTCCCTCTTTTTTTT |
| 3 | 11 | SEQ ID NO: 85 | 4 | AA_215G (2) | TTTTTTTTTGCGTGGTCTCCCTTTTTTTTT |
| 3 | 12 | SEQ ID NO: 86 | 5 | AA K417N | TTTTAACTGGAAAKATTGCTGATTATTTTT |
| 4 | 1 | SEQ ID NO: 87 | 5 | AA K417_ (1) | TTTCTTCTCTGGAAAGATTGCTGCTTTTTT |
| 4 | 2 | SEQ ID NO: 88 | 5 | AA K417_ (2) | TTCTTCTCTGGAAAGATTGCTGACTTTTTT |

TABLE 10-continued

Clade chip probe layout

| Row | Col. | SEQ ID NOS. | Amplimer # | Target | Probe Sequence (5' to 3') |
|---|---|---|---|---|---|
| 4 | 3 | SEQ ID NO: 89 | 5 | AA_417N (1) | TTTTTCTCTGGAAATATTGCTGACTTTTTT |
| 4 | 4 | SEQ ID NO: 90 | 5 | AA_417N (2) | TTTTCTCTGGAAATATTGCTGATCTTTTTT |
| 4 | 5 | SEQ ID NO: 91 | 5 | AA_417T (1) | TTTTTTTACTGGAACGATTGCTTTTTTTTT |
| 4 | 6 | SEQ ID NO: 92 | 5 | AA_417T (2) | TTTTTTCCTGGAACGATTGCTGTTTTTTTT |
| 4 | 7 | SEQ ID NO: 42 | 5 | AA N439K + N440K | TTTTTAATTCTAAMAAKCTTGATTCTAATTTT |
| 4 | 8 | SEQ ID NO: 93 | 5 | AA N439_ + N440_ (1) | TTTTTTATTCTAACAATCTTGATTTCTTTT |
| 4 | 9 | SEQ ID NO: 43 | 5 | AA N439_ + N440_ (2) | TTTTTAATTCTAACAATCTTGATTTCTTTT |
| 4 | 10 | SEQ ID NO: 94 | 5 | AA N439_ + _440K (1) | TTTTTTTTTCTAACAAGCTTGATTTTTTTT |
| 4 | 11 | SEQ ID NO: 44 | 5 | AA N439_ + _440K (2) | TTTTTTATTCTAACAAGCTTGATTTTTTTT |
| 4 | 12 | SEQ ID NO: 45 | 5 | AA_439K + N440_ (1) | TTTTCTATTCTAAAAATCTTGATTTCTTTT |
| 5 | 1 | SEQ ID NO: 95 | 5 | AA_439K + N440_ (2) | TTCTTAATTCTAAAAATCTTGATTTCTTTT |
| 5 | 2 | SEQ ID NO: 46 | 5 | AA L452R | TTTCTATAATTACCTGTATAGATTGTCTTT |
| 5 | 3 | SEQ ID NO: 96 | 5 | AA L452_ (1) | TTTTTCATAATTACCTGTATAGACTTTCTT |
| 5 | 4 | SEQ ID NO: 47 | 5 | AA L452_ (2) | TTTTTTTAATTACCTGTATAGATTTCTTTT |
| 5 | 5 | SEQ ID NO: 48 | 5 | AA_452R (1) | TTTTTCATAATTACTGGTATAGATCTTTTT |
| 5 | 6 | SEQ ID NO: 97 | 5 | AA_452R (2) | TTTTTTCAATTACCGGTATAGATCTTTTTT |
| 5 | 7 | SEQ ID NO: 49 | 6 | AA S477_ | TTTTTTCGCCGGTAGCACACCTCTTTTTTT |
| 5 | 8 | SEQ ID NO: 98 | 6 | AA_478I (1) | TTTTTTTTGGTAGCATACCTTGTTTTTTTT |
| 5 | 9 | SEQ ID NO: 99 | 6 | AA_478I (2) | TTTTTTTCGGTAGCATACCTTGTTTTTTT |
| 5 | 10 | SEQ ID NO: 50 | 6 | AA_477N (1) | TTTTCTTCCGGTAACACACCTTTTTTTTTT |
| 5 | 11 | SEQ ID NO: 100 | 6 | AA_477N (2) | TTTTTTCGCCGGTAACACACCTCTTTTTTT |
| 5 | 12 | SEQ ID NO: 101 | 6 | AA_476S (1) | TTTTTTTTCAGGCCAGTAGCACTTTTTTTT |
| 6 | 1 | SEQ ID NO: 51 | 6 | AA V483A + E484K | TTTTTAATGGTGTTRAAGGTTTTAATTTTTT |
| 6 | 2 | SEQ ID NO: 52 | 6 | AA V483_ + E484_ (1) | TTTTTTCTGGTGTTGAAGGTTTTACTTTTT |
| 6 | 3 | SEQ ID NO: 102 | 6 | AA V483_ + E484_ (2) | TTTTTCTGGTGTTGAAGGTTTTATCTTTTT |
| 6 | 4 | SEQ ID NO: 103 | 6 | AA V483_ + _484K (1) | TTTTTTCTGGTGTTAAAGGTTTTACTTTTT |
| 6 | 5 | SEQ ID NO: 53 | 6 | AA V483_ + _484K (2) | TTTTTTTATGGTGTTAAAGGTTTTCTTTTT |
| 6 | 6 | SEQ ID NO: 54 | 6 | AA_483A + E484_ (1) | TTTTTTTATGGTGCTGAAGGTTCTTTTTTT |
| 6 | 7 | SEQ ID NO: 104 | 6 | AA_483A + E484_ (2) | TTTTTTCAATGGTGCTGAAGGTTCTTTTTT |
| 6 | 8 | SEQ ID NO: 55 | 6 | AA N501Y | TTTTTTTTCCAACCCACTWATGGTGTTTTTTTT |
| 6 | 9 | SEQ ID NO: 56 | 6 | AA N501_ (1) | TTTTTTTTACCCACTAATGGTGTCTTTTTT |
| 6 | 10 | SEQ ID NO: 105 | 6 | AA N501_ (2) | TTTTTTTAACCCACTAATGGTGTCTTTTTT |
| 6 | 11 | SEQ ID NO: 57 | 6 | AA_501Y (1) | TTTTTTTTACCCACTTATGGTGTCTTTTTT |
| 6 | 12 | SEQ ID NO: 106 | 6 | AA_501Y (2) | TTTTTTTAACCCACTTATGGTGTCTTTTTT |
| 7 | 1 | SEQ ID NO: 107 | 7 | AA D614G | TTTTTCTCTTTATCARGRTGTTAACTGCTTTTTT |
| 7 | 2 | SEQ ID NO: 108 | 7 | AA D614_ | TTTTTCTTATCAGGATGTTAACTTTTTTTT |
| 7 | 3 | SEQ ID NO: 109 | 7 | AA_614G + 613 (CAG) | TTTTTTCCTATCAGGGTGTTAACTTTTTTT |

TABLE 10-continued

Clade chip probe layout

| Row | Col. | SEQ ID NOS. | Amplimer # | Target | Probe Sequence (5' to 3') |
|---|---|---|---|---|---|
| 7 | 4 | SEQ ID NO: 110 | 7 | AA_614G + 613 (CAA) | TTTTTTCCTATCAAGGTGTTAACTTTTTTT |
| 7 | 5 | SEQ ID NO: 111 | 7 | AA_614G | TTTTTTCCTATCARGGTGTTAACTTTTTTT |
| 7 | 6 | SEQ ID NO: 58 | 8 | AA P681H | TTTTTTCAGACTAATTCTCMTCGGCTTTTT |
| 7 | 7 | SEQ ID NO: 112 | 8 | AA P681_ (1) | TTTTTTTTAATTCTCCTCGGCGTTTTTTTT |
| 7 | 8 | SEQ ID NO: 59 | 8 | AA P681_ (2) | TTTTTTTCTAATTCTCCTCGGCGTTTTTTT |
| 7 | 9 | SEQ ID NO: 60 | 8 | AA_681H (1) | TTTTTTTTTAATTCTCATCGGCGTTTTTTT |
| 7 | 10 | SEQ ID NO: 113 | 8 | AA_681H (2) | TTTTTTTCTAATTCTCATCGGCGTTTTTTT |
| 7 | 11 | SEQ ID NO: 61 | 8 | AA A701V | TTTTCACTTGGTGYAGAAAATTCAGTTTTT |
| 7 | 12 | SEQ ID NO: 62 | 8 | AA A701_ (1) | TCTTCTTCTTGGTGCAGAAAATTATTCTTT |
| 8 | 1 | SEQ ID NO: 114 | 8 | AA A701_ (2) | TTCTTCTACTTGGTGCAGAAAATTATTCTT |
| 8 | 2 | SEQ ID NO: 63 | 8 | AA_701V (1) | TCTTCTTCTTGGTGTAGAAAATTATTCTTT |
| 8 | 3 | SEQ ID NO: 115 | 8 | AA_701V (2) | TTTCTTTCTTGGTGTAGAAAATTCTTTTTT |
| 8 | 4 | SEQ ID NO: 116 | | N2 | TTTTTTACAATTTGCCCCCAGCGTCTTTTT |
| 8 | 5 | SEQ ID NO: 117 | | SARS-2003 N2 | TTTTTTTTTGCTCCRAGTGCCTCTTTTTTT |
| 8 | 6 | SEQ ID NO: 70 | | Negative Control | TTTTTTCTACTACCTATGCTGATTCACTCTTTTT |
| 8 | 7 | EMPTY | | | |
| 8 | 8 | EMPTY | | | |
| 8 | 9 | EMPTY | | | |
| 8 | 10 | EMPTY | | | |
| 8 | 11 | EMPTY | | | |
| 8 | 12 | EMPTY | | | |

TABLE 11

Amplimer primer sequences

| SEQ ID NOS. | Amplimer # | Target | Gene | Primer Sequence (5' to 3') |
|---|---|---|---|---|
| SEQ ID NO: 25 | 2 | AA66-85 | Spike | TTCTTTTCCAATGTTACTTGGTT CCATG |
| SEQ ID NO: 26 | 2 | AA66-85 | Spike | Cy3-TTTCAAAATAAACACCATC ATTAAATGG |
| SEQ ID NO: 11 | 3 | AA126-157 | Spike | TTTCTTATTGTTAATAACGCTAC TAATG |
| SEQ ID NO: 12 | 3 | AA126-157 | Spike | Cy3-TTTCATTCGCACTAGAATA AACTCTGAA |
| SEQ ID NO: 27 | 5 | AA413-458 | Spike | TTTGATGAAGTCAGACAAATCG CCCAG |
| SEQ ID NO: 28 | 5 | AA413-458 | Spike | Cy3-TTTCTCTCAAAAGGTTTGA GATTAGACT |
| SEQ ID NO: 15 | 6 | AA475-506 | Spike | TTTTATTTCAACTGAAATYTATCA GGCC |
| SEQ ID NO: 16 | 6 | AA475-506 | Spike | Cy3-TTTAAAGTACTACTACTCT GTATGGTTG |

TABLE 11-continued

| Amplimer primer sequences | | | | |
|---|---|---|---|---|
| SEQ ID NOS. | Amplimer # | Target | Gene | Primer Sequence (5' to 3') |
| SEQ ID NO: 29 | 7 | AA610-618 | Spike | TTTCAAATACTTCTAACCAGGTT GCTGT |
| SEQ ID NO: 24 | 7 | AA610-618 | Spike | Cy3-TTTTGCATGAATAGCAACA GGGACTTCT |
| SEQ ID NO: 17 | 8 | AA677-707 | Spike | TTTTATATGCGCTAGTTATCAGA CTCAG |
| SEQ ID NO: 18 | 8 | AA677-707 | Spike | Cy3-TTTTGGTATGGCAATAGAG TTATTAGAG |

Example 5

Clade Array Functional Characterization

Experiment 1:

Samples Used for Testing. Analysis was performed with a highly characterized, purified Wuhan gRNA standard (Quantitative Standard obtained from ATCC-BEI) or with synthetic "mutant" targets designed by PDx, obtained by SGI fabrication (IDT).

RT-PCR Conditions. RT-PCR was performed using the [UNG+ One-Step RT-PCR] protocol. As is customary in optimization of multiplex RT-PCR, the data presented comprise the use of Single PCR primer pairs as a single reaction. Based on these data multiplex RT-PCR conditions are optimized.

Clade Array Hybridization & Imaging. Conditions of Hybridization, Washing and Imaging were exactly as described. Following the completion of the multiplex RT-PCR, the DNA microarray was prepared for hybridization with brief water washes, and an incubation in prehybridization buffer (0.6 M NaCl, 0.06 M sodium citrate solution, 0.1% Ficoll, 0.1% Polyvinylpyrrolidone 0.1% Bovine Serum Albumin). Following aspiration of the prehybridization buffer, a mixture of amplicon and hybridization buffer (0.6 M NaCl, 0.06 M sodium citrate solution, 0.1% Ficoll, 0.1% Polyvinylpyrrolidone 0.1% Bovine Serum Albumin) was added to the DNA microarray and allowed to incubate for 2 hours. The microarray was prepared for imaging with one quick wash of wash buffer (22.5 mM NaCl, 2.25 mM sodium citrate solution) and a 10-minute incubation (22.5 mM NaCl, 2.25 mM sodium citrate solution). The microarray plate was then spun dry for 5 minutes at 2200 rpm. The underside of the plate was wiped clean with 70% ethanol and lens tissue until all dust particles were removed. The plate was scanned on the Sensospot utilizing Sensovation software. Cy5 exposure time was set at 312 ms, and the Cy3 exposure times at 115 ms and 578 ms. Upon image scanning completion, the folder containing all of the scanned data was saved to a thumb drive and uploaded to Dropbox for Augury Analysis.

Data Analysis. Data for all (11) Core Spike Target Sites are presented in FIGS. 1-11. For all Spike Target sites, data is presented as a bar graph, where the ratio of hybridization signal strength for Wild Type vs Mutant Probes define the specificity of analysis.

a) Left Side of each bar graph shows hybridization data derived from analysis of the "Mutant" synthetic CoV-2 target sequence appropriate for that site.

b) Right Side of each bar graph displays the corresponding data obtained for the "Wild Type" Wuhan gRNA reference sequence.

c) In the analysis of each bar graph at each target site, the parameter of analytical importance is the hybridization signal strength (RFU) ratio obtained by comparison of RT-PCR amplimer hybridization to the Mutant-Specific vs Wild-Type specific probe which can be presented as [$RFU_{wt}$/$RFU_{mt}$].

i. Criterion #1. Primary Data. The [$RFU_{wt}$/$RFU_{mt}$] ratio should differ significantly (>5×) upon comparison of "Wild Type" CoV2 genome hybridization at that site, vs "Mutant" Template hybridization measured at that same site.

ii. Criterion #2. Optimal but not necessarily. The [$RFU_{wt}$/$RFU_{mt}$] ratio should change qualitatively upon CoV2 hybridization analysis of a "Wild Type" CoV2 genome at that site, vs a "Mutant" Template measured at that site. i.e.

Wild-Type Template→[$RFU_{wt}$/$RFU_{mt}$]>1

Mutant Template→[$RFU_{wt}$/$RFU_{mt}$]<1

Clade Array Results a) The Data, Presented in FIGS. 1-11 demonstrate that all (11) Spike Target sites show generally excellent hybridization-based discrimination between Wild Type vs Mutant Sequence Variants by the primary Criterion #1 listed above.

b) For (9) of the 11, Both Criterion #1 and Criterion #2 have been met. All such sites are thus marked among FIGS. 1-11 as "No Additional Probe Optimization Required" and are marked by a "*" below their location in the probe matrix of Table 9.

c) For two of the 11 Spike Target sites (D80A and E484K, FIGS. 2 and 7), Criterion #2 was not met adequately.

d) Only two Probes need Optimization. In two cases (Target Sites D80A and E484K) although the Wild Type (Wuhan gRNA) is easily distinguished from the Mutant based on significant differences in relative hybridization (Criterion #1, above), the Mutant/Wild Type distinction does not change sign (Criterion #2). Thus, although the data obtained at those (2) sites (D80A, E484K) is adequate at present to make accurate "Clade Calls", modest Optimization (1 Probe at each site) can be deployed quickly to enhance the quality of the data obtained there.

e) Experience and general understanding of nucleic acid biophysics suggest that the needed optimization (Target Sites D80A and E484K) was obtainable by simply reducing the length of one probe at each site by 2 bases. As soon as the need for such.

SUMMARY

The Clade Array Probe Content was found to be fully functional. An optimized shorter probe was seen to improve Cov-2 mutant analysis at target sites D80A and E484K.

Experiment 2:

A second 15 Plate Manufacturing Run (#2) of DETECTX-Cv, similar to the one described in Experiment 1 above was implemented to complete validation of the Multiplex assay. In this assessment, print quality passed the test for all 96 (160 probe) arrays among all 15 plates.

The second set of validation tests sought to evaluate the preferred method of multiplexing of the RT-PCR reaction, using the UNG combined with One Step RT-PCR condition. The primary goal was to deliver a first RT-PCR Multiplex capable of distinguishing the five prevalent clade Variants—UK (B.1.1.7), S Africa (B.1.351) Brazil (P.1) Brazil (P.2) US California (B.1.429) shown in Table 12. The validation materials comprised a purified Wuhan gRNA reference (ATCC-BEI). The data obtained subsequent to RT-PCR, hybridization and washing revealed that an initial deployment of a specific 4-plex RT-PCR reaction, comprising amplimers [2, 3, 6, 8] was sufficient to distinguish, as a single multiplex assay, these five prevalent Clade variants (FIGS. 12A-12B).

Figure 12A:
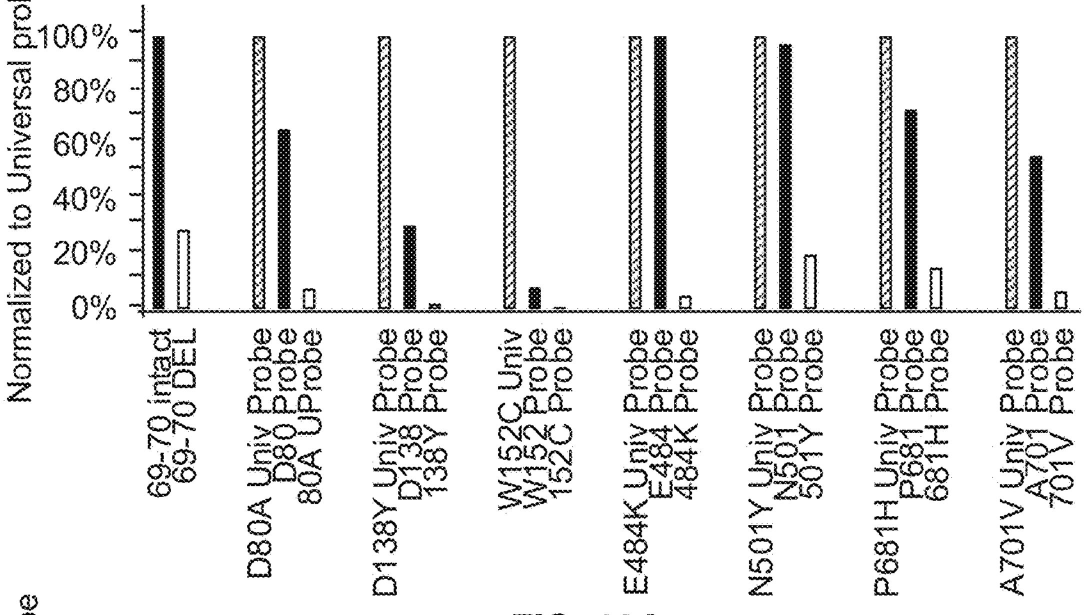
FIGS. 12A-12B shows the results of DETECTX-Cv analysis using a multiplex of Amplimers 2, 3, 6, 8.
Figure 12B:
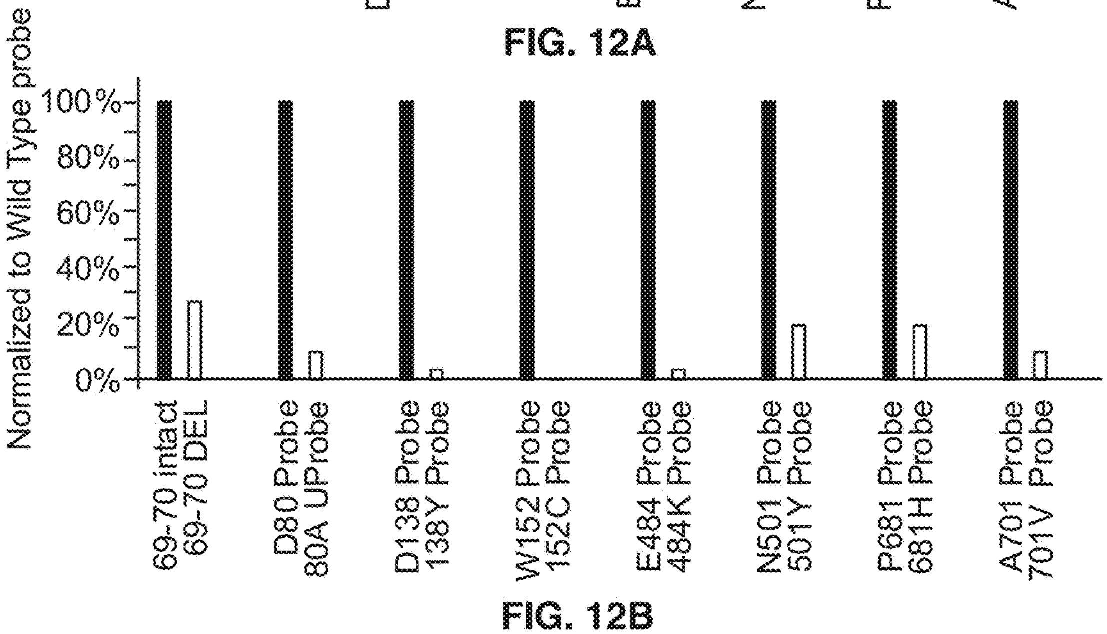

FIG. 12A shows the raw microarray hybridization data for the eight (8) target sites covered by amplimer sets 2, 3, 6 and 8 with data normalized to the Universal Probe at "100%" to emphasize the sensitivity of Universal vs Wild-Type/Mutant Target Detection. FIG. 12B shows the same raw hybridization data for the eight (8) target sites covered by the amplimer sets 2, 3, 6 and 8, but normalized to the Wild-Type probe signal, to emphasize the specificity of discrimination between Wild-Type vs Mutant target sequence.

Experiment 3:

Fully Multiplexed DETECTX-Cv.

A third round of validation was performed to evaluate the preferred method of multiplexing of the RT-PCR reaction, using the UNG combined with One Step RT-PCR condition. The primary goal was to deliver a second (N=5) RT-PCR Multiplex capable of distinguishing the six (6) prevalent US Clade Variants—UK (B.1.1.7), S Africa (B.1.351) Brazil (P.1) Brazil (P.2) a second redundant target in US California (B.1.429) and India N440K. shown in Table 12. The validation materials comprised a purified Wuhan gRNA reference (ATCC-BEI). The data obtained subsequent to RT-PCR, hybridization and washing revealed that a second deployment of a specific 5-plex RT-PCR reaction, comprising a N=5 multiplex of amplimers [2, 3, 5, 6, 8] was sufficient to distinguish, as a single multiplex assay, these six prevalent Clade Variants (FIGS. 13A-13B).

Figure 13A:
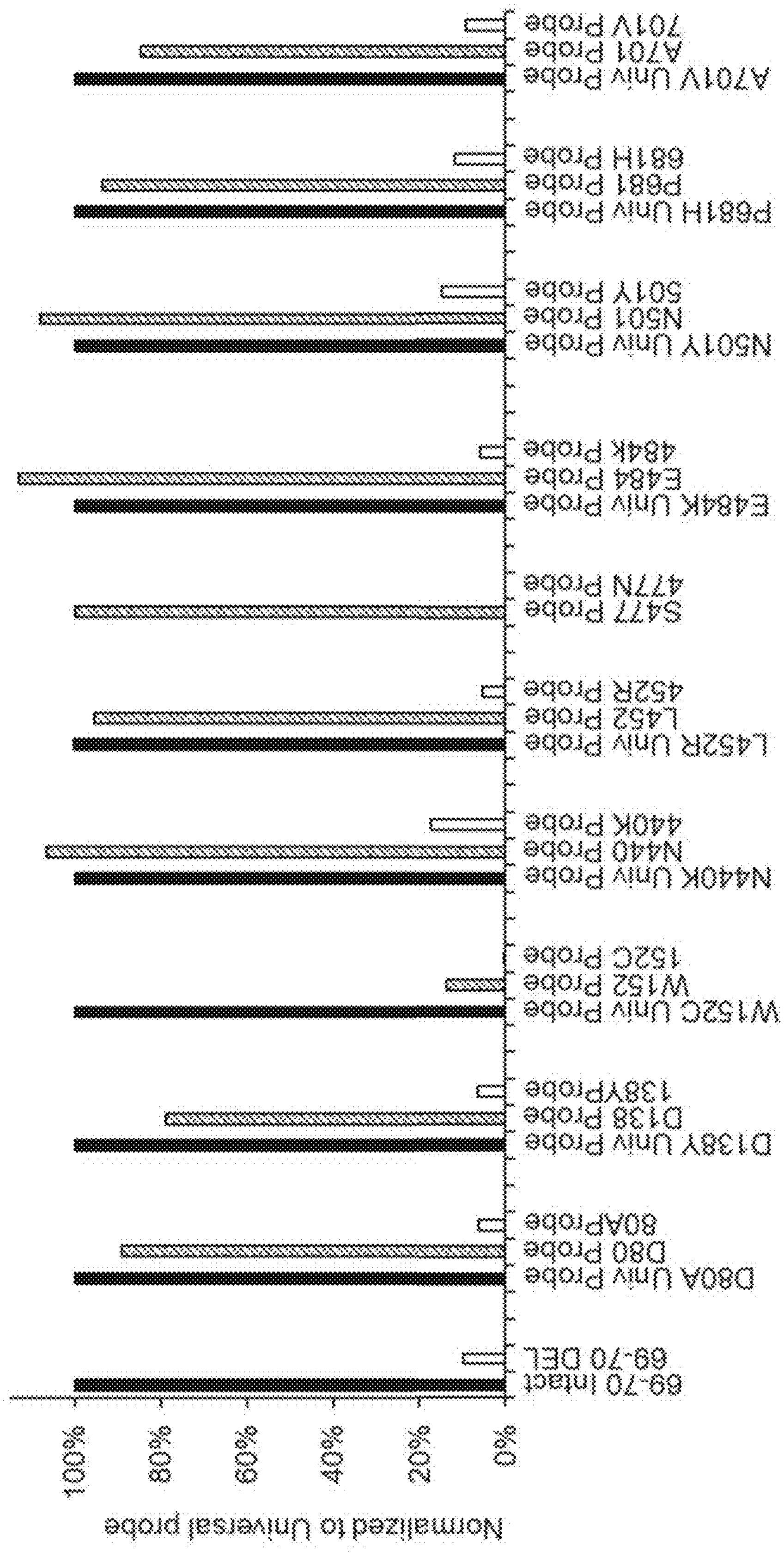
FIGS. 13A-13B shows the results of DETECTX-Cv analysis using a multiplex of Amplimers 2, 3, 5, 6, 8.
Figure 13B:
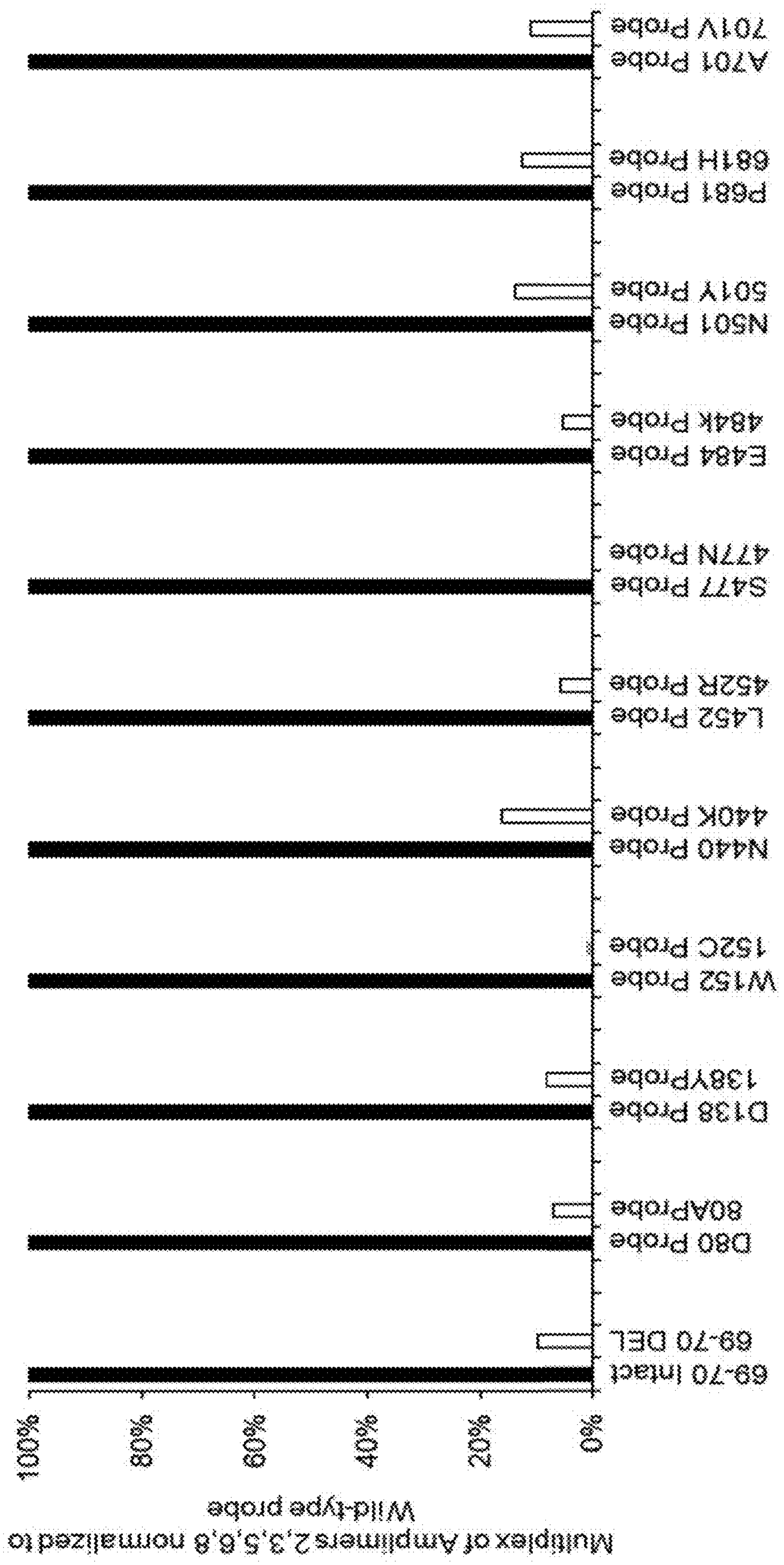

FIG. 13A shows the raw microarray hybridization data for the eleven (11) target sites covered by amplimer sets 2, 3, 5, 6 and 8 with data normalized to the Universal Probe at "100%" to emphasize the sensitivity of Universal vs Wild-Type/Mutant Target Detection. FIG. 13B shows the same raw hybridization data for the eleven (11) target sites covered by the amplimer sets 2, 3, 5, 6 and 8, but normalized to the Wild-Type probe signal, to emphasize the specificity of discrimination between Wild-Type vs Mutant target sequence.

TABLE 12

Validation of test design for the five prevalent Clade variants

| Spike Gene Target Region (Codon) Amino Acid Change | | | S13I | L18F | T20N | P26S | Δ69-70 | D80A | T95I | D138Y | Y144D | W152C | R190S | D215G | A243 del | R246I | D2 53G | K4 17N | N4 40K | L4 52R |
|---|---|---|---|---|---|---|---|---|---|---|---|---|---|---|---|---|---|---|---|---|
| Mutation specific Probe coverage | | | | | | | ✓$^1$ | ✓$^1$ | | ✓$^1$ | | ✓$^1$ | | | ✓$^1$ | ✓$^1$ | ✓$^1$ | ✓$^1$ | ✓$^1$ | ✓$^1$ |
| Wuhan reference specific probe/s coverage | | | | | | | ✓$^2$ | ✓$^2$ | | ✓$^2$ | | ✓$^2$ | | | ✓$^2$ | ✓$^2$ | ✓$^2$ | ✓$^2$ | ✓$^2$ | ✓$^2$ |
| Locus specific Probe coverage | | | | | | | N/A | ✓ | | ✓ | | ✓ | | | ✓ | ✓ | ✓ | ✓ | ✓ | ✓ |
| REGION | LINEAGE DESIGNATION var | | | | | | | | | | | | | | | | | | | |
| Denmark | Mink V | B.1.1.298 | $S^3$ | $L^3$ | $T^3$ | $P^3$ | $\Delta^1$ | $D^2$ | $T^3$ | $D^2$ | $Y^3$ | $W^2$ | $R^3$ | $D^3$ | $A^2$ | $R^2$ | $D^2$ | $K^2$ | $N^2$ | $L^2$ |
| UK | GR/501Y.V1 | B.1.1.7 | $S^3$ | $L^3$ | $T^3$ | $P^3$ | $\Delta^1$ | $D^2$ | $T^3$ | $D^2$ | $\Delta^3$ | $W^2$ | $R^3$ | $D^3$ | $A^2$ | $R^2$ | $D^2$ | $K^2$ | $N^2$ | $L^2$ |
| SA | GH/501Y.V2 | B.1.351 | $S^3$ | $L^3$ | $T^3$ | $P^3$ | $HV^2$ | $A^2$ | $T^3$ | $D^2$ | $Y^3$ | $W^2$ | $R^3$ | $G^3$ | $\Delta^1$ | $I^1$ | $D^2$ | $N^1$ | $N^2$ | $L^2$ |
| Brazil | P.1 | | $S^3$ | $F^3$ | $N^3$ | $S^3$ | $HV^2$ | $D^2$ | $T^3$ | $Y^1$ | $Y^3$ | $W^2$ | $S^3$ | $D^3$ | $A^2$ | $R^2$ | $D^2$ | $T^1$ | $N^2$ | $L^2$ |
| Brazil | P.2 | | $S^3$ | $L^3$ | $T^3$ | $P^3$ | $HV^2$ | $D^2$ | $T^3$ | $D^2$ | $Y^3$ | $W^2$ | $R^3$ | $D^3$ | $A^2$ | $R^2$ | $D^2$ | $K^2$ | $N^2$ | $L^2$ |
| California | CAL.20C-GH/452R.V1 | B.1.429 | $I^3$ | $L^3$ | $T^3$ | $P^3$ | $HV^2$ | $D^2$ | $T^3$ | $D^2$ | $Y^3$ | $C^1$ | $R^3$ | $D^3$ | $A^2$ | $R^2$ | $D^2$ | $K^2$ | $N^2$ | $R^1$ |
| India | (Andhra Pradesh) | N440K | $S^3$ | $L^3$ | $T^3$ | $P^3$ | $HV^2$ | $D^2$ | $T^3$ | $D^2$ | $Y^3$ | $W^2$ | $R^3$ | $D^3$ | $A^2$ | $R^2$ | $D^2$ | $K^2$ | $K^1$ | $L^2$ |
| S. US | B.1.596/B.1.2 | Q677P/H | $S^3$ | $L^3$ | $T^3$ | $P^3$ | $HV^2$ | $D^2$ | $T^3$ | $D^2$ | $Y^3$ | $W^2$ | $R^3$ | $D^3$ | $A^2$ | $R^2$ | $D^2$ | $K^2$ | $N^2$ | $L^2$ |
| NY | Ho et al. | B.1.526a | $S^3$ | $L^3$ | $T^3$ | $P^3$ | $HV^2$ | $D^2$ | $I^3$ | $D^2$ | $Y^3$ | $W^2$ | $R^3$ | $D^3$ | $A^2$ | $R^2$ | $G^1$ | $K^2$ | $N^2$ | $L^2$ |
| | | B.1.526b | $S^3$ | $L^3$ | $T^3$ | $P^3$ | $HV^2$ | $D^2$ | $I^3$ | $D^2$ | $Y^3$ | $W^2$ | $R^3$ | $D^3$ | $A^2$ | $R^2$ | $G^1$ | $K^2$ | $N^2$ | $L^2$ |
| WUHAN | | WUHAN | $S^3$ | $L^3$ | $T^3$ | $P^3$ | $HV^2$ ✓$^4$ | $D^2$ ✓$^5$ | $T^3$ | $D^2$ ✓$^4$ | $Y^3$ | $W^2$ ✓$^4$ | $R^3$ | $D^3$ | $A^2$ | $R^2$ | $D^2$ | $K^2$ | $N^2$ ✓$^4$ | $L^2$ ✓$^4$ |
| PCR Amplimer length (bases) | | | | (1) 101 | | | | ($2_B$) 150 | | | (3) 129 | | | | | ($4_B$) 160 | | | (5) 199 | |

| Spike Gene Target Region (Codon) Amino Acid Change | | | Y453F | S477N | E484K | N501Y | A570D | D614G | H655Y | Q677P/H | P681H | I692V | A701V | T716I | S982A | T1 027I | D1 118 | V11 76 | M122 9I |
|---|---|---|---|---|---|---|---|---|---|---|---|---|---|---|---|---|---|---|---|
| Mutation specific Probe coverage | | | | ✓$^1$ | ✓$^1$ | ✓$^1$ | | ✓$^1$ | | ✓$^1$ | ✓$^1$ | | ✓$^1$ | | | | | | |
| Wuhan reference specific probe/s coverage | | | | ✓$^2$ | ✓$^2$ | ✓$^2$ | | ✓$^2$ | | ✓$^2$ | ✓$^2$ | | ✓$^2$ | | | | | | |
| Locus specific Probe coverage | | | | ✓ | ✓ | ✓ | | ✓ | | ✓ | ✓ | | ✓ | | | | | | |
| REGION | LINEAGE DESIGNATION var | | | | | | | | | | | | | | | | | | |
| Denmark | Mink V | B.1.1.298 | $F^3$ | 2 | $E^2$ | $N^2$ | $A^3$ | $G^1$ | $H^3$ | $Q^2$ | $P^2$ | $V^3$ | $A^2$ | $T^3$ | $S^3$ | $T^3$ | $D^3$ | $V^3$ | $I^3$ |
| UK | GR/501Y.V1 | B.1.1.7 | $Y^3$ | 2 | $E^2$ | $Y^1$ | $D^3$ | $G^1$ | $H^3$ | $Q^2$ | $H^1$ | $I^3$ | $A^2$ | $I^3$ | $A^3$ | $T^3$ | $H^3$ | $V^3$ | $M^3$ |
| SA | GH/501Y.V2 | B.1.351 | $Y^3$ | 2 | $K^1$ | $Y^1$ | $A^3$ | $G^1$ | $H^3$ | $Q^2$ | $P^2$ | $I^3$ | $V^1$ | $T^3$ | $S^3$ | $T^3$ | $D^3$ | $V^3$ | $M^3$ |
| Brazil | P.1 | | $Y^3$ | 2 | $K^1$ | $Y^1$ | $A^3$ | $G^1$ | $Y^3$ | $Q^2$ | $P^2$ | $I^3$ | $A^2$ | $T^3$ | $S^3$ | $I^3$ | $D^3$ | $F^3$ | $M^3$ |
| Brazil | P.2 | | $Y^3$ | 2 | $K^1$ | $N^2$ | $A^3$ | $G^1$ | $H^3$ | $Q^2$ | $P^2$ | $I^3$ | $A^2$ | $T^3$ | $S^3$ | $T^3$ | $D^3$ | $F^3$ | $M^3$ |
| California | CAL.20C-GH/452R.V1 | B.1.429 | $Y^3$ | 2 | $E^2$ | $N^2$ | $A^3$ | $G^1$ | $H^3$ | $Q^2$ | $P^2$ | $I^3$ | $A^2$ | $T^3$ | $S^3$ | $T^3$ | $D^3$ | $V^3$ | $M^3$ |
| India | (Andhra Pradesh) | N440K | $Y^3$ | 2 | $E^2$ | $N^2$ | $A^3$ | $G^1$ | $H^3$ | $Q^2$ | $P^2$ | $I^3$ | $A^2$ | $T^3$ | $S^3$ | $T^3$ | $D^3$ | $V^3$ | $M^3$ |

TABLE 12-continued

Validation of test design for the five prevalent Clade variants

| | | | | | | | | | | | | | | | | | | | | |
|---|---|---|---|---|---|---|---|---|---|---|---|---|---|---|---|---|---|---|---|---|
| S. US | B.1.596/B.1.2 | Q677P/H | $Y^3$ | 2 | $E^2$ | $N^2$ | $A^3$ | $G^1$ | $H^3$ | $P/H^1$ | $P^2$ | $I^3$ | $A^2$ | $T^3$ | $S^3$ | $T^3$ | $D^3$ | $V^3$ | $M^3$ |
| NY | Ho et al. | B.1.526a | $Y^3$ | 2 | $K^1$ | $N^2$ | $A^3$ | $G^1$ | $H^3$ | $Q^2$ | $P^2$ | $I^3$ | $A^2$ | $T^3$ | $S^3$ | $T^3$ | $D^3$ | $V^3$ | $M^3$ |
| | | B.1.526b | $Y^3$ | $N^1$ | $E^2$ | $N^2$ | $A^3$ | $G^1$ | $H^3$ | $Q^2$ | $P^2$ | $I^3$ | $A^2$ | $T^3$ | $S^3$ | $T^3$ | $D^3$ | $V^3$ | $M^3$ |
| WUHAN | | WUHAN | $Y^3$ | S2 | $E^2$ | $N^2$ | $A^3$ | $D^2$ | $H^3$ | $Q^2$ | $P^2$ | $I^3$ | $A^2$ | $T^3$ | $S^3$ | $T^3$ | $D^3$ | $V^3$ | $M^3$ |
| | | | | | ✓$^5$ | ✓$^4$ | | ✓$^4$ | | | ✓$^4$ | | ✓$^4$ | | | | | | |
| PCR Amplimer length (bases) | | | (5) 199 | | (6) 151 | | | (7) 88 | | | (8) 135 | | | | | | | | |

[1]AA mutation-hybridizes to mutation specific probe

[2]AA identical to hCoV-19/Wuhan/WIV04/2019 (WIV04)-official reference sequence employed by GISAID (EPI_ISL_402124)

[3]Potential probe target

[4]No Probe Adjustment Necessary

[5]Minor Probe Adjustment Necessary

Table 13 shows the information content for the fully multiplexed (2, 3, 5, 6, 8) data obtained via the multiplex RT-PCR reaction in this DETECTX-Cv assay, which is sufficient to discriminate the five clade variants (superscript "1"). It was determined that including Amplimer 5 to the multiplex adds redundancy (superscript "2") thereby allowing unambiguous discrimination of the India Mutant (B.1.36.29). Similarly, addition of amplimer 4 (for NY B.1.526) and Q677P/H probes (for Southern US B.1.596/13.1.2) to the multiplex enabled discrimination of Southern US and NY Clade variants (superscript "3"). Importantly, the emerging Southern US Clade variants (B.1.596/1.1.2) does not require modification of the present multiplex reaction since inclusion of probes at Q677P/H would be sufficient. Analytical specificity was established as described earlier via analysis of both wild type (Wuhan) gRNA and synthetic, Clade specific fragments.

TABLE 13

Information content obtained by addition of amplimers

| Region | Lineage Designation Var | | Information obtained with Amplimers 2, 3, 6, 8 | Information obtained by adding Amplimer 5 | Information obtained by adding Amplimer 4 + New Clade variant probes |
|---|---|---|---|---|---|
| Denmark | Mink V | B.1.1.298 | ✓[1] | | □ |
| UK | GR/501Y.V1 | B.1.1.7 | ✓[1] | | □ |
| SA | GH/501Y.V2 | B.1.351 | ✓[1] | ✓[2] | ✓[3] |
| Brazil/Japan | P.1 | | ✓[1] | ✓[2] | |
| Brazil | P.2 | | ✓[1] | | |
| California | CAL.20C-GH/452R.V1 | B.1.429 | ✓[1] | ✓[2] | □ |
| India | (Andhra Pradesh) | N440K | | ✓[2] | |
| S. US | B.1.596/13.1.2 | Q677P/H | | | ✓[3] |
| NY | Ho etal. | B.1.526 | | | ✓[3] |
| | | B.1.526.2 | | | ✓[3] |
| WUHAN | | | ✓[1] | ✓[2] | ✓[3] |

Augury Software Modification

Current deployment of Augury software was modified to include automated capacity for determining "Wild-Type" vs "Mutant" at each of the (11) Spike target sites of the present DETECTX-Cv assay described above (the columns in Table 12. As modified, Augury is capable of calling the identity of the clade variant, based on the pattern of mutant presentation among the sites (that is, a "look-up" table comprising the pattern of each row of Table 12). Coding to enable such autonomous calling is based on allelotyping methods previously developed for HLA allelotyping. In the present case, the clade variant test is also an exercise in spike gene allelotyping. Such spike gene allelotypes (the rows in Table 12) have already been determined as being the preferred marker for CoV-2 Clade Variation.

TABLE 14

New Clade variant probe" sequences

| SEQ ID NOS. | Amplimer # | Target | Probe Sequence (5' to 3') |
|---|---|---|---|
| SEQ ID NO: 118 | 4 | AA A243_ | TTTTTTTTCAAACTTTACTTGCTTTACTC TTT |
| SEQ ID NO: 119 | 4 | AA_243DEL | TTTTTTTTCAAACTTTACATAGAAGCCTT TTT |
| SEQ ID NO: 120 | 4 | AA R246_ | TTTTCTACATAGAAGTTATTTGACTCCCT TTT |
| SEQ ID NO: 121 | 4 | AA_246I | TTTTCTGCTTTACATATGACTCCTGGTTT TTT |
| SEQ ID NO: 122 | 4 | AA D253G | TTTCTACTCCTGGTGRTTCTTCTTCATTT T |

TABLE 14-continued

New Clade variant probe" sequences

| SEQ ID NOS. | Amplimer # | Target | Probe Sequence (5' to 3') |
|---|---|---|---|
| SEQ ID NO: 123 | 4 | AA D253_ | TTTTTTCCCTGGTGATTCTTCTTTCTTTT T |
| SEQ ID NO: 124 | 4 | AA_253G | TTTTTTCCCTGGTGGTTCTTCTTTTTTTT T |
| SEQ ID NO: 125 | 8 | AA_Q677P/H | TTTTTTATCAGACTCMGACTAATTCTCTT TTT |
| SEQ ID NO: 126 | 8 | AA Q677_ | TTTTTTCCAGACTCAGACTAATTTCTTTT T |
| SEQ ID NO: 127 | 8 | AA_677P | TTTTTCTTCAGACTCCGACTAATCTTTTT T |
| SEQ ID NO: 128 | 8 | AA_677H1 | TTTTTTCCAGACTCATACTAATTTCTTTT T |
| SEQ ID NO: 129 | 8 | AA_677H2 | TTTTTTCCAGACTCACACTAATTTCTTTT T |

Example 6

Augury Modification with Clade ID Module

The current deployment of the Augury software for wild type COV-2 was modified to include automated capacity for determining "Wild-Type" vs "Mutant" at each of the Spike target sites of the DETECTX-Cv assay (the columns in Table 15) and to identify the Clade variant based on the pattern of mutant presentation among the sites (the rows in Tables 15 and 16). Coding for the software is based on allelotyping formalism previously developed for HLA allelotyping.

Augury Software for DETECTX-Cv

All DETECTX-Cv probe sequences and their information content were added to a database ("Dot Score" file) within Augury. This database defined the DETECTX-Cv probe content (Mutant, Wild Type, Universal) at each of the eleven (11) Spike target regions (the columns in Table 15).

Establishment of DETECTX-Cv Version Control

The Augury Software is configured to read the bar code associated with each 96-well plate of microarrays for DETECTX-Cv and use the information in the bar code to create a "Dot Score" file for the probe content introduced into DETECTX-Cv. Further, Augury is configured to incorporate a new "Dot Score" file as appropriate for any new Clade Variant content with additional probes in the array (Table 15). Additionally, Augury is intrinsically cloud enabled and configured to deploy software modification downloaded from the cloud. When useful for analysis of DETECTX-Cv, data such as those from the RADx Rosalind initiative can also be introduced directly into Augury autonomously, to update the list of prevalent clade variants.

Manual Deployment Version of Augury for DETECTX-Cv

The core functionality of Augury has been used as a manual product for deployment at TriCore. This version of Augury automatically is enabled to read DETECTX-Cv plate bar codes, perform microarray image analysis, create "Dot Score" files and present the resulting averaged, background subtracted DETECTX-Cv data as a spread sheet matrix, which can be compared to the Clade Variant Hybridization patterns such as described in Table 15. This manual deployment version has been tested on DETECTX-Cv synthetic Clade variant standards.

Clade Variant "Look Up Table"

All prevalent Cov-2 Clades have been programmed into Augury to generate a "Look-up Table" (equivalent in content to the pattern of boxes having superscript 1 and 2 in Table 15). The Augury internal "Lookup Table" is formatted to function as part of a Boolean pattern search as developed previously for allelotype analysis of all genes.

TABLE 15

Validation of Glade variants

| Spike Gene Target Region (Codon) Amino Acid Change | | S13I | L18F | T20N | P26S | Q52R | Δ67/ Δ69- 70 | D80A | T95I | D138Y | Y144- DEL | W152C | F157L | R190S | D215- G | A222- V | A243- del | R246- I | D253G | V367F |
|---|---|---|---|---|---|---|---|---|---|---|---|---|---|---|---|---|---|---|---|---|
| Mutation specific Probe coverage | | | | | | | $\checkmark^1$ | $\checkmark^1$ | | $\checkmark^1$ | $\checkmark^1$ | $\checkmark^1$ | | | | | $\checkmark^1$ | $\checkmark^1$ | $\checkmark^1$ | |
| Wuhan reference specific probe/s coverage | | | | | | | $\checkmark^2$ | $\checkmark^2$ | | $\checkmark^2$ | $\checkmark^2$ | $\checkmark^2$ | | | | | $\checkmark^2$ | $\checkmark^2$ | $\checkmark^2$ | |
| Locus specific Probe coverage | | | | | | | N/A | ✓ | | ✓ | ✓ | ✓ | | | | | ✓ | ✓ | ✓ | |
| Street name | Pango lineage- (Clade Nexstrain) | | | | | | | | | | | | | | | | | | | |
| UK | B.1.1.7- (20I/ 501Y.V1) | $S^3$ | $L^3$ | $T^3$ | $P^3$ | $Q^3$ | $\Delta^1$ | $D^2$ | $T^3$ | $D^2$ | $\Delta^1$ | $W^2$ | $F^3$ | $R^3$ | $D^3$ | $A^3$ | $A^2$ | $R^2$ | $D^2$ | $V^3$ |
| SA | B.1.351- (20H/ 501Y.V2) | $S^3$ | $L^3$ | $T^3$ | $P^3$ | $Q^3$ | $HV^2$ | $A^1$ | $T^3$ | $D^2$ | $Y^2$ | $W^2$ | $F^3$ | $R^3$ | G | $A^3$ | $\Delta^1$ | $I^1$ | $D^2$ | $V^3$ |
| US | B.1.375 | $S^3$ | $L^3$ | $T^3$ | $P^3$ | $Q^3$ | $\Delta^1$ | $D^2$ | $T^3$ | $D^2$ | $Y^2$ | $W^2$ | $F^3$ | $R^3$ | $D^3$ | $A^3$ | $A^2$ | $R^2$ | $D^2$ | $V^3$ |
| Brazil | P.1- (20J/ 501Y.V3) | $S^3$ | F | N | S | $Q^3$ | $HV^2$ | $D^2$ | $T^3$ | $Y^1$ | $Y^2$ | $W^2$ | $F^3$ | S | $D^3$ | $A^3$ | $A^2$ | $R^2$ | $D^2$ | $V^3$ |
| Cal L452R | B.1.429/ 427-(20C/ S: 452R) | $I^3$ | $L^3$ | $T^3$ | $P^3$ | $Q^3$ | $HV^2$ | $D^2$ | $T^3$ | $D^2$ | $Y^2$ | $C^1$ | $F^3$ | $R^3$ | $D^3$ | $A^3$ | $A^2$ | $R^2$ | $D^2$ | $V^3$ |
| Rio de Jan. | B.1.28 | $S^3$ | $L^3$ | $T^3$ | $P^3$ | $Q^3$ | $HV^2$ | $D^2$ | $T^3$ | $D^2$ | $Y^2$ | $W^2$ | $F^3$ | $R^3$ | $D^3$ | $A^3$ | $A^2$ | $R^2$ | $D^2$ | $V^3$ |
| Andrah Pradesh | B.1.36.29 | $S^3$ | $L^3$ | $T^3$ | $P^3$ | $Q^3$ | $HV^2$ | $D^2$ | $T^3$ | $D^2$ | $Y^2$ | $W^2$ | $F^3$ | $R^3$ | $D^3$ | $A^3$ | $A^2$ | $R^2$ | $D^2$ | $V^3$ |
| S. US/ Q677P/ H | (S: 677P. B.1.596) (S: 677H. B.1.2) | $S^3$ | $L^3$ | $T^3$ | $P^3$ | $Q^3$ | $HV^2$ | $D^2$ | $T^3$ | $D^2$ | $Y^2$ | $W^2$ | $F^3$ | $R^3$ | $D^3$ | $A^3$ | $A^2$ | $R^2$ | $D^2$ | $V^3$ |
| NYC (Ho etal) | B.1.526a- (20C/S: 484K) | $S^3$ | $L^3$ | $T^3$ | $P^3$ | $Q^3$ | $HV^2$ | $D^2$ | I | $D^2$ | $Y^2$ | $W^2$ | $F^3$ | $R^3$ | $D^3$ | $A^3$ | $A^2$ | $R^2$ | $G^1$ | $V^3$ |
| | B1.526b | $S^3$ | $L^3$ | $T^3$ | $P^3$ | $Q^3$ | $HV^2$ | $D^2$ | I | $D^2$ | $Y^2$ | $W^2$ | $F^3$ | $R^3$ | $D^3$ | $A^3$ | $A^2$ | $R^2$ | $G^1$ | $V^3$ |
| NYC | B.1.525- (20A/S: 484K) | $S^3$ | $L^3$ | $T^3$ | $P^3$ | R | $V/\Delta^1$ | $D^2$ | $T^3$ | D | $\Delta^1$ | $W^2$ | $F^3$ | $R^3$ | $D^3$ | $A^3$ | $A^2$ | R | D | $V^3$ |

TABLE 15-continued

| Validation of Glade variants | | | | | | | | | | | | | | | | | | | | | | | | |
|---|---|---|---|---|---|---|---|---|---|---|---|---|---|---|---|---|---|---|---|---|---|---|---|---|
| | A.23.1 | $S^3$ | $L^3$ | $T^3$ | $P^3$ | $Q^3$ | $HV^2$ | $D^2$ | $T^3$ | $D^2$ | $Y^2$ | $W^2$ | L | $R^3$ | $D^3$ | $A^3$ | $A^2$ | $R^2$ | | $D^2$ | | | F | |
| | B.1.358-(20A/S: 439K) | $S^3$ | $L^3$ | $T^3$ | $P^3$ | $Q^3$ | $\Delta^1$ | $D^2$ | $T^3$ | $D^2$ | $Y^2$ | $W^2$ | $F^3$ | $R^3$ | $D^3$ | $A^3$ | $A^2$ | $R^2$ | | $D^2$ | | | $V^3$ | |
| | B.1.1.33 | $S^3$ | $L^3$ | $T^3$ | $P^3$ | $Q^3$ | $HV^2$ | $D^2$ | $T^3$ | $D^2$ | $Y^2$ | $W^2$ | $F^3$ | $R^3$ | $D^3$ | $A^3$ | $A^2$ | $R^2$ | | $D^2$ | | | $V^3$ | |
| | B.1.177-(20E (EU1) (S: A222V)) | $S^3$ | $L^3$ | $T^3$ | $P^3$ | $Q^3$ | $HV^2$ | $D^2$ | $T^3$ | $D^2$ | $Y^2$ | $W^2$ | $F^3$ | $R^3$ | $D^3$ | V | $A^2$ | $R^2$ | | $D^2$ | | | $V^3$ | |
| | B1.1.207 | $S^3$ | $L^3$ | $T^3$ | $P^3$ | $Q^3$ | $HV^2$ | $D^2$ | $T^3$ | $D^2$ | $Y^2$ | $W^2$ | $F^3$ | $R^3$ | $D^3$ | $A^3$ | $A^2$ | $R^2$ | | $D^2$ | | | $V^3$ | |
| Mink/ Cluster V | B.1.1.298 (S: Y453F) | $S^3$ | $L^3$ | $T^3$ | $P^3$ | $Q^3$ | $\Delta^1$ | $D^2$ | $T^3$ | $D^2$ | $Y^2$ | $W^2$ | $F^3$ | $R^3$ | $D^3$ | $A^3$ | $A^2$ | $R^2$ | | $D^2$ | | | $V^3$ | |
| WU-HAN | WUHAN | $S^3$ | $L^3$ | $T^3$ | $P^3$ | $Q^3$ | $HV^2$ | $D^2$ | $T^3$ | $D^2$ | $Y^2$ | $W^2$ | $F^3$ | $R^3$ | $D^3$ | $A^3$ | $A^2$ | $R^2$ | | $D^2$ | | | $V^3$ | |
| | | | | | | | ✓$^4$ | ✓$^5$ | | ✓$^4$ | | ✓$^4$ | | | | | | | | | | | | |
| PCR Amplimer length (bases) | | | | (1) 101 | | | | ($2_B$) 150 | | | (3) 129 | | | | | | | | ($4_B$) 160 | | | | | |
| Spike Gene Target Region (Codon) Amino Acid Change | | K417-N/T | N439K | N440K | L452R | Y453F | S477N | E484K | N501Y | A570D | Q613H | D614G | H655Y | Q677P/H | P681-H | I692-V | A701-V | T716-I | F888-L | S9 82-A | T10 27-I | D1 118-H | V1 176-F | M12 29-I |
| Mutation specific Probe coverage | | ✓$^1$ | ✓$^1$ | ✓$^1$ | ✓$^1$ | ✓$^1$ | ✓$^1$ | ✓$^1$ | ✓$^1$ | | ✓$^1$ | ✓$^1$ | | ✓$^1$ | ✓$^1$ | ✓$^1$ | ✓$^1$ | | | | | | | |
| Wuhan reference specific probe/s coverage | | ✓$^2$ | ✓$^2$ | ✓$^2$ | ✓$^2$ | ✓$^2$ | ✓$^2$ | ✓$^2$ | ✓$^2$ | | ✓$^2$ | ✓$^2$ | | ✓$^2$ | ✓$^2$ | ✓$^2$ | ✓$^2$ | | | | | | | |
| Locus specific Probe coverage | | ✓ | ✓ | ✓ | ✓ | ✓ | N/A | ✓ | ✓ | | ✓ | ✓ | | ✓ | ✓ | ✓ | ✓ | | | | | | | |
| Street name | Pango lineage-(Clade Nexstrain) | | | | | | | | | | | | | | | | | | | | | | | |
| UK | B.1.1.7-(20I/ 501Y.V1) | $K^2$ | $N^2$ | $N^2$ | $L^2$ | $Y^2$ | $S^2$ | $E^2$ | $Y^1$ | D | $Q^2$ | $G^1$ | $H^3$ | $Q^2$ | $H^1$ | $I^2$ | $A^2$ | I | $F^3$ | A | T | H | $V^3$ | $M^3$ |
| SA | B.1.351-(20H/ 501Y.V2) | $N^1$ | $N^2$ | $N^2$ | $L^2$ | $Y^2$ | $S^2$ | $K^1$ | $Y^1$ | $A^3$ | $Q^2$ | $G^1$ | $H^3$ | $^3Q^2$ | $P^2$ | $I^2$ | $V^1$ | $T^3$ | $F^3$ | $S^3$ | $T^3$ | $D^3$ | $V^3$ | $M^3$ |
| US | B.1.375 | $K^2$ | $N^2$ | $N^2$ | $L^2$ | $Y^2$ | $S^2$ | $E^2$ | $N^2$ | $A^3$ | $Q^2$ | $G^1$ | $H^3$ | $Q^2$ | $P^2$ | $I^2$ | $A^2$ | $T^3$ | $F^3$ | $S^3$ | $T^3$ | $D^3$ | $V^3$ | $M^3$ |
| Brazil | P.1-(20J/ 501Y.V3) | $T^1$ | $N^2$ | $N^2$ | $L^2$ | $Y^2$ | $S^2$ | $K^1$ | $Y^1$ | $A^3$ | $Q^2$ | $G^1$ | Y | $Q^2$ | $P^2$ | $I^2$ | $A^2$ | $T^3$ | $F^3$ | $S^3$ | I | $D^3$ | F | $M^3$ |
| Cal L452R | B.1.429/ 427-(20C/ S: 452R) | $K^2$ | $N^2$ | $N^2$ | $R^1$ | $Y^2$ | $S^2$ | $E^2$ | $N^2$ | $A^3$ | $Q^2$ | $G^1$ | $H^3$ | $Q^2$ | $P^2$ | $I^2$ | $A^2$ | $T^3$ | $F^3$ | $S^3$ | $T^3$ | $D^3$ | $V^3$ | $M^3$ |

TABLE 15-continued

| Validation of Glade variants | | | | | | | | | | | | | | | | | | | | | | | | |
|---|---|---|---|---|---|---|---|---|---|---|---|---|---|---|---|---|---|---|---|---|---|---|---|---|
| Rio de Jan. | B.1.28 | K[2] | N[2] | N[2] | L[2] | Y[2] | S[2] | K[1] | N[2] | A[3] | Q[2] | G[1] | H[3] | Q[2] | P[2] | I[2] | A[2] | T[3] | F[3] | S[3] | T[3] | D[3] | F | M[3] |
| Andrah Pradesh | | K[2] | N[2] | N[2] | L[2] | Y[2] | S[2] | E[2] | N[2] | A[3] | Q[2] | G[1] | H[3] | Q[2] | P[2] | I[2] | A[2] | T[3] | F[3] | S[3] | T[3] | D[3] | V[3] | M[3] |
| S. US/ Q677P/ H | (S: 677P. B.1.596) (S: 677H. B.1.2) | K[2] | N[2] | N[2] | L[2] | Y[2] | S[2] | E[2] | N[2] | A[3] | Q[2] | G[1] | H[3] | P/H[1] | P[2] | I[2] | A[2] | T[3] | F[3] | S[3] | T[3] | D[3] | V[3] | M[3] |
| NYC (Ho etal) | B.1.526a- (20C/S: 484K) | K[2] | N[2] | N[2] | L[2] | Y[2] | S[2] | K[1] | N[2] | A[3] | Q[2] | G[1] | H[3] | Q[2] | P[2] | I[2] | A[2] | T[3] | F[3] | S[3] | T[3] | D[3] | V[3] | M[3] |
| | B.1.526b | K[2] | N[2] | N[2] | L[2] | Y[2] | N[1] | E[2] | N[2] | A[3] | Q[2] | G[1] | H[3] | Q[2] | P[2] | I[2] | V[1] | T[3] | F[3] | S[3] | T[3] | D[3] | V[3] | M[3] |
| NYC | B.1.525- (20A/S: 484K) | K | N | N | L | Y | S | K[1] | N | A[3] | Q | G[1] | H[3] | H[1] | P[2] | I[2] | A/V[1] | T[3] | L | S[3] | T[3] | D[3] | V[3] | M[3] |
| | A23.1 | K[2] | N[2] | N[2] | L[2] | Y[2] | S[2] | E[2] | N[2] | A[3] | H[1] | D[2] | H[3] | Q[2] | P | I | A | T[3] | F[3] | S[3] | T[3] | D[3] | V[3] | M[3] |
| | B.1.358- (20A/S: 439K) | K[2] | K[1] | N[2] | L[2] | Y[2] | S[2] | E[2] | N[2] | A[3] | Q[2] | G[1] | H[3] | Q[2] | P[2] | I[2] | A[2] | T[3] | F[3] | S[3] | T[3] | D[3] | V[3] | M[3] |
| | B.1.1.33 | K[2] | N[2] | N[2] | L[2] | Y[2] | S[2] | K | N[2] | A[3] | Q[2] | G | H[3] | Q[2] | P[2] | I[2] | A[2] | T[3] | F[3] | S[3] | T[3] | D[3] | V[3] | M[3] |
| | B.1.177- (20E (EU1) (S: A222V)) | K[2] | N[2] | N[2] | L[2] | Y[2] | S[2] | E[2] | N[2] | A[3] | Q[2] | G | H[3] | Q[2] | P[2] | I[2] | A[2] | T[3] | F[3] | S[3] | T[3] | D[3] | V[3] | M[3] |
| | (22.5 mM NaCl, 2.25 mM sodium citrate) | K[2] | N[2] | N[2] | L[2] | Y[2] | S[2] | E[2] | N[2] | A[3] | Q[2] | G | H[3] | Q[2] | H | I[2] | A[2] | T[3] | F[3] | S[3] | T[3] | D[3] | V[3] | M[3] |
| Mink/ Cluster V | B.1.298 (S: Y453F) | K[2] | N[2] | N[2] | L[2] | F | S[2] | E[2] | N[2] | A[3] | Q[2] | G | H[3] | Q[2] | P[2] | V | A[2] | T[3] | F[3] | S[3] | T[3] | D[3] | V[3] | I |
| WU- HAN | WUHAN | K[2] | N[2] | N[2] | L[2] | Y[2] | S[2] | E[2] | N[2] | A[3] | Q[2] | D[2] | H[3] | Q[2] | P[2] | I[2] | A[2] | T[3] | F[3] | S[3] | T[3] | D[3] | V[3] | M[3] |
| | | | | ✓[4] | ✓[4] | | | ✓[5] | ✓[4] | | | ✓[4] | | | ✓[4] | | ✓[4] | | | | | | | |
| PCR Amplimer length (bases) | | | | (5) 199 | | | | (6) 151 | | | | (7) 88 | | | (8) 135 | | | | | | | | | |

[1]AA mutation-hybridizes to mutation specific probe
[2]AA identical to hCoV-19/Wuhan/WIV04/2019 (WIV04)-official reference sequence employed by GISAID (EPI_ISL_402124)
[3]Potential probe target
[4]No Probe Adjustment Necessary
[5]Minor Probe Adjustment Necessary

TABLE 16

Information content obtained by addition of amplimers

| Street Name | Pango lineage (Clade Nextstrain open-source toolkit) | Amplimers 2, 3, 6, 8 | Amplimer 5 | Potential Probe content as described in Table 14 | Amplimer 4 + New Clade variant probes |
|---|---|---|---|---|---|
| UK | B.1.1.7 - (20I/501Y.V1) | ✓[1] | | ✓[3] | □ |
| SA | B.1.351 - (20H/501Y.V2) | ✓[1] | ✓[2] | □ | ✓[4] |
| US | B.1.375 | ✓[1] | | | |
| Brazil | P.1 - (20J/501Y.V3) | ✓[1] | ✓[2] | | |
| California L452R | B.1.429/427 - (20C/S: 452R) | ✓[1] | ✓[2] | □ | □ |
| Rio de Janeiro | B.1.1.28 | ✓[1] | | | |
| Andhra Pradesh | | | ✓[2] | □ | □ |
| S.US/Q677P/H | (S: 677P.Pelican) (S: 677H.Robin1) | | | ✓[3] | □ |
| NYC (Ho etal.) | B.1.526a - (20C/S: 484K) | | | □ | ✓[4] |
| | B.1.526a - (20C/S: 484K) | | | □ | ✓[4] |
| NYC | B.1.525 - (20A/S: 484K) | | | ✓[3] | □ |
| Mink/Cluster V | (S: Y453F) | ✓[1] | | ✓[3] | □ |
| WUHAN | | ✓[1] | ✓[2] | ✓[3] | ✓[4] |

[1]Information obtained by adding Amplimers 2, 3, 6 and 8
[2]Information obtained by adding Amplimer 5
[3]Information obtained by adding Potential probe content
[4]Information obtained by adding Amplimer 4 + New Glade variant probes Analytical Threshold Values Multiplex RT-PCR [2, 3, 5, 6, 8] were performed in the absence of template (0 copies/reaction) to obtain the mean and STD from the mean for LoB signals. This "blank" data collection data is used by Augury to obtain the analytical threshold for each probe (3.2×STD+Mean) to yield Mutant threshold (Tm), Wild Type threshold (Tw) and Universal threshold (Tu) values for all thirty-three (33) probes comprising the content of DETECTX-Cv.

Deployment of Automatic Mutant Vs Wild Type Detection ("Delta").

Threshold values were introduced as constants into Augury for autonomous Mutant vs Wild Type determination at all eleven (11) sites. This was performed using the following relationship analytical approach;

$$\text{Delta}=([RFU_m-T_m]/T_m)-([RFU_w-T_w]/T_w) \qquad \text{(Equation 1)}$$

where, $RFU_m$=mutant probe RFU signal in a sample $RFU_w$=wild type probe RFU signal in a sample $T_m$=mutant probe RFU Threshold—a constant obtained from CLSI (LoB) analysis $T_w$=wild type probe RFU Threshold—a constant obtained from CLSI (LoB) analysis $[RFU_m-T_m]$=Mutant Probe Signal strength above Threshold. By definition, this is a non-zero value.

$[RFU_w-T_w]$=Wild Type Signal strength above Threshold. By definition, this is a non-zero value.

Delta=Difference in Signal Strength above Threshold normalized to Threshold

If Delta>0, within experimental accuracy, then "Mutant" (i.e. boxes having superscript 1 in Table 15). If Delta<0, within experimental accuracy, then "Wild Type" (i.e. boxes having superscript 2 in Table 15).

Example 7

Clade Variant Array Deployment-1

1. Analytical LoD Determination. A first determination of analytical LoD was performed for DETECTX-Cv, among all eleven (11) Spike target sites deployed using the [UNG+One Step RT-PCR] conditions. For this analysis, validation materials comprised a purified Wuhan gRNA reference (ATCC-BEI) and a cocktail of five (5) synthetic fragments designed by PathogenDx and fabricated by Integrated DNA Technologies, Inc. (IDT, Coralville, Iowa), comprising each region targeted for amplification via the [2, 3, 5, 6, 8] multiplex RT-PCR reaction (deployed as N=5 multiplex).

To support the multiplex reaction, all 5 synthetic CoV-2 fragments were mixed [1:1:1:1:1] in strand equivalents. Copy number values listed in Table 15 refer to the copy number of each fragment (in the equimolar mix) applied to the RT-PCR reaction. The primary goal here is to deploy the (N=5) RT-PCR multiplex to obtain a preliminary analytical LoD in units of copies/reaction for each of the probes comprising the set associated with each of the (n) target sites—$LoD_n$ (Universal), $LoD_n$ (Wild Type), $LoD_n$ (Mutant). The analytical LoD associated with the Universal probes ($LoD_n$) were lower than that of either $LoD_n$ or $LoD_n$, due to the intentionally longer probe sequence for the universal probe, which is associated with a higher affinity for its complementary amplicon sequence.

Results

Subsequent to RT-PCR the DNA microarray was prepared for hybridization with brief water washes, and an incubation in prehybridization buffer (0.6 M NaCl, 0.06 M sodium citrate solution, 0.1% Ficoll, 0.1% Polyvinylpyrrolidone 0.1% Bovine Serum Albumin). Following aspiration of the prehybridization buffer, a mixture of amplicon and hybridization buffer (0.6 M NaCl, 0.06 M sodium citrate, 0.1% Ficoll, 0.1% Polyvinylpyrrolidone 0.1% Bovine Serum Albumin) was added to the DNA microarray and allowed to incubate for 2 hours. The microarray is then washed with wash buffer (22.5 mM NaCl, 2.25 mM sodium citrate) and dried via centrifugation. The glass portion of the microarray was cleaned with lens tissue and 70% ethanol and images were acquired on the Sensospot. Images were then uploaded for Augury analysis. Following image acquisition and upload to Augury, it was found that the 5-plex RT-PCR reaction, comprising a N=5 multiplex of amplimers [2, 3, 5, 6, 8] was sufficient to obtain a first determination of analytical LODs [$LoD_n$ (Universal), $LoD_n$ (Wild Type), and $LoD_n$ (Mutant)].

Figure 14A:
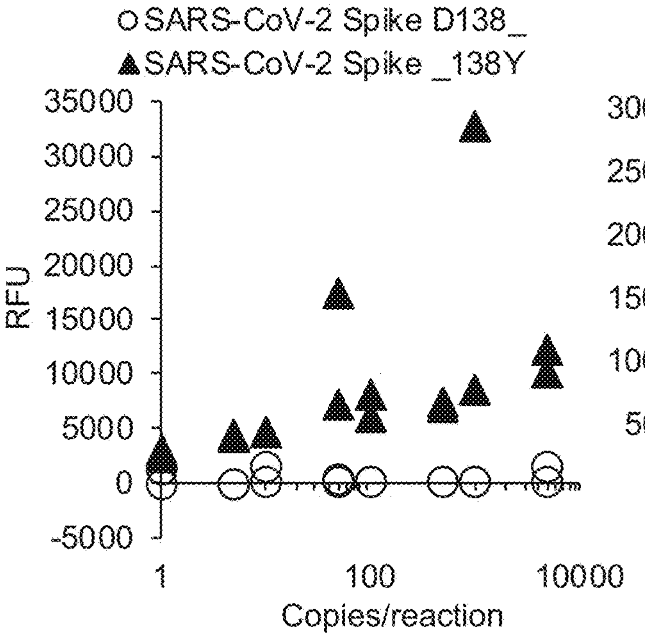
FIGS. 14A-14Y shows analytical LoD data for a series of synthetic G-block fragments, used as "synthetic clade variant standards", corresponding to domains 2-8.
Figure 14B:
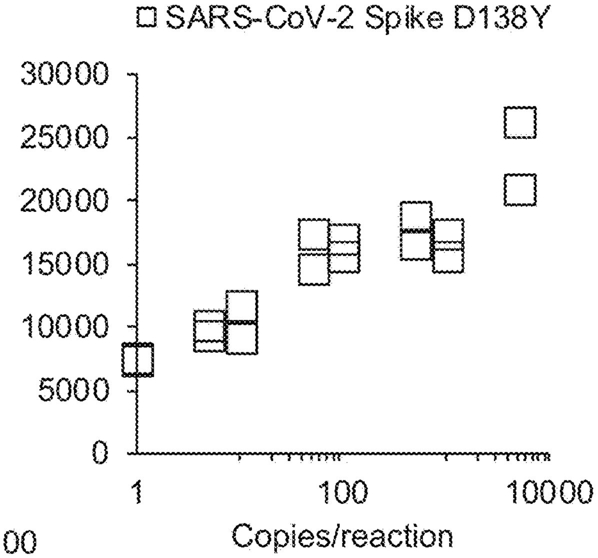
FIG. 14B shows DETECTX-Cv analysis for the indicated variants corresponding to the Brazil region.
Figure 14C:
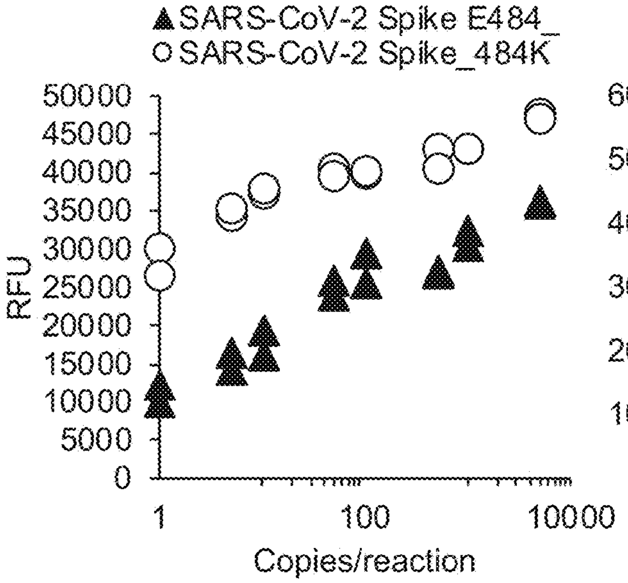
FIG. 14C shows DETECTX-Cv analysis for the indicated variants corresponding to the Brazil region.
Figure 14D:
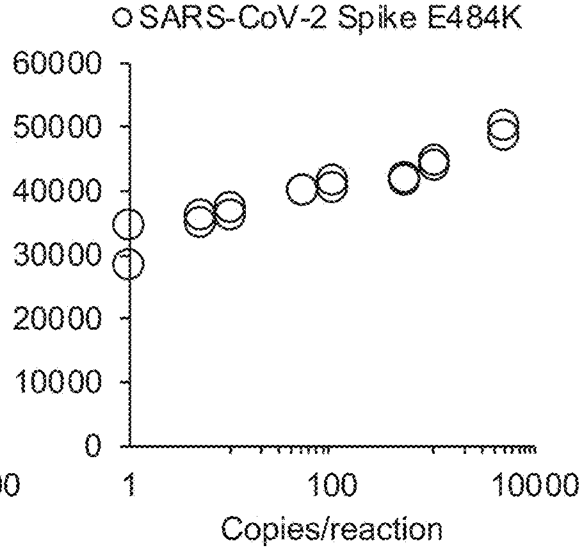
FIG. 14D shows DETECTX-Cv analysis for the indicated variants corresponding to the Brazil region.
Figure 14E:
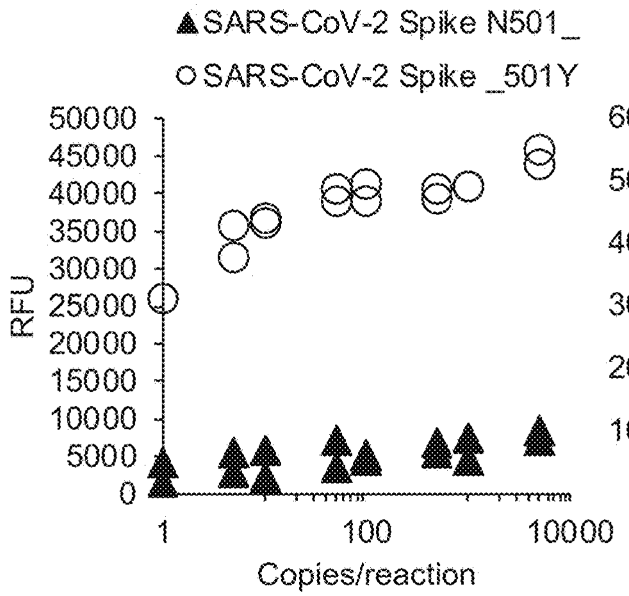
FIG. 14E shows DETECTX-Cv analysis for the indicated variants corresponding to the Brazil region.
Figure 14F:
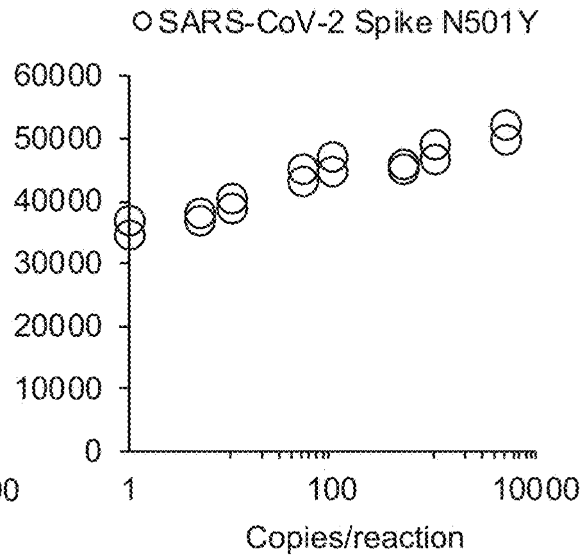
FIG. 14F shows DETECTX-Cv analysis for the indicated variants corresponding to the Brazil region.
Figure 14G:
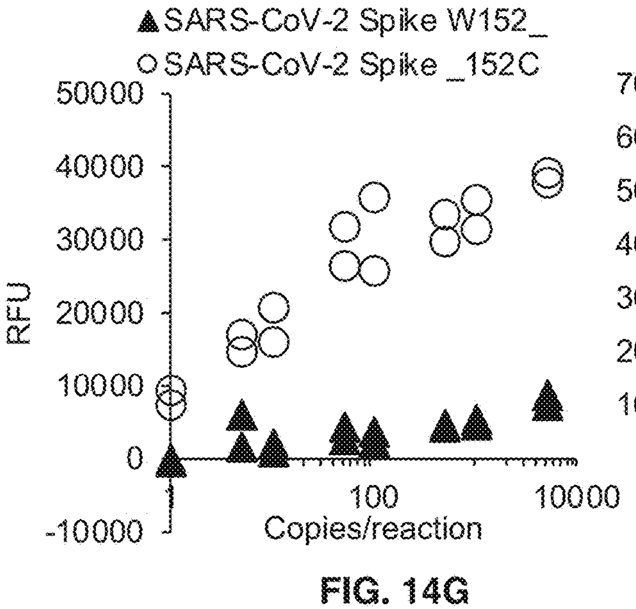
FIG. 14G shows DETECTX-Cv analysis for the indicated variants corresponding to the California region.
Figure 14H:
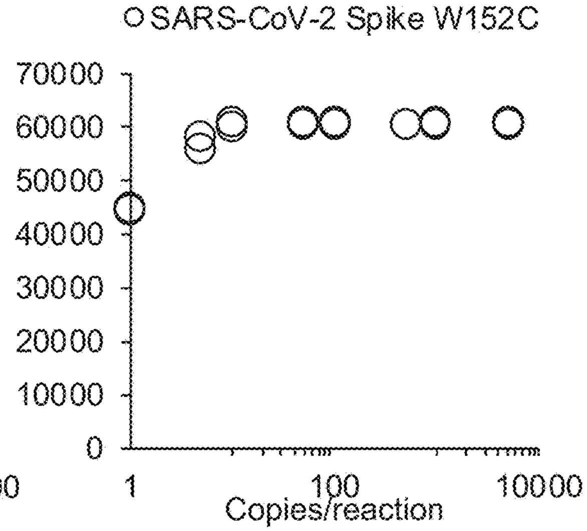
FIG. 14H shows DETECTX-Cv analysis for the indicated variants corresponding to the California region.
Figure 14I:
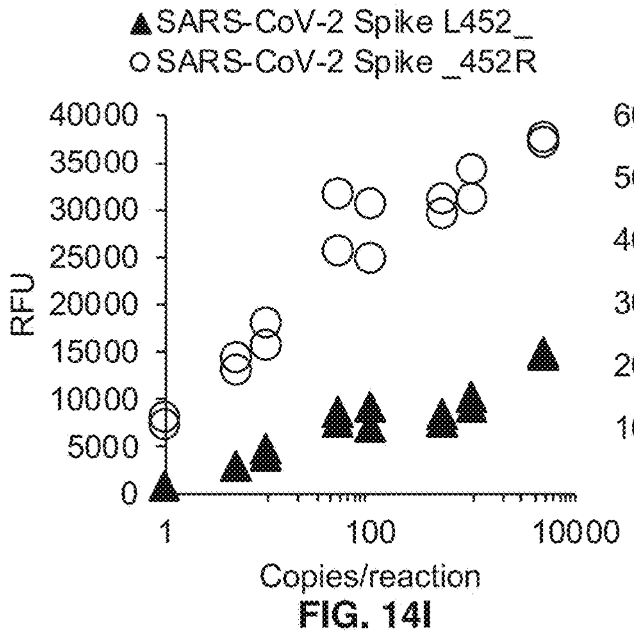
FIG. 14I shows DETECTX-Cv analysis for the indicated variants corresponding to the California region.
Figure 14J:
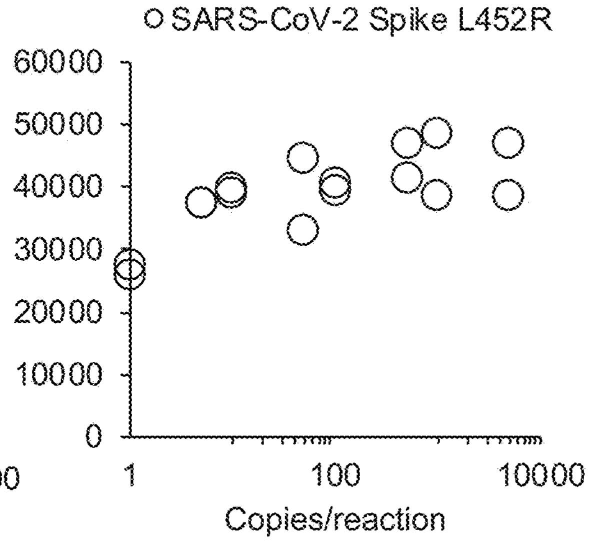
FIG. 14J shows DETECTX-Cv analysis for the indicated variants corresponding to the California region.
Figure 14K:
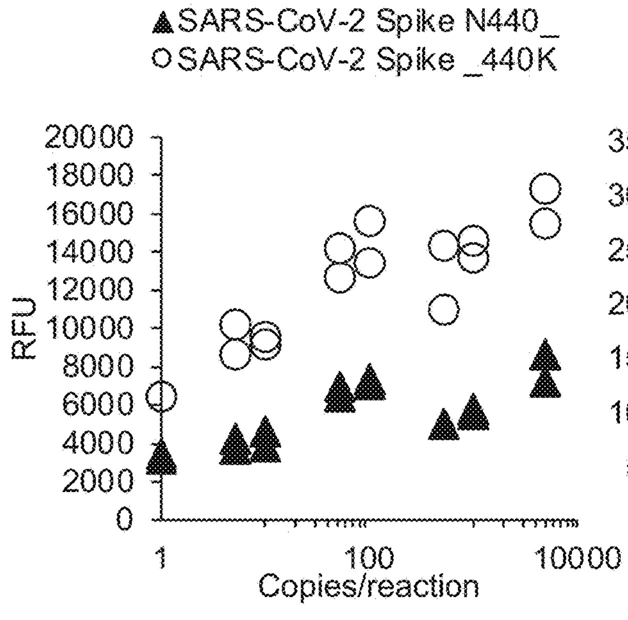
FIG. 14K shows DETECTX-Cv analysis for the indicated variants corresponding to the Indian region.
Figure 14L:
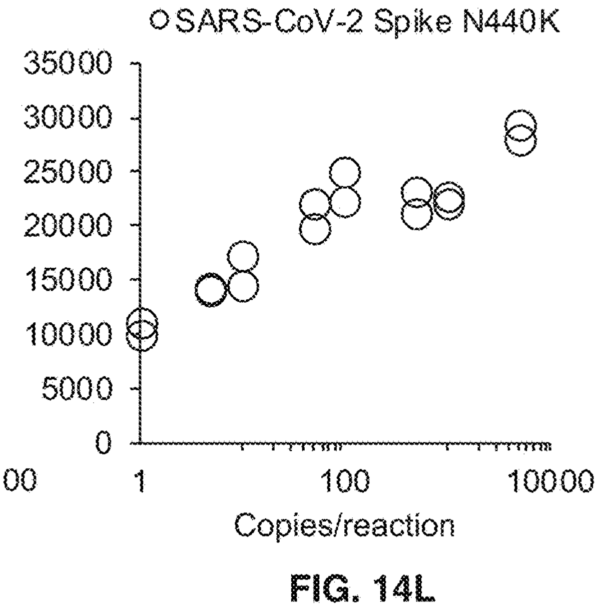
FIG. 14L shows DETECTX-Cv analysis for the indicated variants corresponding to the Indian region.
Figure 14M:
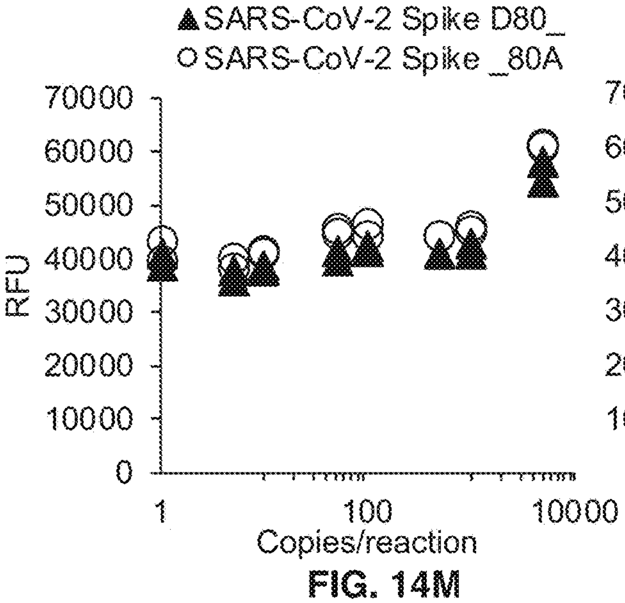
FIG. 14M shows DETECTX-Cv analysis for the indicated variants corresponding to the South Africa region.
Figure 14N:
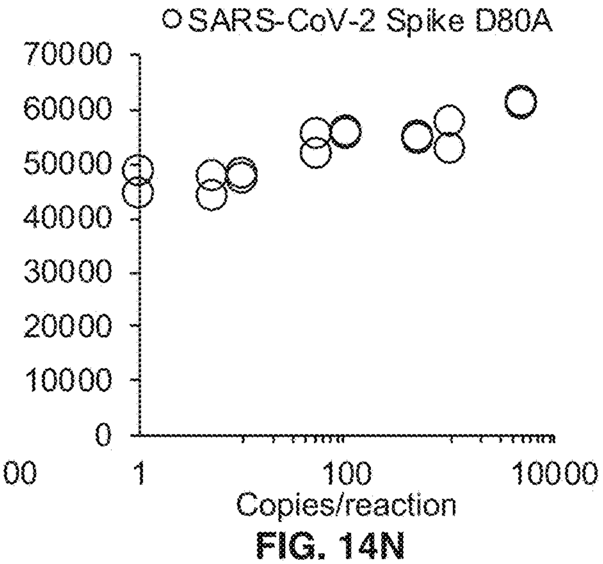
FIG. 14N shows DETECTX-Cv analysis for the indicated variants corresponding to the South Africa region.
Figure 14O:
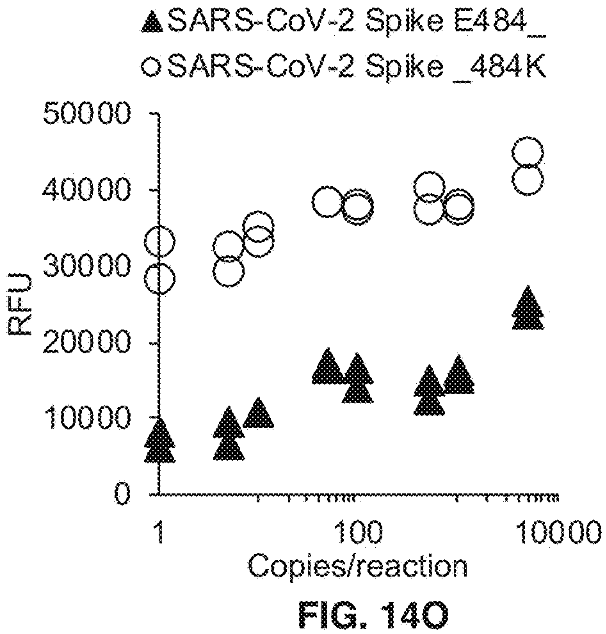
FIG. 14O shows DETECTX-Cv analysis for the indicated variants corresponding to the South Africa region.
Figure 14P:
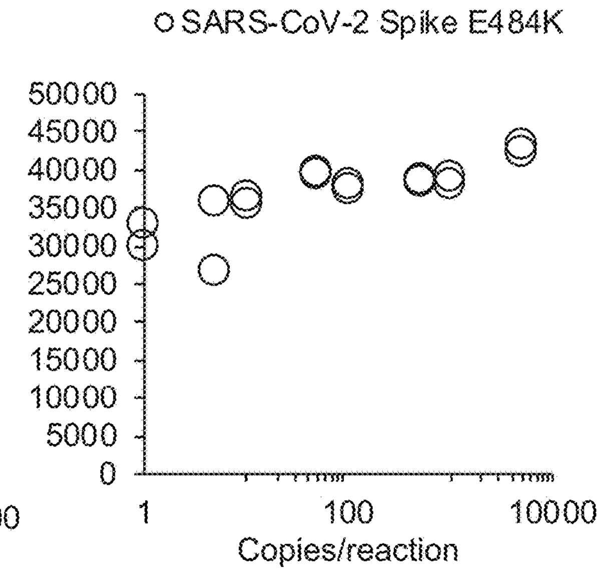
FIG. 14P shows DETECTX-Cv analysis for the indicated variants corresponding to the South Africa region.
Figure 14Q:
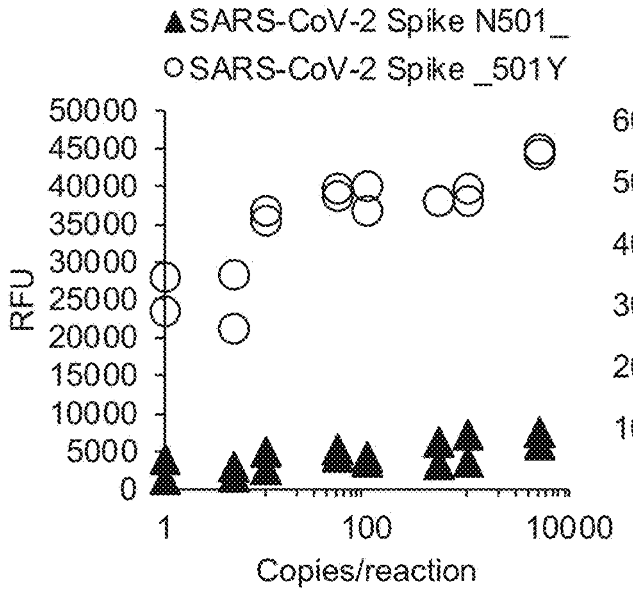
FIG. 14Q shows DETECTX-Cv analysis for the indicated variants corresponding to the South Africa region.
Figure 14R:
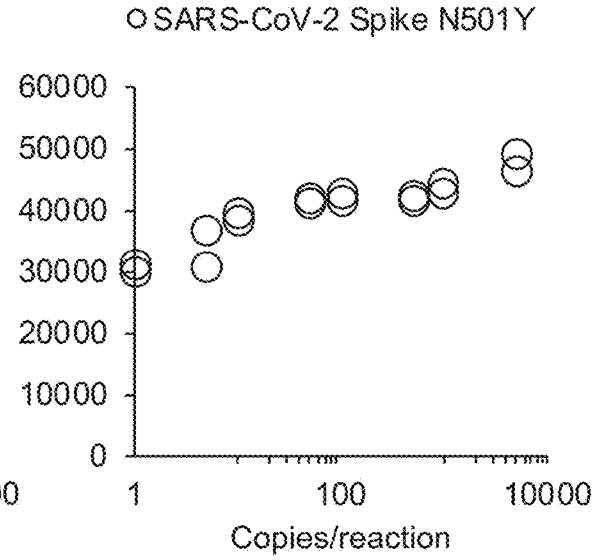
FIG. 14R shows DETECTX-Cv analysis for the indicated variants corresponding to the South Africa region.
Figure 14S:
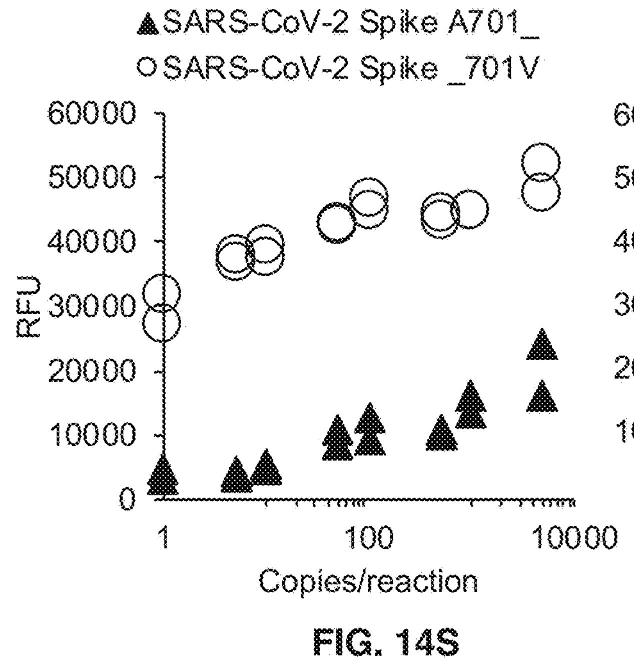
FIG. 14S shows DETECTX-Cv analysis for the indicated variants corresponding to the South Africa region.
Figure 14T:
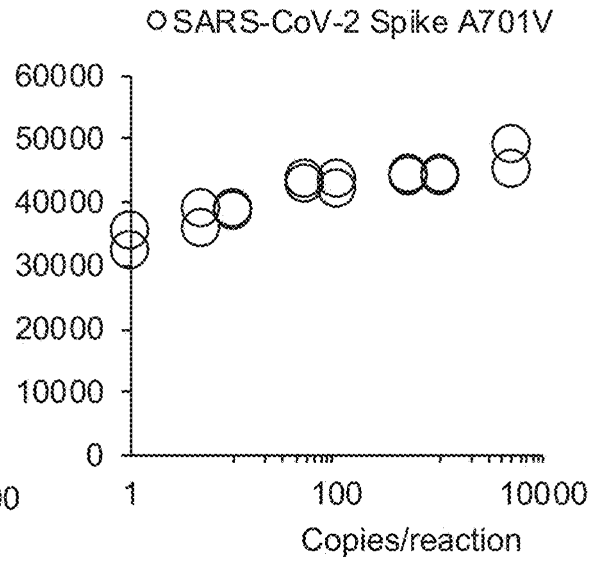
FIG. 14T shows DETECTX-Cv analysis for the indicated variants corresponding to the South Africa region.
Figure 14U:
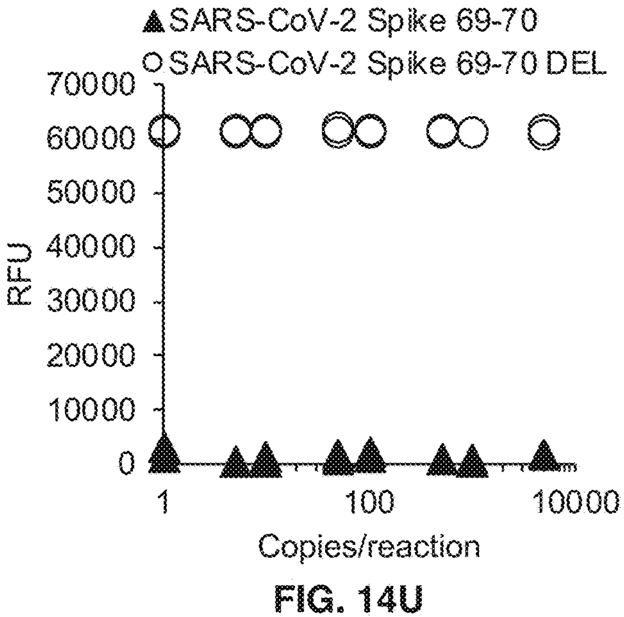
FIG. 14U shows DETECTX-Cv analysis for the indicated variants corresponding to the UK region.
Figure 14V:
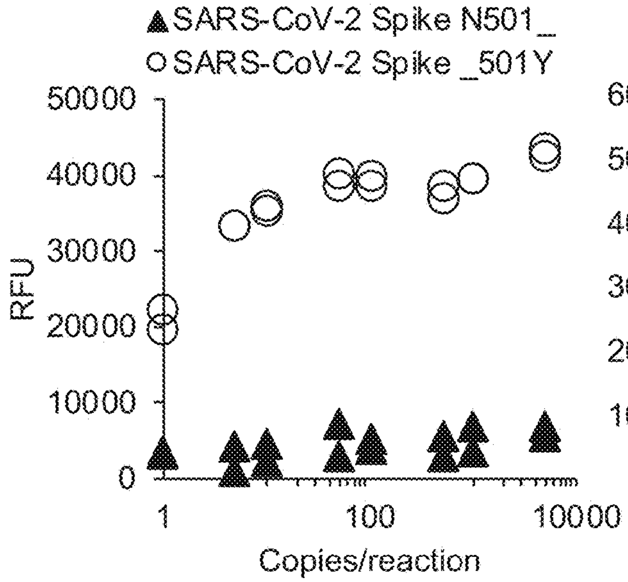
FIG. 14V shows DETECTX-Cv analysis for the indicated variants corresponding to the UK region.
Figure 14W:
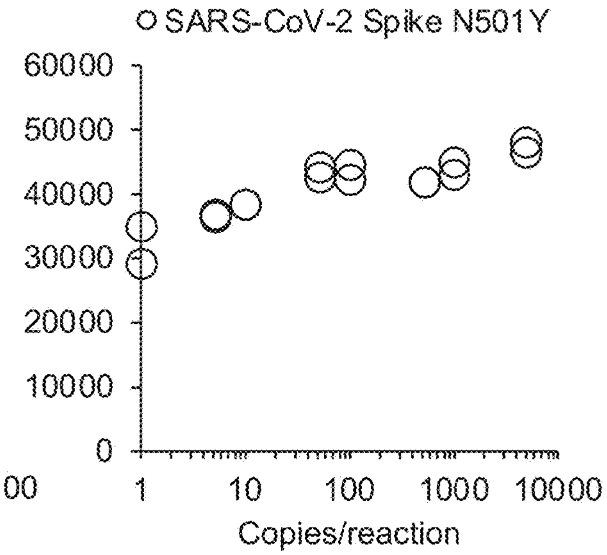
FIG. 14W shows DETECTX-Cv analysis for the indicated variants corresponding to the UK region.
Figure 14X:
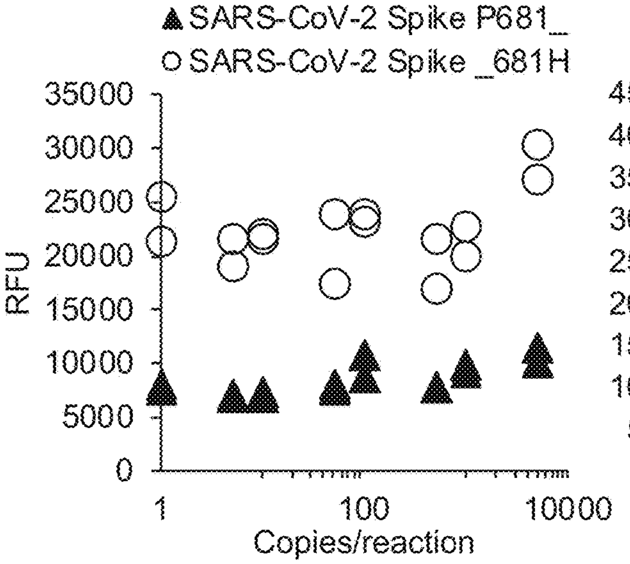
FIG. 14X shows DETECTX-Cv analysis for the indicated variants corresponding to the UK region.
Figure 14Y:
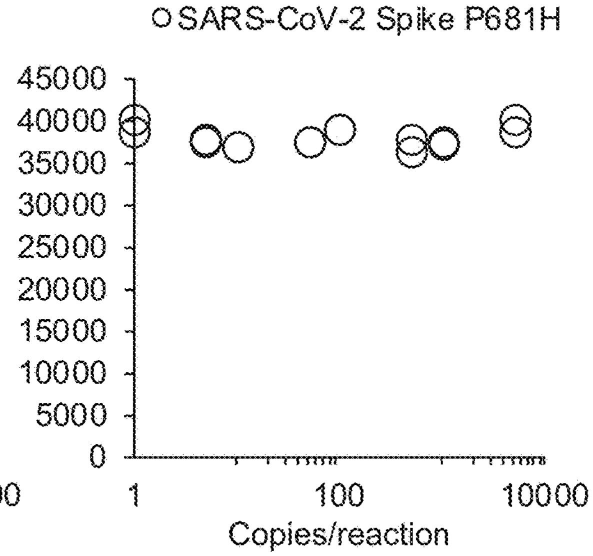
Figure 15A:
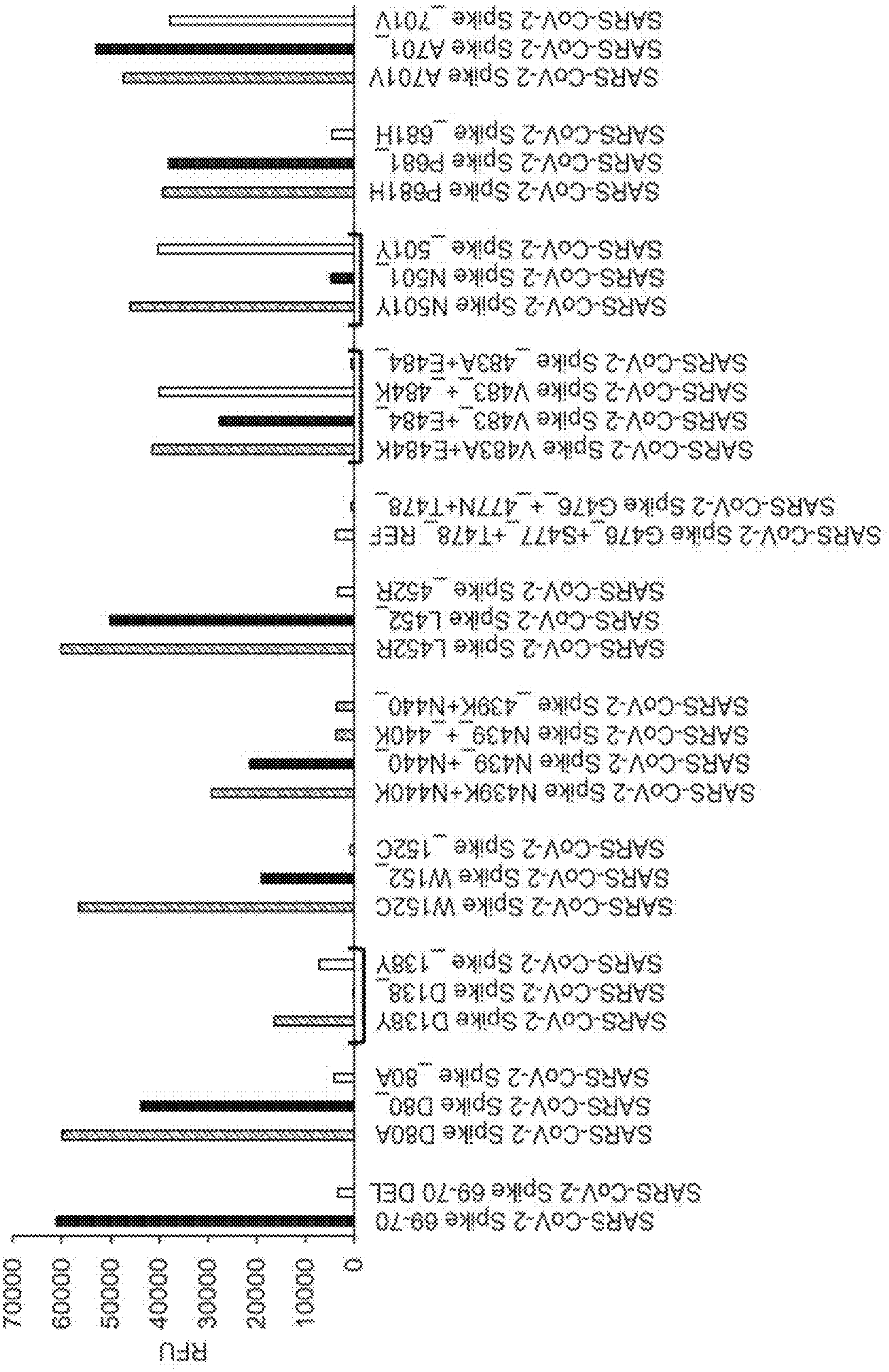
FIGS. 15A-15E shows DETECTX-Cv analysis using synthetic Clade Variant standards.
Figure 15B:
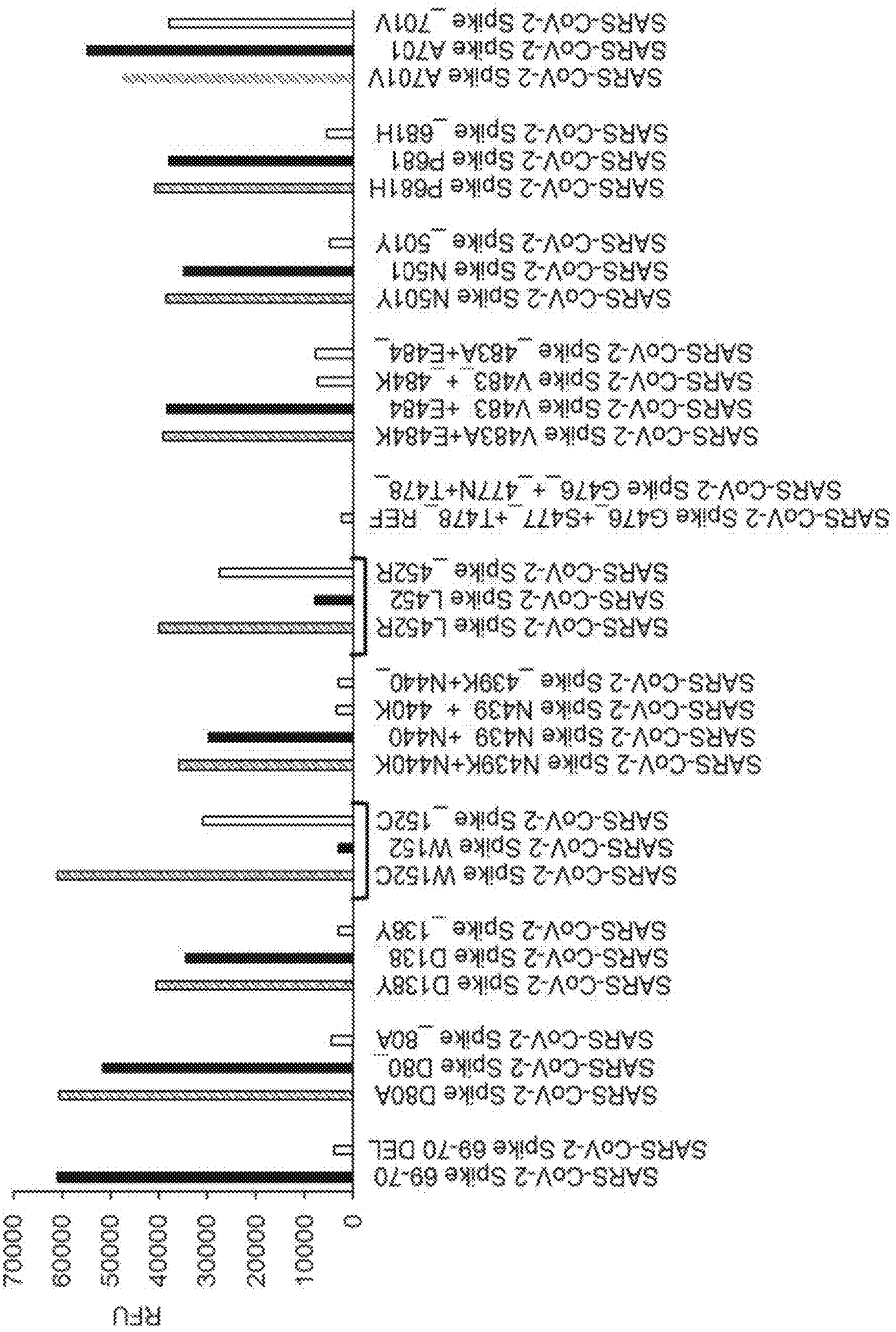
Figure 15C:
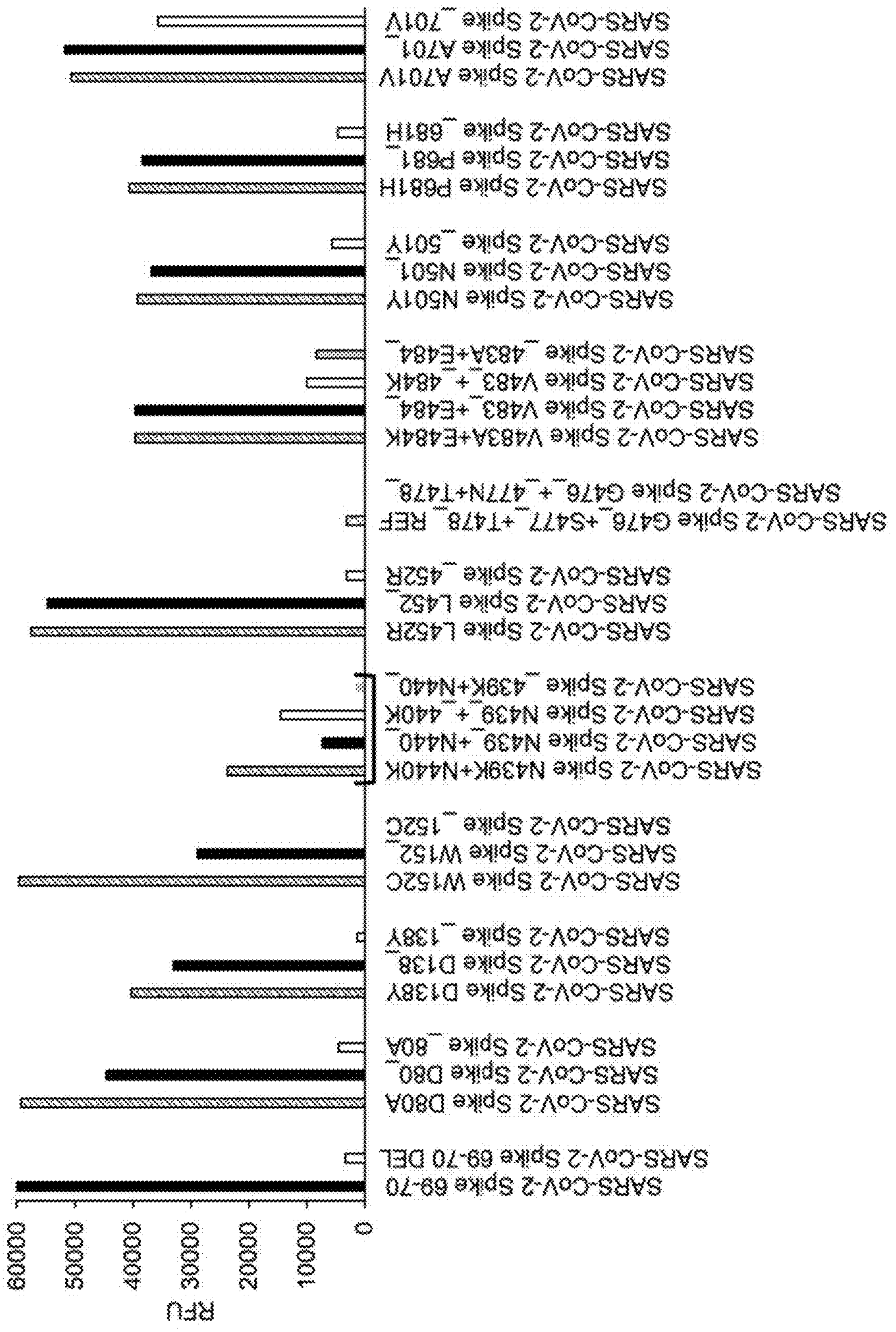
Figure 15D:
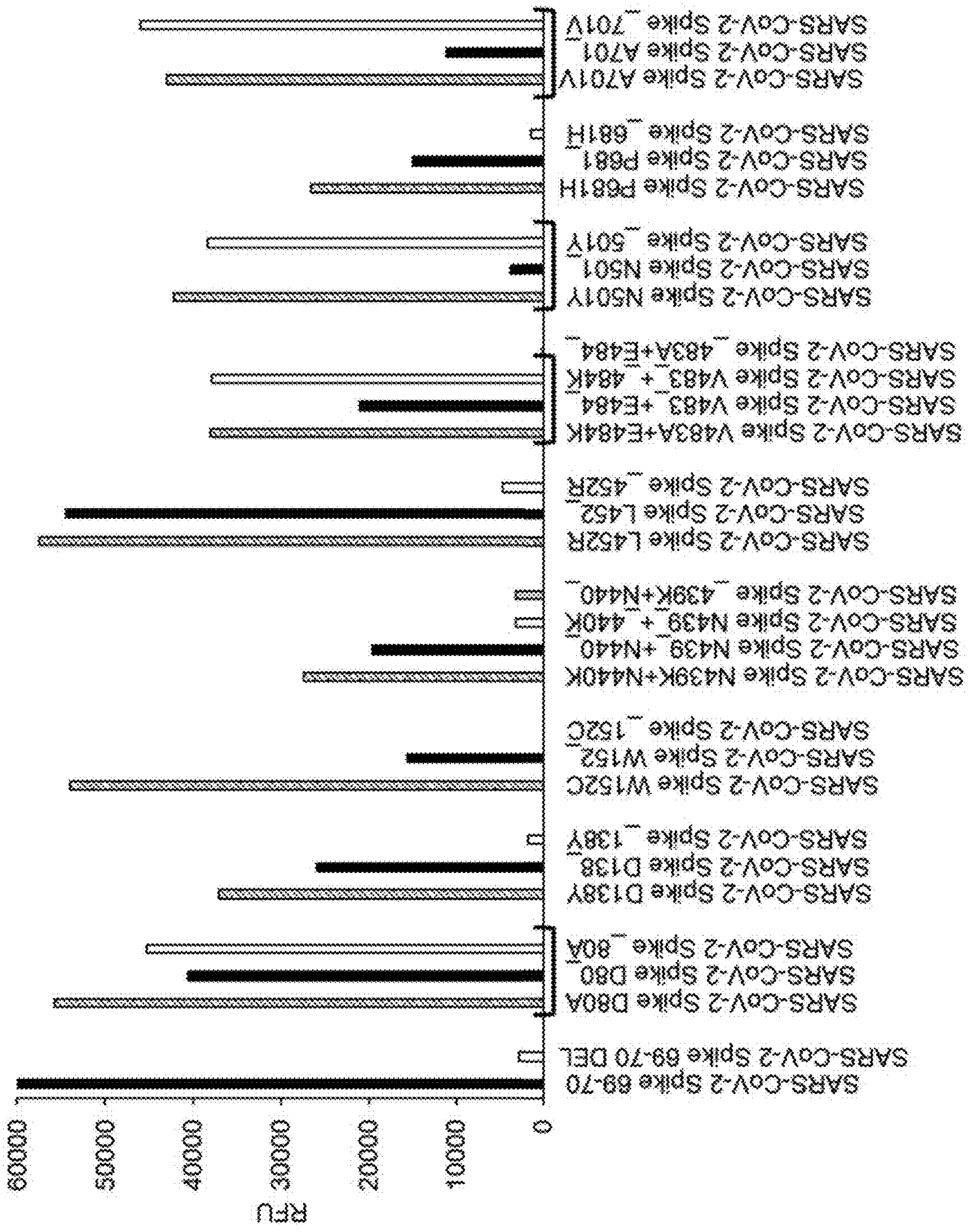
Figure 15E:
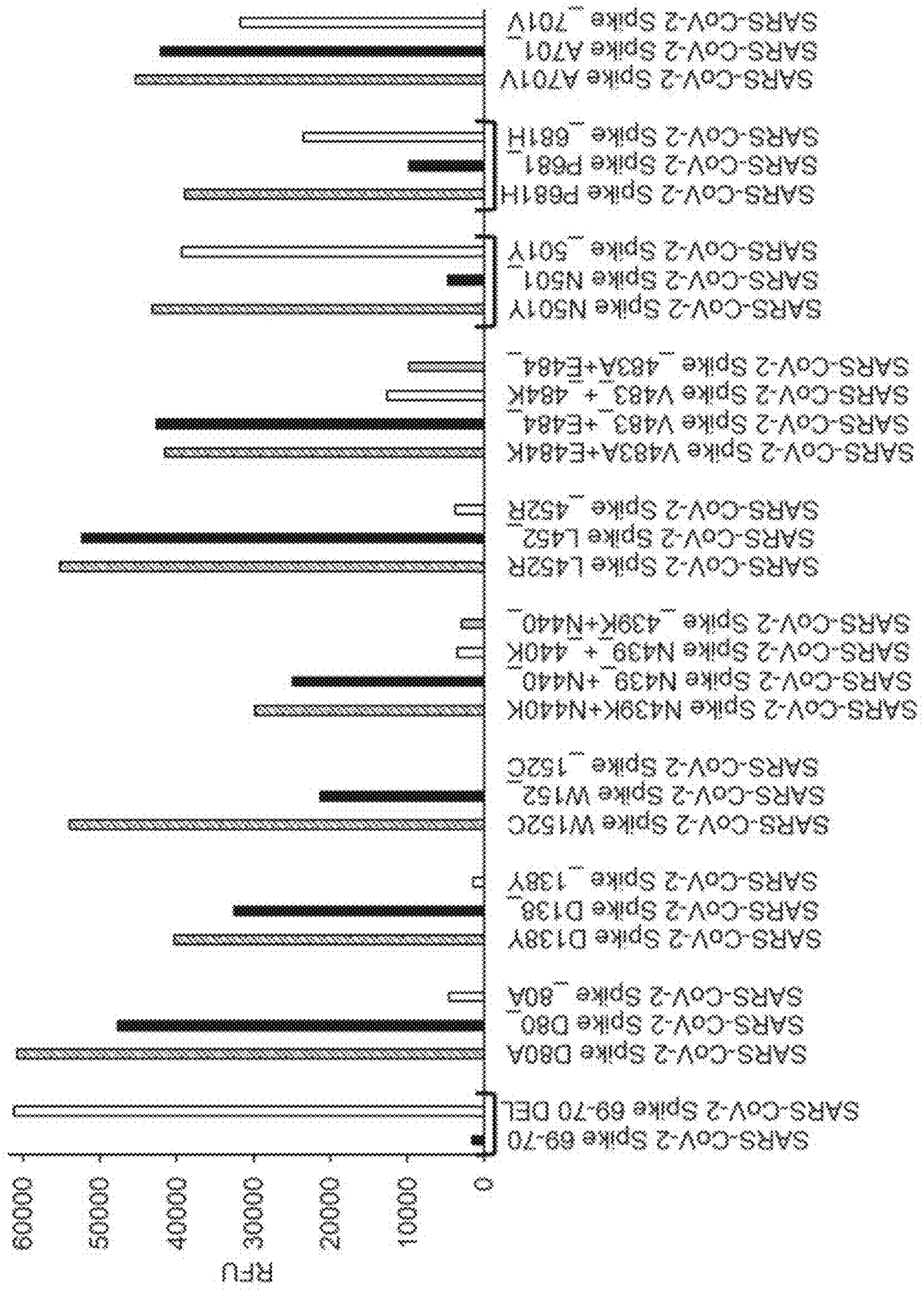

FIGS. 14A-14Y shows analytical LoD data for a series of synthetic G-block fragments corresponding to domains 2-8. The synthetic copy number was determined by IDT and used as such, in subsequent dilutions. Fragments fabricated to display "signature" mutations as defined in boxes showing superscript 1 in Table 15 were mixed into a series of "cocktails" to emulate different clade variant types.

FIGS. 14A, 14C, 14E, 14G, 14I, 14K, 14M, 14O, 14Q, 14S, 14U, 14V and 14X FIGS. 4(*a-q*) show a comparison of signals for Mutant (Synthetic) Cov-2, followed by hybridization to DETECTX-Cv to yield Wild-Type Probe (open circle) vs Mutant Probe (closed triangle) to emphasize the specificity of discrimination between Wild-Type vs Mutant target sequence. The signals were derived from microarray hybridization data (N=2 Repeats) for the N=5 multiplex RT-PCR amplification of Mutant (Synthetic) Cov-2, followed by hybridization to DETECTX-Cv. Table 17 summarizes the analytical $LoD_n$ (Wild Type) and $LoD_n$ (Mutant) values. FIGS. 14B, 14D, 14F, 14H, 14J, 14L, 14N, 14P, 14R, 14T, 14W and 14Y FIGS. 4(*a-q*) show microarray hybridization data (N=2 Repeats) for the N=5 multiplex RT-PCR amplification of Mutant (Synthetic) Cov-2, followed by hybridization to DETECTX-Cv, to yield Universal Probe Hybridization probe signals (open square). These data emphasize the high sensitivity of analysis obtained via hybridization to the (longer) Universal Probe, generally manifested as a lower $LoD_n$ (Universal).

TABLE 17

Summary of analytical LoD values measured for each of the eleven Spike gene target sites, for Universal, Wild-Type and Mutant probes.

| Target Site (n) | Amplicon | $LoD_n$* (Universal) WT | $LoD_n$* (Universal) MT | $LoD_n$§ (Wild Type) | $LoD_n$¶ (Mutant) |
|---|---|---|---|---|---|
| 69-70 (del) | 2 | NA | NA | 50 | <10** |
| D80A | 2 | 50 | <10 | 50 | <10 |
| D138Y | 3 | 100 | <10 | 100 | <10 |
| W152C | 3 | 100 | <10 | 500 | <10 |
| N440K | 5 | 50 | <10 | 50 | <10 |
| L452R | 5 | 50 | <10 | 50 | <10 |
| S477N | 6 | 10 | <10 | 50 | <10 |
| E484K | 6 | 10 | <10 | 10 | <10 |
| N501Y | 6 | 100 | <10 | 100 | <10 |
| P681H | 8 | 10 | <10 | 10 | <10 |
| A701V | 8 | 10 | <10 | 50 | <10 |

*$LoD_n$ (Universal). Analytical LoD Values for Universal Probes as defined from the input target density (in copies per RT-PCR reaction) at which the signal obtained from the Universal probe becomes indistinguishable from the present estimate of background. There are two related values obtained for $LoD_n$ (Universal). One value is obtained upon titration with Wild Type (Wuhan) genomic gRNA ($LoD_n$ (Universal) and the other obtained upon titration with Mutant Synthetic Fragments ($LoD_n$ (Universal) MT)

§$LoD_n$ (Wild Type). Analytical LoD Values for Analysis of Wild Type (Wuhan)as defined from the input target density (measured in copies per RT-PCR reaction) at which the signal obtained from the Wild Type probe becomes indistinguishable from background.

¶$LoD_n$ (Mutant). Analytical LoD Values for Analysis of Mutant (Synthetic Fragnnent)as defined from the input target density (measured in copies per RT-PCR reaction) at which the signal obtained from the Mutant probe becomes indistinguishable from background.

Example 8

Analysis of "Synthetic Clade Variant" Standards for Deployment to TriCore and Other Labs 1. Synthetic Clade Variant Analysis.

The (N=5) RT-PCR Multiplex (2, 3, 5, 6, 8) described in Example 7 was deployed to obtain a full eleven (11) site clade variant profile using standard hybridization and wash procedures described above.

2. Synthetic Clade Variant Cocktails.

A set of five (5) different "Synthetic clade Variant Standards" corresponding to UK (B.1.1.7), SA (B.1.351), CA452 (B.1.429), Brazil (P.1) and India N440K (B.1.36.29) were prepared each containing a synthetic gene fragment (IDT, Coralville, Iowa) identical to each of the Spike domains amplified by the present RT-PCR multiplex.

3. Synthetic Clade Variant Data Analysis.

Data were obtained at 100 copies/reaction for each of the five (5) synthetic cocktails. Hybridization analysis was performed, and the hybridization data thus obtained was plotted as described above.

4. Results.

Raw data from this analysis presented in FIGS. 15A-15E shows that the ratio of Mutant (open bars) to Wild Type signal (black bars) readily identify the state of each of the eleven (11) target domains. Spike target sites expected to display a "Mutant" Signal (i.e. open bars>black bars) are marked with brackets.

Example 9

CoV-2 Detection and Pooling Via (Oasis) Pure-SAL Saliva Collection.

Clinical LoD Range Finding and Clinical LoD analysis were performed on contrived samples, comprising clinical negatives from healthy volunteers, collected in PURE-SAL™ collection device (OASIS DIAGNOSTICS® Corporation, WA). The samples were contrived with heat attenuated CoV-2 (Wuhan, BEI).

Contrived samples were subjected to viral gRNA capture and purification on Zymo silica magnetic beads or Ceres magnetic beads. Five microliters of purified RNA was added to the RT-PCR mix in a PCR plate. The plate was sealed and placed in a thermocycler to undergo 20 minutes of reverse transcription and 45 cycles of asymmetric PCR. Upon PCR completion, the DNA microarray was prepared for hybridization with brief water washes, and an incubation in pre-hybridization buffer (0.6 M NaCl, 0.06 M sodium citrate solution, 0.1% Ficoll, 0.1% Polyvinylpyrrolidone 0.1% Bovine Serum Albumin). Following aspiration of the pre-hybridization buffer, a mixture of amplicon and hybridization buffer (0.6 M NaCl, 0.06 M sodium citrate, 0.1% Ficoll, 0.1% Polyvinylpyrrolidone 0.1% Bovine Serum Albumin) was added to the DNA microarray and allowed to incubate for 2 hours. The microarray is then washed with wash buffer (22.5 mM NaCl, 2.25 mM sodium citrate) and dried via centrifugation. The glass portion of the microarray was cleaned with lens tissue and 70% ethanol and images were acquired on the Sensospot. Images were then uploaded for Augury analysis.

Figure 16:
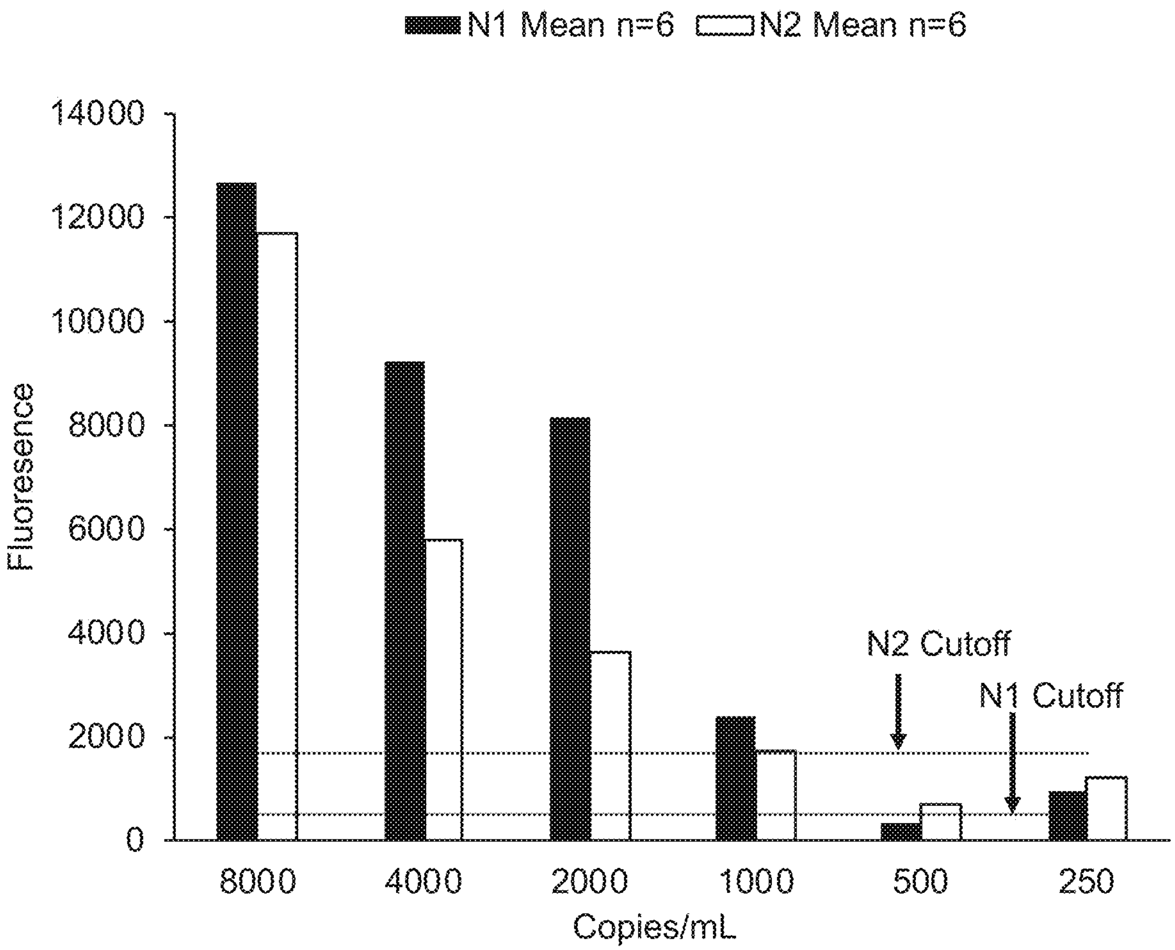
FIG. 16 shows LoD range finding DETECTX-Cv analysis for clinical samples processed using Zymo bead capture.

Clinical LoD Results: Clinical LoD range finding was performed as described above (N=6 repeats) using clinically negative saliva samples (PURE-SAL™) to which were added heat inactivated CoV-2 that were processed using Zymo bead capture. FIG. 16 shows that the clinical LoD is close to 1000 copies/ml. A follow-up experiment was performed at N=20, where the resulting clinical LoD is defined as the point at which nineteen of the twenty (19/20) repeated samples produced positive detection (Table 18), which corresponds to a clinical LoD of 1000 copies/ml, a value that is identical within experimental accuracy to that obtained via the same DETECTX-Cv assay of contrived NP-VTM samples with Ceres bead collection as follows. Twenty microliters of beads were added to 400 μL of clinical sample and 800 μL of viral DNA/RNA buffer and mixed on a shaker at 1200 rpm for 10 minutes. The samples were placed on the magnet and supernatant was removed before the addition and pipette-mixing of Zymo Wash Buffer 1. This was repeated for Zymo Wash Buffer 2 and two washes with 100% ethanol. All washes were performed at a volume of 500 μL. The beads were dried at 55° C. Once completely dried, 50 μL of water was added to the beads and mixed well. After placing the samples on the magnet, the supernatant was transfer to another plate for RNA storage. Five microliters of purified RNA were added to the RT-PCR mix in a PCR plate. The plate was sealed and placed in a thermocycler to undergo 20 minutes of reverse transcription and 45 cycles of asymmetric PCR. Upon PCR completion, the DNA microarray was prepared for hybridization with brief water washes, and an incubation in prehybridization buffer (0.6 M NaCl, 0.06 M sodium citrate solution, 0.1% Ficoll, 0.1% Polyvinylpyrrolidone 0.1% Bovine Serum Albumin). Following aspiration of the prehybridization buffer, a mixture of amplicon and hybridization buffer (0.6 M NaCl, 0.06 M sodium citrate solution, 0.1% Ficoll, 0.1% Polyvinylpyrrolidone 0.1% Bovine Serum Albumin) was added to the DNA microarray and allowed to incubate for 2 hours. The microarray is then washed with wash buffer (22.5 mM NaCl, 2.25 mM sodium citrate) and dried via centrifugation. The glass portion of the microarray was cleaned with lens tissue and 70% ethanol and images were acquired on the Sensospot. Images were then uploaded for Augury analysis.

TABLE 18

Summary of LoD Experiment Results

| Input Concentration | SARS-CoV-2 N1 | SARS-CoV-2 N2 | Positive Final Call | % Positive Final Call |
|---|---|---|---|---|
| 1500 cp/mL | 20/20 | 19/20 | 20/20 | 100% |
| 1000 cp/mL | 19/20 | 13/20 | 19/20 | 95% |

Final LoD

| Input Concentration | SARS-CoV-2 N1 | SARS-CoV-2 N2 | Positive Final Call | % Positive Final Call |
|---|---|---|---|---|
| 1000 cp/mL | 19/20 | 13/20 | 19/20 | 95% |

Pure-SAL Saliva. Pooling Range Finding.

Figure 17:
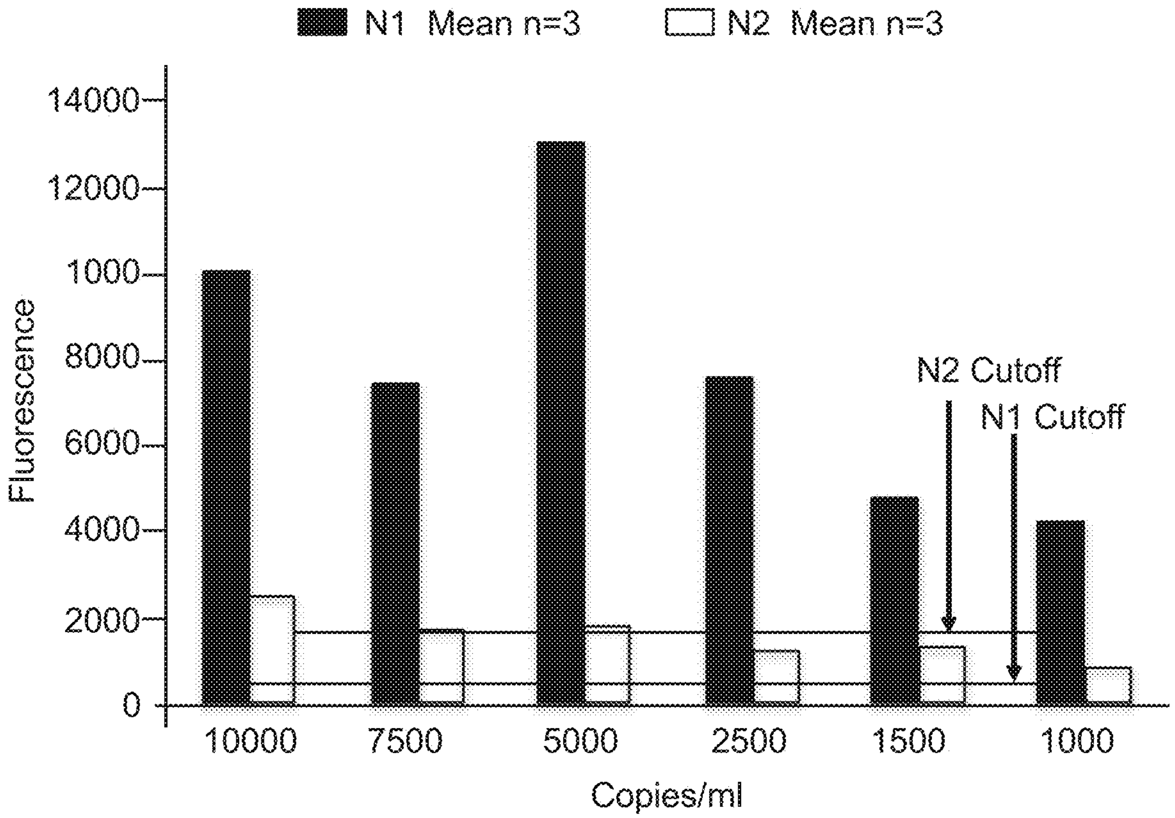
FIG. 17 shows LoD range finding DETECTX-Cv analysis for clinical negative saliva samples processed using Zymo bead capture.

The ability to pool CoV-2 contrived clinical negative PURE-SAL™ saliva samples was tested. Contrived clinical negative samples were pooled at (1) Positive Clinical Sample (100 ⌈L)+(4) Clinical samples (100 ⌈L each), to yield a final pooled sample where the viral complement of the original contrived clinical positive is diluted 5×. The entire pooled specimen was then subjected to Zymo magnetic bead purification, RT-PCR and Hybridization to DETECTX-Cv as described above. The results shown in FIG. 17 suggest that subsequent to 5× pooling, the LoD is reduced less than the full 5× expected from a simple 5× dilution, thus demonstrating feasibility of the N=5 PURE-SAL™ pooling.

Example 10

Autonomous Analysis

DETECTX-Cv analysis was performed by hands-free, autonomous analysis of raw DETECTX-microarray data obtained from Sensovation Scans to generate "Mutant" vs "Wild Type" calls among the ten (10) Spike target sites Table 19. These calls were subsequently used for Clade identification. The autonomous analysis is presented here along with manual Augury analysis.

The following multiple functional modules were added to Augury to enable autonomous analysis of DETECTX-Cv data as follows;

(1) Look-Up Table. A database (a "Look-Up Table") directly related to a Clade Variant vs Mutation data matrix (Table 19) was programmed into Augury. The database is flexible, resident within Augury and can be increased in size as needed to include a larger number of Spike Gene Targets (i.e. more columns as in Table 19) or Clade Variant Targets (i.e. more Rows as in Table 19). Augury is intrinsically linked to the cloud. Further, the clade Variant Look-Up Table in Augury can be updated in real time via secure inputs such as those which could be provided by Rosalind (San Diego, Calif.).

(2) Comparison among probe data sets. Augury was modified to compare probe information to be used for data quality (QA/QC) and for interpretation of the RFU data (clade ID):

a) QA/QC based on signal strength (signal intensity). The universal probes described earlier were used to measure data quality. If universal probe signals were <10,000 (resulting from sample degradation or low concentration), the data associated with the corresponding Mutant and Wild type data at a Spike Target Site are not used by Augury for clade variant identification.

b) Data Interpretation: Primary. "Wild Type" and "Mutant" Probe data (RFU) were compared automatically, along with clinical threshold data stored in Augury to generate a "Delta" value (see Example 6). A Delta value greater than 0 returns a "Mutant" call, whereas a Delta value less than 0 returns a "Wild Type" call at each Spike Target Site.

c) Data Interpretation: Secondary. The pattern of Wild Type vs Mutant calls (i.e. the rows in Table 19) obtained from the Primary Data Interpretation were automatically compared to patterns associated with known clade variants. The most likely clade variant pattern is automatically reported. A statistical probability is also assignable to the clade Variant call and alternative calls based on DETECTX-Cv analysis of multiple clade Variant samples.

d) Data Reports. A Standard Report Format was chosen.

DETECTX-Cv Analysis of Synthetic Clade Variant Standards at TriCore.

Five (5) synthetic clade variant standards described earlier (UK, SA, CA452, Brazil P.1, India, Examples 8 and 9) were used for on-site validation. Each standard contained a synthetic gene fragment (IDT) identical to each of the Spike domains amplified by the RT-PCR multiplex. DETECTX-Cv data were obtained at TriCore at 100 copies/reaction for each of the five (5) synthetic cocktails. Analysis of the hybridization data were plotted as described previously. Table 20 shows a plate map, PCR recipe and cycling conditions for this analysis. DNA fragment cocktails were utilized as reference.

TABLE 19

| | | | | | Spike Gene Target Region (Codon) Amino Acid Change | | | | | | | | | | | | | | | |
|---|---|---|---|---|---|---|---|---|---|---|---|---|---|---|---|---|---|---|---|---|
| | | | | | L5F | S13I | L18F | T20N | P26S | Q52R | A67V | Δ69-70 | D80A/G | T95I | D138Y | Y144DEL | W152C | F157L/S | L189F | R190S |
| | Street name | Pango lineage | CDC % Mar. 14-27, 2021 (US) | Incidence % Gisaid March 2021 | Signal (1-13) | | S1 subunit (14-685) N-terminal domain (14-305) | | | | | | | | | | | | | |
| VOC | UK | B.1.1.7 | 44.10% | 49.81% | $L^3$ | $S^2$ | $L^3$ | $T^2$ | $P^3$ | $Q^3$ | $A^3$ | $Δ^1$ | $D^2$ | $T^3$ | $D^2$ | $Δ^1$ | $W^2$ | $F^3$ | $L^3$ | $R^3$ |
| VOC | California L452R | B.1.427 | 6.90% | 2.08% | $L^3$ | $I^1$ | $L^3$ | $T^2$ | $P^3$ | $Q^3$ | $A^3$ | $HV^2$ | $D^2$ | $T^3$ | $D^2$ | $Y^2$ | $C^1$ | $F^3$ | $L^3$ | $R^3$ |
| VOC | | B.1.427 | 2.90% | 0.90% | $L^3$ | $S/I^1$ | $L^3$ | $T^2$ | $P^3$ | $Q^3$ | $A^3$ | $HV^2$ | $D^2$ | $T^3$ | $D^2$ | $Y^2$ | $W/C^2$ | $F^3$ | $L^3$ | $R^3$ |
| VOC | Brazil | P.1 | 1.40% | 0.39% | $L^3$ | $S^2$ | F | $N^1$ | S | $Q^3$ | $A^3$ | $HV^2$ | $D^2$ | $T^3$ | $Y^1$ | $Y^2$ | $W^2$ | $F^3$ | $L^3$ | S |
| VOC | SA | B.1.351 | 0.70% | 1.13% | $L^3$ | $S^2$ | $L^3$ | $T^2$ | $P^3$ | $Q^3$ | $A^3$ | $HV^2$ | $A^1$ | $T^3$ | $D^2$ | $Y^2$ | $W^2$ | $F^3$ | $L^3$ | $R^3$ |
| VOC | NYC (ho et al.) | B.1.526 | 9.20% | 0.82% | L/F | $S^2$ | $L^3$ | $T^2$ | $P^3$ | $Q^3$ | $A^3$ | $HV^2$ | $D^2$ | I | $D^2$ | $Y^2$ | $W^2$ | $F^3$ | $L^3$ | $R^3$ |
| VOC | NYC | B.1.525 | 0.50% | 0.10% | $L^3$ | $S^2$ | $L^3$ | $T^2$ | $P^3$ | R | V | $Δ^1$ | $D^2$ | $T^3$ | $D^2$ | $Δ^1$ | $W^2$ | $F^3$ | $L^3$ | $R^3$ |
| VOC | Rio de Janeiro | P.2 | 0.30% | 0.36% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1.2 | 10.00% | 7.83% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1, B.1.1, B.1.234 | 2.4%/ 0.9%/ 0.5% | 2.6%/ 1.5%/ 0.5% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1.1.519 | 4.10% | 1.50% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1.526.1 | 3.90% | 0.35% | F | $S^2$ | $L^3$ | $T^2$ | $P^3$ | $Q^3$ | $A^3$ | $HV^2$ | G | I | $D^2$ | $Δ^1$ | $W^2$ | S | $L^3$ | $R^3$ |
| | | B.1.526.2 | 2.90% | 0.18% | F | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1.596 | 1.70% | 1.04% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | R.1 | 1.20% | 0.20% | $L^3$ | $S^2$ | $L^3$ | $T^2$ | $P^3$ | $Q^3$ | $A^3$ | $HV^2$ | $D^2$ | $T^3$ | $D^2$ | $Y^2$ | L | $F^3$ | $L^3$ | $R^3$ |
| | | B.1.575 | 1.10% | 0.19% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1.243, B.1.1.207 | 0.60% | 0.84% | | | | | | | | | | | | | | | | |
| | US | B.1.375 | <1% | 0.03% | $L^3$ | $S^2$ | $L^3$ | $T^2$ | $P^3$ | $Q^3$ | $A^3$ | $Δ^1$ | $D^2$ | $T^3$ | $D^2$ | $Y^2$ | $W^2$ | $F^3$ | $L^3$ | $R^3$ |
| | | B.1.1.1, B.1.416, B.1.1.33, B.1.311, B.1.1.122 | <1% | 0.50% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | Brazil (Original) | B.1.1.28 | <1% | 0.10% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | Andhra Pradesh | B.1.36.29 | <1% | 0.08% | $L^3$ | $S^2$ | F | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | A.23.1 | <1% | 0.05% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | L | $L^3$ | $R^3$ |
| | | A.27 | <1% | 0.05% | $L^3$ | $S^2$ | F | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | A.28 | <1% | 0.02% | $L^3$ | $S^2$ | $L^3$ | $T^2$ | $P^3$ | $Q^3$ | $A^3$ | $Δ^1$ | $D^2$ | $T^3$ | $D^2$ | $Y^2$ | $W^2$ | $F^3$ | $L^3$ | $R^3$ |
| | Mink/ Cluster V | B.1.1.298 | <1% | 0.00% | $L^3$ | $S^2$ | $L^3$ | $T^2$ | $P^3$ | $Q^3$ | $A^3$ | $Δ^1$ | $D^2$ | $T^3$ | $D^2$ | $Y^2$ | $W^2$ | $F^3$ | $L^3$ | $R^3$ |
| | | B.1.1.318 | <1% | 0.01% | $L^3$ | $S^2$ | $L^3$ | $T^2$ | $P^3$ | $Q^3$ | $A^3$ | $HV^2$ | $D^2$ | $T^3$ | $D^2$ | $Δ^1$ | $W^2$ | $F^3$ | $L^3$ | $R^3$ |
| | | B.1.160 | <1% | 1.76% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1.177 | <1% | 3.19% | $L^3$ | $S^2$ | F | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1.177.80 | <1% | 0.04% | $L^3$ | $S^2$ | F | $T^2$ | $P^3$ | $Q^3$ | $A^3$ | $HV^2$ | $D^2$ | $T^3$ | $D^2$ | $Δ/Y^1$ | $W^2$ | $F^3$ | $L^3$ | $R^3$ |

TABLE 19-continued

| | | | | | Spike Gene Target Region (Codon) Amino Acid Change | | | | | | | | | | | | | | | |
|---|---|---|---|---|---|---|---|---|---|---|---|---|---|---|---|---|---|---|---|---|
| | | B.1.258 | <1% | 1.15% | $L^3$ | $S^2$ | $L^3$ | $T^2$ | $P^3$ | $Q^3$ | $A^3$ | $HV/\Delta^1$ | $D^2$ | $T^3$ | $D^2$ | $Y^2$ | $W^2$ | $F^3$ | $L^3$ | $R^3$ |
| | | B.1.258.14 | <1% | 0.06% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | | B.1.258/17 | <1% | 1.02% | $L^3$ | $S^2$ | $L^3$ | $T^2$ | $P^3$ | $Q^3$ | $A^3$ | $\Delta^1$ | $D^2$ | $T^3$ | $D^2$ | $Y^2$ | $W^2$ | $F^3$ | $L^3$ | $R^3$ |
| | | B.1.517 | <1% | 0.25% | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | WUHAN | WUHAN | — | — | $L^3$ | $S^2$ | $L^3$ | $T^2$ | $P^3$ | $Q^3$ | $A^3$ | $HV^2$ | $D^2$ | $T^3$ | $D^2$ | $Y^2$ | $W^2$ | $F^3$ | $L^3$ | $R^3$ |
| | PCR Amplimer length (bases) | | | | | | | (1) 101 | | | | $(2_B)$ 150 | | | | (3) 129 | | | | |
| | | | | | D215G | A222V | A243del | G252V | D253G | V367F | K417N/T | N439K | N440K | L452R | Y453F | S477N | V483A | E484K | S494P | N501Y/T |
| | Street name | Pango lineage | CDC % Mar. 14-27, 2021 (US) | Incidence % Gisaid March 2021 | | | S1 subunit (14-685) N-terminal domain (14-305) | | | | | | | | | S1 subunit (14-685) RBD (319-541) | | | | |
| VOC | UK | B.1.1.7 | 44.10% | 49.81% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E/K^1$ | S/P | $Y^1$ |
| VOC | California L452R | B.1.427 | 6.90% | 2.08% | $D^3$ | $A^3$ | $A^2$ | $G^3$ | $D^2$ | $V^3$ | $K^2$ | $N^2$ | $N^2$ | $R^1$ | $Y^2$ | $S^2$ | $V^2$ | $E^2$ | $S^3$ | $N^2$ |
| VOC | | B.1.427 | 2.90% | 0.90% | $D^3$ | $A^3$ | $A^2$ | $G^3$ | $D^2$ | $V^3$ | $K^2$ | $N^2$ | $N^2$ | $R^1$ | $Y^2$ | $S^2$ | $V^2$ | $E^2$ | $S^3$ | $N^2$ |
| VOC | Brazil | P.1 | 1.40% | 0.39% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $K^1$ | $S^3$ | $Y^1$ |
| VOC | SA | B.1.351 | 0.70% | 1.13% | G | $A^3$ | $\Delta^1$ | $G^3$ | $D^2$ | $V^3$ | $K^2$ | $N^2$ | $N^2$ | $L^2$ | $Y^2$ | $S^2$ | $V^2$ | $K^1$ | $S^3$ | $Y^1$ |
| VOC | NYC (ho et al.) | B.1.526 | 9.20% | 0.82% | $D^3$ | $A^3$ | $A^2$ | $G^3$ | $D^2$ | $V^3$ | $K^2$ | $N^2$ | $N^2$ | $L^2$ | $Y^2$ | $S/N^1$ | $V^2$ | $E/K^1$ | $S^3$ | $N^2$ |
| VOC | NYC | B.1.525 | 0.50% | 0.10% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $K^1$ | $S^3$ | $N^2$ |
| VOC | Rio de Janeiro | P.2 | 0.30% | 0.36% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $K^1$ | $S^3$ | $N^2$ |
| | | B.1.2 | 10.00% | 7.83% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $Y^1$ |
| | | B.1, B.1.1, B.1.234 | 2.4%/ 0.9%/ 0.5% | 2.6%/ 1.5%/ 0.5% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | | B.1.1.519 | 4.10% | 1.50% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | | B.1.526.1 | 3.90% | 0.35% | $D^3$ | $A^3$ | $A^2$ | $G^3$ | $D/G^1$ | $V^3$ | $K^2$ | $N^2$ | $N^2$ | $R^1$ | $Y^2$ | $S^2$ | $V^2$ | $K^1$ | $S^3$ | $N^2$ |
| | | B.1.526.2 | 2.90% | 0.18% | $D^3$ | $A^3$ | $A^2$ | $G^3$ | $G^1$ | $V^3$ | $N/T^1$ | $N^2$ | $N^2$ | $L^2$ | $Y^2$ | $N^1$ | $V^2$ | $E^2$ | $S^3$ | $N^2$ |
| | | B.1.596 | 1.70% | 1.04% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | | R.1 | 1.20% | 0.20% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $K^1$ | $S^3$ | $N^2$ |
| | | B.1.575 | 1.10% | 0.19% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | | B.1.243, B.1.1.207 | 0.60% | 0.84% | | | | | | $V^3$ | $K^2$ | $N^2$ | $N^2$ | $L^2$ | $Y^2$ | $S^2$ | $V^2$ | $E^2$ | $S^3$ | $N^2$ |
| | US | B.1.375 | <1% | 0.03% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | | B.1.1.1, B.1.416, B.1.1.33, B.1.311, B.1.1.122 | <1% | 0.50% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | Brazil (Original) | B.1.1.28 | <1% | 0.10% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | Andhra Pradesh | B.1.36.29 | <1% | 0.08% | $D^3$ | $A^3$ | $A^2$ | $G^3$ | $D^2$ | $V^3$ | $K^2$ | $N^2$ | $K^1$ | $L^2$ | $Y^2$ | $S^2$ | $V^2$ | $E^2$ | $S^3$ | $N^2$ |
| | | A.23.1 | <1% | 0.05% | $D^3$ | $A^3$ | $A^2$ | $G^3$ | $D^2$ | F | $K^2$ | $N^2$ | $N^2$ | $L^2$ | $Y^2$ | $S^2$ | $V^2$ | $E/K^1$ | $S^3$ | $N^2$ |
| | | A.27 | <1% | 0.05% | $D^3$ | $A^3$ | $A^2$ | $G^3$ | $D^2$ | $V^3$ | $K^2$ | $N^2$ | $N^2$ | $R^1$ | $Y^2$ | $S^2$ | $V^2$ | $E^2$ | $S^3$ | $Y^1$ |
| | | A.28 | <1% | 0.02% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | T |

TABLE 19-continued

| | | | | | Spike Gene Target Region (Codon) Amino Acid Change | | | | | | | | | | | | | | | |
|---|---|---|---|---|---|---|---|---|---|---|---|---|---|---|---|---|---|---|---|---|
| | Mink/ Cluster V | B.1.1.298 | <1% | 0.00% | $D^3$ | $A^3$ | $A^2$ | $G^3$ | $D^2$ | $V^3$ | $K^2$ | $N^2$ | $N^2$ | $L^2$ | $F^1$ | $S^2$ | $V^2$ | $E^2$ | $S^3$ | $N^2$ |
| | | B.1.1.318 | <1% | 0.01% | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $K^1$ | $S^3$ | $N^2$ |
| | | B.1.160 | <1% | 1.76% | $D^3$ | $A^3$ | $A^2$ | $G^3$ | $D^2$ | $V^3$ | $K^2$ | $N^2$ | $N^2$ | $L^2$ | $Y^2$ | $N^1$ | $V^2$ | $E^2$ | $S^3$ | $N^2$ |
| | | B.1.177 | <1% | 3.19% | $D^3$ | V | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | | B.1.177.80 | <1% | 0.04% | $D^3$ | V | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | | B.1.258 | <1% | 1.15% | $D^3$ | $A^3$ | $A^2$ | $G^3$ | $D^2$ | $V^3$ | $K^2$ | $K^1$ | $N^2$ | $L^2$ | $Y^2$ | $S^2$ | $V^2$ | $E^2$ | $S^3$ | $N^2$ |
| | | B.1.258.14 | <1% | 0.06% | $D^3$ | $A^3$ | $A^2$ | $G^3$ | $D^2$ | $V^3$ | $K^2$ | $K^1$ | $N^2$ | $L^2$ | $Y^2$ | $S^2$ | $V^2$ | $E^2$ | $S^3$ | $N^2$ |
| | | B.1.258/17 | <1% | 1.02% | $D^3$ | $A^3$ | $A^2$ | $G^3$ | $D^2$ | $V^3$ | $K^2$ | $K^1$ | $N^2$ | $L^2$ | $Y^2$ | $S^2$ | $V^2$ | $E^2$ | $S^3$ | $N^2$ |
| | | B.1.517 | <1% | 0.25% | $D^3$ | $A^3$ | $A^2$ | G/V | $D^2$ | $V^3$ | $K^2$ | $N^2$ | $N^2$ | $L^2$ | $Y^2$ | $S^2$ | $V^2$ | $E^2$ | $S^3$ | T |
| | WUHAN | WUHAN | | — | $D^3$ | $A^3$ | $A^2$ | $G^3$ | $D^2$ | $V^3$ | $K^2$ | $N^2$ | $N^2$ | $L^2$ | $Y^2$ | $S^2$ | $V^2$ | $E^2$ | $S^3$ | $N^2$ |
| | PCR Amplimer length (bases) | | | | | | | $(4_B)$ 160 | | | | | (5) 199 | | | | | (6) 151 | | |
| | | | | | A570D | Q613H | D614G | H655Y | Q677P/H | P681H | I692V | A701V | T716I | G760V | D796V | F888L | S982A | T1027I | D1118H | V1176F |
| | | Pango | CDC % Mar. 14-27, 2021 | Incidence % Gisaid March | | | | | | | | | S2 subunit (686-1273) | | | | | | | |
| | Street name | lineage | (US) | 2021 | S1 subunit (14-685) | | | | | | | | | | | | | Fusion peptide (788-806) | | |
| VOC | UK | B.1.1.7 | 44.10% | 49.81% | D | $Q^2$ | $G^1$ | $H^3$ | $Q^2$ | $H^1$ | $I^2$ | $A^2$ | I | $G^3$ | $D^3$ | $F^3$ | A | $T^3$ | H | $V^3$ |
| VOC | California L452R | B.1.427 | 6.90% | 2.08% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| VOC | | B.1.427 | 2.90% | 0.90% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| VOC | Brazil | P.1 | 1.40% | 0.39% | $A^3$ | $Q^2$ | $G^1$ | Y | $Q^2$ | $P^2$ | $I^2$ | $A^2$ | $T^3$ | $G^3$ | $D^3$ | $F^3$ | $S^3$ | I | $D^3$ | F |
| VOC | SA | B.1.351 | 0.70% | 1.13% | $A^3$ | $Q^2$ | $G^1$ | $H^3$ | $Q^2$ | $P^2$ | $I^2$ | $V^1$ | $T^3$ | $G^3$ | $D^3$ | $F^3$ | $S^3$ | $T^3$ | $D^3$ | $V^3$ |
| VOC | NYC (ho et al.) | B.1.526 | 9.20% | 0.82% | $A^3$ | $Q^2$ | $G^1$ | $H^3$ | $Q^2$ | $P^2$ | $I^2$ | $A/V^1$ | $T^3$ | $G^3$ | $D^3$ | $F^3$ | $S^3$ | $T^3$ | $D^3$ | $V^3$ |
| VOC | NYC | B.1.525 | 0.50% | 0.10% | $A^3$ | $Q^2$ | $G^1$ | $H^3$ | $H^1$ | $P^2$ | $I^2$ | $A^2$ | $T^3$ | $G^3$ | $D^3$ | L | $S^3$ | $T^3$ | $D^3$ | $V^3$ |
| VOC | Rio de Janeiro | P.2 | 0.30% | 0.36% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | F |
| | | B.1.2 | 10.00% | 7.83% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | | B.1, B.1.1, B.1.234 | 2.4%/ 0.9%/ 0.5% | 2.6%/ 1.5%/ 0.5% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | | B.1.1.519 | 4.10% | 1.50% | $A^3$ | $Q^2$ | $G^1$ | $H^3$ | $Q^2$ | $H^1$ | $I^2$ | $A^2$ | $T^3$ | $G^3$ | $D^3$ | $F^3$ | $S^3$ | $T^3$ | $D^3$ | $V^3$ |
| | | B.1.526.1 | 3.90% | 0.35% | $A^3$ | $Q^2$ | $G^1$ | $H^3$ | $Q^2$ | $P^2$ | $I^2$ | $A/V^1$ | $T^3$ | $G^3$ | $D^3$ | $F^3$ | $S^3$ | $T^3$ | $D^3$ | $V^3$ |
| | | B.1.526.2 | 2.90% | 0.18% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | | B.1.596 | 1.70% | 1.04% | $A^3$ | $Q^2$ | $G^1$ | $H^3$ | $Q/P^1$ | $P^2$ | $I^2$ | $A^2$ | $T^3$ | $G^3$ | $D^3$ | $F^3$ | $S^3$ | $T^3$ | $D^3$ | $V^3$ |
| | | R.1 | 1.20% | 0.20% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | | B.1.575 | 1.10% | 0.19% | $A^3$ | $Q^2$ | $G^1$ | $H^3$ | $Q^2$ | $H^1$ | $I^2$ | $A^2$ | $T^3$ | $G^3$ | $D^3$ | $F^3$ | $S^3$ | $T^3$ | $D^3$ | $V^3$ |
| | | B.1.243, B.1.1.207 | 0.60% | 0.84% | $A^3$ | $Q^2$ | $G^1$ | $H^3$ | $Q^2$ | $H^1$ | $I^2$ | $A^2$ | $T^3$ | $G^3$ | $D^3$ | $F^3$ | $S^3$ | $T^3$ | $D^3$ | $V^3$ |
| | US | B.1.375 | <1% | 0.03% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |
| | | B.1.1.1, B.1.416, B.1.1.33, B.1.311, B.1.1.122 | <1% | 0.50% | $A^3$ | $Q^2$ | $G^1$ | $H^3$ | $Q^2$ | $P^2$ | $I^2$ | $A^2$ | $T^3$ | $G^3$ | $D^3$ | $F^3$ | $S^3$ | $T^3$ | $D^3$ | $V^3$ |

TABLE 19-continued

| | | | | Spike Gene Target Region (Codon) Amino Acid Change | | | | | | | | | | | | | | | |
|---|---|---|---|---|---|---|---|---|---|---|---|---|---|---|---|---|---|---|---|
| Brazil (Original) | B.1.1.28 | <1% | 0.10% | A[3] | Q[2] | G[1] | H[3] | Q[2] | P[2] | I[2] | A[2] | T[3] | G[3] | D[3] | F[3] | S[3] | T[3] | D[3] | F |
| Andhra Pradesh | B.1.36.29 | <1% | 0.08% | A[3] | Q[2] | G[1] | H[3] | Q[2] | R[1] | I[2] | A[2] | T[3] | G[3] | D[3] | F[3] | S[3] | T[3] | D[3] | V[3] |
| | A.23.1 | <1% | 0.05% | A[3] | H[1] | D[2] | Y | Q[2] | P[2] | I[2] | A[2] | T[3] | G[3] | D[3] | F[3] | S[3] | T[3] | D[3] | V[3] |
| | A.27 | <1% | 0.05% | A[3] | Q[2] | D[2] | Y | Q[2] | P[2] | I[2] | A[2] | T[3] | G[3] | Y | F[3] | S[3] | T[3] | D[3] | V[3] |
| | A.28 | <1% | 0.02% | A[3] | Q[2] | D[2] | H[3] | Q[2] | P[2] | I[2] | A[2] | T[3] | G[3] | D[3] | F[3] | S[3] | T[3] | D[3] | V[3] |
| Mink/ Cluster V | B.1.1.298 | <1% | 0.00% | A[3] | Q[2] | G[1] | H[3] | Q[2] | P[2] | I[2] | A[2] | T[3] | G[3] | D[3] | F[3] | S[3] | T[3] | D[3] | V[3] |
| | B.1.1.318 | <1% | 0.01% | A[3] | Q[2] | G[1] | H[3] | Q[2] | P[2] | I[2] | A[2] | T[3] | G[3] | D[3] | F[3] | S[3] | T[3] | D[3] | V[3] |
| | B.1.160 | <1% | 1.76% | A[3] | Q[2] | G[1] | H[3] | Q[2] | P[2] | I[2] | A[2] | T[3] | G[3] | D[3] | F[3] | S[3] | T[3] | D[3] | V[3] |
| | B.1.177 | <1% | 3.19% | A[3] | Q[2] | G[1] | H[3] | Q[2] | P[2] | I[2] | A[2] | T[3] | G[3] | D[3] | F[3] | S[3] | T[3] | D[3] | V[3] |
| | B.1.177.80 | <1% | 0.04% | A[3] | Q[2] | G[1] | H[3] | Q[2] | P[2] | I[2] | A[2] | T[3] | G[3] | D[3] | F[3] | S[3] | T[3] | D[3] | V[3] |
| | B.1.258 | <1% | 1.15% | A[3] | Q[2] | G[1] | H[3] | Q[2] | P[2] | I[2] | A[2] | T[3] | G[3] | D[3] | F[3] | S[3] | T[3] | D[3] | V[3] |
| | B.1.258.14 | <1% | 0.06% | A[3] | Q[2] | G[1] | H[3] | Q[2] | P[2] | I[2] | A[2] | T[3] | G[3] | D[3] | F[3] | S[3] | T[3] | D[3] | V[3] |
| | B.1.258/17 | <1% | 1.02% | A[3] | Q[2] | G[1] | H[3] | Q[2] | P[2] | I[2] | A[2] | T[3] | G[3] | D[3] | F[3] | S[3] | T[3] | D[3] | V[3] |
| | B.1.517 | <1% | 0.25% | A[3] | Q/H[1] | G[1] | H[3] | Q[2] | P[2] | I[2] | A[2] | T[3] | G[3] | D[3] | F[3] | S[3] | T[3] | D[3] | V[3] |
| WUHAN | WUHAN | — | — | A[3] | Q[2] | D[2] | H[3] | Q[2] | P[2] | I[2] | A[2] | T[3] | G[3] | D[3] | F[3] | S[3] | T[3] | D[3] | V[3] |
| PCR Amplimer length (bases) | | | | | (7) 88 | | | | (8) 135 | | | | | | | | | | |

[1]AA mutation-hybridizes to mutation specific probe
[2]AA identical to hCoV-19/Wuhan/WIV04/2019 (WIV04)-official reference sequence employed by GISAID (EPI_ISL_402124)
[3]Potential probe target

TABLE 20

Plate map, PCR recipe and Cycling conditions used in the analysis

| | Plate Map 1 | Plate Map 2 | RT-PCR Mix Components | RT-PCR Mix Per reaction (µL) | RT-PCR conditions Steps | RT-PCR conditions Temp (° C.) | RT-PCR conditions Time | RT-PCR conditions Cycles |
|---|---|---|---|---|---|---|---|---|
| A | 300 copies S. Africa | 300 copies UK | ACCESSQUICK ™ Mastermix | 25 | 1 | 55 | 20 min | 1 |
| B | 100 copies S. Africa | 100 copies UK | Primer | 2 | 2 | 94 | 2 min | 1 |
| C | 300 copies California | 300 copies Wuhan gRNA | Avian Myeloblastosis Virus (AMV) Enzyme mix | 1 | 3 | 94 | 30 s | 45 |
| D | 100 copies California | 100 copies Wuhan gRNA | Water | 17 | 4 | 55 | 30 s | |
| E | 300 copies India | NTC | Total | 45 | 5 | 68 | 30 s | |
| F | 100 copies India | NTC | | | 6 | 68 | 7 min | 1 |
| G | 300 copies Brazil | NTC | | | 7 | 4 | ∞ | |
| H | 100 copies Brazil | NTC | | | | | | |

Results

FIGS. 18A-18E and Table 21 show the results from analysis of synthetic clade variant standards at TriCore. The data shows that the raw data, i.e. the ratio of Mutant (open bars) to Wild Type signal (black bars) readily identifies the state of each of the ten (10) target domains. Spike target sites, which were expected to display a "Mutant" signal (i.e. open bar>black bars), are marked in square brackets. As shown, the Mutant vs Wild type signals obtained by TriCore on synthetic Clade variant standards were as expected. The data established that the DETECTX-Cv workflow is easily deployable in any high throughput COVID-19 clinical testing lab.

TABLE 21

DETECTX-Cv analysis of synthetic Clade variant standards at TriCore

Figure 18A:
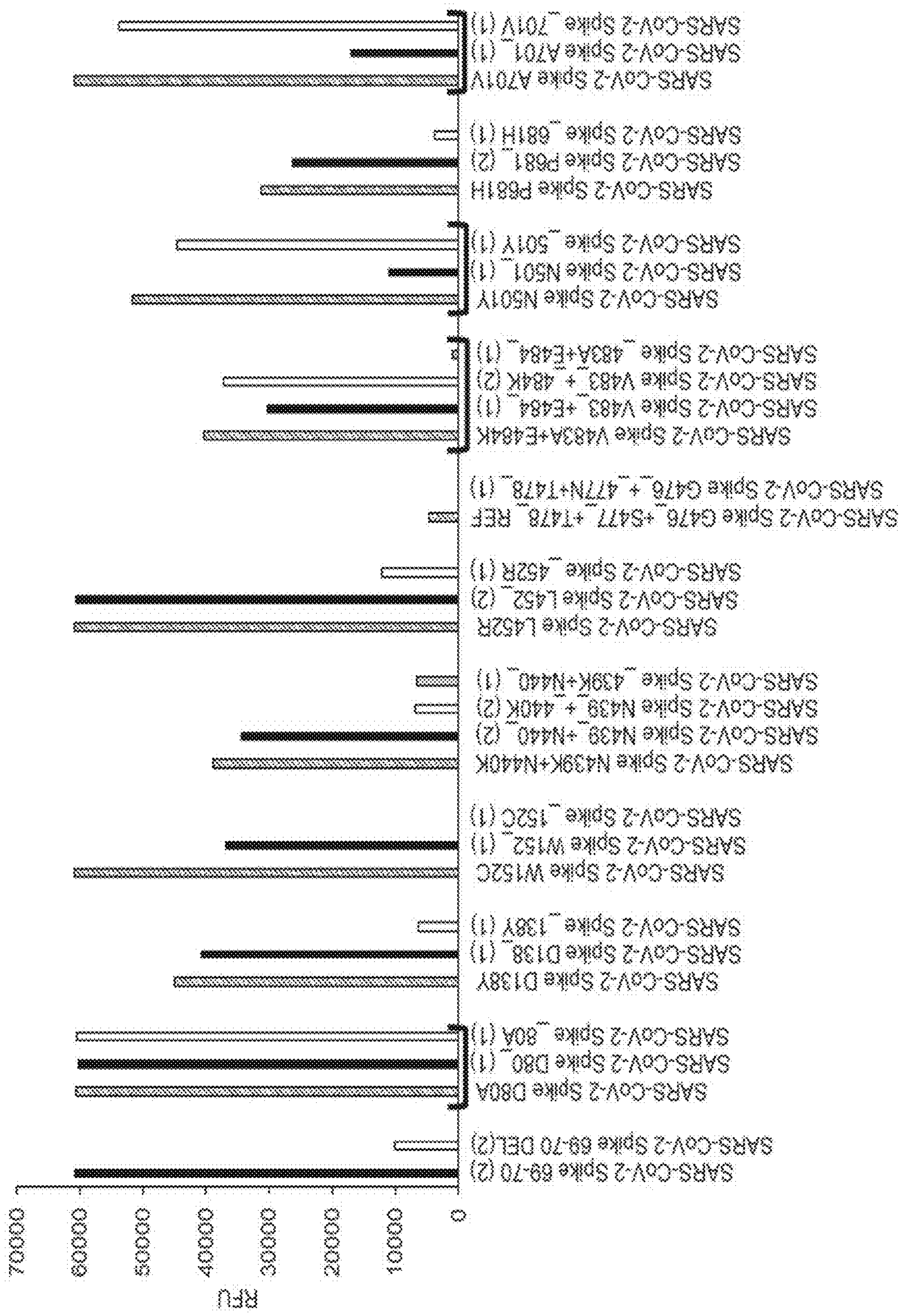
FIGS. 18A-18E shows representative DETECTX-Cv analysis of synthetic Clade variant standards.

| Probe | Wild Type | Mutant Type | Confidence |
|---|---|---|---|
| | Reference FIG. 18A HYBRIDIZED PROBES | | |
| H/V69_ | ON | | 100.00% |
| _80A | | ON | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | | ON | 100.00% |
| _501Y | | ON | 100.00% |
| P681_ | ON | | 100.00% |
| _701V | | ON | 100.00% |
| | UNHYBRIDIZED PROBES | | |
| _152C | | OFF | 98.80% |
| _681H | | OFF | 100.00% |
| A701_ | OFF | | 97.40% |

TABLE 21-continued

DETECTX-Cv analysis of synthetic Clade variant standards at TriCore

Figure 18B:
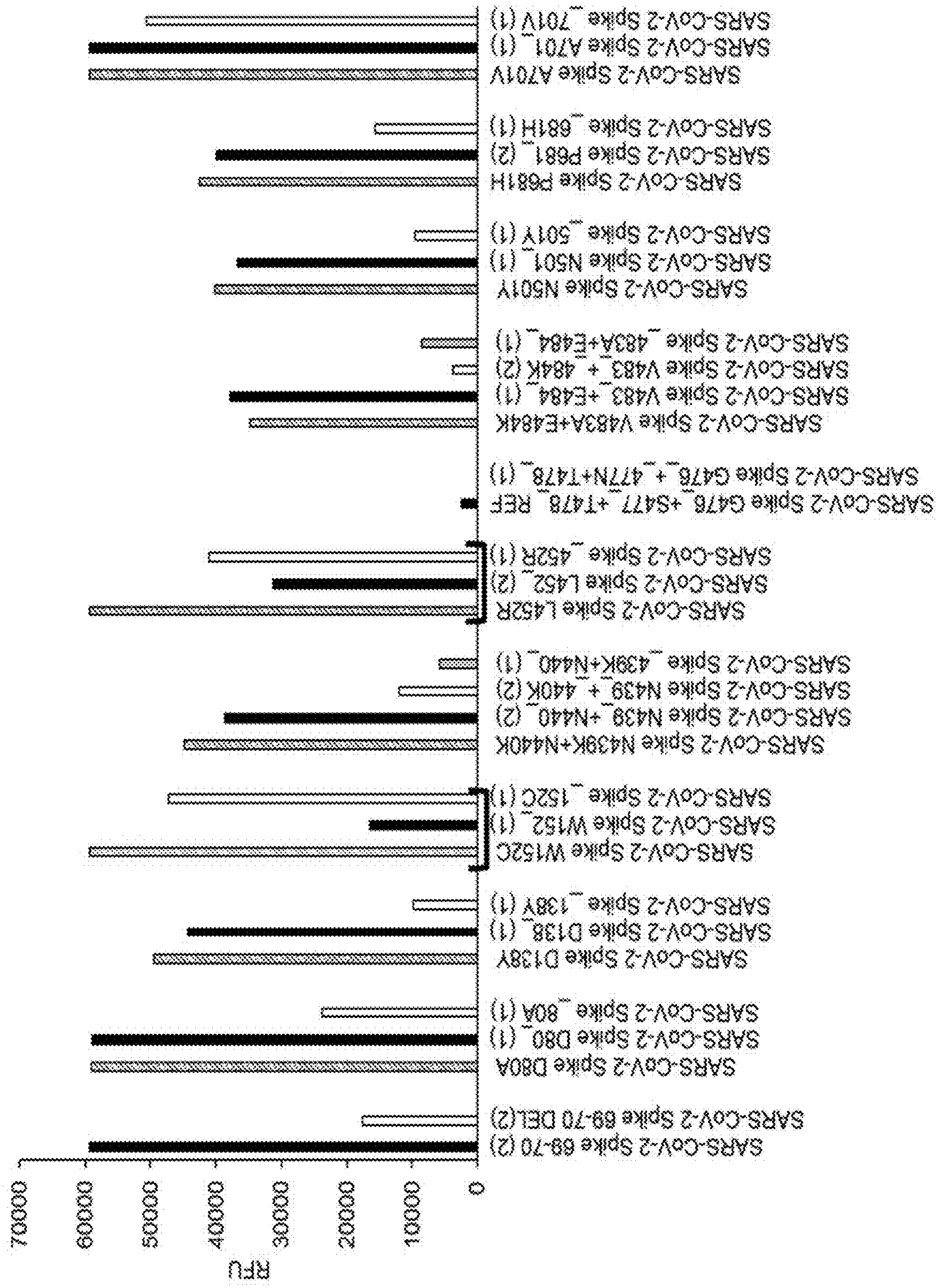
Figure 18C:
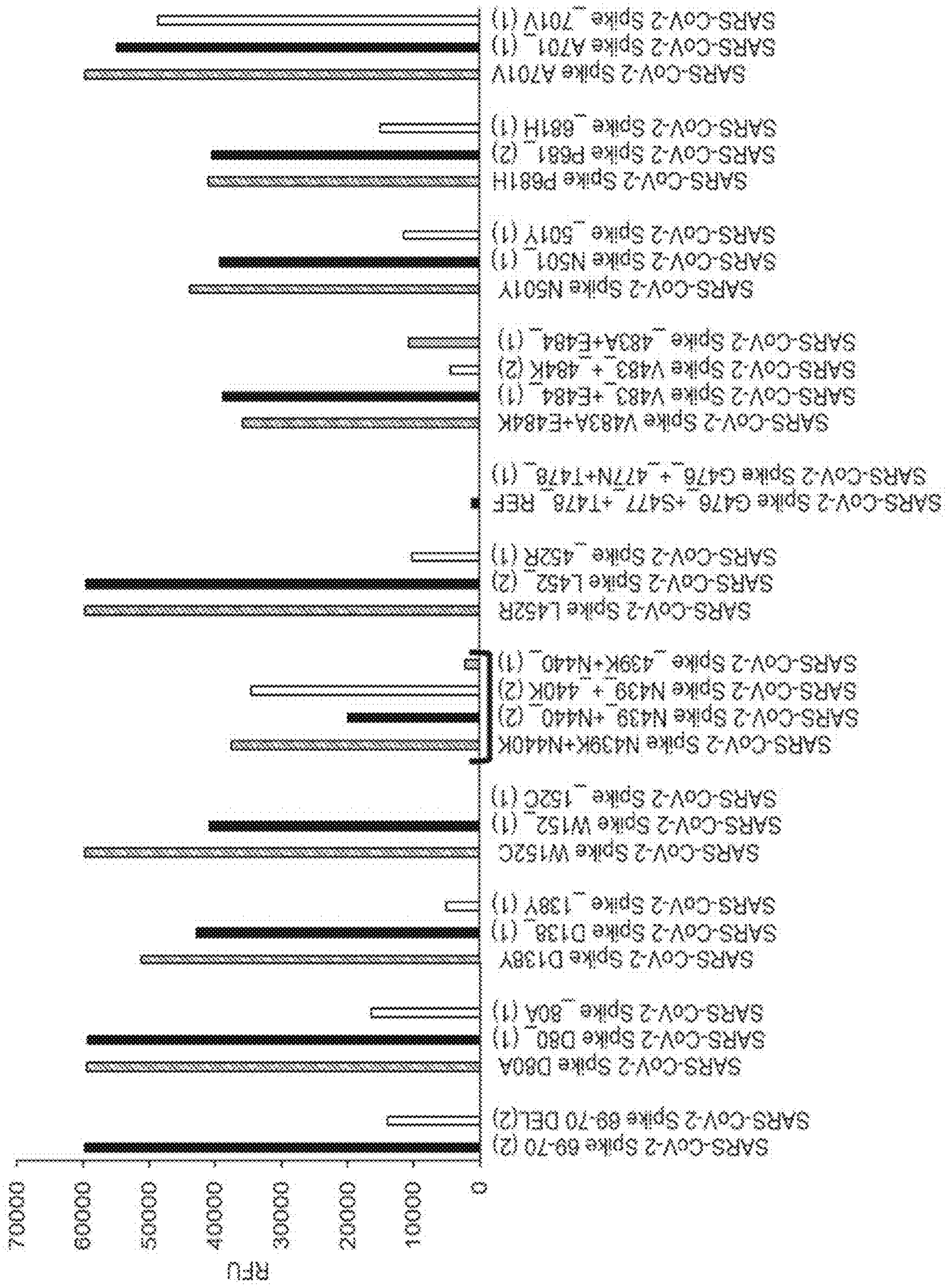

| Probe | Wild Type | Mutant Type | Confidence |
|---|---|---|---|
| Pattern consistent with | S Africa (B.1.351) Reference FIG. 18B HYBRIDIZED PROBES | | |
| H/V69_ | ON | | 100.00% |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| | UNHYBRIDIZED PROBES | | |
| _484K | | OFF | 100.00% |
| _501Y | | OFF | 99.80% |
| Pattern consistent with | California (B.1.429/427) Reference FIG. 18C HYBRIDIZED PROBES | | |
| H/V69_ | ON | | 100.00% |
| D80_ | ON | | 100.00% |
| D138_ | ON | | 100.00% |
| W152_ | ON | | 100.00% |
| N439_ | ON | | 100.00% |
| _440K | | ON | 100.00% |
| L452_ | ON | | 100.00% |
| E484_ | ON | | 100.00% |
| N501_ | ON | | 100.00% |
| P681_ | ON | | 100.00% |
| A701_ | ON | | 100.00% |

TABLE 21-continued

DETECTX-Cv analysis of synthetic Clade variant standards at TriCore

Figure 18D:
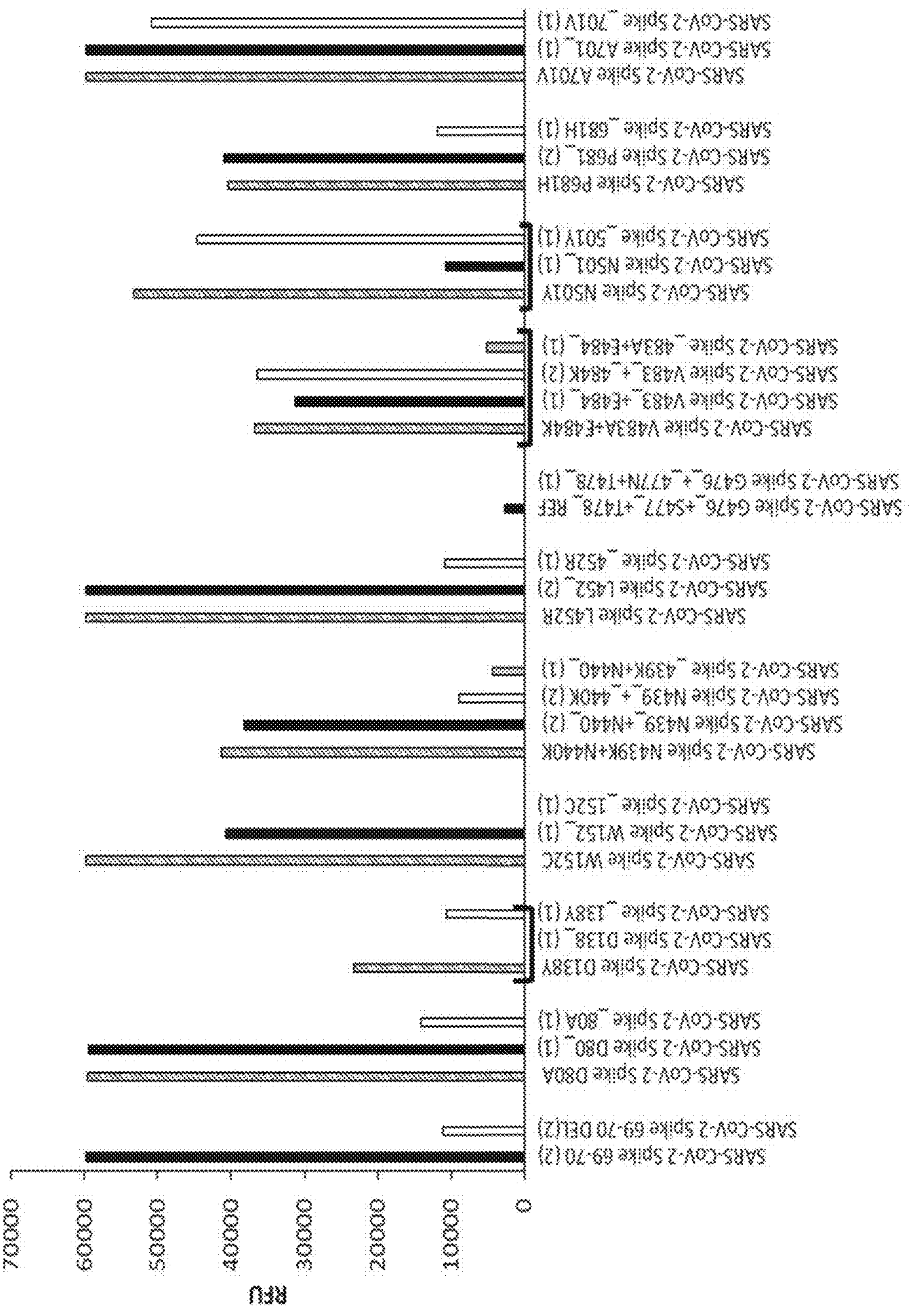
Figure 18E:
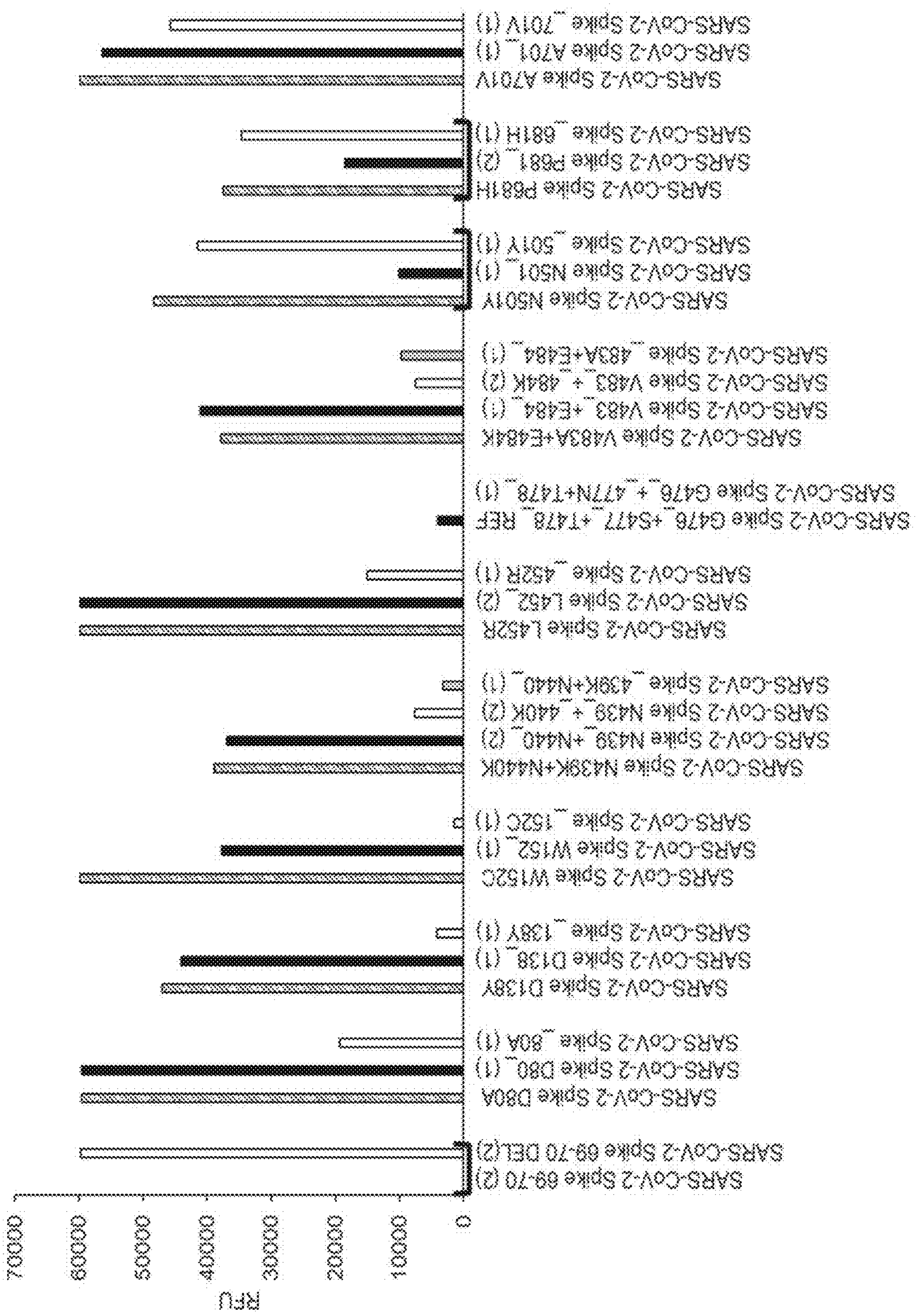

| Probe | Wild Type | Mutant Type | Confidence |
|---|---|---|---|
| UNHYBRIDIZED PROBES | | | |
| _152C | | OFF | 98.80% |
| _484K | | OFF | 100.00% |
| _501Y | | OFF | 98.20% |
| Pattern consistent with | India (N440K) | | |
| Reference FIG. 18D | | | |
| HYBRIDIZED PROBES | | | |
| H/V69_ | ON | | 100.00% |
| D80_ | ON | | 100.00% |
| _138Y | | ON | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| _501Y | | ON | 100.00% |
| P681_ | ON | | 100.00% |
| A701_ | ON | | 100.00% |
| UNHYBRIDIZED PROBES | | | |
| D138_ | OFF | | 100.00% |
| _152C | | OFF | 98.80% |
| Pattern consistent with | Brazil (P1) | | |
| Reference FIG. 18E | | | |
| HYBRIDIZED PROBES | | | |
| _69(del) | | ON | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| _501Y | | ON | 100.00% |
| _681H | | ON | 100.00% |
| A701_ | ON | | 100.00% |
| UNHYBRIDIZED PROBES | | | |
| H/V69_ | OFF | | 100.00% |
| _484K | | OFF | 100.00% |
| Pattern consistent with | UK (B.1.1.7) | | |

TABLE 22

Hybridization plate map for 28 SARS-CoV-2 positive clinical samples

| | 3 | 4 | 5 | 6 |
|---|---|---|---|---|
| A | Sample 1 | Sample 9 | Sample 17 | Sample 25 |
| B | Sample 2 | Sample 10 | Sample 18 | Sample 26 |
| C | Sample 3 | Sample 11 | Sample 19 | Sample 27 |
| D | Sample 4 | Sample 12 | Sample 20 | Sample 28 |
| E | Sample 5 | Sample 13 | Sample 21 | |
| F | Sample 6 | Sample 14 | Sample 22 | |
| G | Sample 7 | Sample 15 | Sample 23 | |
| H | Sample 8 | Sample 16 | Sample 24 | |

DETECTX-Cv Analysis of Clinical Positive Samples Performed at Tricore

The Biomerieux EASYMAG® Magnetic Bead platform (bioMérieux, St. Louis, Mo.) was used to extract Covid-19 RNA from 28 clinical positive (NP-VTM) samples (positivity previously determined by Cobas 6800 analysis). The extracted RNA (5 (L) was processed using the DETECTX-Cv method. Table 22 shows a plate map for 28 SARS-CoV-2 positive clinical samples. The PCR recipe and cycling conditions were as described in Table 20.

Results

FIGS. 19A-19K and Table 23 show the results of the DETECTX-Cv analysis for the clinical samples. It was determined that 68% (19/28) of samples generated data that passed QA/QC in terms of Universal Probe signal strength and were therefore fit for manual or autonomous Augury clade calls. These data thus demonstrate that high quality DETECTX-Cv data is obtainable with minimal training on clinical positive samples.

TABLE 23

DETECTX-Cv analysis of clinical positive samples performed at TriCore

Figure 19A:
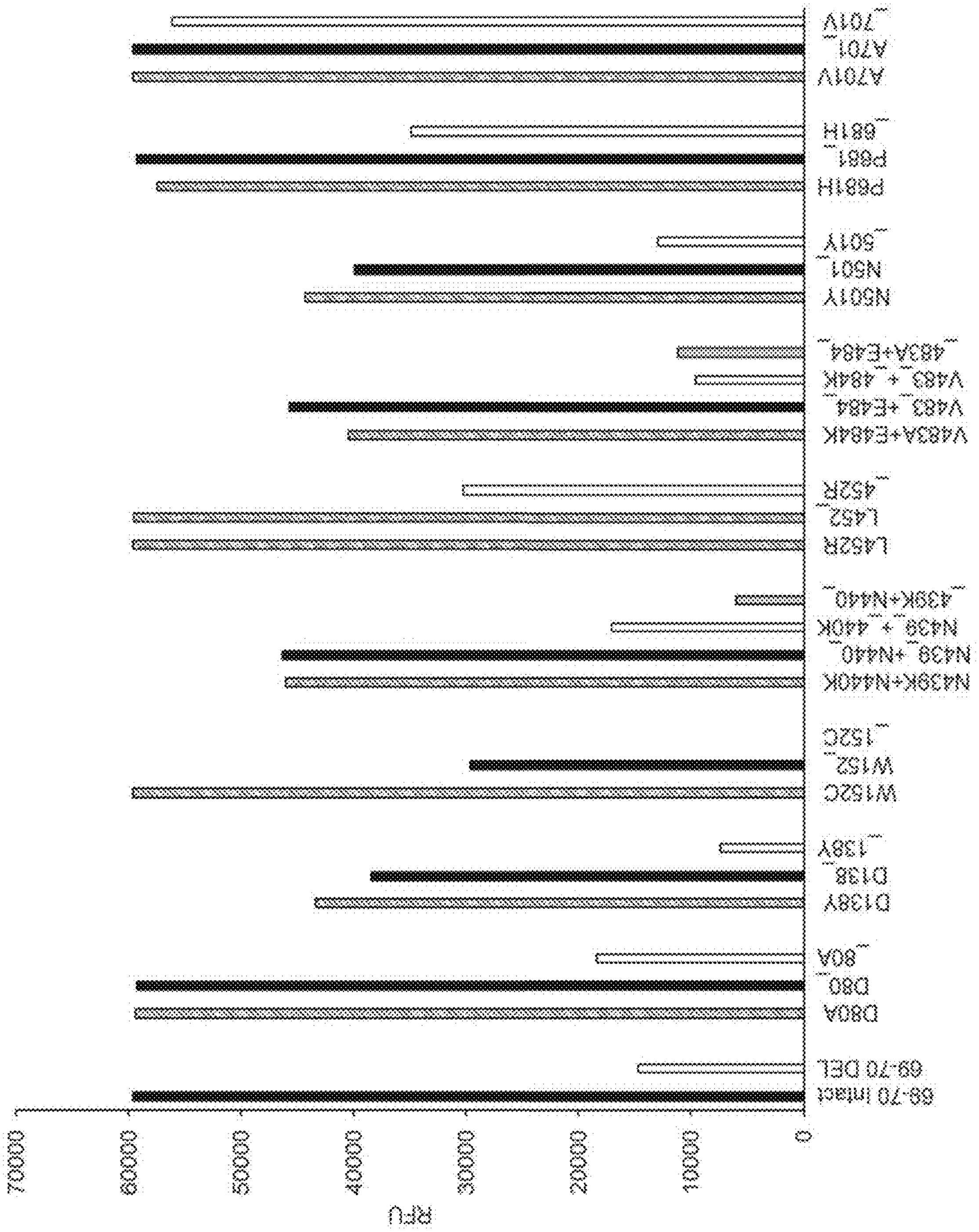
FIGS. 19A-19K show representative data for DETECTX-Cv analysis of clinical positive samples performed at TriCore.
Figure 19B:
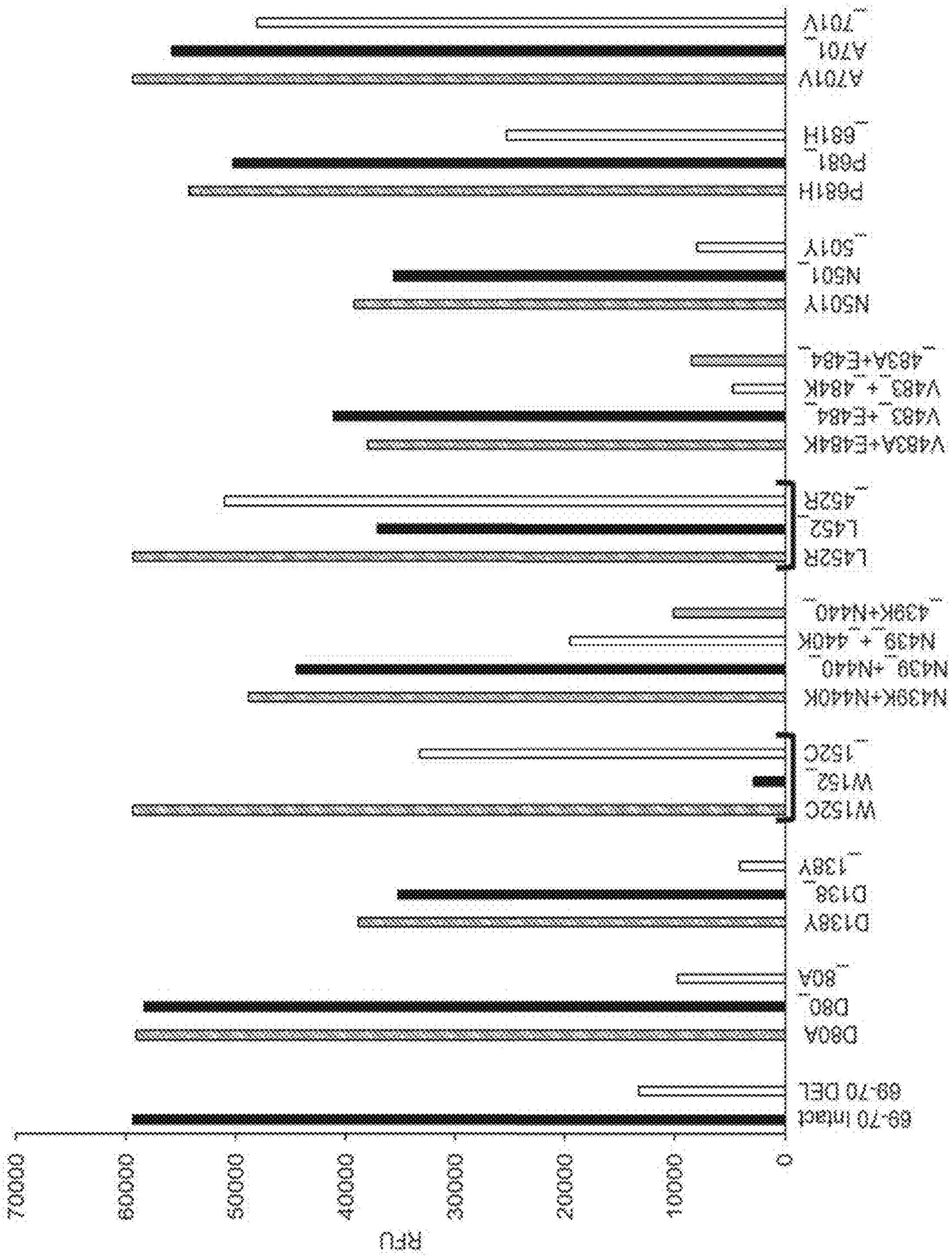
Figure 19C:
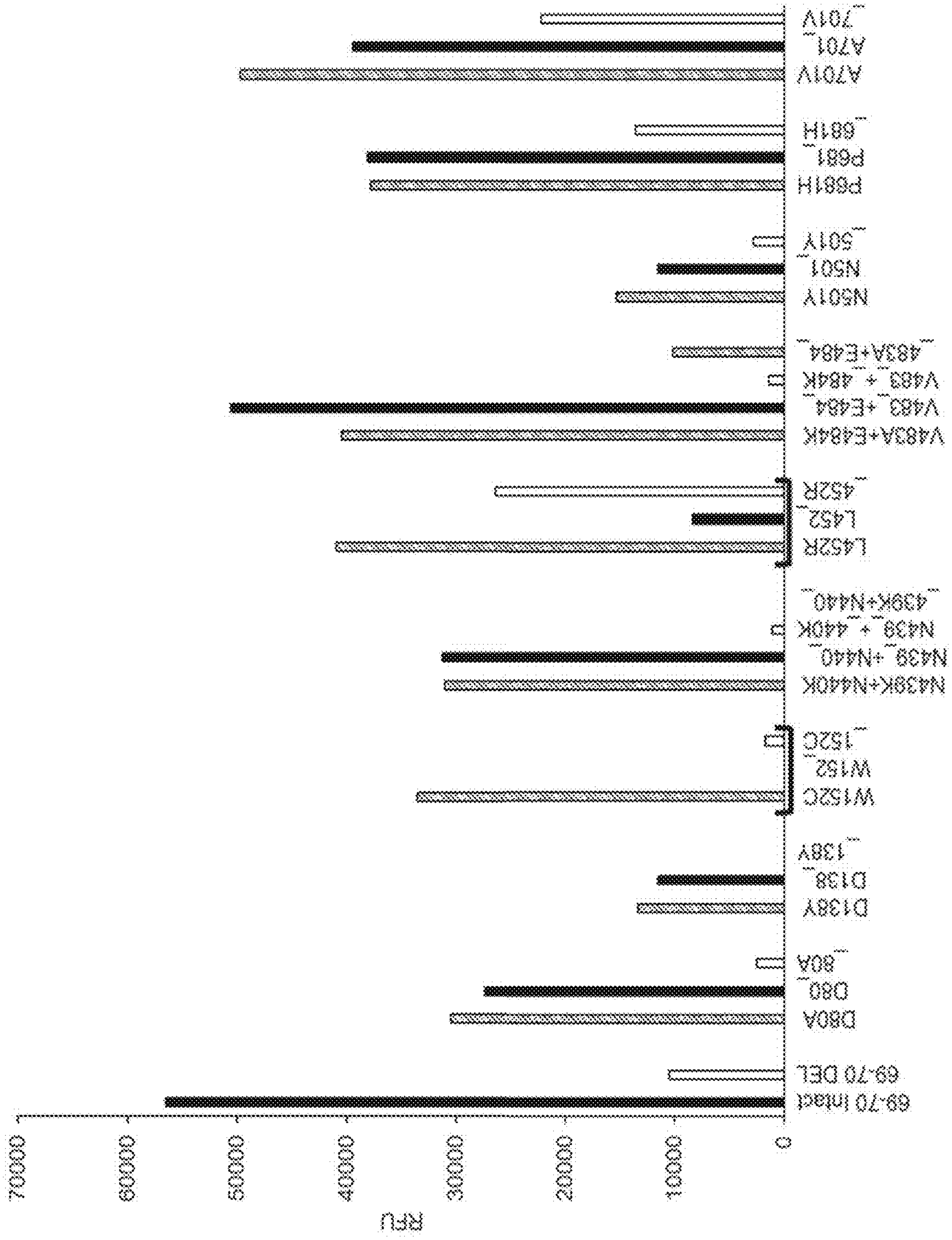
Figure 19D:
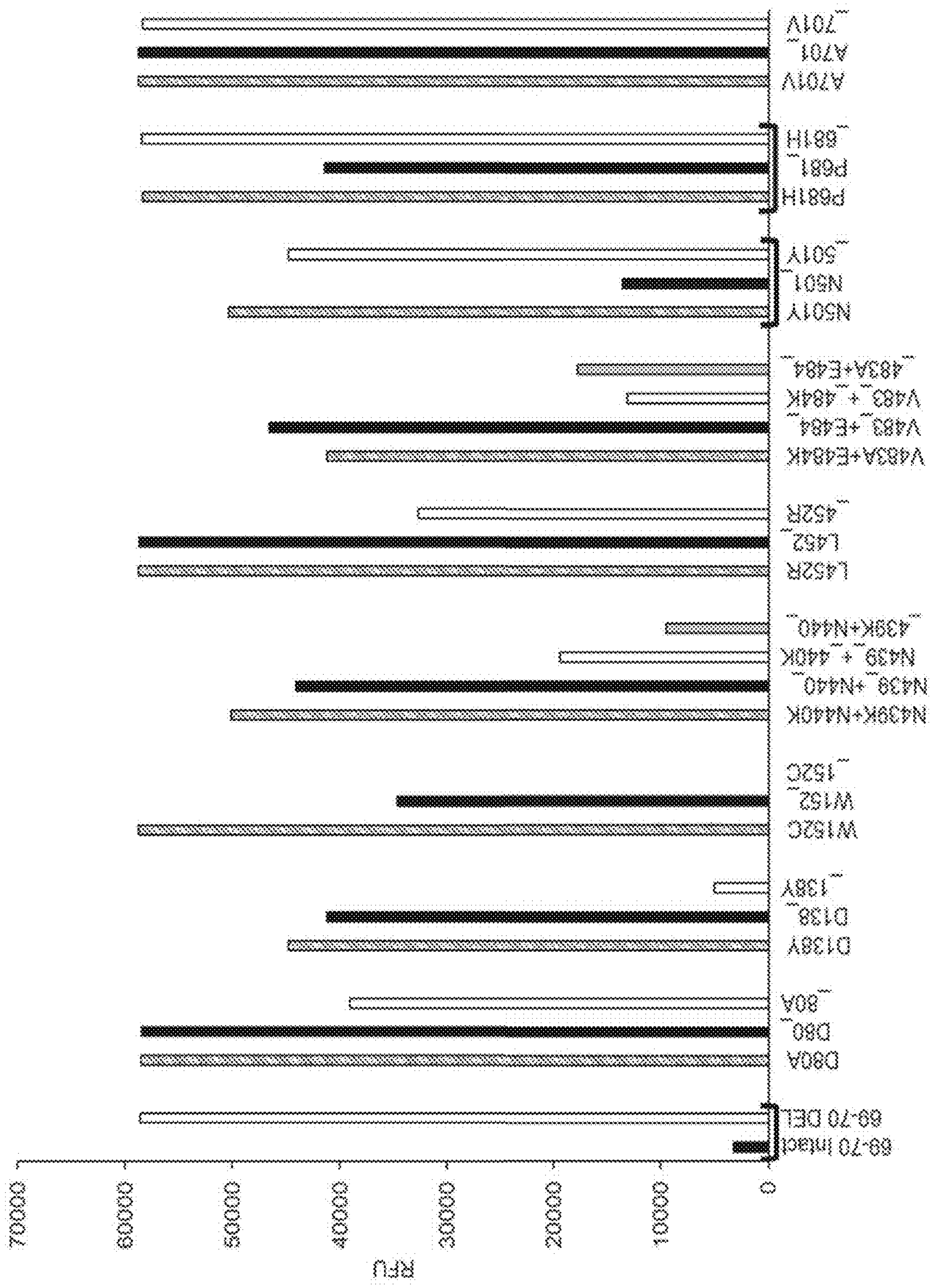
Figure 19E:
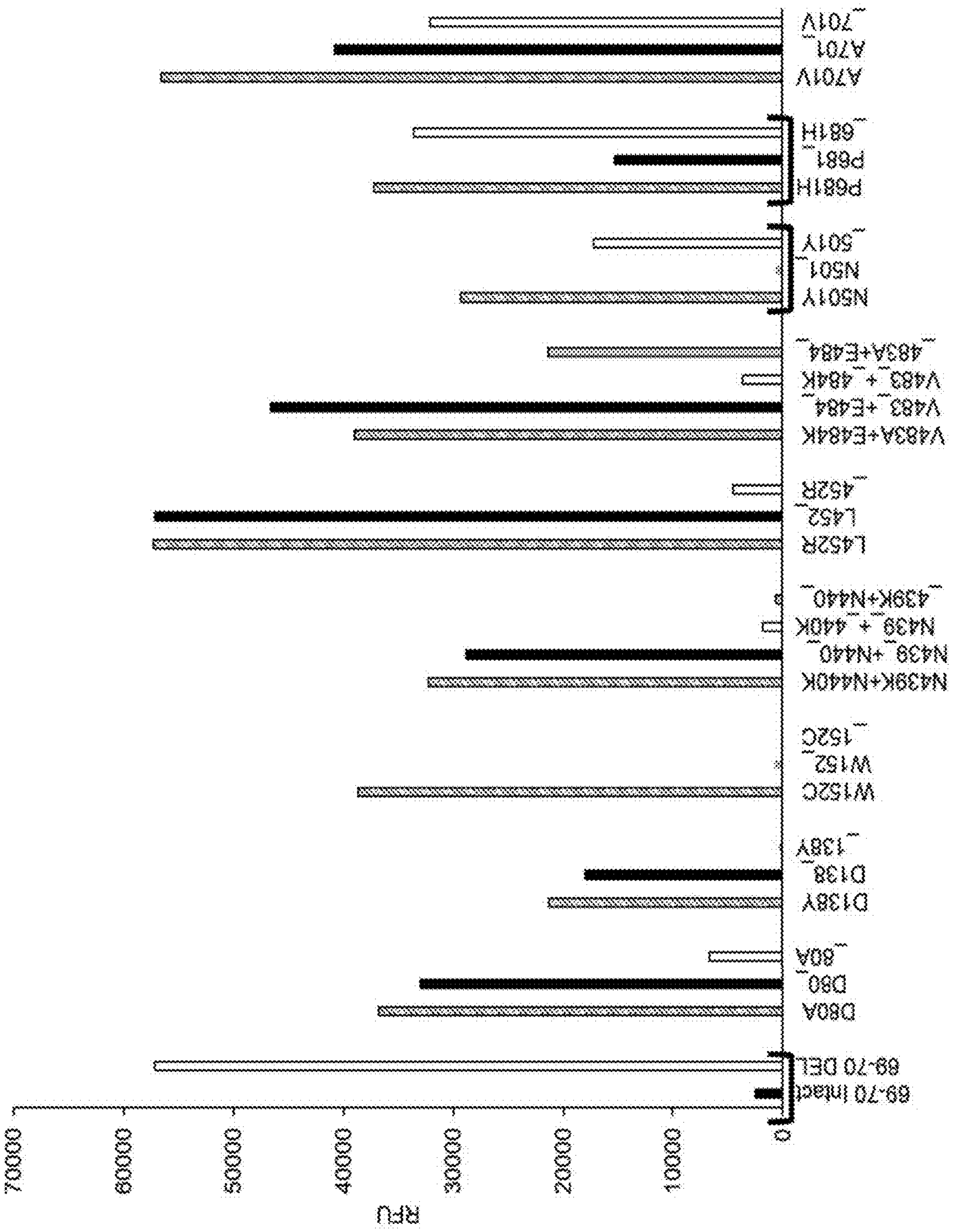
Figure 19F:
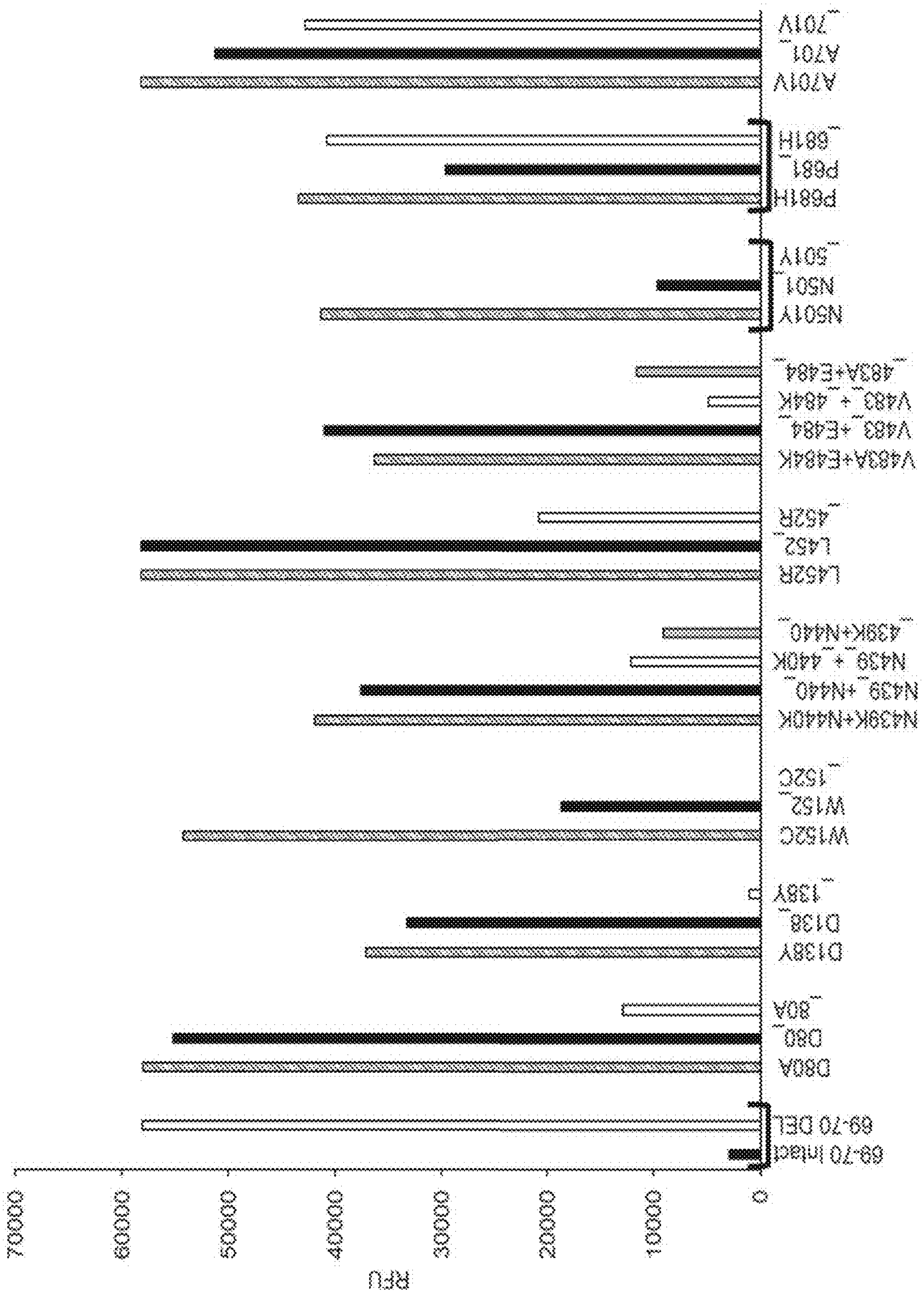
Figure 19G:
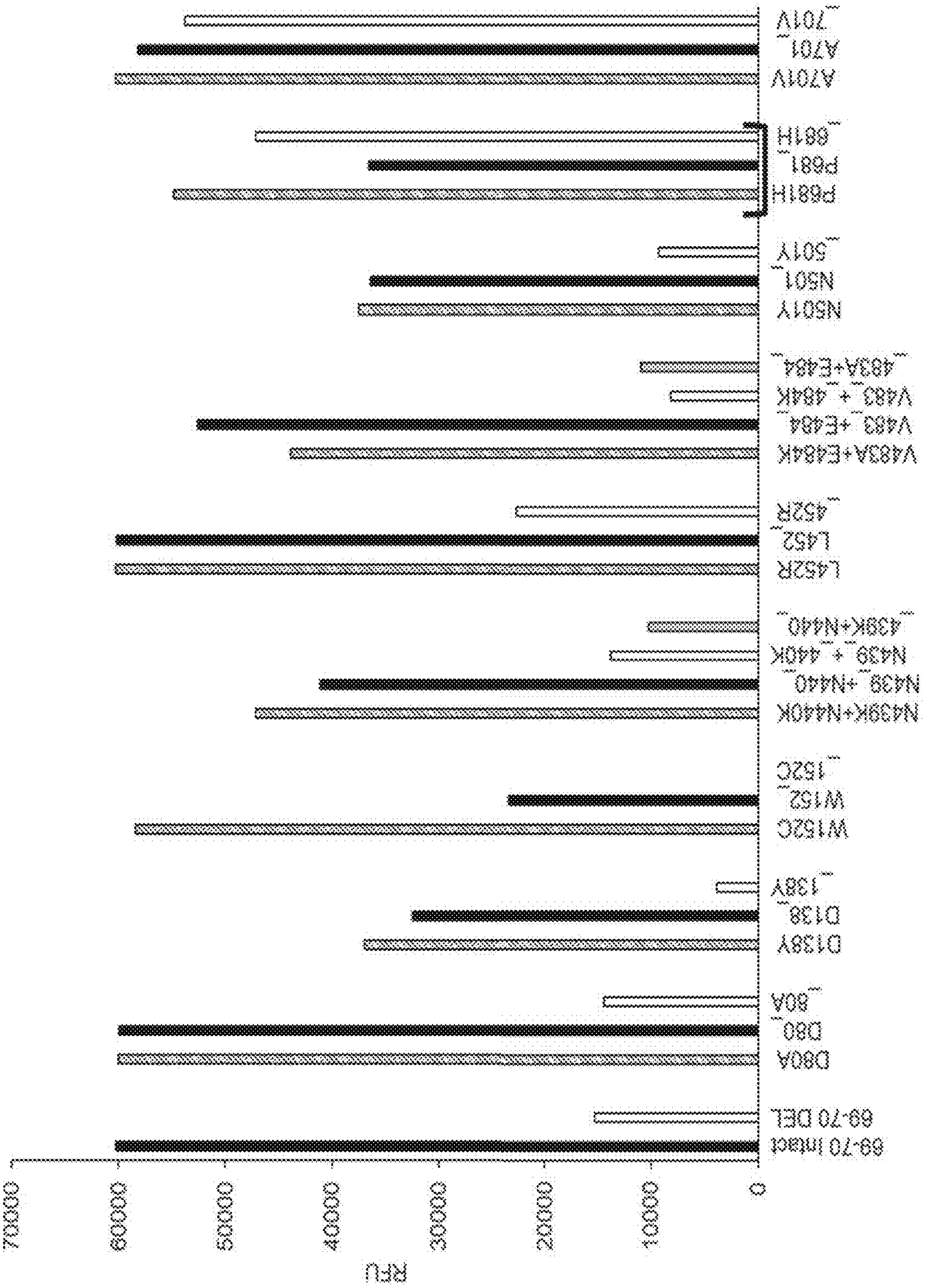
Figure 19H:
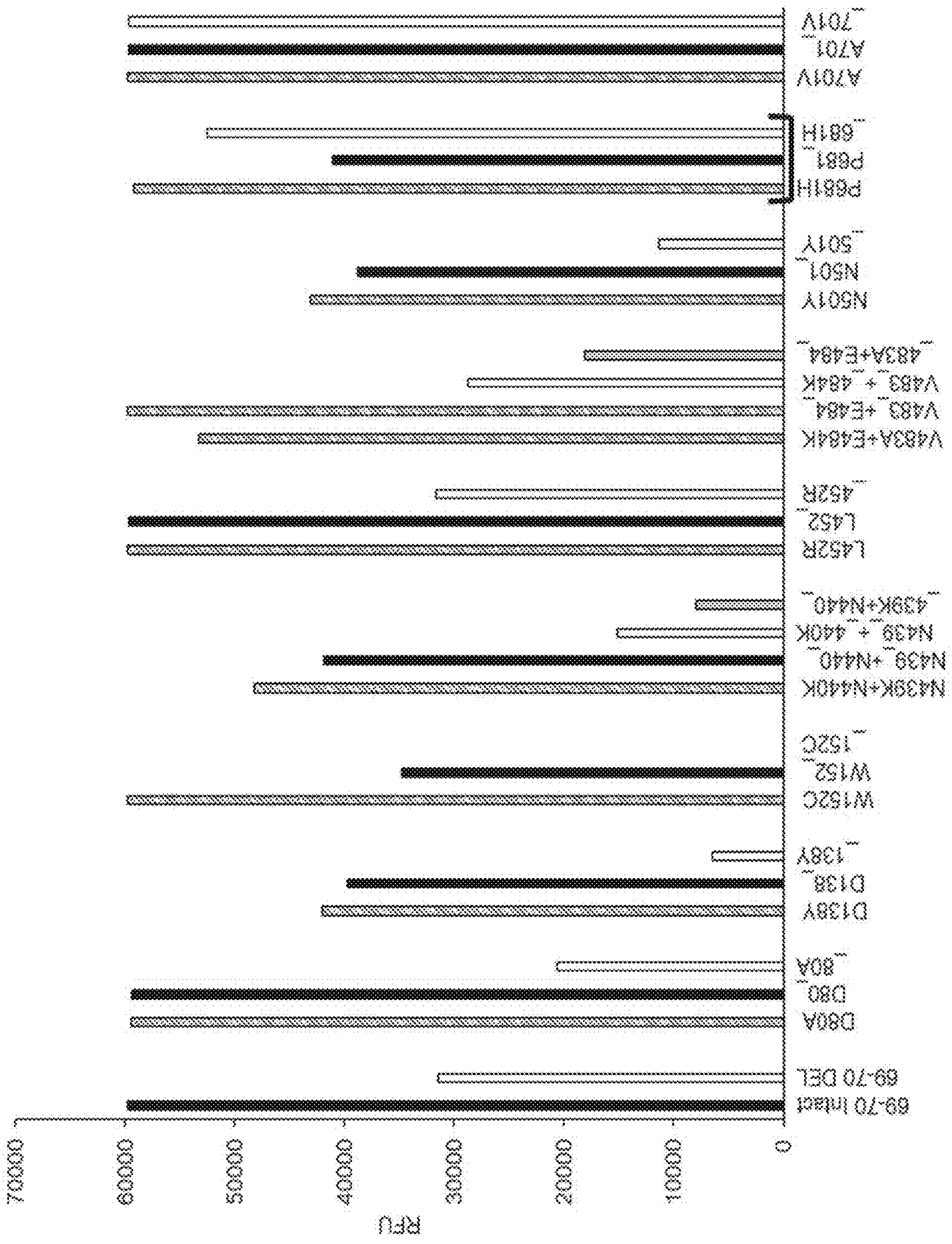
Figure 19I:
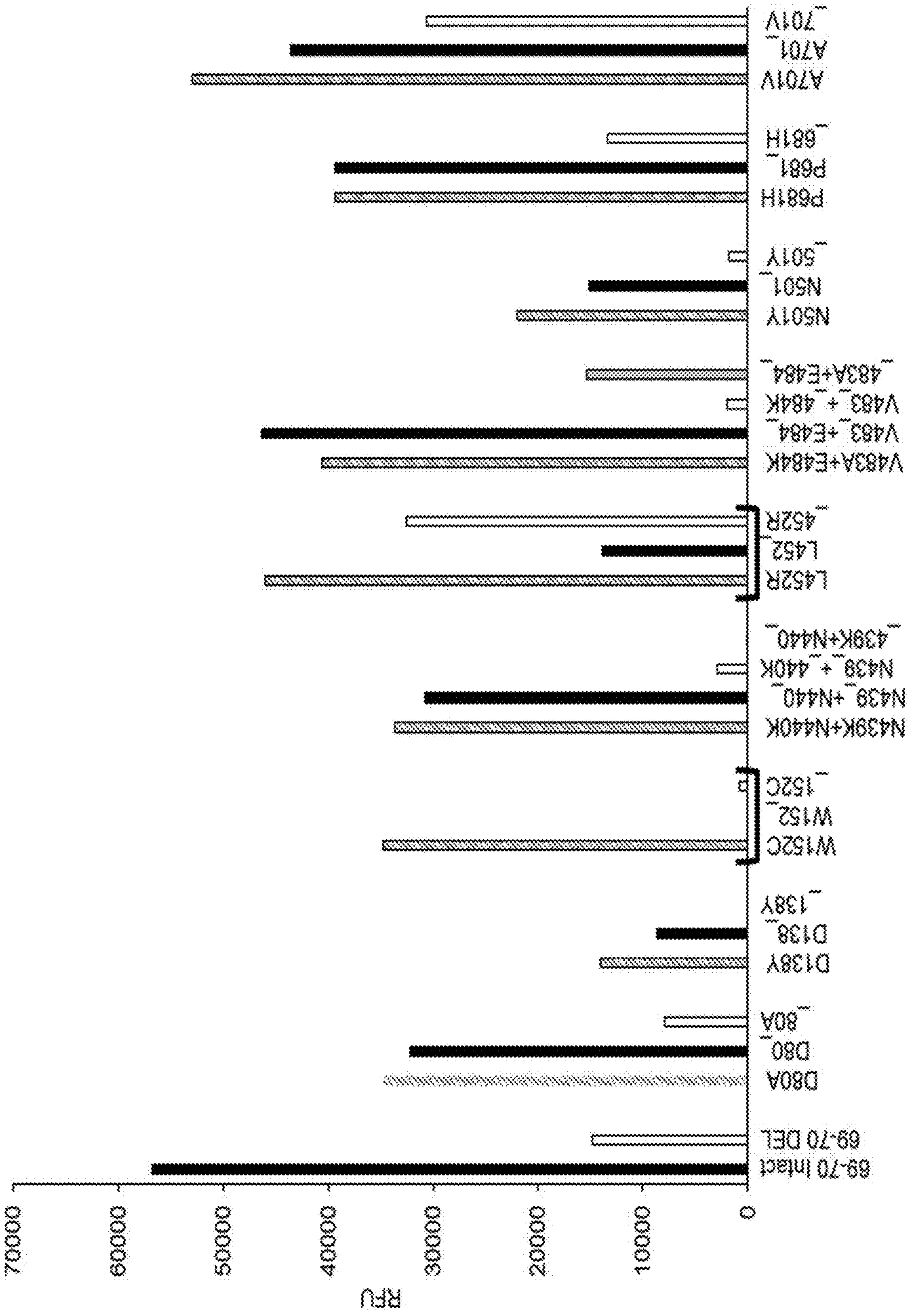
Figure 19J:
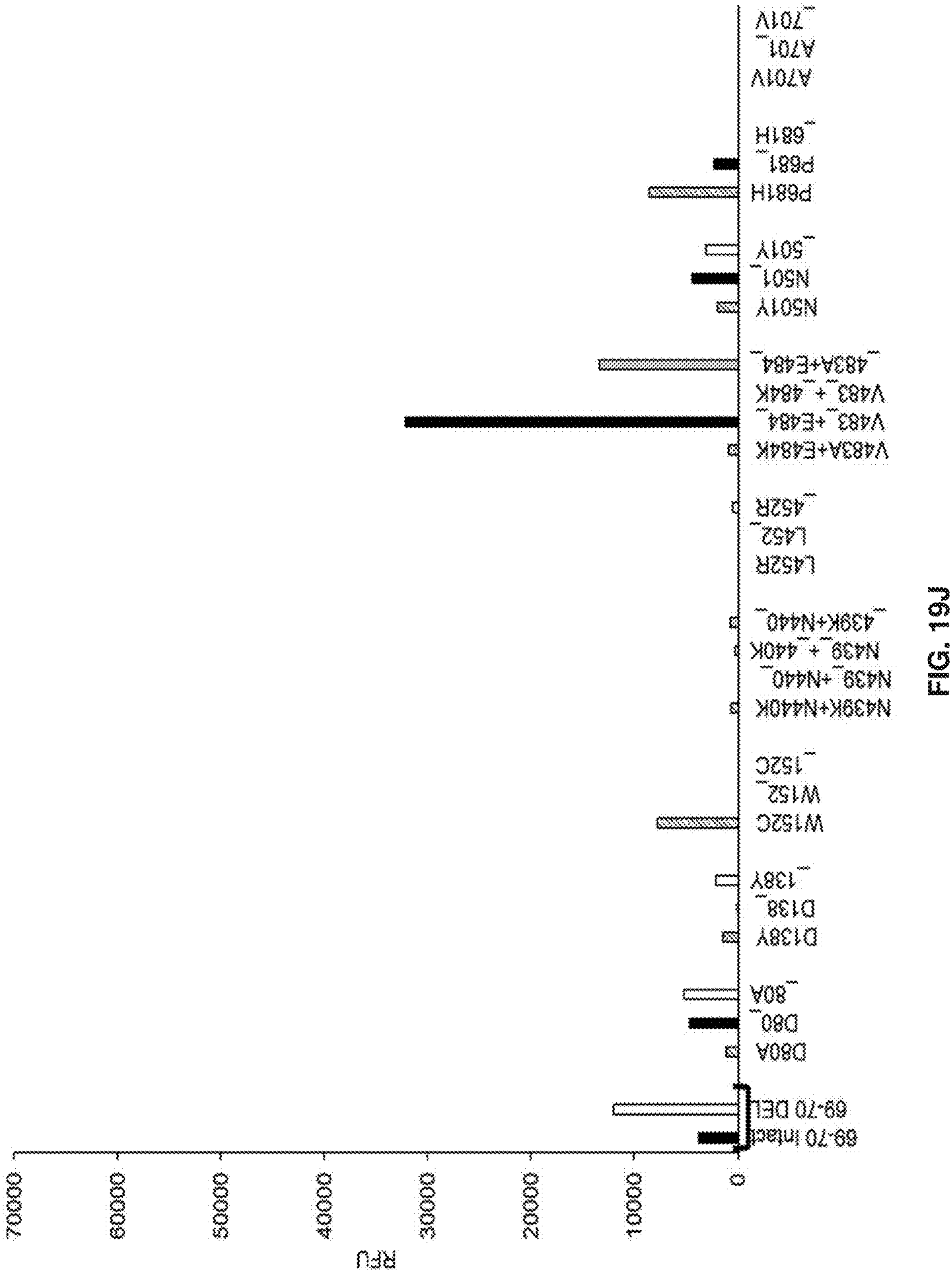

| Probe | Wild Type | Mutant Type | Confi-dence |
|---|---|---|---|
| Reference FIG. 19A TriCore Sample 2-B | | | |
| HYBRIDIZED PROBES | | | |
| H/V69_ | ON | | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _152C | | OFF | 98.80% |
| _484K | | OFF | 100.00% |
| _501Y | | OFF | 93.30% |
| Pattern consistent with: | Wuhan Progenitor | | |
| Reference FIG. 19B TriCore Sample 7-B | | | |
| HYBRIDIZED PROBES | | | |
| H/V69_ | ON | | 100.00% |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _80A | | OFF | 100.00% |
| _484K | | OFF | 100.00% |
| _501Y | | OFF | 100.00% |
| Pattern consistent with: | California (B.1.429/427) | | |
| Reference FIG. 19C TriCore Sample 9-B | | | |
| HYBRIDIZED PROBES | | | |
| H/V69_ | ON | | 100.00% |
| D80_ | ON | | 100.00% |
| D138_ | ON | | 100.00% |
| N439_ | ON | | 100.00% |
| N440_ | ON | | 100.00% |
| _452R | | ON | 100.00% |
| E484_ | ON | | 100.00% |
| N501_ | ON | | 69.70% |
| P681_ | ON | | 100.00% |
| A701_ | ON | | 100.00% |
| UNHYBRIDIZED PROBES | | | |
| _80A | | OFF | 100.00% |
| _138Y | | OFF | 100.00% |
| W152_ | OFF | | 100.00% |
| N439_/_440K | | OFF | 100.00% |
| L452_ | OFF | | 97.40% |
| _484K | | OFF | 100.00% |
| _501Y | | OFF | 100.00% |
| _701V | | OFF | 95.40% |

TABLE 23-continued

DETECTX-Cv analysis of clinical positive samples performed at TriCore

| Probe | Wild Type | Mutant Type | Confidence |
|---|---|---|---|
| Pattern consistent with: California (B.1.429/427) | | | |
| Reference FIG. 19D TriCore Sample 17-B | | | |
| HYBRIDIZED PROBES | | | |
| _69(del) | | ON | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| _501Y | | ON | 100.00% |
| _681H | | ON | 100.00% |
| A701_ | ON | | 100.00% |
| UNHYBRIDIZED PROBES | | | |
| H/V69_ | OFF | | 100.00% |
| _152C | | OFF | 98.80% |
| _484K | | OFF | 100.00% |
| Pattern consistent with: UK (B.1.1.7) | | | |
| Reference FIG. 19E TriCore Sample 18-B | | | |
| HYBRIDIZED PROBES | | | |
| _69(del) | | ON | 100.00% |
| D80_ | ON | | 100.00% |
| D138_ | ON | | 100.00% |
| N439_ | ON | | 100.00% |
| N440_ | ON | | 100.00% |
| L452_ | ON | | 100.00% |
| E484_ | ON | | 100.00% |
| 501Y | | ON | 100.00% |
| 681H | | ON | 100.00% |
| A701_ | ON | | 100.00% |
| UNHYBRIDIZED PROBES | | | |
| H/V69_ | OFF | | 100.00% |
| _80A | | OFF | 100.00% |
| _138Y | | OFF | 100.00% |
| _152C | | OFF | 98.80% |
| W152_ | OFF | | 98.30% |
| N439_/_440K | | OFF | 100.00% |
| _484K | | OFF | 100.00% |
| N501_ | OFF | | 100.00% |
| Pattern consistent with: UK ( B.1.1.7) | | | |
| Reference FIG. 19F TriCore Sample 21-B | | | |
| HYBRIDIZED PROBES | | | |
| _69(del) | | ON | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| _501Y | | ON | 100.00% |
| _681H | | ON | 100.00% |
| A701_ | ON | | 100.00% |
| UNHYBRIDIZED PROBES | | | |
| H/V69_ | OFF | | 100.00% |
| _138Y | | OFF | 100.00% |
| _152C | | OFF | 98.80% |
| _484K | | OFF | 100.00% |
| Pattern consistent with: UK (B.1.1.7) | | | |
| Reference FIG. 19G TriCore Sample 22-B | | | |
| HYBRIDIZED PROBES | | | |
| H/V69_ | ON | | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |

TABLE 23-continued

DETECTX-Cv analysis of clinical positive samples performed at TriCore

| Probe | Wild Type | Mutant Type | Confidence |
|---|---|---|---|
| L452_ | ON | | 100.00% |
| E484_ | ON | | 100.00% |
| N501_ | ON | | 100.00% |
| _681H | | ON | 100.00% |
| A701_ | ON | | 100.00% |
| UNHYBRIDIZED PROBES | | | |
| _152C | | OFF | 98.80% |
| _484K | | OFF | 100.00% |
| _501Y | | OFF | 99.80% |
| Pattern consistent with: B.1.1.207 | | | |
| Reference FIG. 19H TriCore Sample 24-B | | | |
| HYBRIDIZED PROBES | | | |
| H/V69_ | ON | | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| _681H | | ON | 100.00% |
| A701_ | ON | | 100.00% |
| UNHYBRIDIZED PROBES | | | |
| _152C | | OFF | 97.60% |
| _501Y | | OFF | 98.60% |
| Pattern consistent with: B.1.1.207 | | | |
| Reference FIG. 191 TriCore Sample 27-B | | | |
| HYBRIDIZED PROBES | | | |
| H/V69_ | ON | | 100.00% |
| D80_ | ON | | 100.00% |
| D138_ | ON | | 100.00% |
| 152C | | ON | 85.40% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _80A | | OFF | 100.00% |
| _138Y | | OFF | 100.00% |
| _152C | | OFF | 69.40% |
| W152_ | OFF | | 100.00% |
| N439_/_440K | | OFF | 98.30% |
| _484K | | OFF | 100.00% |
| _501Y | | OFF | 100.00% |
| Pattern consistent with: California (B.1.429/427) | | | |
| Reference FIG. 19J TriCore Sample 1-B | | | |
| HYBRIDIZED PROBES | | | |
| _69(del) | | ON | 87.50% |
| UNHYBRIDIZED PROBES | | | |
| H/V69_ | OFF | | 99.70% |
| Pattern consistent with: | | | |
| 1 | UK (B.1.1.7) | | |
| 2 | B.1.525 | | |
| 3 | B.1.375 | | |
| 4 | Denmark | | |
| 5 | B.1.258 | | |

TABLE 23-continued

Figure 19K:
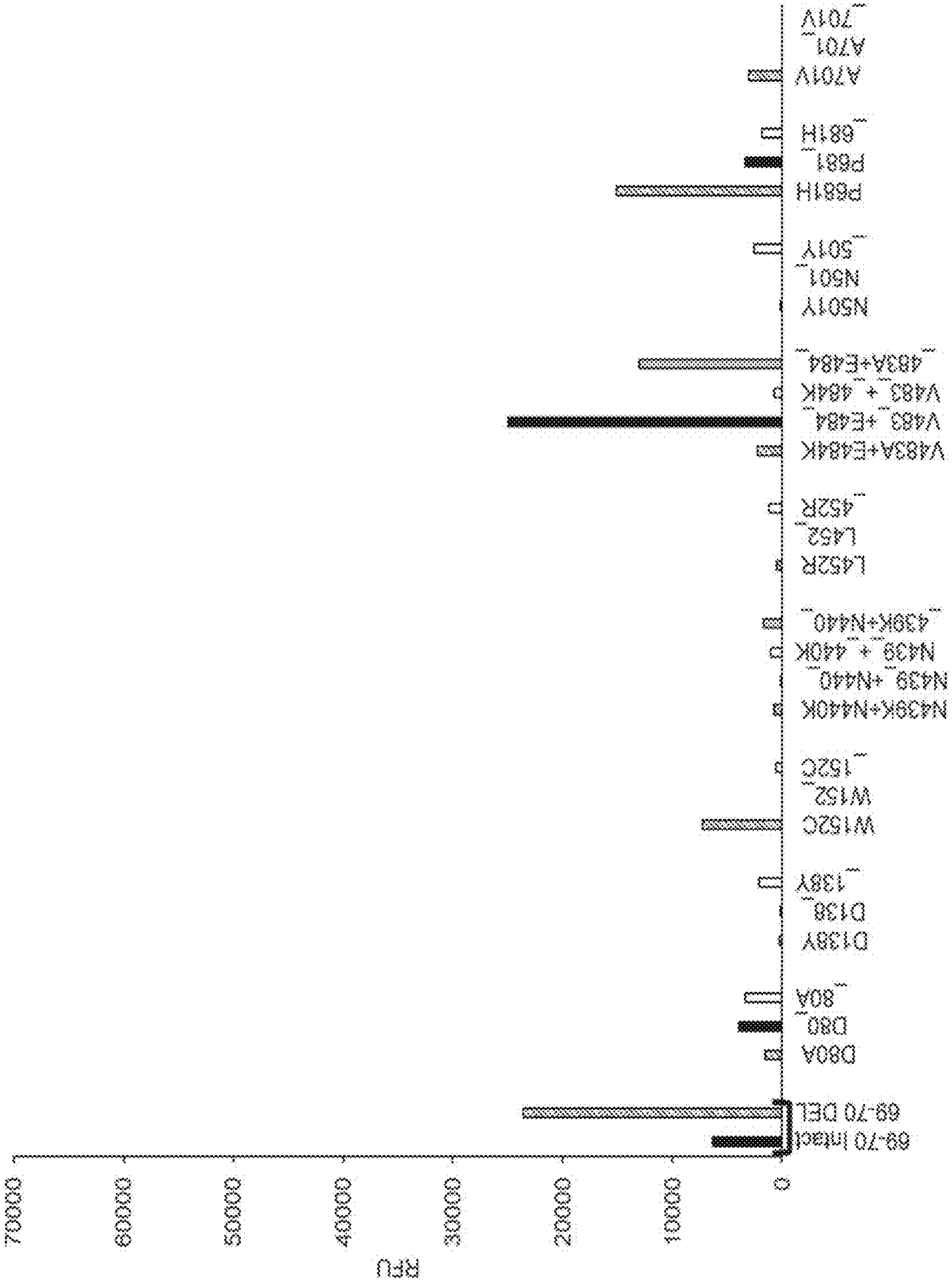

| DETECTX-Cv analysis of clinical positive samples performed at TriCore | | | |
|---|---|---|---|
| Probe | Wild Type | Mutant Type | Confi-dence |
| Reference FIG. 19K TriCore Sample 4-B | | | |
| START_WELL_20 | | | |
| SPECTMEN_FD | Sample #20 | | |
| HYBRIDIZED PROBES | | | |
| _69(del) | | ON | 100.00% |
| UNHYBRIDIZED PROBES | | | |
| Pattern consistent with: | NA | | |
| END_WELL_20 | | | |

DETECTX-Cv Analysis of TriCore Clinical Positive Samples at PathogenDx.

Sixty (60) clinical positive NP-VTM samples collected by TriCore were sent to PathogenDx for DETECTX-Cv analysis. RNA was extracted from these samples using the Zymo Magnetic Bead platform. The extracted RNA (5 (L) was processed using the DETECTX-Cv method. The PCR recipe and cycling conditions were as described in Table 20.

Results

FIGS. 20A-20J and Table 24 show the results of this analysis. It was determined that 65% (39/60) of these samples generated data which passed QC/QA in terms of signal strength and were thus fit for manual or autonomous Augury Clade calls. The data shows all NP-VTM specimens which passed QA/QC and which displayed nonstandard clade variants (other than Wuhan) and representative data (2) for which QA/QC were inadequate either due to low RNA concentration or degraded RNA in the sample.

TABLE 24

Figure 20A:
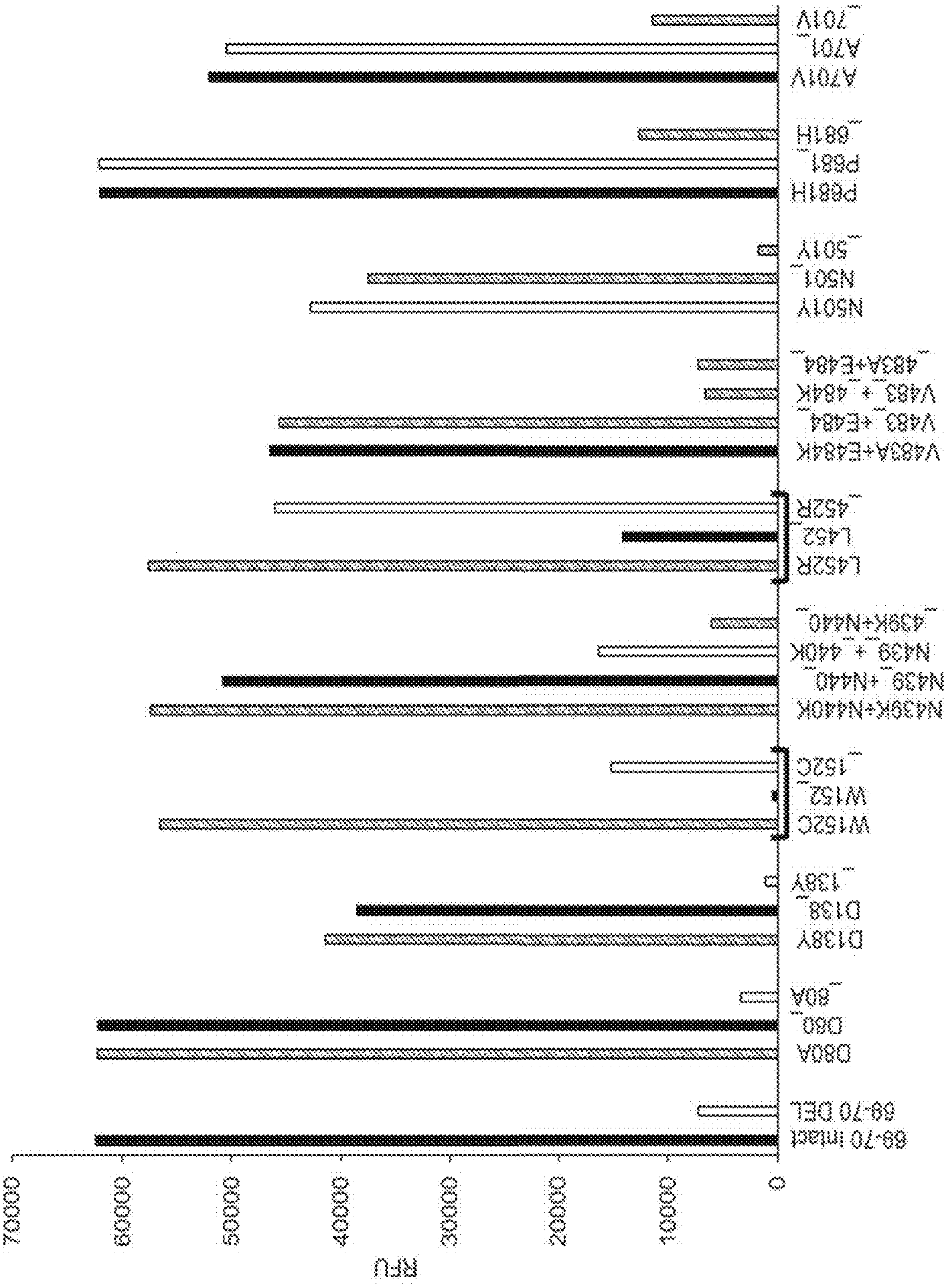
FIGS. 20A-20J show representative data for DETECTX-Cv analysis of clinical positive samples performed at PathogenDx.
Figure 20B:
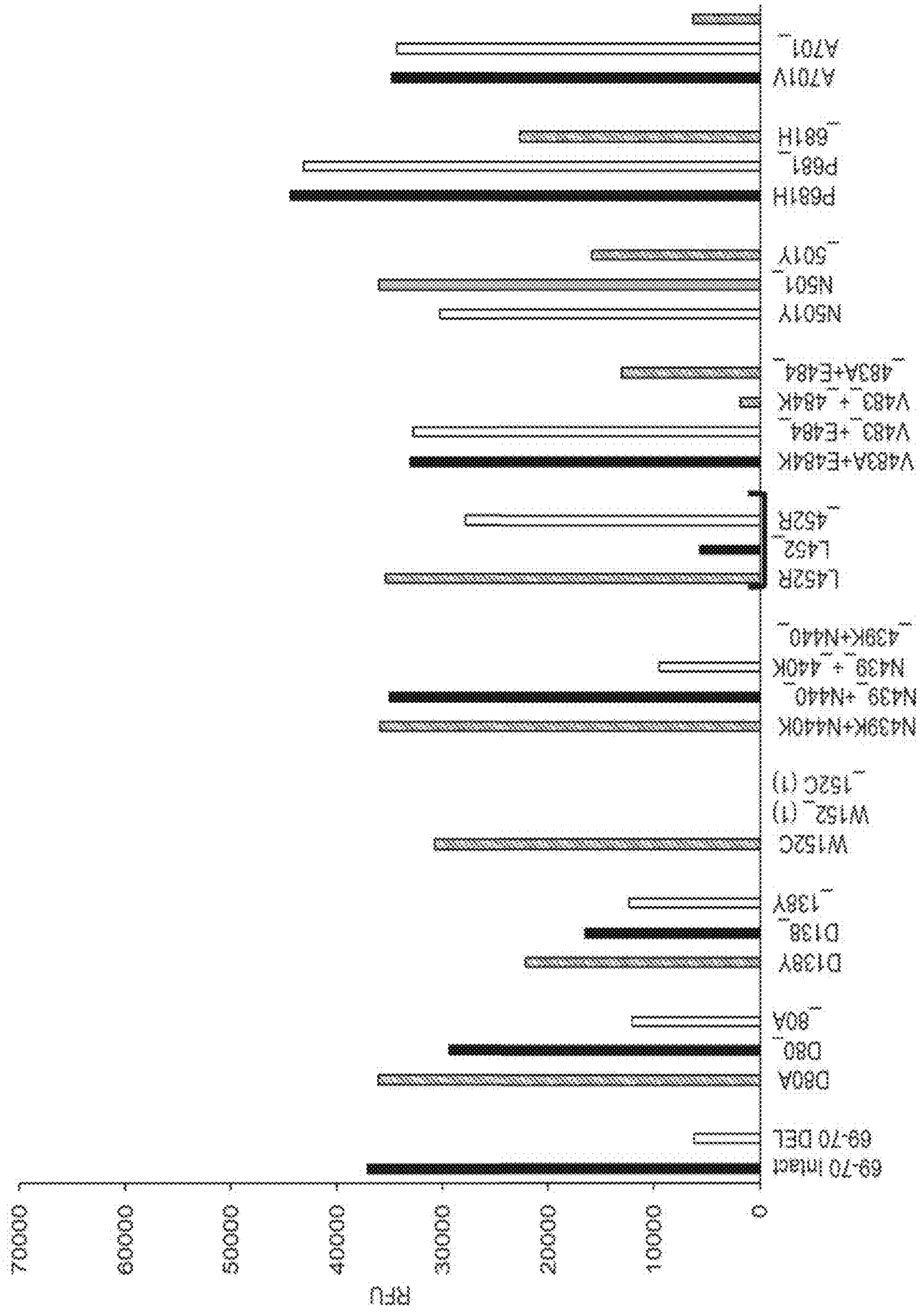

| DETECTX-Cv analysis of clinical positive samples performed at PathogenDx | | | |
|---|---|---|---|
| Probe | Wild Type | Mutant Type | Confidence |
| Reference FIG. 20A TriCore 238480-d Sample 1 | | | |
| HYBRIDIZED PROBES | | | |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| _138Y | | OFF | 100.00% |
| _152C | | OFF | 98.80% |
| _452R | | OFF | 98.00% |
| _484K | | OFF | 100.00% |
| _501Y | | OFF | 100.00% |
| _681H | | OFF | 87.00% |
| _701V | | OFF | 100.00% |
| Pattern consistent with: | Wuhan Progenitor | | |
| Reference FIG. 20B TriCore 238484-d Sample 4 | | | |
| HYBRIDIZED PROBES | | | |
| D80_ | ON | | 100.00% |
| D138_ | ON | | 100.00% |
| N439_ | ON | | 100.00% |

TABLE 24-continued

Figure 20C:
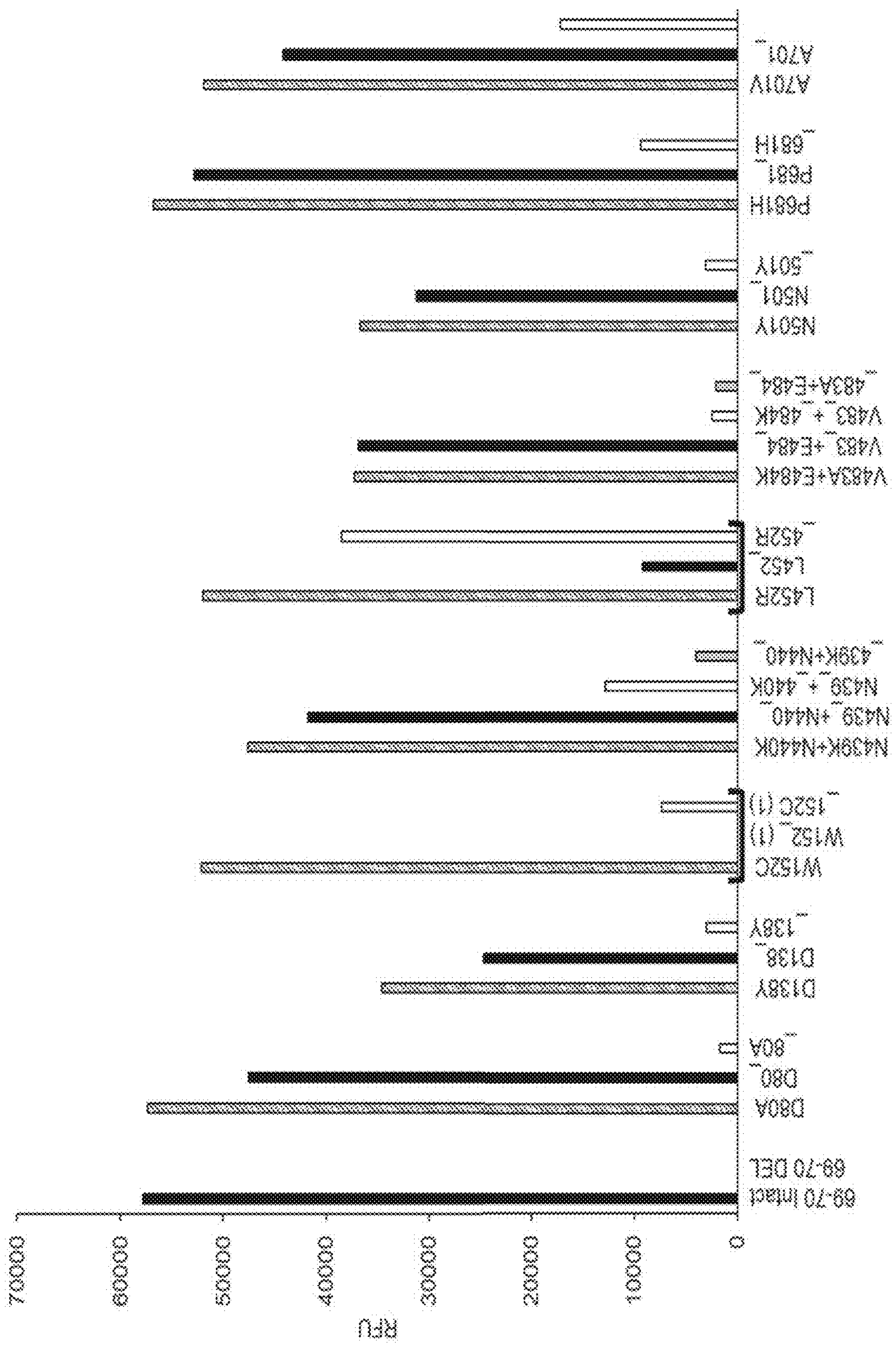
Figure 20D:
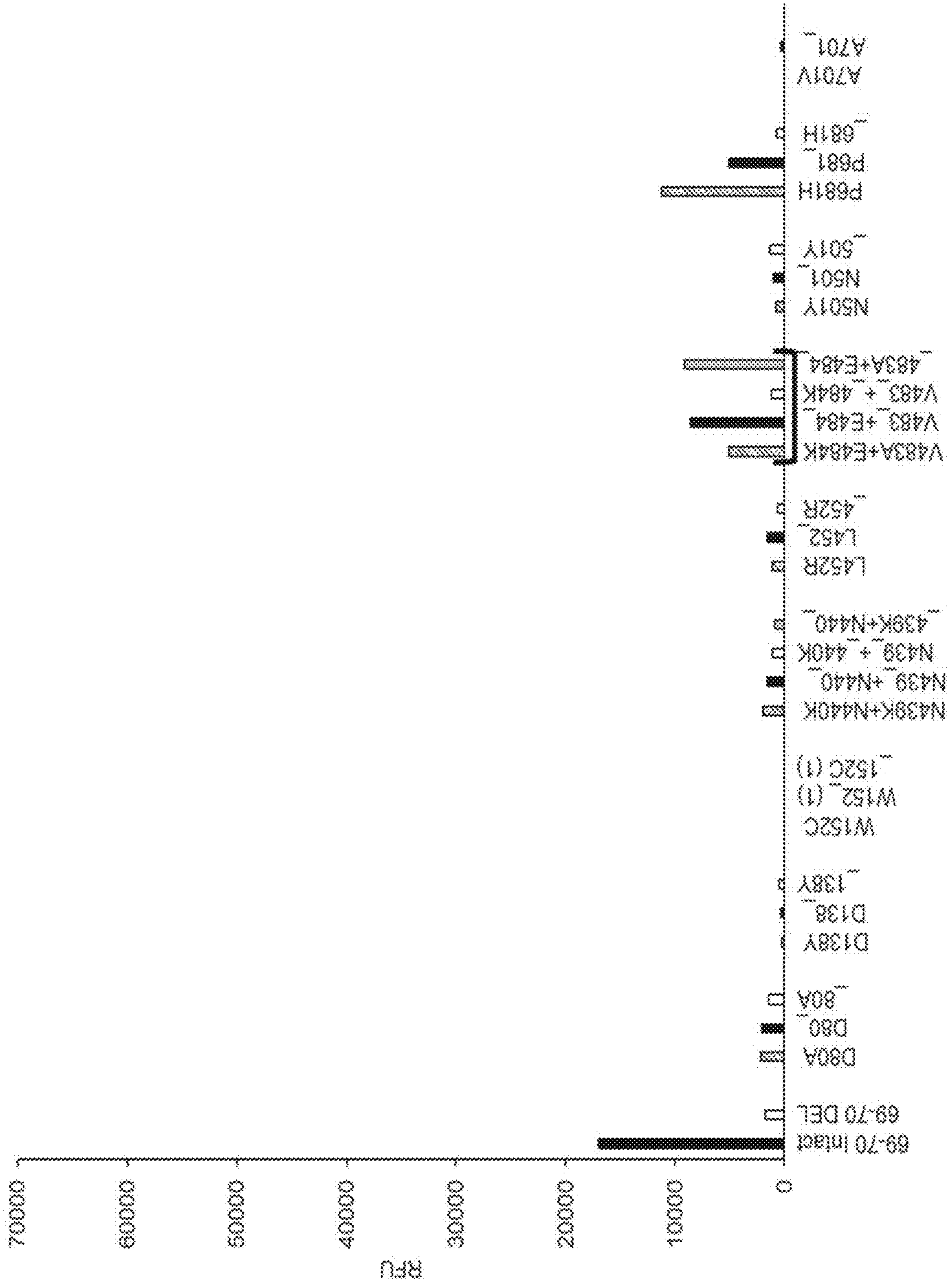
Figure 20E:
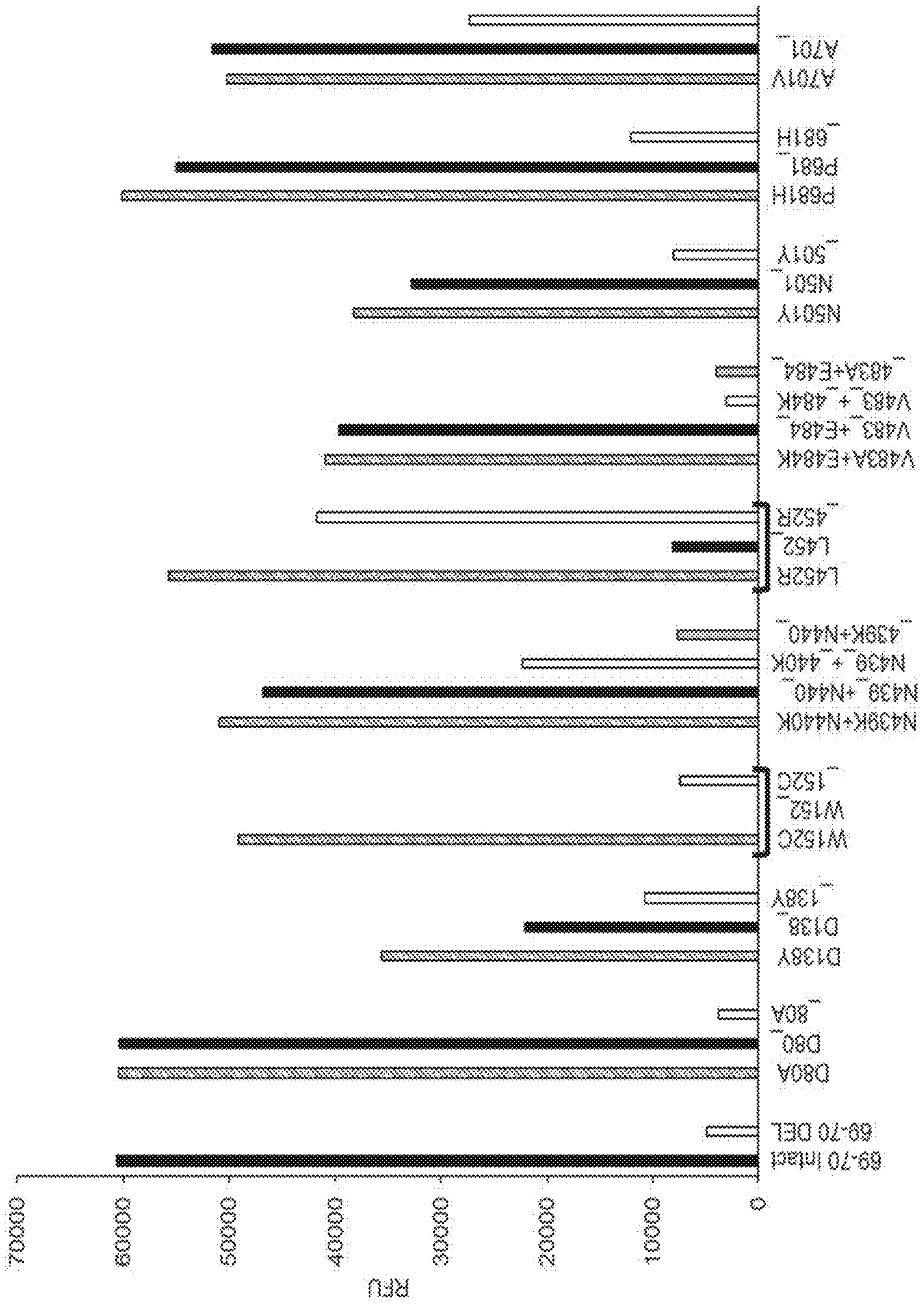
Figure 20F:
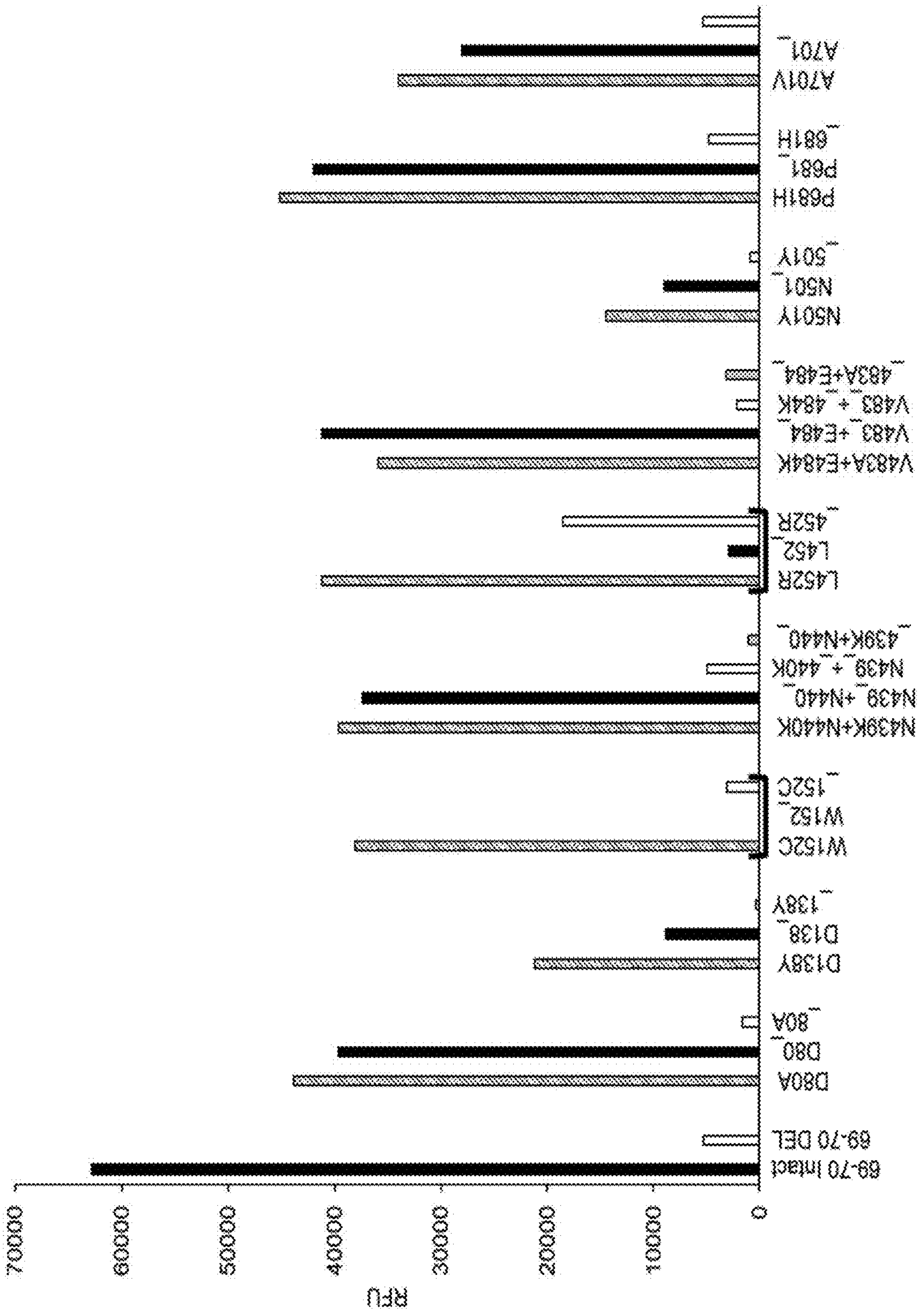

| DETECTX-Cv analysis of clinical positive samples performed at PathogenDx | | | |
|---|---|---|---|
| Probe | Wild Type | Mutant Type | Confidence |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 99.90% |
| UNHYBRIDIZED PROBES | | | |
| _69(del) | | OFF | 100.00% |
| _80A | | OFF | 89.00% |
| _152C | | OFF | 98.80% |
| W152_ | OFF | | 100.00% |
| L452_ | OFF | | 100.00% |
| _484K | | OFF | 100.00% |
| _701V | | OFF | 100.00% |
| Pattern consistent with: | No Glade Call, likely California | | |
| Reference FIG. 20C TriCore 238485-d Sample 5 | | | |
| HYBRIDIZED PROBES | | | |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| W152_ | OFF | | 100.00% |
| L452_ | OFF | | 90.50% |
| _484K | | OFF | 100.00% |
| _501Y | | OFF | 100.00% |
| _681H | | OFF | 83.60% |
| _701V | | OFF | 99.90% |
| Pattern consistent with: | California (B.1.429/427) | | |
| Reference FIG. 20D TriCore 238487-d Sample 6 | | | |
| HYBRIDIZED PROBES | | | |
| UNHYBRIDIZED PROBES | | | |
| _69(del) | | OFF | 100.00% |
| Pattern consistent with: | NA | | |
| Reference FIG. 20E TriCore 238488-d Sample 7 | | | |
| HYBRIDIZED PROBES | | | |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| W152_ | OFF | | 100.00% |
| L452_ | OFF | | 98.50% |
| _484K | | OFF | 100.00% |
| _501Y | | OFF | 100.00% |
| Pattern consistent with: | California (B.1.429/427) | | |
| Reference FIG. 20F TriCore 238498-d Sample 12 | | | |
| HYBRIDIZED PROBES | | | |
| D80_ | ON | | 100.00% |
| D138_ | ON | | 100.00% |
| _152C | | ON | 97.60% |
| N439_ | ON | | 100.00% |

TABLE 24-continued

Figure 20G:
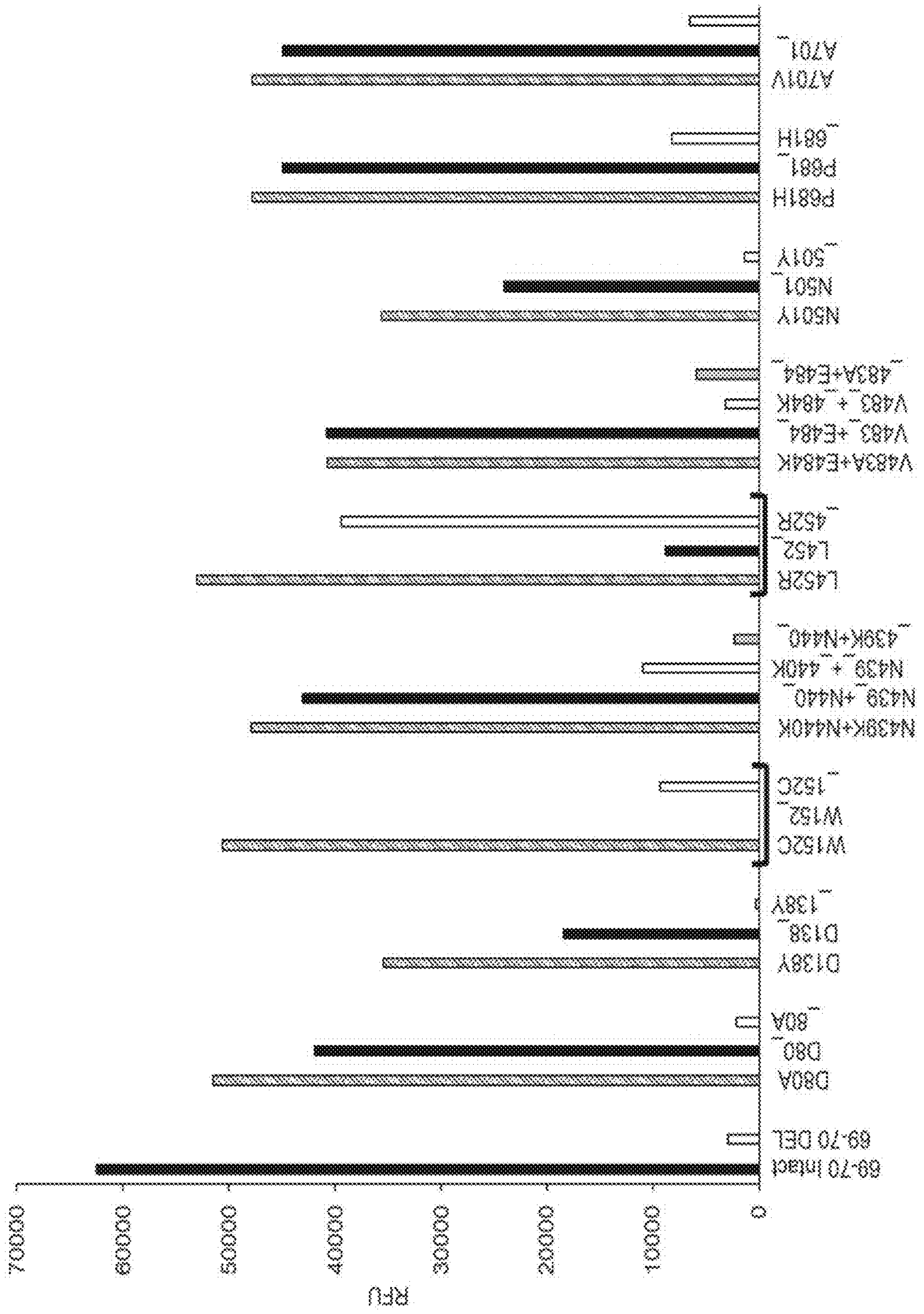
Figure 20H:
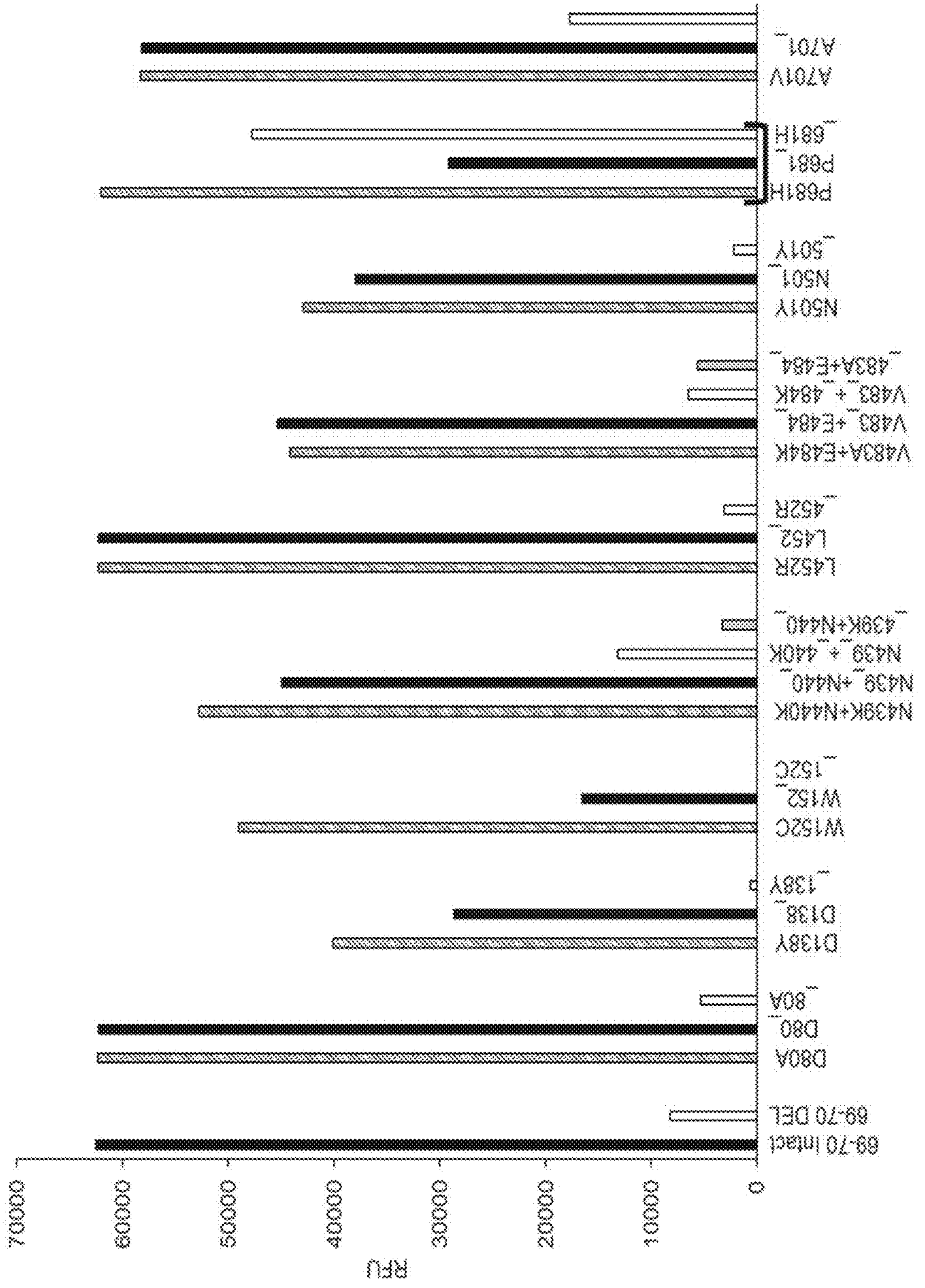
Figure 20I:
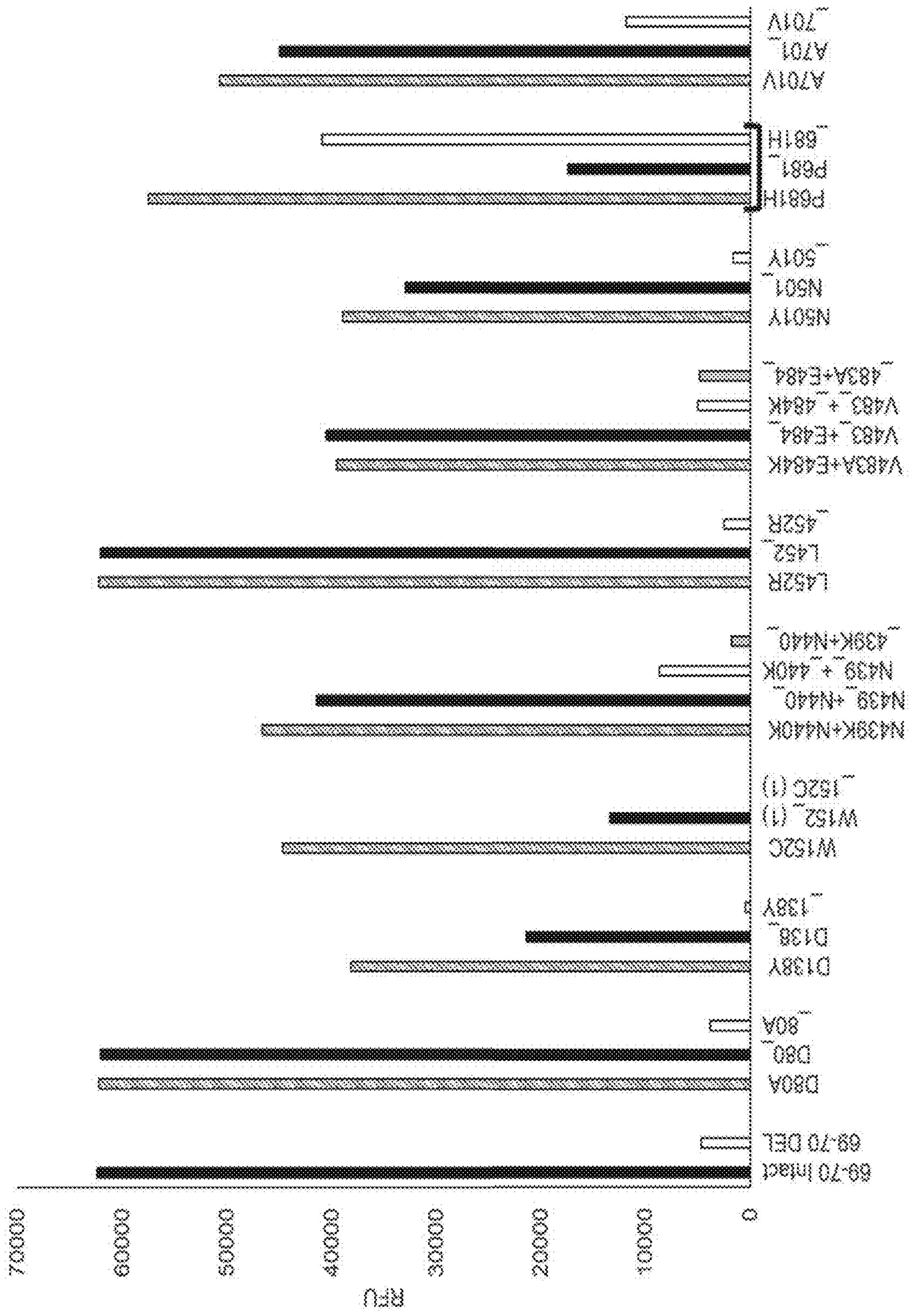

| DETECTX-Cv analysis of clinical positive samples performed at PathogenDx | | | |
|---|---|---|---|
| Probe | Wild Type | Mutant Type | Confidence |
| N440_ | ON | | 100.00% |
| _452R | | ON | 100.00% |
| E484_ | ON | | 100.00% |
| P681_ | ON | | 100.00% |
| A701_ | ON | | 78.60% |
| UNHYBRIDIZED PROBES | | | |
| _69(del) | | OFF | 100.00% |
| _80A | | OFF | 100.00% |
| _138Y | | OFF | 100.00% |
| W152_ | OFF | | 100.00% |
| L452_ | OFF | | 100.00% |
| _484K | | OFF | 100.00% |
| _501Y | | OFF | 100.00% |
| _681H | | OFF | 100.00% |
| _701V | | OFF | 100.00% |
| Pattern consistent with: | California (B.1.429/427) | | |
| Reference FIG. 20G TriCore 238499-d Sample 13 | | | |
| HYBRIDIZED PROBES | | | |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| _138Y | | OFF | 100.00% |
| W152_ | OFF | | 100.00% |
| L452_ | OFF | | 94.40% |
| _484K | | OFF | 100.00% |
| _501Y | | OFF | 100.00% |
| _681H | | OFF | 98.40% |
| _701V | | OFF | 100.00% |
| Pattern consistent with: | California (B.1.429/427) | | |
| Reference FIG. 20H TriCore 238504-d Sample 16 | | | |
| HYBRIDIZED PROBES | | | |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| _681H | | ON | 100.00% |
| A701_ | ON | | 100.00% |
| UNHYBRIDIZED PROBES | | | |
| _69(del) | | OFF | 99.70% |
| _80A | | OFF | 100.00% |
| _138Y | | OFF | 100.00% |
| _152C | | OFF | 97.40% |
| _452R | | OFF | 94.60% |
| _484K | | OFF | 100.00% |
| _501Y | | OFF | 100.00% |
| _701V | | OFF | 99.80% |
| Pattern consistent with: | B.1.1.207 | | |
| Reference FIG. 201 TriCore 236310-P Sample 39 | | | |
| HYBRIDIZED PROBES | | | |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |

TABLE 24-continued

Figure 20J:
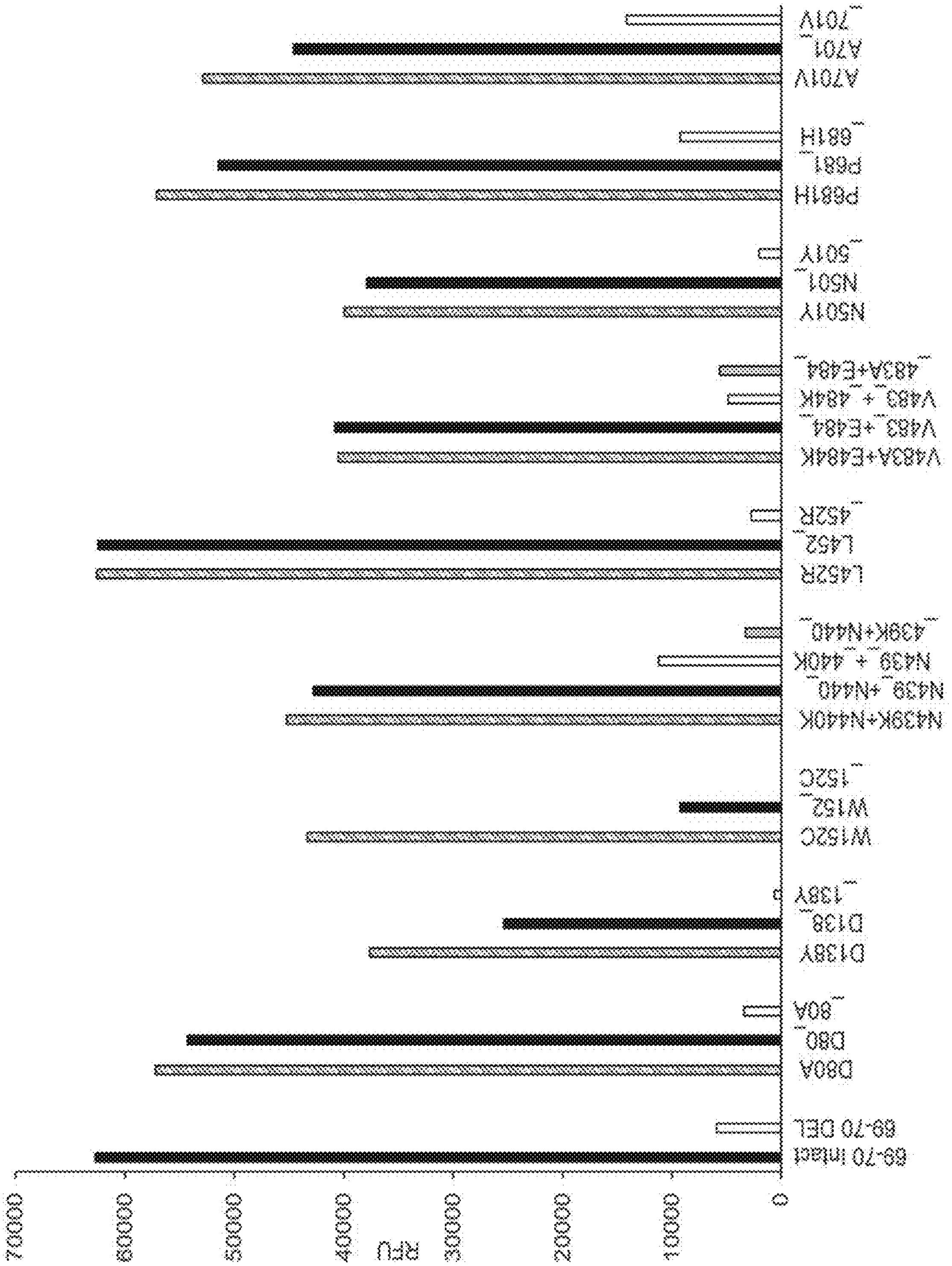

| DETECTX-Cv analysis of clinical positive samples performed at PathogenDx | | | |
|---|---|---|---|
| Probe | Wild Type | Mutant Type | Confidence |
| E484_ | ON | | 100.00% |
| N501_ | ON | | 100.00% |
| _681H | | ON | 100.00% |
| A701_ | ON | | 100.00% |
| UNHYBRIDIZED PROBES | | | |
| _69(del) | | OFF | 100.00% |
| _80A | | OFF | 100.00% |
| _138Y | | OFF | 100.00% |
| _152C | | OFF | 98.80% |
| _452R | | OFF | 98.90% |
| _484K | | OFF | 100.00% |
| _501Y | | OFF | 100.00% |
| _701V | | OFF | 100.00% |
| Pattern consistent with: | B.1.1.207 | | |
| Reference FIG. 20J TriCore 236315-P Sample 42 | | | |
| HYBRIDIZED PROBES | | | |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| _138Y | | OFF | 100.00% |
| _152C | | OFF | 98.80% |
| _452R | | OFF | 98.00% |
| _484K | | OFF | 100.00% |
| _501Y | | OFF | 100.00% |
| _681H | | OFF | 87.00% |
| _701V | | OFF | 100.00% |
| Pattern consistent with: | Wuhan Progenitor | | |

Example 11

Detection of Stable Genetic Variation

The method of nucleic acid analysis to detect stable genetic variations in a pathogen is based on simultaneous analysis of multiple sequence domains in a gene or group of genes, such as the Spike gene or the LINK domain of the Nucleoprotein (N) gene in SARS-CoV-2 or a combination of the Spike gene and the N gene in the RNA genome to measure clade variations in SARS-CoV-2. For SARS-CoV-2 (CoV-2), the sequence domains are processed for nucleic acid analysis by converting them into a set of amplicons via a multiplex RT-PCR reaction. In one preferred implementation, the sequence of the multiplex RT-PCR products is identified relative to that of the underlying CoV-2 Spike gene, by the Horizontal Black Bars in the bottom of Table 25 or is identified relative to that of the underlying CoV-2 N gene LINK region, by the Horizontal Black Bar at the bottom of Table 26.

The product of the multiplex RT-PCR reaction is analyzed by hybridization to a matrix of synthetic oligonucleotide probes positioned as a microarray. In one preferred implementation of the present invention for CoV-2, there are (32) such Spike Gene Target Regions (Table 25 & 28) and (11) N gene Target Regions (Table 26, 28) containing meaningful local sequence variation which may be used to measure a pattern of mutation for SARS-CoV2, which in combination, can be used for SARS-CoV-2 Variant Identification. See the top Row of Table 25 for localization of those Target sites in the Spike gene and the top row of Table 26 for their location in the LINK domain of the N protein.

In terms of detailed test design, the forward and reverse Primers deployed for multiplex amplification of the Spike gene (Amplicons S:1-S:8) and those for PCR amplification of the N gene LINK region (Amplicon N:9) are listed in Table 27.

In terms of detailed test design, the Hybridization Probes resident at each target region of the Spike surface protein and each target region of the N gene LINK domain are each produced as 3 closely related types of probe variants, which may be referred to as "Wild Type", "Mutant" and "Universal". Those Spike gene and N gene Hybridization probe sequences are listed in Table 28.

TABLE 25

Spike Gene Variant Lookup Table

| VOC/VOI/VUM LIST COMBINED WHO & CDC Oct. 21, 2021 | | S: L5F | S: S131 | S: L18F | S: T19R | S: T20N | S: A67V | S: HV60-70del | S: G75V. T76I | S: D80A | S: D80G | S: T95I | S: D138Y | S: Y144del | S: ins143T | S: G142D | S: L141Y. 142-144del | S: Y145H | S: W152C |
|---|---|---|---|---|---|---|---|---|---|---|---|---|---|---|---|---|---|---|---|
| Alpha | B1.1.7(Q) | | | | | | | 97 | | | | | | 95 | | | | | |
| Beta | B.1.351 | | | | | | | | | 97 | | | | | | | | | |
| Gamma | P.1 | | | 98 | | 97 | | | | | | | 97 | | | | | | |
| Delta | B.1.617.2(AY) | | | | 98 | | | | | | | 35 | | | | 59 | | | |
| Lambda | C.37 | | | | | | | | 96 | | | | | | | | | | |
| MU | B.1.621 | | | | | | | | | | | 94 | | | 80 | | | | |
| | R.1 | | | | | | | | | | | | | | | | | | |
| | B.1.466.2 | | | | | | | | | | | | | | | | | | |
| | B1.1.318 | | | | | | | | | | | 98 | | 91 | | | | | |
| | B1.1.519 | | | | | | | | | | | | | | | | | | |
| | C.36.3 | | | | | | | 78 | | | | | | | | | | | |
| | B.1.214.2 | | | | | | | | | | | | | | | | | | |
| Epsilon | B.1.429/427 | | 94 | | | | | | | | | | | | | | | | 92 |
| | B.1.523 | | | | | | | | | | | | | | | | | | |
| | B.1.619 | | | | | | | | | | | | | | | | | | |
| | B.1.620 | | | | | | | 98 | | | | | | 99 | | | | | |
| | C.1.2 | | | | | | | | | | | | | 77 | | | | | |
| Kappa | B.1.617.1 | | | | | | | | | | | 48 | | | | 57 | | | |
| Iota | B.1.526 | 96 | | | | | | | | | | 99 | | | | | | | |
| Eta | B.1.525 | | | | | | 95 | 94 | | | | | | 93 | | | | | |
| | B.1.630 | | | | | | | | | | | | | 92 | | | | | |
| Zeta | P.2 | | | | | | | | | | | | | | | | | | |
| Theta | P.3 | | | | | | | | | | | | | | | | | | |
| | B.1.617.3 | | | | 95 | | | | | | | | | | | 16 | | | |

| VOC/VOI/VUM LIST COMBINED WHO & CDC Oct. 21, 2021 | | S: W152L | S: W152R | S: E154K | S: E156G. 157-158del | S: D215G | S: A222V | S: 242-244deL | S: R246N. 247-354del | S: D253G | S: K417N | S: K417T | S: N439K | S: N440K | S: L452R | S: L452Q | S: S477N | S: T478K |
|---|---|---|---|---|---|---|---|---|---|---|---|---|---|---|---|---|---|---|
| Alpha | B1.1.7(Q) | | | | | | | | | | | | | | | | | |
| Beta | B.1.351 | | | | | 94 | | 68 | | | 93 | | | | | | | |
| Gamma | P.1 | | | | | | | | | | | 96 | | | | | | |
| Delta | B.1.617.2(AY) | | | | 91 | | | | | | | | | | 98 | | | 98 |
| Lambda | C.37 | | | | | | | | 85 | | | | | | | 98 | | |
| MU | B.1.621 | | | | | | | | | | | | | | | | | |
| | R.1 | 99 | | | | | | | | | | | | | | | | |
| | B.1.466.2 | | | | | | | | | | | | 92 | | | | | |
| | B1.1.318 | | | | | | | | | | | | | | | | | |
| | B1.1.519 | | | | | | | | | | | | | | | | | 93 |
| | C.36.3 | | 97 | | | | | | | | | | | | 98 | | | |
| | B.1.214.2 | | | | | | | | | | | | | | | | | |

TABLE 25-continued

Spike Gene Variant Lookup Table

| | | | | | | | | | | | | | | | | | |
|---|---|---|---|---|---|---|---|---|---|---|---|---|---|---|---|---|---|
| Epsilon | B.1.429/427 | | | | | | | | | | | | | 96 | | | |
| | B.1.523 | | | | | | | | | | | | | | | | |
| | B.1.619 | | | | | | | | | | | | 87 | | | | |
| | B.1.620 | | | | | | 77 | | | | | | | | | 99 | |
| | C.1.2 | | | | 96 | | | | | | | | | | | | 19 |
| Kappa | B.1.617.1 | | 63 | | | | | | | | | | | 93 | | | |
| Iota | B.1.526 | | | | | | | | 97 | | | | | | | 38 | |
| Eta | B.1.525 | | | | | | | | | | | | | | | | |
| | B.1.630 | | | | | 94 | | | | | | | | 96 | | | |
| Zeta | P.2 | | | | | | | | | | | | | | | | |
| Theta | P.3 | | | | | | | | | | | | | | | | |
| | B.1.617.3 | | | 87 | | | | | | | | | | 89 | | | |
| | VOC/VOI/VUM LIST COMBINED WHO & CDC Oct. 21, 2021 | S: V483A | S: E484K | S: E484Q | S: F490S | S: S494P | S: N501Y | S: N501T | S: Q613H | S: D614G | S: Q677P | S: Q677H2 | S: Q677H1 | S: P681R | S: P681H | S: A688V | S: A701V |
| Alpha | B1.1.7(Q) | | | | | | 98 | | | 99 | | | | | 99 | | |
| Beta | B.1.351 | | 86 | | | | 87 | | | 98 | | | | | | | 96 |
| Gamma | P.1 | | 95 | | | | 95 | | | 99 | | | | | | | |
| Delta | B.1.617.2(AY) | | | | | | | | | 99 | | | | 99 | | | |
| Lambda | C.37 | | | | 97 | | | | | 99 | | | | | | | |
| MU | B.1.621 | | 94 | | | | 94 | | | 97 | | | | | 97 | | |
| | R.1 | | 99 | | | | | | | 99 | | | | | | | |
| | B.1.466.2 | | | | | | | | | 99 | | | | 87 | | | |
| | B1.1.318 | | 97 | | | | | | | 99 | | | | | 98 | | |
| | B1.1.519 | | | | | | | | | 99 | | | | | 98 | | |
| | C.36.3 | | | | | | | | | 99 | | 98 | | | | | |
| | B.1.214.2 | | | | | | | | | 99 | | | | | | | |
| Epsilon | B.1.429/427 | | | | | | | | | 99 | | | | | | | |
| | B.1.523 | | | | | | | | | 99 | | | | | | | |
| | B.1.619 | | 97 | | | | | | | 99 | | | | | | | |
| | B.1.620 | | 99 | | | | | | | 99 | | | | | 99 | | |
| | C.1.2 | | 86 | | | | 84 | | | 99 | | | | | | | |
| Kappa | B.1.617.1 | | | 93 | | | | | | 98 | | | | 97 | | | |
| Iota | B.1.526 | | 55 | | | | | | | 99 | | | | | | | 65 |
| Eta | B.1.525 | | 97 | | | | | | | 99 | | 98 | | | | | |
| | B.1.630 | | | 95 | | | | | | 99 | | | | | | | |
| Zeta | P.2 | | 94 | | | | | | | 99 | | | | | | | |
| Theta | P.3 | | 86 | | | | 86 | | | 98 | | | | | 95 | | |
| | B.1.617.3 | | | 92 | | | | | | 99 | | | | 98 | | | |

TABLE 26

N Gene (LINK doman) Variant Lookup Table

| VOC/VOI/VUM LIST<br>COMBINED WHO & CDC Oct. 21, 2021 | | NUCLEOCAPSID (N) GENE MUTATIONS DETECTED IN THE PRESENT INVENTION<br>N: S194L | N: S197L | N: P199L | N: S201I | N: S202N | N: R203M | N: R203K | N: K G204R | N: T205I |
|---|---|---|---|---|---|---|---|---|---|---|
| Alpha | B.1.1.7(Q) | | | | | | | 91 | 91 | |
| Beta | B.1.351 | | | | | | | | 99 | |
| Gamma | P.1 | | | | | | | 95 | 95 | |
| Delta | B.1.617.2(AY) | | | | | | 99 | | | |
| Lambda | C.37 | | | | | | | 97 | 97 | |
| Mu | B.1.621 | | | | | | | | | 95 |
| | R.1 | | | | | | | 99 | 99 | |
| | B.1.466.2 | | | | | | | | | 97 |
| | B.1.1.318 | | | | | | | 96 | 96 | |
| | B.1.1.519 | | | | | | | 97 | 97 | |
| | C.36.3 | | | | | | | 99 | 99 | |
| | B.1.214.2 | | | | | | | | | 94 |
| Epsilon | B.1.429/427 | | | | | | | | | 98 |
| | B.1.523 | | | | | | | | | |
| | B.1.619 | | | | 97 | | | | | 97 |
| | B.1.620 | | | | | | | | | |
| | C.1.2 | | | | | | | 97 | 97 | |
| Kappa | B.1.617.1 | | | | | | 95 | | | |
| Iota | B.1.526 | | | 68 | | | | | | |
| Eta | B.1.525 | | | | | | | | | 92 |
| | B.1.630 | | | | | | | | | 97 |
| Zeta | P.2 | | | | | | | 97 | 97 | |
| Theta | P.3 | | | | | | | 93 | 93 | |
| | B.1.617.3 | | | | | | 93 | | | |

| VOC/VOI/VUM LIST<br>COMBINED WHO & CDC Oct. 21, 2021 | | NUCLEOCAPSID (N) GENE MUTATIONS DETECTED IN THE PRESENT INVENTION<br>N: A208G | N: R209del | N: G212V | N: N213Y | N: 214C | N: G215C | N: M234I | N: S235F |
|---|---|---|---|---|---|---|---|---|---|
| Alpha | B.1.1.7(Q) | | | | | | | | 99 |
| Beta | B.1.351 | | | | | | | | |
| Gamma | P.1 | | | | | | | | |
| Delta | B.1.617.2(AY) | | | | | | 85 | | |
| Lambda | C.37 | | | | | 98 | | | |
| Mu | B.1.621 | | | | | | | | |
| | R.1 | | | | | | | | |
| | B.1.466.2 | | | | | | | | |
| | B.1.1.318 | 94 | 94 | | | | | | |
| | B.1.1.519 | | | | | | | | |
| | C.36.3 | | | 98 | | | | | |
| | B.1.214.2 | | | | | | | | |
| Epsilon | B.1.429/427 | | | | | | | 29 | |
| | B.1.523 | | | | | | | 99 | |
| | B.1.619 | | | | | | | | |
| | B.1.620 | | | | | | | | |
| | C.1.2 | | | | | | | | |
| Kappa | B.1.617.1 | | | | | | | | |
| Iota | B.1.526 | | | | | | | 67 | |
| Eta | B.1.525 | | | | | | | | |
| | B.1.630 | | | | | | | | |
| Zeta | P.2 | | | | | | | 97 | |
| Theta | P.3 | | | | | | | | |
| | B.1.617.3 | | | | | | | | |

% Mutation prevalence across lineages

The number associated with each element of the matrix in Tables 25 and 26 is the prevalence of that mutation at each location in the N Gene being analyzed (columns) across each of the lineages comprising the Combined WHO and CDC VOC/VOI/VUM lists (rows). Those percentages are calculated by use of the informatics tools provided by Latif et al. based on the aggregated GISAID database (Oct. 20, 2021 update). Where there is no number presented, that location remains as Wild Type in that lineage, Wild Type being defined as the original Wuhan reference sequence.

Table 27 lists S-gene primers to generate amplimers S:1-S:8 and N-gene amplimer N:9 in the DetectX-Cv assay.

TABLE 27

| RT-PCR Primers for S-Gene (Amplimers S:1-S:8) and N-Gene (Amplimer N:9) | | | | |
|---|---|---|---|---|
| SEQ ID NOS. | Amplimer # | Target | Gene | Primer Sequence (5' to 3') |
| SEQ ID NO: 137 | S:1 | (AA$^{(-)}$15-$^{(-)}$11) | S | TTTAGAGTTGTTATTTCTAGTG<br>ATGTTC |
| SEQ ID NO: 20 | | (AA 33-41) | | Cy3-TTTTTGTCAGGGTAATAAA<br>CACCACGTG |
| SEQ ID NO: 9 | S:2 | (AA 57-65) | S | ACCTTTCTTTTCCAATGTTACT<br>TGGTTC |
| SEQ ID NO: 138 | | (AA 98-105) | | Cy3-<br>TTTAATCCAGCCTCTTATTATG<br>TTAGAC |
| SEQ ID NO: 11 | S:3 | (AA 118-126) | S | TTTCTTATTGTTAATAACGCTA<br>CTAATG |
| SEQ ID NO: 139 | | (AA 161-169) | | Cy3-<br>TTTCAAAAGTGCAATTATTCGC<br>ACTAGA |
| SEQ ID NO: 21 | S:4 | (AA 205-213) | S | TTTTAAGCACACGCCTATTAAT<br>TTAGTG |
| SEQ ID NO: 22 | | (AA 260-268) | | Cy3-<br>TTTCCACATAATAAGCTGCAG<br>CACCAGC |
| SEQ ID NO: 13 | S:5 | (AA 400-408) | S | TTTTGTAATTAGAGGTGATGAA<br>GTCAGA |
| SEQ ID NO: 14 | | (AA 456-464) | | Cy3-<br>TTTAAAGGTTTGAGATTAGACT<br>TCCTAA |
| SEQ ID NO: 140 | S:6 | (AA 471-463) | S | TTTCTTTTGAGAGAGATATTTC<br>AACTGA |
| SEQ ID NO: 16 | | (AA 506-514) | | Cy3-<br>TTTAAAGTACTACTACTCTGTA<br>TGGTTG |
| SEQ ID NO: 23 | S:7 | (AA 596-604) | S | TTTAGTGTTATAACACCAGGAA<br>CAAATA |
| SEQ ID NO: 24 | | (AA 618-626) | | Cy3-TTTTGCATGAAT<br>AGCAACAGGGACTTCT |
| SEQ ID NO: 141 | S:8 | (AA 666-673) | S | TTTATTGGTGCAGGTATATGC<br>GCTAG |
| SEQ ID NO: 18 | | (AA 707-715) | | Cy3-<br>TTTTGGTATGGCAATAGAGTTA<br>TTAGAG |
| SEQ ID NO: 142 | N:9 | (AA167-175) | N | TTTGCCAAAAGGCTTCTACGC<br>AGAAG |
| SEQ ID NO: 143 | | (AA 253-261) | | Cy3-<br>TTTTTTGCCGAGGCTTCTTAGA<br>AGCC |

Table 28A lists S-gene robes used with the N-gene specific probes to detect hybridization to the S gene regions in amplimers S:1-S:8, that are generated via RT-PCR from the representative primer pairs described in Table 27. Table 28B lists N-gene probes used with the S-gene specific probes to detect hybridization to the N gene region (aa183-aa252), amplimer N:9 that are generated via RT-PCR from the representative primer pairs described in Table 27.

TABLE 28A

| Hybrdization Probes (Spike gene region) | | | | |
|---|---|---|---|---|
| SEQ ID NOS. | Amplimer # | Target | U/W/M | Probe Sequence (5' to 3') |
| SEQ ID NO: 144 | S:1 | S: L5F | U | TTTTCGTTTGTTTTTYTT<br>GTTTTATTGCTTTT |
| SEQ ID NO: 145 | | S: L5_ | W | TTTTCGTTTGTTTTTCTT<br>GTTTTATTTTTT |
| SEQ ID NO: 146 | | S: _5F | M | TTTTCGTTTGTTTTTTTT<br>GTTTTATTTTTT |

TABLE 28A-continued

Hybrdization Probes (Spike gene region)

| SEQ ID NOS. | Amplimer # | Target | U/W/M | Probe Sequence (5' to 3') |
|---|---|---|---|---|
| SEQ ID NO: 30 | S:1 | S: S13I | U | TTTTTCTAGTCTCTAKTC AGTGTGTTTTTT |
| SEQ ID NO: 64 | | S: S13_ | W | TTTTTTTGTCTCTAGTCA GTGTTTTTTTTT |
| SEQ ID NO: 67 | | S:_13I | M | TTTTTTTAGTCTCTATTC AGTGTTTTTTTT |
| SEQ ID NO: 233 | S:1 | S: L18F.T19R.T20N | U | TTTTTTAATYTTASAAMC AGAACTCTTTTT |
| SEQ ID NO: 69 | | S: L18_.T19_.T20_ | W | TTTTTTTATCTTACAACC AGAACCTTTTTT |
| SEQ ID NO: 234 | | S: _18F.T19_.T20N | M | TTTTTCTTGTTAATTTTA CAAMCATTTTTT |
| SEQ ID NO: 148 | | S: L18_._19R.T20_ | M | TTTTTCTTTAATCTTAGA ACCAGACTTTTT |
| SEQ ID NO: 71 | | S: L18_.T19_._20N | M | TTTTTTATTTTACAAACA GAACTTTTTTTT |
| SEQ ID NO: 235 | S:2 | S:A67V.HV69-70del (MIX) | U | TTTTTCCCATGYTATAC ATGTCTCTGTTTTTT |
| SEQ ID NO: 236 | | | | TTTTTTTTTCCATGYTAT CTCTGGGATTTTTT |
| SEQ ID NO: 149 | | S: A67.HV69-70_ | W | TTTTTCTCCATGCTATA CATGTCCTTTTTT |
| SEQ ID NO: 150 | | S: A67_._69-70del | M | TTTTTTTTTCCATGCTAT CTCTGTTTTTTT |
| SEQ ID NO: 151 | | S: _67V._69-70del | M | TTTTTTTTTCCATGTTAT CTCTGTTTTTTT |
| SEQ ID NO: 31 | S:2 | S: HV69-70del (Mix) | U | TTTTTCCCATGCTATAC ATGTCTCTGTTTTTT |
| SEQ ID NO: 32 | | | | TTTTTTTTTCCATGCTAT CTCTGGGATTTTTT |
| SEQ ID NO: 31 | | S: HV69-70_ | W | TTTTTCCCATGCTATAC ATGTCTCTGTTTTTT |
| SEQ ID NO: 32 | | S: _69-70del | M | TTTTTTTTTCCATGCTAT CTCTGGGATTTTTT |
| SEQ ID NO: 237 | S:2 | S: G75V.T76I | U | TTTTTTGACCAATGGTA CTAAGAGTTTTTT |
| SEQ ID NO: 238 | | S: G75_.T76_ | W | TTTTTTACCAATGGTAC TAAGAGTCTTTTT |
| SEQ ID NO: 239 | | S: _75V._76I | M | TTTTTTACCAATGTTATT AAGAGTCTTTTT |
| SEQ ID NO: 240 | S:2 | S: D80A/G | U | TTTTTCAGAGGTTTGVT AACCCTGTCTTTTTT |
| SEQ ID NO: 34 | | S: D80_ | W | TTTTTTTGGTTTGATAAC CCTGCTTTTTTT |
| SEQ ID NO: 35 | | S: _80A | M | TTTTTTTGGTTTGCTAA CCCTGCTTTTTTT |
| SEQ ID NO: 152 | | S: _80G | M | TTTTTTTGGTTTGGTAA CCCTGCTTTTTTT |
| SEQ ID NO: 153 | S:2 | S: T95I | U | TTTCTTTTTGCTTCCAYT GAGAAGTCTTTTTT |
| SEQ ID NO: 154 | | S: T95_ | W | TTTTTTCCGCTTCCACT GAGAAGCATTTTT |
| SEQ ID NO: 155 | | S: _95I | M | TTTTTTCCGCTTCCATT GAGAAGCATTTTT |
| SEQ ID NO: 36 | S:3 | S: D138Y | U | TTTTATTTTGTAATKATC CATTTTTGTTTT |
| SEQ ID NO: 37 | | S: D138_ | W | TTTTTCTTTGTAATGATC CATTTTCTTTTT |
| SEQ ID NO: 38 | | S: _138Y | M | TTTTTTTTTGTAATTATC CATTTTCTTTTT |
| SEQ ID NO: 241 | S:3 | L141Y.G142D.V143insT. Y144S/del.Y145N (Mix) | U | TTTCTTTGGRTGTTTATT ACCACAAAAATTTT |
| SEQ ID NO: 157 | | | | TTTTTTTTTGGGTGTTTA CCACAAAAACTTTT |
| SEQ ID NO: 158 | | | | TTTATTTTTGGGTGTTA CTTATTACCACATTT |

TABLE 28A-continued

Hybrdization Probes (Spike gene region)

| SEQ ID NOS. | Amplimer # | Target | U/W/M | Probe Sequence (5' to 3') |
|---|---|---|---|---|
| SEQ ID NO: 160 | | | | TTCGTAATGATCCATTT TATTACCACAAATTT |
| SEQ ID NO: 156 | | S: L141_.G142_.V143_ .Y144_.Y145_ | W | TTTCTTTGGGTGTTTAT TACCACAAAAATTTT |
| SEQ ID NO: 157 | | S: L141_.G142_.V143_ ._144del.Y145_ | | TTTTTTTTTGGGTGTTTA CCACAAAAACTTTT |
| SEQ ID NO: 158 | | S: L141_.G142_.ins143T ._144S._145N | M | TTTATTTTTGGGTGTTA CTTATTACCACATTT |
| SEQ ID NO: 159 | | S: L141_._142D.V143_ .Y144_.Y145_ | M | TTCTTTTGGATGTTTATT ACCACAAAAACTTT |
| SEQ ID NO: 160 | | S: _141Y._142del. _V143del._144del. Y145_ | M | TTCGTAATGATCCATTT TATTACCACAAATTT |
| SEQ ID NO: 242 | S:3 | S: Y145H | U | TTTCTGTGTTTATYACC ACAAAAACTTCTT |
| SEQ ID NO: 243 | | S: Y145_ | W | TTTTTCTGTGTTTATTAC CACAAATCTTTTT |
| SEQ ID NO: 244 | | S: _145H | M | TTTTTTATGTTTATCACC ACAAATCTTTTT |
| SEQ ID NO: 39 | S:3 | S: W152C/L/R.E154K | U | TTTTTAGTWKKATGGAA AGTGAGTTCTTTT |
| SEQ ID NO: 40 | | S: W152_.E154_ | W | TTTCTCTAAAAGTTGGA TGGAAACTCTTCT |
| SEQ ID NO: 41 | | S: _152C.E154_ | M | TTTCTTCAAAGTTGTAT GGAAAGCCTTCTT |
| SEQ ID NO: 161 | | S: _152L.E154_ | M | TCTCTTCAAAAGTTTGA TGGAAATCTCTTT |
| SEQ ID NO: 162 | | S: _152R.E154_ | M | TTTCTTTACAAAAGTAG GATGGATTTCTTT |
| SEQ ID NO: 163 | | S: _152C._154K | M | TTTCTTTGTTGGATGAA AAGTGATCTTCTT |
| SEQ ID NO: 164 | S:3 | S: E156G/del.F157del. R158del (Mix) | U | TTTTGAAAGTGAGTTCA GAGTTTACCTTTT |
| SEQ ID NO: 165 | | | | TTCTTTGGAAAGTGGAG TTTATTCTCTTTT |
| SEQ ID NO: 164 | | S: E156_.F157_.R158_ | W | TTTTGAAAGTGAGTTCA GAGTTTACCTTTT |
| SEQ ID NO: 165 | | S: 156G._157del. _158del | M | TTCTTTGGAAAGTGGAG TTTATTCTCTTTT |
| SEQ ID NO: 81 | S:4 | S: D215G | U | TTTTTTAGTGCGTGRTC TCCCTCATTTTTT |
| SEQ ID NO: 245 | | S: D215_ | M | TTTTTTTTTGCGTGATCT CCCTTTTTTTTT |
| SEQ ID NO: 246 | | S: _215G | W | TTTTTTTTTGCGTGGTC TCCCCTTTTTTTT |
| SEQ ID NO: 247 | S:4 | S: A222V | U | TTTTGTTTTTCGGYTTTA GAACCATCTTTT |
| SEQ ID NO: 248 | | S: A222_ | M | TTTTTTTTTTTCGGCTTT AGAACTTTTTTT |
| SEQ ID NO: 249 | | S: _222V | W | TTTTTTGTTTTTCGGTTT TAGAATTTTTTT |
| SEQ ID NO: 166 | S:4 | S: L242del.A243del. L244deL (Mix) | U | TTTTTTTTCAAACTTTAC TTGCTTTACTCTTT |
| SEQ ID NO: 167 | | | | TTTTTTTTCAAACTTTAC ATAGAAGCCTTTTT |
| SEQ ID NO: 166 | | S: L242_.A243_.L244_ | W | TTTTTTTTCAAACTTTAC TTGCTTTACTCTTT |
| SEQ ID NO: 167 | | S: 242del._243del ._244deL | M | TTTTTTTTCAAACTTTAC ATAGAAGCCTTTTT |
| SEQ ID NO: 168 | S:4 | S: R246N.5247del. Y248del.L249del. | U | TTTTCTACATAGAAGTT ATTTGACTCCCTTTT |
| SEQ ID NO: 169 | | T250del.P251del. D253del (Mix) | | TTTTCTGCTTTACATAT GACTCCTGGTTTTTT |
| SEQ ID NO: 168 | | S: R246_.5247_.Y248_. L249_.T250_.P251_. D253_ | W | TTTTCTACATAGAAGTT ATTTGACTCCCTTTT |

TABLE 28A-continued

Hybrdization Probes (Spike gene region)

| SEQ ID NOS. | Amplimer # | Target | U/W/M | Probe Sequence (5' to 3') |
|---|---|---|---|---|
| SEQ ID NO: 169 | | S: _246N._247del._248del._249del._250del._251del._253del (Mix) | M | TTTTCTGCTTTACATATGACTCCTGGTTTTTT |
| SEQ ID NO: 170 | S:4 | S: D253G | U | TTTCTACTCCTGGTGRTTCTTCTTCATTTT |
| SEQ ID NO: 171 | | S: D253_ | W | TTTTTTCCCTGGTGATTCTTCTTTCTTTTT |
| SEQ ID NO: 172 | | S: _253G | M | TTTTTTCCCTGGTGGTTCTTCTTTTTTTTT |
| SEQ ID NO: 250 | S:5 | S: K417N/T | U | TTTTAACTGGAAMKATTGCTGATTATTTTT |
| SEQ ID NO: 88 | | S: K417_ | W | TTCTTCTCTGGAAAGATTGCTGACTTTTTT |
| SEQ ID NO: 89 | | S: _417N | M | TTTTTCTCTGGAAATATTGCTGACTTTTTT |
| SEQ ID NO: 92 | | S: _417T | M | TTTTTTCCTGGAACGATTGCTGTTTTTTTT |
| SEQ ID NO: 42 | S:5 | S: N439K.N440K | U | TTTTTAATTCTAAMAAKCTTGATTCTAATTTT |
| SEQ ID NO: 43 | | S: N439_.N440_ | W | TTTTTAATTCTAACAATCTTGATTTCTTTT |
| SEQ ID NO: 44 | | S: N439_._440K | M | TTTTTTATTCTAACAAGCTTGATTTTTTTT |
| SEQ ID NO: 45 | | S: _439K.N440_ | M | TTTTCTATTCTAAAAATCTTGATTTCTTTT |
| SEQ ID NO: 251 | S:5 | S: L452R/Q | U | TTTCTATAATTACCDGTATAGATTGTCTTT |
| SEQ ID NO: 47 | | S: L452_ | W | TTTTTTTAATTACCTGTATAGATTTCTTTT |
| SEQ ID NO: 48 | | S: _452R | M | TTTTTCATAATTACCGGTATAGATCTTTTT |
| SEQ ID NO: 173 | | S: _452Q | M | TTTTTTTAATTACCAGTATAGATCCTTTTT |
| SEQ ID NO: 252 | S:6 | S: S477N.T478K | U | TTTTTCGCCGGTARCAMACCTTGTATTTTT |
| SEQ ID NO: 253 | | S: S477_.T478_ | W | TTTTTTTCCGGTAGCACACCTTTTTTTTTT |
| SEQ ID NO: 50 | | S: _477N.T478_ | M | TTTTCTTCCGGTAACACACCTTTTTTTTTT |
| SEQ ID NO: 254 | | S: S477_._478K | M | TTTTTCTGGTAGCAAACCTTGTTTTTTTTT |
| SEQ ID NO: 174 | S:6 | S: T478K | U | TTTTTCGGTAGCAMACCTTGTAATGTTTTT |
| SEQ ID NO: 175 | | S: _478K | W | TTTTTTTGTAGCACACCTTGTATTTTTTTT |
| SEQ ID NO: 176 | | S: T478_ | M | TTTTTTTGTAGCAAACCTTGTATTTTTTTT |
| SEQ ID NO: 255 | S:6 | S: V483A.E484K/Q | U | TTTTTTAATGGTGYTRAAGGTTTTAATTTTTT |
| SEQ ID NO: 52 | | S: V483_.E484_ | W | TTTTTTCTGGTGTTGAAGGTTTTACTTTTT |
| SEQ ID NO: 53 | | S: V483_._484K | M | TTTTTTTATGGTGTTAAAGGTTTTCTTTTT |
| SEQ ID NO: 177 | | S: V483_._484Q | M | TTTTTTATGGTGTTCAAGGTTTTCTTTTTT |
| SEQ ID NO: 54 | | S: _483A.E484_ | M | TTTTTTTATGGTGCTGAAGGTTCTTTTTTT |
| SEQ ID NO: 256 | S:6 | S: F490S | U | TTTTCTAATTGTTACTYTCCTTTACAATTTTT |
| SEQ ID NO: 179 | | S: F490_ | W | TTTTTTTTTGTTACTTTCCTTTACTTTTTT |
| SEQ ID NO: 180 | | S: _490S | M | TTTTTTTTTGTTACTCTCCTTTACTTTTTT |
| SEQ ID NO: 181 | S:6 | S: S494P | U | TTTTTCTCCTTTACAAYTATATGGTTTTTTT |

TABLE 28A-continued

Hybrdization Probes (Spike gene region)

| SEQ ID NOS. | Amplimer # | Target | U/W/M | Probe Sequence (5' to 3') |
|---|---|---|---|---|
| SEQ ID NO: 182 | | S: S494_ | W | TTTTTCTCTTTACAATCA TATGGTCTTTTT |
| SEQ ID NO: 183 | | S: _494P | M | TTTTTCTCTTTACAACCA TATGGTCTTTTT |
| SEQ ID NO: 257 | S:6 | S: N501Y/T | U | TTTTTTTTCCAACCCAC TWMTGGTGTTTTTTTT |
| SEQ ID NO: 56 | | S: N501_ | W | TTTTTTTTACCCACTAAT GGTGTCTTTTTT |
| SEQ ID NO: 57 | | S: _501Y | M | TTTTTTTTACCCACTTAT GGTGTCTTTTTT |
| SEQ ID NO: 184 | | S: _501T | M | TTTTTTTACCCACTACT GGTGTCTTTTTTT |
| SEQ ID NO: 107 | S:7 | S: Q613H.D614G | U | TTTTTCTCTTTATCARG RTGTTAACTGCTTTTTT |
| SEQ ID NO: 108 | | S: Q613_.D614_ | W | TTTTTCTTATCAGGATG TTAACTTTTTTTT |
| SEQ ID NO: 109 | | S: Q613_._614G | M | TTTTTTCCTATCAGGGT GTTAACTTTTTTT |
| SEQ ID NO: 110 | | S: Q2613_._614G | M | TTTTTTCCTATCAAGGT GTTAACTTTTTTT |
| SEQ ID NO: 258 | | S: _613H.D614_ | M | TTTTTCCCTTTATCATGA TGTTAATCTTTT |
| SEQ ID NO: 259 | S:8 | S: Q677P/H | U | TTTTTTATCAGACTCMB ACTAATTCTCTTTTT |
| SEQ ID NO: 186 | | S: Q677_ | W | TTTTTTCCAGACTCAGA CTAATTTCTTTTT |
| SEQ ID NO: 187 | | S: _677P | M | TTTTTCTTCAGACTCCG ACTAATCTTTTTT |
| SEQ ID NO: 188 | | S: _677H2 | M | TTTTTTCCAGACTCACA CTAATTTCTTTTT |
| SEQ ID NO: 189 | | S: _677H1 | M | TTTTTTCCAGACTCATA CTAATTTCTTTTT |
| SEQ ID NO: 260 | S:8 | S: P681H/R | U | TTTTTTCAGACTAATTCT CVTCGGCTTTTT |
| SEQ ID NO: 59 | | S: P68_ | W | TTTTTTTCTAATTCTCCT CGGCGTTTTTTT |
| SEQ ID NO: 60 | | S: _681H | M | TTTTTTTTTAATTCTCAT CGGCGTTTTTTT |
| SEQ ID NO: 190 | | S: _681R | M | TTTTTTTTTAATTCTCGT CGGCGTTTTTTT |
| SEQ ID NO: 261 | S:8 | S: A688V-RE1.1 | U | TTTTTTAGTGTAGYTAG TCAATCCACTTTT |
| SEQ ID NO: 262 | | S: A688_-RE1.1 | W | TTTTTTCAGTGTAGCTA GTCAATTTTTTTT |
| SEQ ID NO: 263 | | S:_688V-RE1.1 | M | TTTTTTCAGTGTAGTTA GTCAATTTTTTTT |
| SEQ ID NO: 61 | S:8 | S: A701V | U | TTTTCACTTGGTGYAGA AAATTCAGTTTTT |
| SEQ ID NO: 62 | | S: A701_ | W | TCTTCTTCTTGGTGCAG AAAATTATTCTTT |
| SEQ ID NO: 63 | | S: _701V | M | TCTTCTTCTTGGTGTAG AAAATTATTCTTT |
| SEQ ID NO: 134 | | RNAseP control | | TTTTTTTTCTGACCTGA AGGCTCTGCGCGTTTTT |
| SEQ ID NO: 136 | | NEG CONTROL | | TTTTTTCTACTACCTATG CTGATTCACTCTTTTT |

TABLE 28B

| Hybrdization Probes (Nucleocapsid gene region) | | | | |
|---|---|---|---|---|
| SEQ ID NOS. | Amplimer # | Target | U/W/M | Probe Sequence (5' to 3') |
| SEQ ID NO: 191 | N:9 (AA183-252) | N: S194L | U | TTTTCCGCAACAGTTYAA GAAATTCATTTT |
| SEQ ID NO: 192 | | N: S194_ | W | TTTTTTTAACAGTTCAAGA AATTTTTTTTT |
| SEQ ID NO: 193 | | N: _194L | M | TTTTTTTAACAGTTTAAGA AATTTTTTTTT |
| SEQ ID NO: 194 | N:9 (AA183-252) | N: S197L | U | TTTTCTCAAGAAATTYAAC TCCAGGCTTTT |
| SEQ ID NO: 195 | | N: S197_ | W | TTTTTCTAAGAAATTCAAC TCCATTTTTTT |
| SEQ ID NO: 196 | | N: _197L | M | TTTTTCTAAGAAATTTAAC TCCATTTTTTT |
| SEQ ID NO: 197 | N:9 (AA183-252) | N: P199L | U | TTTTTAAATTCAACTCYAG GCAGCATCTTT |
| SEQ ID NO: 198 | | N: P199_ | W | TTTTTTTTTCAACTCCAGG CAGCTTTTTTT |
| SEQ ID NO: 199 | | N: _199L | M | TTTTTTTTTCAACTCTAGG CAGCTTTTTTT |
| SEQ ID NO: 200 | N:9 (AA183-252) | N: S201I | U | TTTTTACTCCAGGCAKCW STADRSGATTTT |
| SEQ ID NO: 201 | | N: S20I_ | W | TTTTTTTTCCAGGCAGCA GTADRTTTTTTT |
| SEQ ID NO: 202 | | N: _201I | M | TTTTTTTTCCAGGCATCAG TAGGTTTTTTT |
| SEQ ID NO: 203 | N:9 (AA183-252) | N: S202N | U | TTTTCCCAGGCAGCARTA DRSGAACCTTTT |
| SEQ ID NO: 204 | | N: S202_ | W | TTTTTTTAGGCAGCAGTA DRSGATTTTTTT |
| SEQ ID NO: 205 | | N: _202N | M | TTTTTTTAGGCAGCAATA GGGGATTTTTTT |
| SEQ ID NO: 206 | N:9 (AA183-252) | N: R203M/K G204R | U | TTTTGCAGCWSTADRSGA ACTTCTCTTTTT |
| SEQ ID NO: 207 | | N: R203_G204_ | W | TTTTTTTCAGCAGTAGGG GAACTCTTTTTT |
| SEQ ID NO: 208 | | N: 203M G204_ | M | TTTTTTTCAGCAGTATGG GAACTCTTTTTT |
| SEQ ID NO: 219 | | N: _203K G204R | M | TTTTTTTCAGCAGTAAACG AACTCTTTTTT |
| SEQ ID NO: 210 | | N: _203K G204R (2) | M | TTTTTTTCAGCTCTAAACG AACTCTTTTTT |
| SEQ ID NO: 211 | N:9 (AA183-252) | N: T205I | U | TTTTCSTADRSGAAYTTCT CCTGCTATTTT |
| SEQ ID NO: 212 | | N: T205_ | W | TTTTTTTGGGGAACTTCTC CTGCCTTTTTT |
| SEQ ID NO: 213 | | N: _205I | M | TTTTTTTGGGGAATTTCTC CTGCCTTTTTT |
| SEQ ID NO: 214 | N:9 (AA183-252) | N: A208G R209del (MIX) | U | TTTTAAYTTCTCCTGCTAG AATGGCTGTTT |
| SEQ ID NO: 215 | | | | TTTTACGAACTTCTCCTG GAATGGCTGTTT |
| SEQ ID NO: 216 | | N: A208_R209_ | W | TTTTCTCTCCTGCTAGAAT GGCTGTTTTTT |
| SEQ ID NO: 217 | | N: _208G_209del | M | TTTTTACTTCTCCTGGAAT GGCTGTTTTTT |
| SEQ ID NO: 218 | N:9 (AA183-252) | N: G212V N213Y | U | TTTTTTGGCTGKCWATKG CKGTGATTTTTT |
| SEQ ID NO: 219 | | N: G212_N213Y | W | TTTTTTTAATGGCTGGCW ATKGCTTTTTTT |
| SEQ ID NO: 220 | | N: _212V N213_ | M | TTTTTTTAATGGCTGTCAA TGGCTTTTTTT |
| SEQ ID NO: 221 | | N: G212V N213_ | W | TTTTTTTTGGCTGKCAATK GCKGCTTTTTT |
| SEQ ID NO: 222 | | N: G212_ _213Y | M | TTTTTTTTGGCTGGCTATG GCGGCTTTTTT |
| SEQ ID NO: 223 | N:9 (AA183-252) | N: G214C G215C | U | TTTTTTGGCTGKCWATKG CKGTGATTTTTT |

TABLE 28B-continued

Hybrdization Probes (Nucleocapsid gene region)

| SEQ ID NOS. | Amplimer # | Target | U/W/M | Probe Sequence (5' to 3') |
|---|---|---|---|---|
| SEQ ID NO: 224 | | N: G214_G215C | W | TTTTTTTTGKCWATGGCK GTGATTTTTTTT |
| SEQ ID NO: 225 | | N: _214C G215_ | M | TTTTTTTTGGCAATTGCG GTGATTTTTTTT |
| SEQ ID NO: 226 | | N: G214C G215_ | W | TTTTTTTCWATKGCGGTG ATGCTTTTTTTT |
| SEQ ID NO: 227 | | N: G214_ _215C | M | TTTTTTTCAATGGCTGTGA TGCTTTTTTTT |
| SEQ ID NO: 228 | N:9 (AA183-252) | N: M234I S235F | U | TTTTTGAGCAAAATDTYTG GTAAAGTTTTT |
| SEQ ID NO: 229 | | N: M234_S235_ | W | TTTTTTTCAAAATGTCTGG TAAATTTTTTT |
| SEQ ID NO: 230 | | N: _234I S235_ | M | TTTTTCTAGCAAAATTTCT GGTATCTTTTT |
| SEQ ID NO: 231 | | N: _234I S235_ (2) | M | TTTTTCTAGCAAAATATCT GGTATCTTTTT |
| SEQ ID NO: 232 | | N: M234_ _235F | M | TTTTTCTCAAAATGTTTGG TAAATCTTTTT |

CONCLUSION

Described here is a “DETECTX-Cv” technology designed to combine the practicality of field deployable Q-RT-PCR testing with the high-level information content of targeted NGS. Population scale deployment of DETECTX-Cv is enabled in a way that is simple enough that it can be “drop-shipped” with minimal set up cost and training into any laboratory performing conventional Q-RT-PCR based COVID-19 screening. Initial field deployment demonstrated the ability of DETECTX-Cv to identify clinical positives per shift per Q-RT-PCR screening and analysis without additional sample prep for a large panel of CoV-2 clade variants (UK, Denmark, South Africa, Brazil, US (California, New York, Southern US) and Wuhan and the remainder of the present list of Variants of Concern, Variants of Interest and other Variants as known and classified by the World Health Organization; who.int/en/activities/tracking-SARS-CoV-2-variants/) incorporated into the content of the assay.

In conclusion, the technology encompassed in this invention enables DETECTX-Cv to perform very low-cost microarray analyses in a field-deployable format. DETECTX-Cv is based on proprietary technology of PathogenDx for designing DNA microarray probes and so, the resulting microarrays can be mass produced to deliver >24,000 tests/day. DETECTX-Cv also enables sequence-based testing on these microarrays via open-format room temperature hybridization and washing, much like the processing of ELISA assays. Like an ELISA plate, DETECTX-Cv is mass produced in a 96-well format, ready for manual or automated fluid handling and has the capability to handle up to 576 probe spots per well, at full production scale.

DETECTX-Cv is a combinatorial assay with several targets in the CoV-2 Spike gene and the N gene comprising an exceptionally large set of gain-of-function Spike and/or N gene mutants, which are believed to be selected for enhanced infectivity or resistance to natural or vaccine induced host immunity. Based on analysis of the rapidly growing CoV-2 resequencing effort (600,000 genomes in GISAID, April 2021 and over 5,000,000 genomes in GISAID, November 2021; gisaid.org) “terminal differentiation” of the Spike gene marker “basis set” into a set of informative Spike gene and N gene target sites is expected, which can be built into and mass produced into the same 96-well format described above. DETECTX-Cv is therefore expected to be beneficial as a true discovery tool that is capable of unbiased identification of new CoV-2 clade variants based on detection of novel combinations of the underlying Spike Variant “basis set”. Thus, DETECTX-Cv is expected to become the basis for field deployed seasonal COVID testing with military and civilian applications The DETECTX-Cv test content comprises Spike Gene Target sequence analysis among 32 discrete information-rich domains, and N gene Target sequence analysis among 11 discrete information-rich domains produced as triplicate tests per array, with positive and negative controls, to produce core content that is deployed as about 160 independent hybridization tests (per well) on each sample. The DETECTX-Cv technology described here is based on multiplex asymmetric, endpoint RT-PCR amplification of viral RNA purified as for Q-RT-PCR screening. The RT-PCR product resulting from amplification is fluorescently tagged and used as-is without cleanup for the subsequent steps of hybridization and washing, which are performed at room temperature (RT). Subsequent to hybridization and washing, the DETECTX-Cv plate is subjected to fluorescent plate reading, data processing and analysis that occurs automatically with no intervention by a human user to result in an output of detected CoV-2 clades which can be used locally for diagnosis and/or simultaneously uploaded to a secure, cloud-based portal for use by medical officials for military or public health tracking and epidemiology analysis.

What is claimed is:

1. A method for detecting clade variants in a Coronavirus disease 2019 virus (COVID-19) in a sample, comprising:

obtaining the sample;

harvesting viruses from the sample;

isolating total RNA from the harvested viruses;

performing a combined reverse transcription and asymmetric PCR amplification on the total RNA using at least one fluorescent labeled first primer pair comprising an unlabeled primer and a fluorescently labeled primer, selective for a target sequence in all genes of COVID-19 viruses to generate at least one fluorescent labeled COVID-19 virus cDNA amplicon;

performing a second amplification using the COVID-19 virus cDNA amplicons as template and at least one fluorescent labeled second primer pair selective for a target nucleotide sequence in the COVID-19 virus cDNA to generate at least one fluorescent labeled COVID-19 virus amplicon;

hybridizing the fluorescent labeled COVID-19 virus amplicons to a plurality of nucleic acid probes, each having a sequence corresponding to a sequence determinant that discriminates among the clade variants of the COVID-19 virus, said nucleic acid probes attached to a solid microarray support;

washing the microarray at least once;

imaging the microarray to detect at least one fluorescent signal from the hybridized fluorescent labeled COVID-19 virus amplicons; and generating an intensity distribution profile from said at least one fluorescent signal that is unique to one of the clade variants, thereby detecting the clade variant of the COVID-19 virus in the sample.

2. The method of claim 1, wherein prior to the harvesting step the method further comprises mixing the sample with an RNA stabilizer.

3. The method of claim 1, wherein at least one of the fluorescent labeled second primer pairs is selective for a panel of target nucleotide sequences within a target region of a gene in the COVID-19 virus; and wherein the nucleic acid probes are specific to the target region of the gene, whereby the at least one fluorescent labeled COVID-19 virus amplicon generated is hybridized to the nucleic acid probe thereby discriminating the clade variants of the COVID-19 virus in the sample.

4. The method of claim 3, said imaging and generating steps comprising:

detecting the at least one fluorescent signal from the hybridized at least one fluorescent labeled COVID-19 virus amplicons associated with the panel of target nucleotide sequences within the target region of the gene; and generating an intensity distribution profile unique to each of the clade variants, whereby each of the clade variants is distinguishable from the others.

5. The method of claim 1, wherein the gene is a spike gene or a nucleoprotein gene or a combination thereof.

6. The method of claim 1, wherein the clade variant of the COVID-19 virus is identified as a variant of concern, a variant of interest, or a Wuhan variant, or a combination thereof.

7. The method of claim 1, wherein the clade variants of the COVID-19 virus are Denmark (B.1.1.298), UK (B.1.1.7), South African (B.1.351), Brazil/Japan (P1), Brazil (P.2), California USA, L452R (1.429), or India (N440K), or Wuhan or a combination thereof.

8. The method of claim 1, wherein the gene is a spike gene, wherein said performing step comprises a fluorescent labeled second primer pair comprising the nucleotide sequences of SEQ ID NO: 9 and SEQ ID NO: 10, or SEQ ID NO: 11 and SEQ ID NO: 12, or SEQ ID NO: 13 and SEQ ID NO: 14, or SEQ ID NO: 15 and SEQ ID NO: 16, or SEQ ID NO: 17 and SEQ ID NO: 18, or SEQ ID NO: 19 and SEQ ID NO: 20, or SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 24, SEQ ID NO: 137 and SEQ ID NO: 20, or SEQ ID NO: 9 and SEQ ID NO: 138, or SEQ ID NO: 11 and SEQ ID NO: 139, or SEQ ID NO: 140 and SEQ ID NO: 16, or SEQ ID NO: 141 and SEQ ID NO: 18, or a combination thereof.

9. The method of claim 1, wherein the gene is a Nucleoprotein gene, said fluorescent labeled second primer pair comprising the nucleotide sequences of SEQ ID NO: 142 and SEQ ID NO: 143.

10. The method of claim 1, wherein the fluorescently labeled primer is in an excess of about 4-fold to about 8-fold over the unlabeled primer in the fluorescent labeled primer pair.

11. The method of claim 1, wherein the gene is a Spike gene, said nucleic acid probes comprising at least one of the nucleotide sequences of SEQ ID NOS: 30-129, 144-190 or 233-263.

12. The method of claim 1, wherein the gene is a Nucleoprotein gene, said nucleic acid probes comprising at least one of the nucleotide sequences of SEQ ID NOS: 191-232.

13. The method of claim 1, wherein the sample comprises at least one of a nasopharyngeal swab, a nasal swab, a mouth swab, a mouthwash, an aerosol, or a swab from a hard surface.

* * * * *

SEQUENCE LISTING

<160> NUMBER OF SEQ ID NOS: 265

<210> SEQ ID NO 1
<211> LENGTH: 28

```
<212> TYPE: DNA
<213> ORGANISM: Artificial Sequence
<220> FEATURE:
<223> OTHER INFORMATION: Forward primer sequence for SARS CoV-2 Spike
      gene

<400> SEQUENCE: 1

tttaacagag ttgttatttc tagtgatg                                         28


<210> SEQ ID NO 2
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
      gene

<400> SEQUENCE: 2

ttttctaaag tagtaccaaa aatccagc                                         28


<210> SEQ ID NO 3
<211> LENGTH: 28
<212> TYPE: DNA
<213> ORGANISM: Artificial Sequence
<220> FEATURE:
<223> OTHER INFORMATION: Forward primer sequence for SARS CoV-2 Spike
      gene

<400> SEQUENCE: 3

tttccctact tattgttaat aacgctac                                         28


<210> SEQ ID NO 4
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
      gene

<400> SEQUENCE: 4

tttagataac ccacataata agctgcag                                         28


<210> SEQ ID NO 5
<211> LENGTH: 28
<212> TYPE: DNA
<213> ORGANISM: Artificial Sequence
<220> FEATURE:
<223> OTHER INFORMATION: Forward primer sequence for SARS CoV-2 Spike
      gene

<400> SEQUENCE: 5

tttatctctg ctttactaat gtctatgc                                         28


<210> SEQ ID NO 6
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
      gene

<400> SEQUENCE: 6

tttacaaaca gttgctggtg catgtaga                                         28


<210> SEQ ID NO 7
<211> LENGTH: 28
<212> TYPE: DNA
```

```
<213> ORGANISM: Artificial Sequence
<220> FEATURE:
<223> OTHER INFORMATION: Forward primer sequence for SARS CoV-2 Spike
      gene

<400> SEQUENCE: 7

ttttggtgtc agtgttataa caccagga                                      28


<210> SEQ ID NO 8
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
      gene

<400> SEQUENCE: 8

ttttgtcttg gtcatagaca ctggtaga                                      28


<210> SEQ ID NO 9
<211> LENGTH: 28
<212> TYPE: DNA
<213> ORGANISM: Artificial Sequence
<220> FEATURE:
<223> OTHER INFORMATION: Forward primer sequence for SARS CoV-2 Spike
      gene

<400> SEQUENCE: 9

acctttcttt tccaatgtta cttggttc                                      28


<210> SEQ ID NO 10
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
      gene
<220> FEATURE:
<221> NAME/KEY: modified_base
<222> LOCATION: 1
<223> OTHER INFORMATION: Thymidine at position 1 is modified with a
      fluorescent label

<400> SEQUENCE: 10

ttttatgtta gacttctcag tggaagca                                      28


<210> SEQ ID NO 11
<211> LENGTH: 28
<212> TYPE: DNA
<213> ORGANISM: Artificial Sequence
<220> FEATURE:
<223> OTHER INFORMATION: Forward primer sequence for SARS CoV-2 Spike
      gene

<400> SEQUENCE: 11

tttcttattg ttaataacgc tactaatg                                      28


<210> SEQ ID NO 12
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
      gene
<220> FEATURE:
<221> NAME/KEY: modified_base
<222> LOCATION: 1
<223> OTHER INFORMATION: Thymidine at position 1 is modified with a
      fluorescent label
```

-continued

<400> SEQUENCE: 12
tttcattcgc actagaataa actctgaa 28

<210> SEQ ID NO 13
<211> LENGTH: 25
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 13
tgtaattaga ggtgatgaag tcaga 25

<210> SEQ ID NO 14
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 14
tttaaaggtt tgagattaga cttcctaa 28

<210> SEQ ID NO 15
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 15
ttttatttca actgaaatyt atcaggcc 28

<210> SEQ ID NO 16
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 16
tttaaagtac tactactctg tatggttg 28

<210> SEQ ID NO 17
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 17
ttttatatgc gctagttatc agactcag 28

<210> SEQ ID NO 18
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 18
ttttggtatg gcaatagagt tattagag 28

<210> SEQ ID NO 19
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 19
tttttttctt gttttattgc cactagtc 28

<210> SEQ ID NO 20
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 20
tttttgtcag ggtaataaac accacgtg 28

<210> SEQ ID NO 21
<211> LENGTH: 28
<212> TYPE: DNA
<213> ORGANISM: Artificial Sequence
<220> FEATURE:
<223> OTHER INFORMATION: Forward primer sequence for SARS CoV-2 Clade variant Spike gene

<400> SEQUENCE: 21
ttttaagcac acgcctatta atttagtg 28

<210> SEQ ID NO 22
<211> LENGTH: 28
<212> TYPE: DNA
<213> ORGANISM: Artificial Sequence
<220> FEATURE:
<223> OTHER INFORMATION: Reverse primer sequence for SARS CoV-2 Clade variant Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 22
tttccacata ataagctgca gcaccagc 28

<210> SEQ ID NO 23
<211> LENGTH: 28
<212> TYPE: DNA
<213> ORGANISM: Artificial Sequence
<220> FEATURE:
<223> OTHER INFORMATION: Forward primer sequence for SARS CoV-2 Clade variant Spike gene

<400> SEQUENCE: 23
tttagtgtta taacaccagg aacaaata 28

<210> SEQ ID NO 24
<211> LENGTH: 28
<212> TYPE: DNA
<213> ORGANISM: Artificial Sequence
<220> FEATURE:
<223> OTHER INFORMATION: Reverse primer sequence for SARS CoV-2 Clade variant Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 24
ttttgcatga atagcaacag ggacttct 28

<210> SEQ ID NO 25
<211> LENGTH: 28
<212> TYPE: DNA
<213> ORGANISM: Artificial Sequence
<220> FEATURE:
<223> OTHER INFORMATION: Forward primer sequence for SARS CoV-2 Clade variant Spike gene

<400> SEQUENCE: 25
ttcttttcca atgttacttg gttccatg 28

<210> SEQ ID NO 26
<211> LENGTH: 28
<212> TYPE: DNA
<213> ORGANISM: Artificial Sequence
<220> FEATURE:
<223> OTHER INFORMATION: Reverse primer sequence for SARS CoV-2 Clade variant Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 26
tttcaaaata aacaccatca ttaaatgg 28

<210> SEQ ID NO 27
<211> LENGTH: 28
<212> TYPE: DNA
<213> ORGANISM: Artificial Sequence
<220> FEATURE:
<223> OTHER INFORMATION: Forward primer sequence for SARS CoV-2 Clade variant Spike gene

<400> SEQUENCE: 27
tttgatgaag tcagacaaat cgctccag 28

<210> SEQ ID NO 28

```
<211> LENGTH: 28
<212> TYPE: DNA
<213> ORGANISM: Artificial Sequence
<220> FEATURE:
<223> OTHER INFORMATION: Reverse primer sequence for SARS CoV-2 Clade
      variant Spike gene
<220> FEATURE:
<221> NAME/KEY: modified_base
<222> LOCATION: 1
<223> OTHER INFORMATION: Thymidine at position 1 is modified with a
      fluorescent label

<400> SEQUENCE: 28

tttctctcaa aaggtttgag attagact                                      28


<210> SEQ ID NO 29
<211> LENGTH: 28
<212> TYPE: DNA
<213> ORGANISM: Artificial Sequence
<220> FEATURE:
<223> OTHER INFORMATION: Forward primer sequence for SARS CoV-2 Clade
      variant Spike gene

<400> SEQUENCE: 29

tttcaaatac ttctaaccag gttgctgt                                      28


<210> SEQ ID NO 30
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 30

tttttctagt ctctaktcag tgtgtttttt                                    30


<210> SEQ ID NO 31
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 31

tttttcccat gctatacatg tctctgtttt tt                                 32


<210> SEQ ID NO 32
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 32

tttttttttc catgctatct ctgggatttt tt                                 32


<210> SEQ ID NO 33
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 33

tttttcagag gtttgmtaac cctgtctttt tt                                 32


<210> SEQ ID NO 34
```

<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 34 ttttttggt ttgataaccc tgcttttttt 30

<210> SEQ ID NO 35
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 35 ttttttggt ttgctaaccc tgcttttttt 30

<210> SEQ ID NO 36
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 36
ttttattttg taatkatcca tttttgtttt 30

<210> SEQ ID NO 37
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 37
tttttctttg taatgatcca ttttcttttt 30

<210> SEQ ID NO 38
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 38 ttttttttg taattatcca ttttcttttt 30

<210> SEQ ID NO 39
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 39
tttttagttg katggaaagt gagttctttt 30

<210> SEQ ID NO 40
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 40

-continued

```
tttctctaaa agttggatgg aaactcttct                                        30


<210> SEQ ID NO 41
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 41

tttcttcaaa gttgtatgga aagccttctt                                        30


<210> SEQ ID NO 42
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 42

tttttaattc taamaakctt gattctaatt tt                                     32


<210> SEQ ID NO 43
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 43

tttttaattc taacaatctt gatttctttt                                        30


<210> SEQ ID NO 44
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 44

ttttttattc taacaagctt gatttttttt                                        30


<210> SEQ ID NO 45
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 45

ttttctattc taaaaatctt gatttctttt                                        30


<210> SEQ ID NO 46
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 46

tttctataat tacctgtata gattgtcttt                                        30


<210> SEQ ID NO 47
<211> LENGTH: 30
<212> TYPE: DNA
```

-continued

<213> ORGANISM: Artificial Sequence
<220> FEATURE:
<223> OTHER INFORMATION: Probe sequence for SARS CoV-2 Clade variant

<400> SEQUENCE: 47 ttttttaat tacctgtata gatttctttt 30

<210> SEQ ID NO 48
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 48
tttttcataa ttactggtat agatcttttt 30

<210> SEQ ID NO 49
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 49
ttttttcgcc ggtagcacac ctcttttttt 30

<210> SEQ ID NO 50
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 50
ttttcttccg gtaacacacc tttttttttt 30

<210> SEQ ID NO 51
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 51
ttttttaatg gtgttraagg ttttaatttt tt 32

<210> SEQ ID NO 52
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 52
ttttttctgg tgttgaaggt tttacttttt 30

<210> SEQ ID NO 53
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 53
tttttttatg gtgttaaagg ttttcttttt 30

<210> SEQ ID NO 54
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 54
tttttttatg gtgctgaagg ttcttttttt 30

<210> SEQ ID NO 55
<211> LENGTH: 33
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 55
ttttttttcc aacccactwa tggtgttttt ttt 33

<210> SEQ ID NO 56
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 56
ttttttttac ccactaatgg tgtctttttt 30

<210> SEQ ID NO 57
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 57
ttttttttac ccacttatgg tgtctttttt 30

<210> SEQ ID NO 58
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 58
ttttttcaga ctaattctcm tcggcttttt 30

<210> SEQ ID NO 59
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 59
tttttttcta attctcctcg gcgttttttt 30

<210> SEQ ID NO 60
<211> LENGTH: 30
<212> TYPE: DNA
<213> ORGANISM: Artificial Sequence
<220> FEATURE:

<223> OTHER INFORMATION: Probe sequence for SARS CoV-2 Clade variant

<400> SEQUENCE: 60 tttttttta attctcatcg gcgttttttt 30

<210> SEQ ID NO 61
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 61
ttttcacttg gtgyagaaaa ttcagttttt 30

<210> SEQ ID NO 62
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 62
tcttcttctt ggtgcagaaa attattcttt 30

<210> SEQ ID NO 63
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 63
tcttcttctt ggtgtagaaa attattcttt 30

<210> SEQ ID NO 64
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 64
tttttttgtc tctagtcagt gttttttttt 30

<210> SEQ ID NO 65
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 65
tttttttagt ctctagtcag tgtttttttt 30

<210> SEQ ID NO 66
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 66
ttttttagtc tctattcagt gttttttttt 30

-continued

<210> SEQ ID NO 67
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 67 ttttttagt ctctattcag tgttttttt 30

<210> SEQ ID NO 68
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 68 tttttaaty ttacaamcag aactcttttt 30

<210> SEQ ID NO 69
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 69
tttttttatc ttacaaccag aacctttttt 30

<210> SEQ ID NO 70
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 70
tttttttatc ttacaaccag aacttttttt 30

<210> SEQ ID NO 71
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 71
ttttttattt tacaaacaga actttttttt 30

<210> SEQ ID NO 72
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 72
tttttcaatt ttacaaacag aacttttttt 30

<210> SEQ ID NO 73
<211> LENGTH: 30
<212> TYPE: DNA
<213> ORGANISM: Artificial Sequence
<220> FEATURE:
<223> OTHER INFORMATION: Probe sequence for SARS CoV-2 Clade variant -continued

<400> SEQUENCE: 73 tttttatgc tatacatgtc tctgtttttt 30

<210> SEQ ID NO 74
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 74 tttttacca tgctatctct gggatttttt 30

<210> SEQ ID NO 75
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 75
tttttctagg tttgataacc ctgctttttt 30

<210> SEQ ID NO 76
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 76 ttttttagg tttgctaacc ctcttttttt 30

<210> SEQ ID NO 77
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 77
ttttttcttt gtaatgatcc atttcttttt 30

<210> SEQ ID NO 78
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 78
tttttctttg taattatcca ttttcttttt 30

<210> SEQ ID NO 79
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 79
ttttcttcaa agttggatgg aaactctttt 30

<210> SEQ ID NO 80
<211> LENGTH: 30

<212> TYPE: DNA
<213> ORGANISM: Artificial Sequence
<220> FEATURE:
<223> OTHER INFORMATION: Probe sequence for SARS CoV-2 Clade variant

<400> SEQUENCE: 80
tttctctaaa agttgtatgg aaactcttct 30

<210> SEQ ID NO 81
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 81 tttttagtg cgtgrtctcc ctcatttttt 30

<210> SEQ ID NO 82
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 82
ttttttctgc gtgatctccc tcattttttt 30

<210> SEQ ID NO 83
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 83
tttttttctg cgtgatctcc ctcttttttt 30

<210> SEQ ID NO 84
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 84
ttttttttgc gtggtctccc tctttttttt 30

<210> SEQ ID NO 85
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 85
tttttttttg cgtggtctcc cttttttttt 30

<210> SEQ ID NO 86
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 86
ttttaactgg aaakattgct gattattttt 30

<210> SEQ ID NO 87
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 87
tttcttctct ggaaagattg ctgctttttt 30

<210> SEQ ID NO 88
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 88
ttcttctctg gaaagattgc tgactttttt 30

<210> SEQ ID NO 89
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 89
tttttctctg gaaatattgc tgactttttt 30

<210> SEQ ID NO 90
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 90
ttttctctgg aaatattgct gatctttttt 30

<210> SEQ ID NO 91
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 91 ttttttttact ggaacgattg cttttttttt 30

<210> SEQ ID NO 92
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 92
ttttttcctg gaacgattgc tgtttttttt 30

<210> SEQ ID NO 93
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 93 tttttattc taacaatctt gatttctttt 30

<210> SEQ ID NO 94
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 94 ttttttttc taacaagctt gatttttttt 30

<210> SEQ ID NO 95
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 95
ttcttaattc taaaaatctt gatttctttt 30

<210> SEQ ID NO 96
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 96
tttttcataa ttacctgtat agactttctt 30

<210> SEQ ID NO 97
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 97
ttttttcaat taccggtata gatctttttt 30

<210> SEQ ID NO 98
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 98
ttttttttgg tagcatacct tgtttttttt 30

<210> SEQ ID NO 99
<211> LENGTH: 29
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 99
tttttttcgg tagcatacct tgttttttt 29

-continued

<210> SEQ ID NO 100
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 100
ttttttcgcc ggtaacacac ctctttttttt 30

<210> SEQ ID NO 101
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 101 tttttttca ggccagtagc acttttttttt 30

<210> SEQ ID NO 102
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 102
tttttctggt gttgaaggtt ttatcttttt 30

<210> SEQ ID NO 103
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 103
ttttttctgg tgttaaaggt tttacttttt 30

<210> SEQ ID NO 104
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 104
ttttttcaat ggtgctgaag gttctttttt 30

<210> SEQ ID NO 105
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 105
tttttttaac ccactaatgg tgtctttttt 30

<210> SEQ ID NO 106
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 106
tttttttaac ccacttatgg tgtctttttt 30

<210> SEQ ID NO 107
<211> LENGTH: 34
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 107
tttttctctt tatcargrtg ttaactgctt tttt 34

<210> SEQ ID NO 108
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 108
tttttcttat caggatgtta actttttttt 30

<210> SEQ ID NO 109
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 109
ttttttccta tcagggtgtt aacttttttt 30

<210> SEQ ID NO 110
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 110
ttttttccta tcaaggtgtt aacttttttt 30

<210> SEQ ID NO 111
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 111
ttttttccta tcarggtgtt aacttttttt 30

<210> SEQ ID NO 112
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 112
ttttttttaa ttctcctcgg cgtttttttt 30

<210> SEQ ID NO 113

<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 113 ttttttcta attctcatcg gcgttttttt 30

<210> SEQ ID NO 114
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 114
ttcttctact tggtgcagaa aattattctt 30

<210> SEQ ID NO 115
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 115
tttctttctt ggtgtagaaa attctttttt 30

<210> SEQ ID NO 116
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 116
ttttttacaa tttgccccca gcgtcttttt 30

<210> SEQ ID NO 117
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 117
tttttttttg ctccragtgc ctcttttttt 30

<210> SEQ ID NO 118
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 118
ttttttttca aactttactt gctttactct tt 32

<210> SEQ ID NO 119
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 119 tttttttca aactttacat agaagccttt tt 32

<210> SEQ ID NO 120
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 120
ttttctacat agaagttatt tgactccctt tt 32

<210> SEQ ID NO 121
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 121
ttttctgctt tacatatgac tcctggtttt tt 32

<210> SEQ ID NO 122
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 122
tttctactcc tggtgrttct tcttcatttt 30

<210> SEQ ID NO 123
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 123
ttttttccct ggtgattctt ctttcttttt 30

<210> SEQ ID NO 124
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 124
ttttttccct ggtggttctt cttttttttt 30

<210> SEQ ID NO 125
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 125
ttttttatca gactcmgact aattctcttt tt 32

<210> SEQ ID NO 126
<211> LENGTH: 30
<212> TYPE: DNA

<213> ORGANISM: Artificial Sequence
<220> FEATURE:
<223> OTHER INFORMATION: Probe sequence for SARS CoV-2 Clade variant

<400> SEQUENCE: 126 tttttccag actcagacta atttcttttt 30

<210> SEQ ID NO 127
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 127
tttttcttca gactccgact aatctttttt 30

<210> SEQ ID NO 128
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 128
ttttttccag actcatacta atttcttttt 30

<210> SEQ ID NO 129
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 129
ttttttccag actcacacta atttcttttt 30

<210> SEQ ID NO 130
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 130
tttacttcag catggcggtg tttgcaga 28

<210> SEQ ID NO 131
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 131
ttttgatagc aacaactgaa tagccaag 28

<210> SEQ ID NO 132
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 132
tttgtttgca gatttggacc tgcgagcg 28

<210> SEQ ID NO 133
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 133
tttaaggtga gcggctgtct ccacaagt 28

<210> SEQ ID NO 134
<211> LENGTH: 34
<212> TYPE: DNA
<213> ORGANISM: Artificial Sequence
<220> FEATURE:
<223> OTHER INFORMATION: Probe sequence for human RNAse P control

<400> SEQUENCE: 134 tttttttct gacctgaagg ctctgcgcgt tttt 34

<210> SEQ ID NO 135
<211> LENGTH: 30
<212> TYPE: DNA
<213> ORGANISM: Artificial Sequence
<220> FEATURE:
<223> OTHER INFORMATION: Probe sequence for human RNAse P control

<400> SEQUENCE: 135
tttttcttga cctgaaggct ctgctttttt 30

<210> SEQ ID NO 136
<211> LENGTH: 34
<212> TYPE: DNA
<213> ORGANISM: Artificial Sequence
<220> FEATURE:
<223> OTHER INFORMATION: Probe sequence for Negative Control

<400> SEQUENCE: 136
ttttttctac tacctatgct gattcactct tttt 34

<210> SEQ ID NO 137
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 137
tttagagttg ttatttctag tgatgttc 28

<210> SEQ ID NO 138
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 138
tttaatccag cctcttatta tgttagac 28

<210> SEQ ID NO 139
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent label

<400> SEQUENCE: 139
tttcaaaagt gcaattattc gcactaga 28

<210> SEQ ID NO 140
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 140
tttcttttga gagagatatt tcaactga 28

<210> SEQ ID NO 141
<211> LENGTH: 26
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 141
tttattggtg caggtatatg cgctag 26

<210> SEQ ID NO 142
<211> LENGTH: 26
<212> TYPE: DNA
<213> ORGANISM: Artificial Sequence
<220> FEATURE:
<223> OTHER INFORMATION: Forward primer sequence for SARS CoV-2 Nucleoprotein gene

<400> SEQUENCE: 142
tttgccaaaa ggcttctacg cagaag 26

<210> SEQ ID NO 143
<211> LENGTH: 26
<212> TYPE: DNA
<213> ORGANISM: Artificial Sequence
<220> FEATURE:
<223> OTHER INFORMATION: Reverse primer sequence for SARS CoV-2 Nucleoprotein gene

<400> SEQUENCE: 143
ttttttgccg aggcttctta gaagcc 26

<210> SEQ ID NO 144
<211> LENGTH: 32
<212> TYPE: DNA
<213> ORGANISM: Artificial Sequence
<220> FEATURE:
<223> OTHER INFORMATION: Reverse primer sequence for SARS CoV-2 Nucleocapsid gene -continued

```
<220> FEATURE:
<221> NAME/KEY: modified_base
<222> LOCATION: 1
<223> OTHER INFORMATION: Thymidine at position 1 is modified with a
      fluorescent label

<400> SEQUENCE: 144

ttttcgtttg tttttyttgt tttattgctt tt                                    32

<210> SEQ ID NO 145
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 145

ttttcgtttg tttttcttgt tttatttttt                                       30

<210> SEQ ID NO 146
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 146

ttttcgtttg tttttcttgt tttatttttt                                       30

<210> SEQ ID NO 147
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 147

tttttcttgt taattttaca accatttttt                                       30

<210> SEQ ID NO 148
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 148

tttttcttta atcttagaac cagacttttt                                       30

<210> SEQ ID NO 149
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 149

tttttctcca tgctatacat gtcctttttt                                       30

<210> SEQ ID NO 150
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 150
```

tttttttttc catgctatct ctgttttttt 30

<210> SEQ ID NO 151
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 151
tttttttttc catgttatct ctgttttttt 30

<210> SEQ ID NO 152
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 152
tttttttggt ttggtaaccc tgcttttttt 30

<210> SEQ ID NO 153
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 153 tttcttttg cttccaytga gaagtctttt tt 32

<210> SEQ ID NO 154
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 154
ttttttccgc ttccactgag aagcattttt 30

<210> SEQ ID NO 155
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 155
ttttttccgc ttccattgag aagcattttt 30

<210> SEQ ID NO 156
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 156
tttctttggg tgtttattac cacaaaaatt tt 32

<210> SEQ ID NO 157
<211> LENGTH: 32
<212> TYPE: DNA

<213> ORGANISM: Artificial Sequence
<220> FEATURE:
<223> OTHER INFORMATION: Probe sequence for SARS CoV-2 Clade variant

<400> SEQUENCE: 157
tttttttttg ggtgtttacc acaaaaactt tt 32

<210> SEQ ID NO 158
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 158
tttatttttg ggtgttactt attaccacat tt 32

<210> SEQ ID NO 159
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 159
ttcttttgga tgtttattac cacaaaaact tt 32

<210> SEQ ID NO 160
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 160
ttcgtaatga tccattttat taccacaaat tt 32

<210> SEQ ID NO 161
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 161
tctcttcaaa agtttgatgg aaatctcttt 30

<210> SEQ ID NO 162
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 162
tttctttaca aaagtaggat ggatttcttt 30

<210> SEQ ID NO 163
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 163
tttctttgtt ggatgaaaag tgatcttctt 30

<210> SEQ ID NO 164
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 164
ttttgaaagt gagttcagag tttacctttt 30

<210> SEQ ID NO 165
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 165
ttctttggaa agtggagttt attctctttt 30

<210> SEQ ID NO 166
<211> LENGTH: 32
<212> TYPE: DNA
<213> ORGANISM: Artificial Sequence
<220> FEATURE:
<223> OTHER INFORMATION: Primer sequence for SARS CoV-2 Clade variant

<400> SEQUENCE: 166 tttttttca aactttactt gctttactct tt 32

<210> SEQ ID NO 167
<211> LENGTH: 32
<212> TYPE: DNA
<213> ORGANISM: Artificial Sequence
<220> FEATURE:
<223> OTHER INFORMATION: Primer sequence for SARS CoV-2 Clade variant

<400> SEQUENCE: 167 tttttttca aactttacat agaagccttt tt 32

<210> SEQ ID NO 168
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 168
ttttctacat agaagttatt tgactccctt tt 32

<210> SEQ ID NO 169
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 169
ttttctgctt tacatatgac tcctggtttt tt 32

<210> SEQ ID NO 170
<211> LENGTH: 30
<212> TYPE: DNA
<213> ORGANISM: Artificial Sequence
<220> FEATURE:

-continued

<223> OTHER INFORMATION: Probe sequence for SARS CoV-2 Clade variant

<400> SEQUENCE: 170
tttctactcc tggtgrttct tcttcatttt 30

<210> SEQ ID NO 171
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 171
ttttttccct ggtgattctt ctttcttttt 30

<210> SEQ ID NO 172
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 172
ttttttccct ggtggttctt cttttttttt 30

<210> SEQ ID NO 173
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 173
tttttttaat taccagtata gatccttttt 30

<210> SEQ ID NO 174
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 174
tttttcggta gcamaccttg taatgttttt 30

<210> SEQ ID NO 175
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 175
tttttttgta gcacaccttg tatttttttt 30

<210> SEQ ID NO 176
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 176
tttttttgta gcaaaccttg tatttttttt 30

```
<210> SEQ ID NO 177
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 177

tttttttatgg tgttcaaggt tttctttttt                                    30

<210> SEQ ID NO 178
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 178

ttttctaatt gttactttcc tttacaatttt tt                                 32

<210> SEQ ID NO 179
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 179

tttttttttg ttactttcct ttactttttt                                     30

<210> SEQ ID NO 180
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 180

tttttttttg ttactctcct ttactttttt                                     30

<210> SEQ ID NO 181
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 181

tttttctcct ttacaaytat atggtttttt tt                                  32

<210> SEQ ID NO 182
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 182

tttttctctt tacaatcata tggtcttttt                                     30

<210> SEQ ID NO 183
<211> LENGTH: 30
<212> TYPE: DNA
<213> ORGANISM: Artificial Sequence
<220> FEATURE:
<223> OTHER INFORMATION: Probe sequence for SARS CoV-2 Clade variant
```

<400> SEQUENCE: 183
tttttctctt tacaaccata tggtcttttt 30

<210> SEQ ID NO 184
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 184
tttttttacc cactactggt gttttttttt 30

<210> SEQ ID NO 185
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 185
ttttttatca gactcmgact aattctcttt tt 32

<210> SEQ ID NO 186
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 186
ttttttccag actcagacta atttcttttt 30

<210> SEQ ID NO 187
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 187
tttttcttca gactccgact aatctttttt 30

<210> SEQ ID NO 188
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 188
ttttttccag actcacacta atttcttttt 30

<210> SEQ ID NO 189
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 189
ttttttccag actcatacta atttcttttt 30

<210> SEQ ID NO 190
<211> LENGTH: 30

-continued

<212> TYPE: DNA
<213> ORGANISM: Artificial Sequence
<220> FEATURE:
<223> OTHER INFORMATION: Probe sequence for SARS CoV-2 Clade variant

<400> SEQUENCE: 190 tttttttta attctcgtcg gcgttttttt 30

<210> SEQ ID NO 191
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 191
ttttccgcaa cagttyaaga aattcatttt 30

<210> SEQ ID NO 192
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 192
tttttttaac agttcaagaa attttttttt 30

<210> SEQ ID NO 193
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 193
tttttttaac agtttaagaa attttttttt 30

<210> SEQ ID NO 194
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 194
ttttctcaag aaattyaact ccaggctttt 30

<210> SEQ ID NO 195
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 195
tttttctaag aaattcaact ccattttttt 30

<210> SEQ ID NO 196
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 196

-continued tttttctaag aaatttaact ccattttttt 30

<210> SEQ ID NO 197
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 197
tttttaaatt caactcyagg cagcatcttt 30

<210> SEQ ID NO 198
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 198
tttttttttc aactccaggc agcttttttt 30

<210> SEQ ID NO 199
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 199
tttttttttc aactctaggc agcttttttt 30

<210> SEQ ID NO 200
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 200
tttttactcc aggcakcwst adrsgatttt 30

<210> SEQ ID NO 201
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 201
ttttttttcc aggcagcagt adrttttttt 30

<210> SEQ ID NO 202
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 202
ttttttttcc aggcatcagt aggttttttt 30

<210> SEQ ID NO 203
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 203
ttttcccagg cagcartadr sgaacctttt 30

<210> SEQ ID NO 204
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 204
tttttttagg cagcagtadr sgattttttt 30

<210> SEQ ID NO 205
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 205
tttttttagg cagcaatagg ggattttttt 30

<210> SEQ ID NO 206
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 206
ttttgcagcw stadrsgaac ttctcttttt 30

<210> SEQ ID NO 207
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 207
tttttttcag cagtagggga actctttttt 30

<210> SEQ ID NO 208
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 208
tttttttcag cagtatggga actctttttt 30

<210> SEQ ID NO 209
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 209
tttttttcag cagtaaacga actctttttt 30

<210> SEQ ID NO 210
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 210
tttttttcag ctctaaacga actctttttt 30

<210> SEQ ID NO 211
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 211
ttttcstadr sgaayttctc ctgctatttt 30

<210> SEQ ID NO 212
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 212
tttttttggg gaacttctcc tgcctttttt 30

<210> SEQ ID NO 213
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 213
tttttttggg gaatttctcc tgcctttttt 30

<210> SEQ ID NO 214
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 214
ttttaayttc tcctgctaga atggctgttt 30

<210> SEQ ID NO 215
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 215
ttttacgaac ttctcctgga atggctgttt 30

<210> SEQ ID NO 216
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 216
ttttctctcc tgctagaatg gctgtttttt 30

<210> SEQ ID NO 217
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 217
tttttacttc tcctggaatg gctgtttttt 30

<210> SEQ ID NO 218
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 218
ttttttggct gkcwatkgck gtgatttttt 30

<210> SEQ ID NO 219
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 219
tttttttaat ggctggcwat kgcttttttt 30

<210> SEQ ID NO 220
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 220
tttttttaat ggctgtcaat ggcttttttt 30

<210> SEQ ID NO 221
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 221
ttttttttgg ctgkcaatkg ckgctttttt 30

<210> SEQ ID NO 222
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 222
ttttttttgg ctggctatgg cggctttttt 30

<210> SEQ ID NO 223

<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 223 tttttggct gkcwatkgck gtgatttttt 30

<210> SEQ ID NO 224
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 224
ttttttttgk cwatggckgt gatttttttt 30

<210> SEQ ID NO 225
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 225
ttttttttgg caattgcggt gatttttttt 30

<210> SEQ ID NO 226
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 226
tttttttcwa tkgcggtgat gctttttttt 30

<210> SEQ ID NO 227
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 227
tttttttcaa tggctgtgat gctttttttt 30

<210> SEQ ID NO 228
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 228
tttttgagca aaatdtytgg taaagttttt 30

<210> SEQ ID NO 229
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 229
tttttttcaa aatgtctggt aaattttttt 30

<210> SEQ ID NO 230
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 230
tttttctagc aaaatttctg gtatcttttt 30

<210> SEQ ID NO 231
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 231
tttttctagc aaaatatctg gtatcttttt 30

<210> SEQ ID NO 232
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 232
tttttctcaa aatgtttggt aaatcttttt 30

<210> SEQ ID NO 233
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 233
ttttttaaty ttasaamcag aactcttttt 30

<210> SEQ ID NO 234
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 234
tttttcttgt taattttaca amcatttttt 30

<210> SEQ ID NO 235
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 235
tttttcccat gytatacatg tctctgtttt tt 32

<210> SEQ ID NO 236
<211> LENGTH: 32
<212> TYPE: DNA

<213> ORGANISM: Artificial Sequence
<220> FEATURE:
<223> OTHER INFORMATION: Probe sequence for SARS CoV-2 Clade variant

<400> SEQUENCE: 236
tttttttttc catgytatct ctgggatttt tt 32

<210> SEQ ID NO 237
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 237
ttttttgacc aatggtacta agagtttttt 30

<210> SEQ ID NO 238
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 238
ttttttacca atggtactaa gagtcttttt 30

<210> SEQ ID NO 239
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 239
ttttttacca atgttattaa gagtcttttt 30

<210> SEQ ID NO 240
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 240
tttttcagag gtttgvtaac cctgtctttt tt 32

<210> SEQ ID NO 241
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 241
tttctttggr tgtttattac cacaaaaatt tt 32

<210> SEQ ID NO 242
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 242
tttctgtgtt tatyaccaca aaaacttctt 30

<210> SEQ ID NO 243
<211> LENGTH: 31
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 243
tttttctgtg tttattacca caaatctttt t 31

<210> SEQ ID NO 244
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 244 tttttatgt ttatcaccac aaatcttttt 30

<210> SEQ ID NO 245
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 245 ttttttttg cgtgatctcc cttttttttt 30

<210> SEQ ID NO 246
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 246 ttttttttg cgtggtctcc cctttttttt 30

<210> SEQ ID NO 247
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 247
ttttgttttt cggytttaga accatctttt 30

<210> SEQ ID NO 248
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 248 ttttttttt tcggctttag aacttttttt 30

<210> SEQ ID NO 249
<211> LENGTH: 30
<212> TYPE: DNA
<213> ORGANISM: Artificial Sequence
<220> FEATURE:

<223> OTHER INFORMATION: Probe sequence for SARS CoV-2 Clade variant

<400> SEQUENCE: 249 tttttgttt ttcggtttta gaattttttt 30

<210> SEQ ID NO 250
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 250
ttttaactgg aamkattgct gattattttt 30

<210> SEQ ID NO 251
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 251
tttctataat taccdgtata gattgtcttt 30

<210> SEQ ID NO 252
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 252
tttttcgccg gtarcamacc ttgtattttt 30

<210> SEQ ID NO 253
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 253
tttttttccg gtagcacacc tttttttttt 30

<210> SEQ ID NO 254
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 254
tttttctggt agcaaacctt gttttttttt 30

<210> SEQ ID NO 255
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 255
ttttttaatg gtgytraagg ttttaatttt tt 32

<210> SEQ ID NO 256
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 256
ttttctaatt gttactytcc tttacaattt tt 32

<210> SEQ ID NO 257
<211> LENGTH: 33
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 257 tttttttcc aacccactwm tggtgttttt ttt 33

<210> SEQ ID NO 258
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 258
tttttccctt tatcatgatg ttaatctttt 30

<210> SEQ ID NO 259
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 259 tttttatca gactcmbact aattctcttt tt 32

<210> SEQ ID NO 260
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 260 tttttcaga ctaattctcv tcggcttttt 30

<210> SEQ ID NO 261
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 261 tttttagtg tagytagtca atccactttt 30

<210> SEQ ID NO 262
<211> LENGTH: 30
<212> TYPE: DNA
<213> ORGANISM: Artificial Sequence
<220> FEATURE:
<223> OTHER INFORMATION: Probe sequence for SARS CoV-2 Clade variant -continued

```
<400> SEQUENCE: 262

tttttcagt gtagctagtc aatttttttt                                    30


<210> SEQ ID NO 263
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 263

tttttcagt gtagttagtc aatttttttt                                    30


<210> SEQ ID NO 264
<211> LENGTH: 26
<212> TYPE: DNA
<213> ORGANISM: Artificial Sequence
<220> FEATURE:
<223> OTHER INFORMATION: Forward primer sequence for SARS CoV-2
      Nucleocapsid gene

<400> SEQUENCE: 264

ttttgccaaa aggcttctac gcagaa                                       26


<210> SEQ ID NO 265
<211> LENGTH: 26
<212> TYPE: DNA
<213> ORGANISM: Artificial Sequence
<220> FEATURE:
<223> OTHER INFORMATION: Reverse primer sequence for SARS CoV-2
      Nucleocapsid gene

<400> SEQUENCE: 265

ttgtttttgc cgaggcttct tagaag                                       26
```